(12) United States Patent
Lillard, Jr.

(10) Patent No.: US 9,783,588 B2
(45) Date of Patent: Oct. 10, 2017

(54) CHEMOKINE-IMMUNOGLOBULIN FUSION POLYPEPTIDES, COMPOSITIONS, METHOD OF MAKING AND USE THEREOF

(71) Applicant: JYANT TECHNOLOGIES, INC., Marietta, GA (US)

(72) Inventor: James W. Lillard, Jr., Smyrna, GA (US)

(73) Assignee: JYANT TECHNOLOGIES, INC., Marietta, GA (US)

( * ) Notice: Subject to any disclaimer, the term of this patent is extended or adjusted under 35 U.S.C. 154(b) by 0 days.

(21) Appl. No.: 15/282,069

(22) Filed: Sep. 30, 2016

(65) Prior Publication Data

US 2017/0015721 A1    Jan. 19, 2017

Related U.S. Application Data

(63) Continuation of application No. 14/978,684, filed on Dec. 22, 2015, now Pat. No. 9,493,531, which is a continuation of application No. 14/612,884, filed on Feb. 3, 2015, now Pat. No. 9,249,204, which is a continuation-in-part of application No. 13/962,401, filed on Aug. 8, 2013, now Pat. No. 8,987,210, which is a continuation of application No. 13/962,110, filed on Aug. 8, 2013, now Pat. No. 8,796,422, which is a continuation-in-part of application No. 13/480,526, filed on May 25, 2012, now Pat. No. 8,541,564.

(60) Provisional application No. 61/492,260, filed on Jun. 1, 2011.

(51) Int. Cl.
| | |
|---|---|
| *A61K 38/00* | (2006.01) |
| *A61K 38/16* | (2006.01) |
| *A61K 39/395* | (2006.01) |
| *A61K 39/00* | (2006.01) |
| *C07K 16/00* | (2006.01) |
| *C07K 14/52* | (2006.01) |
| *C07K 16/18* | (2006.01) |

(52) U.S. Cl.
CPC ............ *C07K 14/521* (2013.01); *C07K 16/18* (2013.01); *A61K 38/00* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,766,897 A | 6/1998 | Braxton | |
| 7,279,460 B2 | 10/2007 | Wang et al. | |
| 7,740,833 B2 | 6/2010 | Proudfoot et al. | |
| 8,012,928 B2 | 9/2011 | Bluth et al. | |
| 8,277,809 B2 | 10/2012 | Bugelski et al. | |
| 2001/0053539 A1 | 12/2001 | Lauffer et al. | |
| 2002/0058800 A1 | 5/2002 | Kingsbury et al. | |
| 2002/0114806 A1 | 8/2002 | Pardo-Semo et al. | |
| 2005/0053579 A1 | 3/2005 | Galipeau et al. | |
| 2007/0036750 A1 | 2/2007 | Chou et al. | |
| 2007/0116669 A1 | 5/2007 | Merzouk et al. | |
| 2008/0253996 A1* | 10/2008 | Boschert ............... | A61K 38/195 424/85.6 |
| 2009/0098101 A1 | 4/2009 | Raines et al. | |
| 2010/0062009 A9* | 3/2010 | Chu ..................... | C07K 14/522 435/69.5 |
| 2010/0166733 A1 | 7/2010 | Levin et al. | |
| 2010/0196406 A1 | 8/2010 | Karin et al. | |
| 2011/0224134 A1* | 9/2011 | Harper ................. | C07K 5/0808 514/4.3 |

FOREIGN PATENT DOCUMENTS

| | | |
|---|---|---|
| CN | 101443357 | 5/2009 |
| JP | 2009-504158 | 2/2009 |
| WO | 2005/037305 | 4/2005 |
| WO | 2007/021807 | 2/2007 |
| WO | 2007/148317 | 12/2007 |

OTHER PUBLICATIONS

Sun et al. 2010. Cancer Metast. Rev. 29:709-722.*
Biragyn, A., et al., "Mediators of Innate Immunity That Target Immature, But Not Mature, Dendritic Cells Induce Antitumor Immunity When Genetically Fused with Nonimmunogenic Tumor Antigens", The Journal of Immunology, Dec. 1, 2001, vol. 167, No. 11, pp. 6644-6653.
Fagete, S., et al., "Specificity turning of antibody fragments to neutralize two human chemokines with a single agent", MAbs, May-Jun. 2009, vol. 1, No. 3, pp. 288-296.
Van Heeke, G., et al. "Expression of Human Asparagine Synthetase in *Escherichia coli*," The Journal of Biological Chemistry, vol. 264, No. 10, Apr. 5, 1989, pp. 5503-5509.
Allen, S.J., et al. "Chemokine: Receptor Structure, Interactions, and Antagonism," Annu. Rev. Immunol., 2007, 25: 787-820.
File history of U.S. Appl. No. 13/480,526, filed on May 25, 2012.
File history of U.S. Appl. No. 13/962,110, filed on Aug. 8, 2013.
File history of U.S. Appl. No. 13/962,401, filed on Aug. 8, 2013.
Nextprot Beta, CCL25-C-C motif chemokine 25, 2011.
File history of U.S. Appl. No. 14/612,884, filed on Feb. 3, 2015.
The International Search report and the Written Opinion of the International Searching Authority (Application No. PCT/US2012/039550, International Filing Date: May 25, 2012), dated Dec. 18, 2012.
European Search Report issued in European Patent Application No. 12792144.3 dated Mar. 5, 2015.
Islam, Sabina A. et al., "Identification of human CCR8 as a CCL18 receptor," Journal of Experimental Medicine, published Sep. 2, 2013, vol. 210 No. 10, pp. 1889-1898.
File history of U.S. Appl. No. 14/978,684, filed on Dec. 22, 2015.

* cited by examiner

*Primary Examiner* — Shulamith H Shafer
(74) *Attorney, Agent, or Firm* — Ping Wang; Andrews Kurth Kenyon LLP

(57) ABSTRACT

This application is directed to chemokine-immunoglobulin fusion polypeptides and chemokine-polymer conjugates. The fusion polypeptides and conjugates can be used for treating chemokine receptor-mediated disorders and modulating inflammation, inflammatory cell motility, cancer cell motility, or cancer cell survival.

13 Claims, 70 Drawing Sheets

FIG.1A
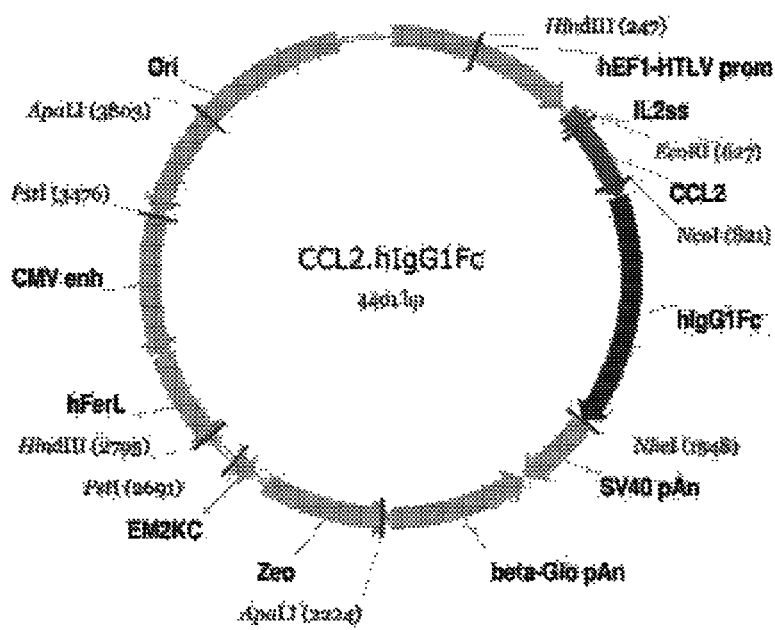
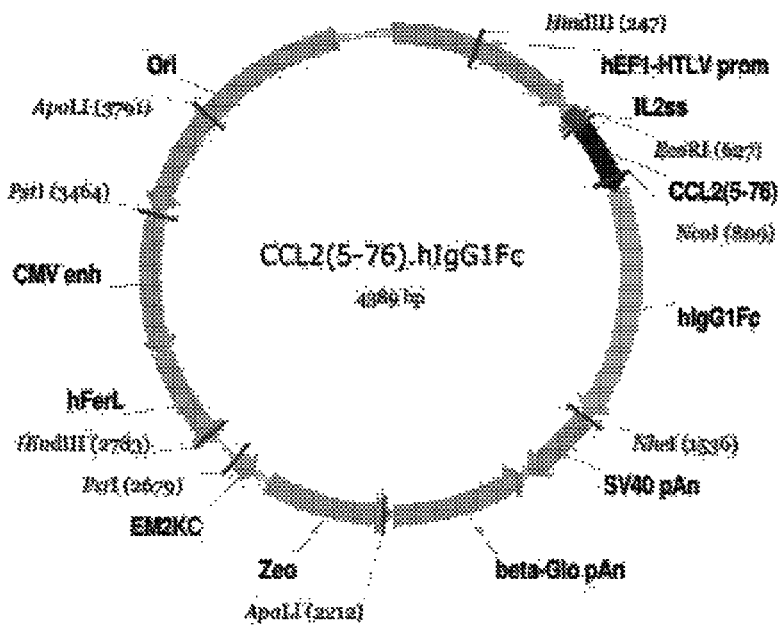
FIG.1B

FIG.1C

IL2ss.CCL2hIgG1Fc GAGless plasmid sequence

Sequence figure not transcribed in detail.

The page shows a DNA/protein sequence listing for "IL2ss.CCL2(5-76).hIgG1Fc GAGless plasmid sequence" which is too low-resolution to transcribe reliably.

IL2ss.CCL2(5-76).hIgG1Fc sequence [Alanine substitutions for removal of GAG binding sites - Lys & His]

IL2ss.CCL7.hIgG1Fc sequence

This figure contains a DNA/protein sequence alignment that is too low-resolution to transcribe reliably. Key annotations visible include:

- EcoRI, KasI, NarI, SfoI, XbeI, BmtI, NheI, AseI restriction sites
- IL-2 secretion signal: MetTyrArg MetGlnLeu LeuSerCysIle...
- CCL7 (1-76)
- human IgG1 Fc (constant region)
- ProGlyLys *** (SEQ ID NO: 55)

```
2401 AGGTCACGT CGTCCCGGAC CACACCGGCG AAGTCGTCCT CCACGAAGTC CCGAGCCGGT CGGTCCAGAA CTCGACCGCT CCGGGCGACGT
2501 CGGCGCGCGT GAGCACCGGA ACGGCACTGG TCAACTTGGC CATGATCGCT CCTCCTGTCA GGAGAAGAAGG GGAGAAGAAGG TTAGTACAAT TGCTATAGTG
                                                 AseI
2601 AGTGTATTA TACTATGCAG ATATACTAATG CCAATGATTA ATTGTCAAAC TAGGCTGCA GGGTTCATAG TGCCACTTCT CCTGCACTGC CCCATCTCCT
2701 GCCCACCCTT TCCCAGGCAT AGACAGTCAG TGACTTACCA AACTTACAAG AGGGAGAAGG CAGAAGCTTTG AGACAGACCC GCGGACACGC CGAACTGCGA
2801 GGGGACGTGG CTAGGGCGGC TTCTTTTATG GTGCGCCGGC CCTCCGAGGC CGGAAGGCTCG GGGAAGGCCTA GCGGCCAATC TGCGGTGGCA GGAGGCGGGG
2901 CCGAGGGCCG TGCCTGACCA CATAGGAGCA CATAGGAGTC TCAGCCCCCC GCCCAAAGC AAGGGAGAAGT CAGCGCCCTG TAGGCGCAGC GTGTTGTGAA
3001 ATGGGGGCTT GGGGGGGTTG GAGCCCTGAC TAGTCAAAAC AAACTCCCAT TGACGTCAAT GGGGTGGAGA CTTGGAAATC CCGTGAGTC AAACGGCTAT
3101 CGACGGGCCAT TGATGTACTG CCAAAACCGC ATCATCATGG TAATAGCGAT TAGATGTACT GCCAAGTAGG AAGTCCCAT AAGTCATGT
3201 ACTGGGCATA ATGCCAAGCG GGCCATTTAC CGTCATAGGG GTCAATAGCG ATATGCGAAC ATATCGTCA CACTTGATGT ACTGCCAAGT GGGCAGTTTA
3301 CCGTAAATAC TCCACCCAT GACGTCAATG GAAAGTCCCT CTATGGAAAC TGTGCAGCAA AGGCCAGCAA AAGACCAGCAA ATGGCGGGG GCTGGTGGGGC
3401 GGGCAGCCAG CTGGCGTTTG TCCATAGGCT TACCGTAAGT CTGCAGTTA GACGAGCATC ACGCTCAAGT CAGAGGTGGC GAAACCCGAC AGGACTATAA
3501 AGATACCAGG CGTTTCCCCC TGGAAGCTCC CTCCTGCGCT CTCCTGTTCC GACCCTGCCG CTTACCGGAT ACCTGTCCGC CTTTCTCCCT TCGGGAAGCG
3601 TGGCGCTTTC TCATAGCTCA CGCTGTAGGT ATCTCAGTTC GGTGTAGGTC GTTCGCTCCA AGCTGGGCTG TGTGCACGAA CCCCCCGTTC AGCCCGACCG
3701 CTGCGCCTTA TCCGGTAACT ATCGTCTTGA GTCCAACCCG GTAAGACACG ACTTATCGCC ACTGGCAGCA ACAGTATTTG GTATCTGCGC ACAGAGGAAGG
3801 TATGTAGGCG GTGCTACAGA GTTCTTGAAG TGGTGGCCTA ACTACGGCTA CACTAGAAGA ACAGTATTG GTATGCCGC AAAGGATAG CCAGTTACCT
3901 TCGGAAAAAG AGTTGGTAGC TCTTGATCCG GCAAACAAAC CACCGCTGGT AGCGGTGGTT TTTTTGTTTG CAAGCAGCAG ATTACGCGCA GAAAAAAGG
4001 ATCTCAAGAA GATCCTTTGA TCTTTTCTAC GGGGTCTGAC GCTCAGTGGA ACGAAAACTC ACGTTAAGGG ATTTTGGTCA TGCGAGTTA ATTAACATTT
4101 AAATCAGCCC CCCAATAAA ATATTTAAT TTTCATTACA TCTGTGTGT GGTTTTTGT GTGAATCGTA ACTAACATAC GCTCTCATC AAAACAAAAC
4201 GAAACAAAAC AAACTAGCAA AATAGGCTGT CCCCAGTGCA AGTGCACGTG TCTCTATCGA A (SEQ ID NO: 62)
```

IL2ss.CCL7(5-76).hIgG1Fc sequence (illegible sequence text - image too low resolution to accurately transcribe nucleotide and amino acid sequences)

(SEQ ID NO: 56)

This figure shows a nucleotide and amino acid sequence for "IL2ss.CCL8.hIgGlFc sequence" which is too low-resolution to reliably transcribe.

Illegible sequence figure (IL2ss-CCL8(5-76)hIgG1Fc sequence, SEQ ID NO: 59).

IL2ss.CCL8(5-76).hIgG1Fc sequence
[Alanine substitutions for GAG binding sites – Lys, Arg & His]

(Illegible sequence data - figure too low resolution to transcribe accurately)

IL2ss.CCL13.hIgG1Fc sequence

[Illegible sequence data - low resolution OCR not feasible]

IL2ss.CCL13(5-75)hIgG1Fc sequence

[Sequence figure illegible for faithful transcription]

IL2ss.CCL13(5-75).hIgG1Fc sequence
[Amine substitutions for removal of GAG binding sites – Lys & His]

(Illegible sequence data - low

Illegible sequence figure content.

```
2101 TTTCTTTATG TTTTAAATGC ACTGACCTCC CACAATTCCT TTTTAGTAAA ATAATTCAGAA AGTAATTTAAA TACATCATTG CAATGAAAAT AAATGTTTTT
2201 TATTAGGCAG AATCCAGATG CTCAAGGCCC TTCATAAATAT CTGCTCCTCT AGTAGTTGGA GCACCGAGTT CTTAGGTGAAC AAAGGAACCT TTCGGACAGCA
2301 AGAAAGCGAG CTTCTAGCTT ATCCTCAGTC GACCGGCCGG GAGGTGTCC GGACACGAACC GGACAGGACT CCGACCACT CGGCAGTACAG CTCGTCCAGG CCCGCCACCG
2401 TGCTCGGCGA TCTCGGTCAT GACCCGGCCG GAGGTGTCCG GGACAGGCTG GGACACGAAGG ATGAACAGGG ATGGAACAGGG TCAGGTGCTC CGGACCCACA CGGCGCAGCC
2501 ACACCCAGGC CAGGGCGTTG TCCGGCACCA GCCGGTCGGT GCCGGTCGGT GCCGGTCGGT GCGGCTCGAGC CGGCGTGAGC ACCGGAACGG CACTGGTCAA CTTGGCCATG
2601 GAAGTCCTGG GAGAACCGGA GCCGGTCGGT GCCGGTCGGT GCCGGTCGGT GCCGGTCGGT GCGGCTCGAGC CGGCGTGAGC ACCGGAACGG CACTGGTCAA CTTGGCCATG AseI
2701 ATGGCTCCTC CTGTCAAGGAG AGGAAAGAGA AGAAGGTAG TACAATTGCT ATAGTGAGTT GTATTATACT ATGCAGATAT ACTATGCCAA TGATTAATTG
2801 TCAAACTAGG GCTGCAGGGT TCATAGTGCC ACTTTTCTG CACTGCCCA TCTCCTGCCC GACCTTTCCC AGGCATAGAC AGTCAGTGAC TTACCAAACT
2901 CACAGCAGGG AGAAGGCAGA AGCTTGAGAC AGACCGGAG CCAATCTGCG GTGGCAGGAA AGTTTACCGT ACGTGGCTAG TTTAGGTGC GCCGGCCTC
3001 GGAGGCAGGG CGCTCGGGGA GGCCTAGCGG CCAATCTGCG GTGGCAGGAA GCGGGCCGA AGGGCGGTGC TGACCAATCC GGAGCACATA GGAGTCTCAG
3101 CCCGCGCCC CAAGCAAGG GGAAGCACG GGAAGTCAG CCTCTGTAGC TGTGAAATGG GGGCTTGGAC CGGCTTGGGAC CCTGACTAGT CAAAACAAAC
3201 TCCCATTGAC GTCAATGGGA GTCATAGCAT TGAGACTTG TGAGTCAAAC CGCTATCCAC GTCAACGATG GTAACTCCAA AACTCATCA TCATGGTAAT
3301 AGCGATGACT AATACGTAGA ATGATACACT TGATGTACTG TCCGATAAGG AGTTACTCGTT CCAATGTGGAC CCGGCGGCC ATTTACCGTC ATTGACGTCA
3401 ATAGGGGGCG TACTTGGCAT GTCAATATAC GTCATTATTG ACGTCAATG CCGGGCGTC TGGCCGCGTC AATACTCCA CCCATGAAAA GTCCTATTG
3501 GCGTTAATTA GGAACATAGT AGAACATGTG AGCAAAAGGC CAGGACCG ACCGGGCAGG ACCAGGGCGG GCCATTAACC GCCATTTTCA TAACGCCTGC
3601 AGGTCACGAC AGAATCGACGC ATAAGTCAGA TCAACCTAG CCGCTAGTGC CCAGGCAGCC TAAAAAACC CTATAAAGAT CCTTTCTCAT TAGGCTCCGC CCCCTGACG
3701 TGTTCCGACC CTGCCGTTA GCTCAAGTCC CGGGCTGTGT GTCCGGCTTT CACGAACCC GGACGCGTC CGGAGGCAGT GCTTCAGGT GCCCCCTG CAGTTCGGTG
3801 TAGGTCGTTC GCTCCAAGCT GGGCTGTGT CACGAACCCG CGGTCAGCC CGGTAGCAGA GATAAGCAGA GCCGTCGTGT TGAAGTGGT GGCCTAACTA
3901 GACACGACTT ATCGCCACTG CCAGCAGCA TATTTGGTAT CTGCGCTCTG GCCGTATAAA TTAAATGATTC AGCGACACTC CGGTATGGT ACCAAACCACC
4001 CGGCTACACT AGAAGAACAG TATTGGTAT CTGCGCTCTG CAGCAGATTA AAAAGAGAGATT GGTAGCTCTT GATCGGCAA ACAAACCACC
4101 GCTGGTAGCG GTGGTTTTT TGTTTGCAAG CAGCAGATTA CAGCAGATTA ACATTTAAAT CAGCAGATTC TTTTATTTTC TCTGACGTC
4201 AGTGGAACGA AAACTCACGT TAAGGGATT TGGTCAGGGC TAGTTAATTA ACATTTAAAT CAGCGGCCG CAAACAAAAA ATTACATCTG ATTACATCTG
4301 TGTGTTGGTT TTGTGTGA ATCGTAACTA ACATACGCTC TCCATCAAGC AATTTAATTAA ACATTTAAAT CAGCGGCCG CAAACAAAAA ATTACATCTG ATTACATCTG
4401 CAGGTCCAG AACATTTCTC TATCGAA (SEQ ID NO: 91)
```

IL2ss.CCL25(4-127).hIgG1Fc sequence (sequence image - illegible at this resolution, SEQ ID NO:65)

IL2ss.CCL25(4-127).hIgG1Fc sequence
[Alanine substitutions for GAG binding sites — Lys, Arg & His]

(sequence illegible at this resolution)

This page shows a nucleotide and amino acid sequence labeled "IL2ss.CXCL11(4-73).hIgG1Fc sequence" which is too low-resolution to transcribe reliably.

```
                                                                                                        AseI
2501 CTCCGGCGAC GTCGCGGGCG GAACGGCACT GTCAACTTG GCCATGATGG CTCCTCCTGT CAGGAGGAGGA AAGAGAAGAA GGTTAGTACA
2601 ATTGCTATAG TGAGTTGTAT TATATACTTA AGATATACTA TGCCAATGAT TAATTGTCAA CAAACTTACA ACTACGGCTG CATGGTTCAT AGTGCCACTT TTCCTCGCACT
2701 GCCCATCTC CTGCCACCC TTTCCCAGGC ATGGACAGTC GCTTCTTTTA AGTGACTTAC CAAACTCACA GGAGGAGAA GCCAGAAGTT TGAGACGGAC CCGCGGACC
2801 GCCGAACTGC GAGGGGACGT GGCTAGGGCG CGTTCCTGAC CAATCCGGAG TGGTGCGCCG GCCCTCAGCC TCTCAGCCC GCCAAGGCGCT TAGCGGCCAA TCTGCGGTGG
2901 CAGGAGGCGG GGCCGAAGGC CGTTGCTGAC CGTTGGGAGT TGGGGGAAGT CACATAGAAG TCTCAGCCCC ACAAACTCCC GCAAGAGGAA GTCACGCGCC TGTAGCGGCA
3001 GGGTGTTGTG AAATGGGGGC TTGGGGAGGT CGTTCCTGA TGGGCCCTG ACTAGTCAA ACAAACTCCC ATTGACGTCA GACTTGGAA TCCCGTGAG
3101 TCAAACGGCT ATCCACGCCC ATTGATGTAC TAATGCCAGG TGCCAAAACC GCATCATCAT GGTAATAGCG RTGACTAATA CGTAGATGTA CTGCCAAGTA GGAAAGTCCC
3201 ATAAGGTCAT GTACTGGGCA TAATGCCAGG TAATGCCAG ACCGTCATTG ACGTCAATAA GGGGCGTACT TGGCATATGA TACACTTGAT GTACTGCCAA
3301 GTGGGCAGTT TACCGTAAAT ACTCACCCA TTGAACGTCAA TGGAAAGTCC CTATTGGCGT ACGTCAATAA TACTATGGGA ACATACGTCA TTATTGACGT CAATGGGCAG
3401 CGGTCCGTTG GCCGTCAGCC AGGCCAGGCA TTTCCATAGG GTTATGTTAA GCCTGCGGT CTGACAGCA TAATTAAGAA CATGTGAGCA AAAGGCCAGC AAAAGGCCAG
3501 GAACCGTAAA AAGGCCGCGT TGCTGGCGTT TTTCCATAGG CTCCGCCCCC CTGACGAGCA TCACAAAAT CGACGCTCAA GTCAGAGGTG GCGAAACCCC
3601 ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701 CTTCGGGAAG CGTGGCGCTTT TCTCATAGCT CACGCTGTAG GTATCGTCAG GAGTCCAACC CGGTAAGACA CGACTTATCG CCACTGGCAG CAGCCACTGG TAACAGGATT
3801 TCAGCCCGAC CGTGCGCCT TATCCGGTAA CTATCGTCTT GAGTCCAACC AGTGGTGGCC TAACACGGC TACTACTAGAA GAACAGTATT TGGTATCTGC GCTCTGCTGA
3901 AGCAGAGCGA GGTATGTAGG CGGTGCTACA AGAGTTCGTA GCTCTTGATC GATCTTTTCT ACGGGGTCTG CGGAAACAA GTAAGCGGTGG TTTTTTTGTT TGCAAGCAGC AGATTACGCG
4001 CAGAAAAAAA CTTCGGAAAA AAGATCCTTT GATCTTTTCT ACGGGTCTG ACGGCTCAGTG GAACGAAAAC TCACGTTAAG GGATTTTGGT CATGAGATTAT
4101 TAATTAACAT TTAAATCAGC CGCCGTAATA AATATCTTT CATTCATTA CATTCTGTGTG TTGGTTTTTTT GTGTGAAATCG TAACTAACGT ACGGTCTCCA
4201 TCAAAACAAA ACGAAACAAA ACAAAACTAGC AAAATAGGGC GTCCCCAGTG CAAGTGCAGG TGCCAGAACA TTTCCTCTATC GAA (SEQ ID NO:95)
```

IL2ss.CXCL11(4-73).hIgG1Fc sequence [Alanine substitutions for removal of GAG binding sites – Lys & His]

```
   1 GGATCTGGAA TGCCTCCAGT GCCCGTCAGT GGGCAGAGCG CACATGCCCA AGAGCCCCG AGAAGGTGG GGG

IL2ss.CXCL11.hIgG4Fc sequence

This figure shows an annotated DNA/protein sequence too low-resolution to transcribe reliably. Annotated features include: MarI, SfoI, KasI, BbeI, BcoRI restriction sites; IL-2 secretion signal; CXCL11 (1-73); human IgG4 Fc (constant region); BmtI, NheI, AseI sites; and the label (SEQ ID NO:70).

```
2501  CTCCGGGCGAAC GTCGCGCGCG GTGAGCACCG GAACGGGCACT GGTCAACTTG GCCATGGATGG CTCCTCCTGT CAGGAGAAGGA AAGAGAAGAA GGTTAGTACA
                                                                    AseI
2601  ATTGCTATAG TGAGTTGTAT TATACTATGC AGATATACTA TGCCAATGAT TAATTGTCAA ACTAGGGCTG CAGGGTTCAT AGTGCCCACTT TTCCTGCGACT
2701  GCCCATCTC CTGCCCACCC TTTCCCAGAGC ATAGACAGTC AGTGACTTAC CAAACTCACA GCAGGGAGAA GGCAGAAAGT TGAGACAGAC CCGCAGGACC
2801  GCGGAACTGC GAAGGGAGCGT GGCTAGGGCG GCTTCTTTTA TGCTGCGCCG GCCCTCGGAG GCCCTCCAAA CCGCCCCAAA GTCAGGGCCC TAGCGGCCAA TCTGCGGTGG
2901  CAGGAGGCGG GGCCGAAGGC CGTGCCTGAC CAATCCGGAG TCTCAGCCG CBAATAGGAAG GCAAGGGGAA GTCACGCGCC TAGCGGCCAA TGTAGCGCCA
3001  GCGTGTTGTG AAATGGGAGC TTGGGGAGT TGGGGAGT ACTAAGTCAA ACAAACTCCC ATTGACGTGA ATGGGTGGA GACTTGGAAA TCCCCGTGAG
3101  TCAACCGCT ATCCACGCCC ATTGATGTAC TGCCAAACC GCATCATCAT GGTAATAGCG ATGACTAGCG CGTAGATGTA CTGCCAGTA GGAAAGTCCC
3201  ATAAGGTCAT GTACTGGGCA TGATGCCAGG CGGGCCATTT ACGTCATATG ACGTCAATAG GGGACGTACT TGGCATATGA TACACTTGAT GTACTGCCAA
3301  GTGGGCAGTT TACCGTAAAT TTGACCGTAA GTTATGTAAC CTATTGGCGT TAATATGGCGT TACTATGGGA ACATACGTCA TAATTGACGT CAATGGCCGG
3401  GGGTCGTTGG GCGGTCAGCG GAGCGGGGCA CCTCCGCCCC CTGACCAGCA TAATGTGCCAA AAGAGCCAGC ATGTGAGCA CATATACGTCC AAAAGCCAGC
3501  GAACCGTAAA AAGGCCGGGT TCGTGGCGTT TTTCAATAGG CTGACACACTG CTAACCGAGC TCAACAAAAT CGACCTTACGG ATACCTGTCC GCGAAACCGG
3601  ACAGGACTAT AAAGATACCA CGTCGCGCTT TCTCATAGCT CCTGGAAGCT CACGCTGTAG GTATCTCAGT TCGGTTGCCGTC CAAGCTGGGC TGTGTGCACG AACCCCCCGT
3701  CTTGGAGAAG CGTGGCGCTT TATCCGGTAA CTATCGTCTT GAGTCCAACC CGGTAAGACA CGACTTATCG CCACTGGCAG CAGCCACTGG TAACAGGATT
3801  AGCAGAGCGA GGATATGTAG GCGGTGCTACA GAGTTCTTGA AGTGGTGGCC TAACTACGGC TACACTAGAA GAACAGTATT TGGTATCTGC GCTCTGCTGA
3901  AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4001  CAGAAAAAAA GGATCTCAAG AAGATCCTTT GATCTTTTCT ACGGGGTCTG ACGCTCAGTG GAACGAAAAC TCACGTTAAG GGATTTTGGT CATGAGATTA
4101  TAATTAACAT TTAAATCAGC GAGCCCAATA AAATATTCAATTA ACGTCATTAT CATCTGTGTG TTGGTTTTTT GTGTGAAATCG TAACTAACAT ACGCTCTCCA
4201  TCAAAACAAA ACGAAACAAA ACAAACTAGC ACAAATTAGCT GTCCCAGTG CAAGTGCAGG TGCCAGAACA TTTCTCTATC GAA  (SEQ ID NO:97)
```

IL2ss.CXCL11(4-73).hIgG4Fc sequence (Sequence data illustration — too low resolution to transcribe reliably)

IL2ss.CXCL11(4-73).hIgG4Fc sequence [Alanine substitutions for GAG binding sites – Arg, Lys & His]

(Figure shows DNA/protein sequence too low resolution to transcribe reliably, labeled with features: EcoRI, KasI, SfoI, NarI, BbeI restriction sites; IL-2 secretion signal; CXCL11 (4-73); human IgG4 Fc (constant region); BmtI, NheI, AseI restriction sites; SEQ ID NO: 73)

FIG. 7E (CONT)

FIG. 8A
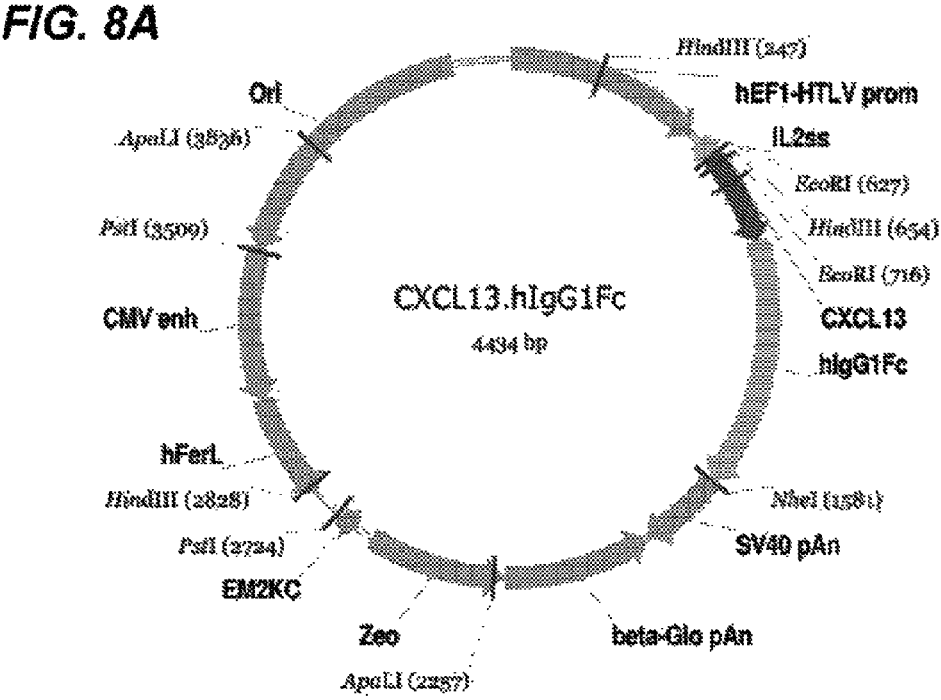
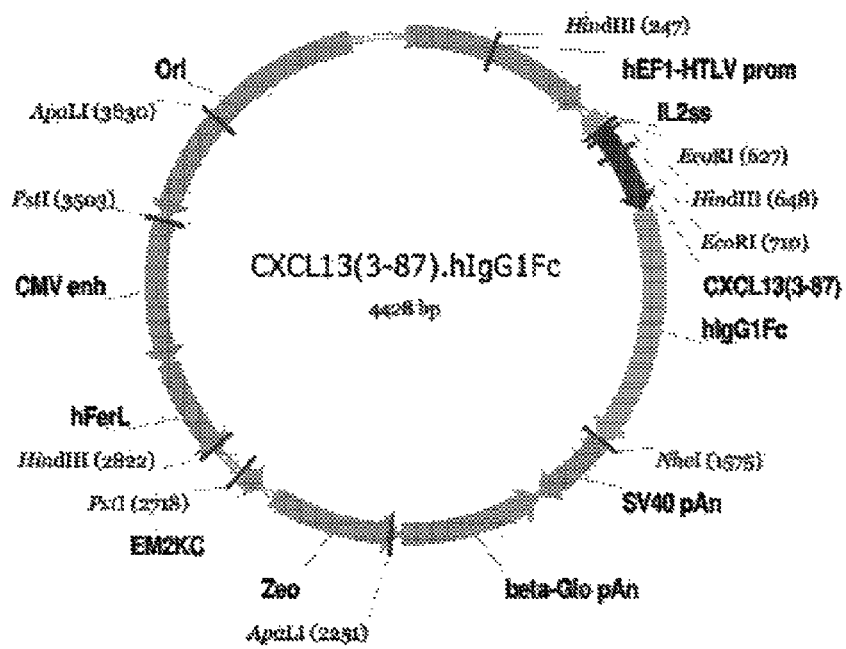
FIG. 8B

FIG. 8C

IL2ss.CXCL13.hIgG1Fc sequence

This figure shows a DNA and protein sequence alignment for the IL2ss.CXCL13.hIgG1Fc construct (SEQ ID NO:73). The sequence is numbered from position 1 to 2201 in increments of 100.

Key annotated features include:
- Restriction sites: EcoRI, KasI, NarI, SfoI, NheI, BmtI, AseI
- IL-2 secretion signal (starting with MetTyrArgMetGlnLeuLeuSerCysIle...)
- CXCL13 (1-87)
- human IgG1 Fc (constant region)

IL2ss.CXCL13(3-87).hIgG1Fc sequence

IL2ss.CXCL13(3-87).hIgG1Fc sequence [Alanine substitutions for removal of GAG binding sites – Lys & His]

```
   1 GGAATCTGGA TCTCTCCAGT GCCCGTCAGT GGGCAGAGCC CACATGCCCC ACAGTGCCCC AGAAGTTGCC GGGAGGGGTC GGCAATTGAA CGGGTGCTA
 101 GAGAAGGTGG CGCGGGGTAA ACTGGAGTA TGATGTCGTG GCAGAGACA AGCTTTCC

Illegible sequence figure.

IL2ss.CXCL13(3-87).hIgG4Fc sequence [Alanine substitutions for removal of GAG binding sites – Lys & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                            NarI
                                            KasI
                                            SfoI
                                            BbeI
                                            ~~~~~~~                                            IL-2 secretion signal
                                                                                               MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                  EcoRI
                                  ~~~~~~~ CXCL13 (3-87)
        AlaLeuSer LeuAlaLeu ValThrAsnSer GluValTyr TyrThrSer LeuArgCysArg CysValGln GluSerSer ValPheIlePro ArgArgPhe
 601   TTGCACTAAG TCTTGCACTT GTCACGAATT CGGAGGTCTA TTACACAAGC TTGAGGTGTA GATGTGTCCA AGAGAGCTCA GTCTTTATCC CTAGACGCTT
            EcoRI
       IleAspAla IleGlnIleLeu ProArgGly AsnGlyCys ProArgLysGlu IleIleVal TrpAlaAla AsnAlaSerIle ValCysVal AspProGln
 701   CATTGATgcc ATTCAAATCT TGCCCCGTGG GAATGGTTGT CCAAGAAAAG AAATCATAGT CTGGgctgcg AACgctTCAA TTGTGTGTGT GGACCCTCAA
                                                                                                   human IgG4 Fc
                                                                                                 (constant region)
       AlaGluTrpIle GlnAlaMet MetGluVal LeuAlaAlaAla SerSerSer ThrLeuPro ValProValPhe AlaAlaAla IleProPro ProCysProSer
 801   GCTGAATGGA TACAAgccAT GATGGAAGTA TTGgctgcgg ctAGTTCTTC AACTCTACCA GTTCCAGTGT TTgccgctgc gATTCCCCCC CCATGCCCAT
        CysProAla ProGluPhe LeuGlyGlyPro SerValPhe LeuPhePro ProLysProLys AspThrLeu MetIleSer ArgThrProGlu ValThrCys
 901   CATGCCCAGC ACCTGAGTTC CTGGGGGGAC CATCAGTCTT CCTGTTCCCC CCAAAACCCA AGGACACTCT CATGATCTCC CGGACCCCTG AGGTCACGTG
        ValValVal AspValSerGln GluAspPro GluValGln PheAsnTrpTyr ValAspGly ValGluVal HisAsnAlaLys ThrLysPro ArgGluGlu
1001   CGTGGTGGTG GACGTGAGCC AGGAAGACCC CGAGGTCCAG TTCAACTGGT ACGTGGATGG CGTGGAGGTG CATAATGCCA AGACAAAGCC GCGGGAGGAG
       GlnPheAsnSer ThrTyrArg ValValSer ValLeuThrVal LeuHisGln AspTrpLeu AsnGlyLysGlu TyrLysCys LysValSer AsnLysGlyLeu
1101   CAGTTCAACA GCACGTACCG TGTGGTCAGC GTCCTCACCG TCCTGCACCA GGACTGGCTG AACGGCAAGG AGTACAAGTG CAAGGTCTCC AACAAAGGCC
        ProSerSer IleGluLys ThrIleSerLys AlaLysGly GlnProArg GluProGlnVal TyrThrLeu ProProSer GlnGluGluMet ThrLysAsn
1201   TCCCGTCCTC CATCGAGAAA ACCATCTCCA AAGCCAAAGG GCAGCCCCGA GAGCCACAGG TGTACACCCT GCCCCCATCC CAGGAGGAGA TGACCAAGAA
        GlnValSer LeuThrCysLeu ValLysGly PheTyrPro SerAspIleAla ValGluTrp GluSerAsn GlyGlnProGlu AsnAsnTyr LysThrThr
1301   CCAGGTCAGC CTGACCTGCC TGGTCAAAGG CTTCTACCCC AGCGACATCG CCGTGGAGTG GGAGAGCAAT GGGCAGCCGG AGAACAACTA CAAGACCACG
       ProProValLeu AspSerAsp GlySerPhe PheLeuTyrSer ArgLeuThr ValAspLys SerArgTrpGln GluGlyAsn ValPheSer CysSerValMet
1401   CCTCCCGTGC TGGACTCCGA CGGCTCCTTC TTCCTCTACA GCAGGCTAAC CGTGGACAAG AGCAGGTGGC AGGAGGGGAA TGTCTTCTCA TGCTCCGTGA
                                                                                 BmtI
                                                                                 NheI
        HisGluAla LeuHisAsn HisTyrThrGln LysSerLeu SerLeuSer ProGlyLys***(SEQ ID NO:78)
1501   TGCATGAGGC TCTGCACAAC CACTACACAC AGAAGAGCCT CTCCCTGTCT CCGGGTAAAT GAGTGCTAGC TGGCCAGACA TGATAAGATA CATTGATGAG
1601   TTTGGACAAA CCACAACTAG AATGCAGTGA AAAAAATGCT TTATTTGTGA AATTTGTGAT GCTATTGCTT TATTTGTAAC CATTATAAGC TGCAATAAAC
1701   AAGTTAACAA CAACAATTGC ATTCATTTTA TGTTTCAGGT TCAGGGGGAG GTGTGGGAGG TTTTTTAAAG CAAGTAAAAC CTCTACAAAT GTGGTATGGA
        AseI
1801   ATTAATTCTA AAATACAGCA TAGCAAAACT TTAACCTCCA AATCAAGCCT CTACTTGAAT CCTTTTCTGA GGGATGAATA AGGCATAGGC ATCAGGGGCT
1901   GTTGCCAATG TGCATTAGCT GTTTGCAGCC TCACCTTCTT TCATGGAGTT TAAGATATAG TGTATTTTCC CAAGGTTTGA ACTAGCTCTT CATTTCTTTA
2001   TGTTTTAAAT GCACTGACCT CCCACATTCC CTTTTTAGTA AAATATTCAG AAATAATTTA AATACATCAT TGCAATGAAA ATAAATGTTT TTTATTAGGC
2101   AGAATCCAGA TGCTCAAGGC CCTTCATAAT ATCCCCCAGT TTAGTAGTTG GACTTAGGGA ACAAAGGAAC CTTTAATAGA AATTGGACAG CAAGAAAGCG
2201   AGCTTCTAGC TTATCCTCAG TCCTGCTCCT CTGCCACAAA GTGCACGCAG TTGCCGGCCG GGTCGCGCAG GGCGAACTCC CGCCCCCACG GCTGCTCGCC
```

```
2301 GATCTCGGTC ATGCCCGGCC CGGAAGCGTC GTGGACACGA CCTCCGACCA CTGGCGTAC AGCTCGTCCA GGCCGCTGCA CGAACCTCAG
2401 GCCAGGGTGT TGTCCGGCAC TGGACCGGGC TGGACCGTCC TGATGAACAG GGTCACCTCG TCCGGACCA CACCGGGAAA GTCGTCCTCC ACGAAGTCCC
2501 GGGAGAACCC GAGCCGGTCG GTCCAGAACT CGACCGTCC CGGCCGGTGA GCACCGGAAC CGCCGGTGA GGCACTGGTC AACTTGGCCA TGATGGCTCC

2601 TCCTGTCAGG AGAGGAAAGA GAAGAAGTT AGTACAATTG CTATAGTGAG TTGTATTATA ATACTATGCC AATGATTAAT TGTCAAACTA
2701 GGGCTGCAGG GTTCATAGTG CCACTTTTCC TGCACTGCCC CATCTCCTGC CCAGGCATAG ACAGTCAGTG ACTTACCAAA CTCAGGGAG
2801 GGAGAAGGCA GAAGCTTGAG ACAGACCGG GGAAGTGCCG AACTGCGAGG GGAAGTGGCTT AGGGCGGCTT CGGCCAGCCC TCGGAGGGAG
2901 GGCGTCGGG GAAGCCTAGC GGCCAATCTG CGGTGGCAGG AGCGCGGGC CCTGACCAAT CGGAAGCACA TAGGAAGTCTC AGCCCCCGC
3001 CCCAAAGCAA GGGGAAGTCA CGGGCCTGTA GGGCCAGCGT GTTGTGAAAT GGGGGTTGGG GCCCTGACTA GTCAAAACAA ACTCCCATTG
3101 ACGTCAATGG CGTGGAGACT TGGAAATCCC CTTGAGTCAA ACCCTATGC AGTCACTGGCC AAAACCGCAT CATCATGGTA ATAGGATGA
3201 CTAATACGTA GATGATACA CAAGTAGAAA AGTCCCATAA GGTCATGTAAC GCCAGGCGG CCATTTACCG TCATTGACGT CAATAGGGG
3301 CGTACTTGGC ATATGATACA CTTGATGTAC TGCCAAGTGG GTAAATACTC CACCCATTGA CGTCAATGGA AAGTCCCTAT TGGCATTACT
3401 ATGGAACAT ACGTCATTAT GGGCGGTAAT GGGCGGGGGT TCAGCCAGGC GGGGCCATTT TGTAACGCCT GCCCCCTGA GCAGCATCAC
3501 TAAGAACATG TGAGCAAAAG GCCAGCAAA GGCCAGGAAC CGTAAAAAGG GACTATAAAG ATACCAGGCG TTTCCCCCTG GAAGCTCCCT CGTGCGCTCT
3601 CCCTGCGCT TACCGGATCA GAGGTCGGA AACCCGACAG GACTATAAAG ATAGCAGGCG GCGTTTCCTC ATAGCTCACG CTGTAGGTAT TGTAGGTCGT
3701 TGGCTCCAAG CTGGGCTGTG TGCACGAACC CCCCGTTCAG CCCGACCGCT GCGCCTTATC CGGTAACTAT CGTCTTGAGT CCAACCCGG
3801 TTATCCCAC TGGCAGCAGC CACTGGTAAC AGGATTAGCA GAGCGAGGTA TGTAGGCGGT GCTACAAGAGT TGGTGACCTC TTGATGCGGC
3901 CTAGAAGAAC AGTATTTGGT ATCTGCGCTC TGCTGAAGCC AGTTACCTTC GGAAAAAGAG TTGGTAGCTC TTGATCCGGC AAACAAACCA
4001 CGGCTGGTTT TTGTTTGCA AGCAGCAGAT TACGCGCAGA AAAAAAGGAT CTCAAGAAGA TCCTTTGATC TTTTCTAGGG GTCTGACGCT
4101 GAAAACTCAC GTTAAGGGAT TTTGGTCATG AGATTATCAA AAAGGATCTT CACCTAGATC CTTTTAAATT AAAAATGAAG TTTTAAATC
4201 TTTTTTTGTCT GAATCGTAAC ATTTGTCATG CTAGTTAAT GCTATTAAAT ATCAGTGAGG CACCTATCTC AGCGATCTGT CTATTTCGTT
4301 AGAACATTTC TCTATCGAA (SEQ ID NO:165)
```

*FIG. 9E (CONT)* indicate potential sites for pegylation of CXCL11.

CCL1   NP_002972   SEQ ID NO:1
mqiittalvc lllagmwped vdskswqvpf srccfsfaeq eiplrailcy rntssicsne
glifklkrgk eacaldtvgw vqrhrkmlrh cpskrk

CCL2   NP_002973   SEQ ID NO:2
mkvsaallcl lliaatfipq glaqpdaina pvtccynftn rkisvqrlas yrritsskcp
keavifktiv akeicadpkq kwvqdsmdhl dkqtqtpkt

CCL3   NP_002974   SEQ ID NO:3
mqvstaalav llctmalcnq fsaslaadtp taccfsytsr qipqnfiady fetssqcskp
gvifltkrsr qvcadpseew vqkyvsdlel sa

CCL4   NP_002975   SEQ ID NO:4
mklcvtvlsl lmlvaafcsp alsapmgsdp ptaccfsyta rklprnfvvd yyetsslcsq
pavvfqtkrs kqvcadpses wvqeyvydle ln

CCL4L1   NP_001001435   SEQ ID NO:5
mklcvtvlsl lvlvaafcsl alsapmgsdp ptaccfsyta rklprnfvvd yyetsslcsq
pavvfqtkrg kqvcadpses wvqeyvydle ln

CCL5   NP_002976   SEQ ID NO:6
mkvsaaalav iliatalcap asaapyssdt tpccfayiar plprahikey fytsgkcsnp
avvfvtrknr qvcanpekkw vreyinslem s

CCL7   NP_006264   SEQ ID NO:7
mkasaallcl lltaaafspq glaqpvgint stccyrfin kkipkqrles yrrttsshcp
reavifktkl dkeicadptq kwvqdfmkhl dkktqtpkl

CCL8   NP_005614   SEQ ID NO:8
mkvsaallcl llmaatfspq glaqpdavsi pitccfnvin rkiplqrles ytritniqcp
keavifktkr gkevcadpke rwvrdsmkhl dqifqnlkp

CCL11   CAG33702   SEQ ID NO:9
mkvsaallwl lliaaafspq glagpasvpt tccfnlanrk iplqrlesyr ritsgkcpqk
avifktklak dicadpkkkw vqdsmkyldq ksptpkp

CCL13   NP_005399   SEQ ID NO:10
mkvsavllcl llmtaafnpq glaqpdalnv pstccftfss kkislqrlks yvittsrcpq
kavifrtklg keicadpkek wvqnymkhlg rkahtlkt

CCL14-1   NP_116739   SEQ ID NO:11
mkisvaaipf fllitialgt ktesssrgpy hpseccftyt tykiprqrim dyyetnsqcs
kpgivfitkr ghsvctnpsd kwvqdyikdm ken

CCL14-2   NP_116738   SEQ ID NO:12
mkisvaaipf fllitialgt ktesssqtgg kpkvvkiqlk lvggpyhpss ccftyttyki
prqrimdyye tnsqcskpgi vfitkrghsv ctnpsdkwvq dyikdmken

FIG. 12 (CONT)

CCL15      NP_116741         SEQ ID NO:13
mkvsvaalsc lmlvavlgsq aqfindaete lmmsklplen pvvlnsfhfa adcctsyisq
sipcslmksy fetssecskp gviflkkgr qvcakpsgpg vqdcmkklkp ysi

CCL16      NP_004581         SEQ ID NO:14
mkvseaalsl lvlillitsa arsqpkvpew vntpstcclk yyakvlprrl vvgyrkalnc
blpaiifvtk rnrevctnpn ddwvqeyikd pnlpllptrn lstvkiitak ngqpqllnsq

CCL17      NP_002978         SEQ ID NO:15
maplkmlalv tlllgaslqh ihaargtnvg reccleyfkg aiplrklktw yqtsedcsrd
aivfvtvqgr aicsdpnnkr vknavkylqs lers

CCL18      NP_002979         SEQ ID NO:16
mkglaaallv lvctmalcsc aqvgtnkelc clvytswqip qkfivdyset spqcpkpgvi
lltkrgrqic adpnkkwvqk yisdlklna

CCL19      NP_006265         SEQ ID NO:17
malllalsll vlwtspaptl sgtndaedcc lsvtqkpipg yivrnfhyll ikdgcrvpav
vfttlrgrql cappdqpwve riiqrlqrts akmkrrss

CCL20-1    NP_004582         SEQ ID NO:18
mcctksllla almsvlllhl cgeseaasnf dcclgytdri lhpkfivgft rqlanegcdi
naiifhtkkk lsvcanpkqt wvkyivrlls kkvknm

CCL20-2    NP_001123518      SEQ ID NO:19
mcctksllla almsvlllhl cgeseasnfd cclgytdril hpkfivgftr qlanegcdin
aiifhtkkkl svcanpkqtw vkyivrllsk kvknm

CCL21      NP_002980         SEQ ID NO:20
maqslalsll ilvlafgipr tqgsdggaqd cclkysqrki pakvvrsyrk qepslgcsip
ailflprkrs qaelcadpke lwvqqlmqhl dktpspqkpa qgcrkdrgas ktgkkgkgsk
gckrtersqt pkgp

CCL22      NP_002981         SEQ ID NO:21
mdrlqtally vlvllavalq ateagpygan medavccrdy vryrlplrvv kbfywtsdsc
prpgvvlltf rdkeicadpr vpwvkmilnk lsq

CCL23-1    NP_665905         SEQ ID NO:22
mkvsvaalsc lmlvtalgsq arvtkdaete fmmsklplen pvlldrfhat sadccisytp
rsipcsiles yfatnsecsk pgviflttkkg rrfcanpsdk qvqvcvrmlk ldtrikt.rkn

CCL23-2    NP_005055         SEQ ID NO:23
mkvsvaalsc lmlvtalgsq arvtkdaete fmmsklplen pvlldmlwrr kigpqmtlsh
aagfhatsad ccisytprsi pcslleasyfa tnsecskpgv ifltkkgrrf canpsdkqvq
vcvrmlkldt riktrkn

CCL24      NP_002982         SEQ ID NO:24
maglmtivts llflgvcahh iiptgsvvip spccmffvak ripenrvvsy qlssretclk
agviftkkg qqfcgdpkqe wvqrymknld akqkkaspra ravavkgpvq rypgnqttc

FIG. 12 (CONT)

CCL25-1  NP_005615  SEQ ID NO:25
mnlwllaclv agflgawapa vhtqgvfedc clayhypigw avlrrawtyr iqevsgscnl
paaifylpkr hrkvcgnpks revqramkll darnkvfakl hhntqtfqag phavkklssg
nsklssskfs npisesskrnv sllisansgl

CCL25-2  NP_683686  SEQ ID NO:26
mnlwllaclv agflgawapa vhtqgvfedc clayhypigw avlrrawtyr iqevsgscnl
paairpscck evefwklqvi ivqv

CCL25-3  EAW68951  SEQ ID NO:27
mnlwllaclv agflgawapa vhtqgvfedc clayhypigw avlrrawtyr iqevsgscnl
paairpscck evefwklqvi iiqv

CCL26  NP_006063  SEQ ID NO:28
mmglslasav llaslIslhl gtatrgsdis ktccfqyshk plpwtwvrsy eftsnscsqr
aviftkkrgk kvcthprkkw vqkyislkt pkql

CCL27  NP_006655  SEQ ID NO:29
mkgpptfcsl llslllspd ptaaflIpps tacctqlyrk plsdkllrkv iqvelqeadg
dchlqafvlh laqrsicihp qnpslsqwfe hqerklhgri pklnfgmlrk mg

CCL28  NP_683513  SEQ ID NO:30
mqqrglaiva lavcaalhas eailplassc ctevshhisr rllervnmcr iqradgdcdl
aavilhvkrr ricvephnht vkqwmkvqaa kkngkgnvch rkkhhgkrns nrahqgkhet
yghktpy

CXCL1  NP_001502  SEQ ID NO:31
maraalsaap snprllrval lllllvaagr raagasvate lrcqclqtlq gihpkniqsv
nvkspgphca qteviatlkn grkaclnpas pivkkiiekm lnsdksn

CXCL2  NP_002080  SEQ ID NO:32
maratlsaap snprllrval llllvaasr raagaplate lrcqclqtlq gihlkniqsv
kvkspgphca qteviatlkn gqkaclnpas pmvkkiiekm lkngksn

CXCL3  NP_002081  SEQ ID NO:33
mahatlsaap snprllrval llllvaasr raagasvvte lrcqclqtlq gihlkniqsv
nvrspgphca qteviatlkn gkkaclnpas pmvqkiieki lnkgstn

CXCL4  NP_002610  SEQ ID NO:34
mssaagfcas rpgllflgll llplvvafas asaeedgdlq clcvkttsqv rprhitslev
ikagphcpta qliatlkngr kicldlqapl ykkiikklle s

CXCL5  NP_002985  SEQ ID NO:35
msllssraar vpgpssalca llvlllltq pgplasagpa aavlrelrcv clqttqgvhp
kmisnlqvfa igpqcskvev vaslkngkei cldpeapflk kviqkildgg nken

CXCL6  NP_002984  SEQ ID NO:36
mslpssraar vpgpsgslca llalIllltp pgplasagpv savltelrct clrvtlrvnp
ktigklqvfp agpqcskvev vaslkngkqv cldpeapflk kviqkildsg nkkn

FIG. 12 (CONT)

CXCL7    NP_002695       SEQ ID NO:37
mslrldttps cnsarplhal qvllllslll talasstkgq tkrnlakgke esldsdlyae
lrcmciktts gihpkniqsl evigkgthcn qveviatlkd grkicldpda prikkivqkk
lagdesad

CXCL8    NP_000575       SEQ ID NO:38
mtsklavall aaflisaalc egavlprsak elrcqcikty skpfhpkfik elrviesgph
canteiivkl sdgrelcldp kenwvqrvve kflkraens

CXCL9    NP_002407       SEQ ID NO:39
mkksgvlfll giillvligv qgtpvvrkgr cscistnqgt ihlqslkdlk qfapspscek
leiiatlkng vqtclnpdsa dvkelikkwe kqvsqkkkqk ngkkhqkkkv lkvrksqrsr
qkktt

CXCL10   NP_001556       SEQ ID NO:40
mnqtailicc lifltlsgiq gvplsrtvrc tcisisnqpv nprsleklei ipasqfcprv
eiiatmkkkg ekrclnpesk aiknllkavs kerskrsp

CXCL11   NP_005400       SEQ ID NO:41
msvkgmaial avilcatvvq gfpmfkrgrc lcigpgvkav kvadiekasi mypsnncdki
eviitlkenk gqrclnpksk qarlliikkve rknf

CXCL12   NP_000600       SEQ ID NO:42
mnakvvvvlv lvltalclsd gkpvslsyrc pcrffeshva ranvkhlkil ntpncalqiv
arlknmnrqv cidpklkwiq eylekalnkr fkm

CXCL13   NP_006410       SEQ ID NO:43
mkfistslll mllvsslspv qgvlevyyts lrcrcvqess vfiprrfidr iqilprgngc
prkeiivwkk nksivcvdpq aewiqrmmev lrkrssstlp vpvfkrkip

CXCL16   NP_071342       SEQ ID NO:44
msgsqsavap spqsprspem grdlrpgsrv lllllllllv yltqpgngne gsvtgscycg
krissdspps vqfmnrlrkh lrayhrclyy trfqllswsv cggnkdpwvq elmscldlke
cghaysgiva hqkhllptsp pisqasegas sdihtpaqml lstlqstqrp tlpvgslssd
kaltrpnett ihtaghalaa gpeagenqkq peknsgptax tsatvpvlcl laiifiltaa
lsyvlckrrr gqspqsspdl pvhyipvapd snt

XCL1     AAH69817        SEQ ID NO:45
mrllilallg icsltayive gvgsevsdkr tcvslttqrl pvsriktyti tegslravif
itkrglkvca dpqatwvrdv vrsmdrksnt rnnmiqtkpt gtqqstntav tltg

XCL2     NP_003166       SEQ ID NO:46
mrllilallg icsltayive gvgsevshrr tcvslttqrl pvsriktyti tegslravif
itkrglkvca dpqatwvrdv vrsmdrksnt rnnmiqtkpt gtqqstntav tltg

FIG. 12 (CONT)

CX3CL1      NP_002987           SEQ ID NO:47
```
mapislswll  rlatfchltv  llagqhhgvt  kcnitcskmt  skipvallih  yqqnqascgk
railletrqh  rlfcadpkeq  wvkdamqhld  rqaaaltrng  gtfekqigev  kprttpaagg
mdesvvlepe  atgesssslep tpssqeaqra  lgtspelptg  vtgssqtrlp  ptpkaqdggp
vgtelfrvpp  vstaatwqss  aphqpgpslw  aeaktseaps  tqdpstqast  asspapeena
pseggrvwgq  gqsprpersl  ereemgpvpa  htdafqdwgp  gsmahvsvvp  vssegtpsre
pvasgswtpk  aeepihatmd  pqrlgvlitp  vpdaqaatrr  qavgllaflg  llfclgvamf
tyqslqgcpr  kmagemaegl  ryiprscgsn  syvlvpv
```

IgG1Fc      CBX54381.1          SEQ ID NO:48
```
aepksodkth  tcppcpapel  lggpsvflfp  pkpkdtlmis  rtpevtcvvv  dvshedpevk
fnwyvdgvev  hnaktkpree  qynstyrvvs  vltvlhqdwl  ngkeykckvs  nkalpapiek
tiskakgqpr  epqvytlpps  rdeltknqvs  ltclvkgfyp  sdiavewesn  gqpennykt
ppvldsdgsf  flyskltvdk  srwqqgnvfs  csvmhealhn  hytqkslsls  pgk
```

IgG2Fc      CBX54382.1          SEQ ID NO:49
```
erkccvecpp  cpappvagps  vflfppkpkd  tlmisrtpev  tcvvvdvshe  dpevqfnwyv
dgvevhnakt  kpreeqfnst  frvvsvltvv  hqdwlngkey  kckvsnkglp  apiektiskt
kgqprepqvy  tlppsreemt  knqvsltclv  kgfypsdiav  ewesngqpem nykttppmld
sdgsfflysk  ltvdksrwqq  gnvfscsvmh eealhnhytqk slslspgk
```

IgG3Fc      CBX54383.1          SEQ ID NO:50
```
elktplgdtt  htcprcpepk  scdtpppcpr  cpepksodtp  ppcprcpepk  scdtpppcpr
cpapellggp  svflfppkpk  dtlmisrtpe  vtcvvvdvsh edpevqfkwy vdgvevhnak
tkpreeqfns  tfrvvsvltv  lhqdwlngke  ykckvsnkal papiektisk tkgqprepqv
ytlppsreem  tknqvsltcl  vkgfypsdia  vewessgqpe nnynttppml dsdgsfflys
kltvdksrwq  qgnifscsvm  healhnrftq  kslslspgk
```

IgG4Fc      CBX54384.1          SEQ ID NO:51
```
eskygppcps  cpapeflggp  svflfppkpk  dtlmisrtpe vtcvvvdvsq edpevqfnwy
vdgvevhnak  tkpreeqfns  tyrvvsvltv  vhqdwlngke ykckvsnkgl psiektisk
akgqprepqv  ytlppsqeem  tknqvsltcl  vkgfypsdia vewesngqpe nnykttppvl
dsdgsfflys  rltvdksrwq  egnvfscsvm  healhnhytq kslslslgk
```

CHEMOKINE-IMMUNOGLOBULIN FUSION POLYPEPTIDES, COMPOSITIONS, METHOD OF MAKING AND USE THEREOF

This application is a continuation of U.S. patent application Ser. No. 14/978,684, filed Dec. 22, 2015, which is a continuation of U.S. patent application Ser. No. 14/612,884, filed Feb. 3, 2015, now U.S. Pat. No. 9,249,204, which is a continuation-in-part of U.S. patent application Ser. No. 13/962,401, filed Aug. 8, 2013, now U.S. Pat. No. 8,987,210, which is a continuation of U.S. patent application Ser. No. 13/962,110, filed Aug. 8, 2013, now U.S. Pat. No. 8,796,422, which is a continuation-in-part application of U.S. patent application Ser. No. 13/480,526, filed May 25, 2012, now U.S. Pat. No. 8,541,564, which claims priority of U.S. Provisional Patent Application No. 61/492,260, filed Jun. 1, 2011. The entirety of the aforementioned applications is incorporated herein by reference.

FIELD

The present application generally relates to compositions that can be used for treating chemokine receptor-mediated disorders and modulating inflammation, inflammatory cell motility, cancer cell motility, or cancer cell survival.

BACKGROUND

Chemokines are chemotactic cytokines, of molecular weight 6-15 kDa, that are released by a wide variety of cells to attract and activate, among other cell types, macrophages, T and B lymphocytes, eosinophils, basophils and neutrophils. There are four classes of chemokines, CXC, CC, C, and CX3C, depending on whether the first two cysteines in the amino acid sequence are separated by a single amino acid (CXC) or are adjacent (CC). Unlike other chemokines, C chemokines have only two cysteines; one N-terminal and one downstream cysteine. The only CX3C chemokine, CX3CL1, has three amino acids between two N-terminal cysteines. The CXC chemokines, such as interleukin-8 (IL-8/CXCL8), neutrophil-activating protein-2 (NAP-2/CXCL7) and melanoma growth stimulatory activity protein (MGSA/CXCL1) are chemotactic primarily for neutrophils and T lymphocytes, whereas the CC chemokines, such as RANTES/CCL5, MIP-1α/CCL3, MIP-1β/CCL4, the monocyte chemotactic proteins (MCP-1/CCL2, MCP-2/CCL8, MCP-3/CCL7, MCP-4/CCL13, and MCP-5/CCL12) and the eotaxins (-1/CCL11 and -2/CCL24) are chemotactic for, among other cell types, macrophages, T lymphocytes, eosinophils, dendritic cells, and basophils. There also exist the chemokines lymphotactin-1/XCL1, lymphotactin-2/XCL2 (both C chemokines), and fractalkine/CX3CL1 (a CX3C chemokine) that do not fall into either of the major chemokine subfamilies, CXC and CC.

Chemokines bind to specific cell-surface receptors belonging to the family of G-protein-coupled seven-transmembrane-domain proteins, which are termed "chemokine receptors." On binding to their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration.

Chemokine receptors have been implicated as being important mediators of inflammatory, infectious, and immunoregulatory disorders and diseases, including cancer, asthma and allergic diseases, as well as autoimmune pathologies such as rheumatoid arthritis and atherosclerosis. For example, the chemokine receptor CCR3 plays a pivotal role in attracting eosinophils to sites of allergic inflammation and in subsequently activating these cells. The chemokine ligands for CCR3 induce a rapid increase in intracellular calcium concentration, increased expression of cellular adhesion molecules, cellular degranulation, and the promotion of eosinophil migration. Another chemokine receptor, CCR2, contributes to cancer progression and can induce tumor cell proliferation or chemotaxis. Accordingly, agents which modulate chemokine receptors would be useful in such disorders and diseases.

Chemokines have also been implicated in the pathogenesis of cell proliferative disorders, including for example induction of tumor angiogenesis and growth. Many tumor cells have also been shown to express chemokine receptors, such as CXCR1, CXCR2, CXCR3, CXCR4, CXCR5, CXCR6, CXCR7, CX3CL1, CCR2, CCR5, and CCR9, and thus tumor cells may also stimulate their own growth, migration, and/or invasion when responding to secreted chemokines.

Chemokines are critical for leukocyte recruitment to injured tissues and play an important role in the wound healing process. Impaired wound healing in diabetic patients is accompanied by decreased early inflammatory cell infiltration, but persistence of neutrophils and macrophages leading to chronic, nonhealing wounds. Chemokines may have both direct and inflammatory-mediated effects on many different aspects of diabetic wound healing, including: impairments in growth factor expression, angiogenesis, extracellular matrix formation, and reepithelialization. Certain chemokine receptor expression in wounds may accelerate healing, and be beneficial in the context of surgery, chronic ulcers, and other conditions.

Chemokine receptors therefore represent promising targets for the development of novel anti-inflammatory and anti-tumor as well as angiostatic, angiogenic, and wound healing agents. Thus, there remains a need for compositions that are capable of modulating activity of chemokine receptors.

SUMMARY

One aspect of the present application relates to an isolated chemokine-immunoglobulin fusion polypeptide having a chemokine moiety and an immunoglobulin moiety. In some embodiments, the chemokine moiety comprises a chemokine selected from the group consisting of human CCL1, CCL2, CCL3, CCL4, CCL4L1, CCL5, CCL7, CCL8, CCL11, CCL13, CCL14-1, CCL14-2, CCL15, CCL16, CCL17, CCL18, CCL19, CCL20-1, CCL20-2, CCL21, CCL22, CCL23-1, CCL23-1, CCL24, CCL25-1, CCL25-2, CCL25-3, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and the immunoglobulin moiety comprises a peptide selected from the group consisting of the constant region of human Ig G1, the constant region of human Ig G2, the constant region of human Ig G3, the constant region of human Ig G4, and functional variants thereof. In one embodiment, the isolated chemokine-immunoglobulin fusion polypeptide is a pegylated chemokine-immunoglobulin fusion polypeptide.

In one particular embodiment, the chemokine-immunoglobulin fusion polypeptide is selected from the group consisting of CCL2-IgG1Fc, CCL2(5-76)-IgG1Fc, CCL2(5-76K/H→A)-IgG1Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG4Fc, CXCL13(3-87)-IgG4Fc, and CXCL13(3-87K/R→A)-IgG4Fc.

Another aspect of the present application is directed to an isolated polynuecleotide encoding a chemokine-immunoglobulin fusion polypeptide having a chemokine moiety and an immunoglobulin moiety, wherein the chemokine moiety comprises a chemokine selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof and wherein the immunoglobulin moiety comprises a peptide selected from the group consisting of the constant regions of human IgG1 (hIgG1Fc), the constant regions of human IgG2 (hIgG2Fc), the constant regions of human IgG3 (hIgG3Fc), the constant regions of human IgG4 (hIgG4Fc), and functional variants thereof.

In a particular embodiment, the isolated polynuecleotide encoding a chemokine-immunoglobulin fusion polypeptide is selected from the group consisting of CCL2-IgG1Fc, CCL2(5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG1Fc, CCL8(5-76)-IgG1Fc, CCL8(5-76K/H/R→A)-IgG1Fc, CCL8-IgG2Fc, CCL8(5-76)-IgG2Fc, CCL8(5-76K/H/R→A)-IgG2Fc, CCL8-IgG3Fc, CCL8(5-76)-IgG3Fc, CCL8(5-76K/H/R→A)-IgG3Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG2Fc, CCL25(4-127)-IgG2Fc, CCL25(4-127K/H/R→A)-IgG2Fc, CCL25-IgG3Fc, CCL25(4-127)-IgG3Fc, CCL25(4-127K/H/R→A)-IgG3Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11-IgG2Fc, CXCL11(4-73)-IgG2Fc, CXCL11(4-73K/R→A)-IgG2Fc, CXCL11-IgG3Fc, CXCL11(4-73)-IgG3Fc, CXCL11(4-73K/R→A)-IgG3Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG2Fc, CXCL12α(3-67)-IgG2Fc, CXCL12α(3-67K/R→A)-IgG2Fc, CXCL12α-IgG3Fc, CXCL12α(3-67)-IgG3Fc, CXCL12α(3-67K/R→A)-IgG3Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG2Fc, CXCL13(3-87)-IgG2Fc, CXCL13(3-87K/R→A)-IgG2Fc, CXCL13-IgG3Fc, CXCL13(3-87)-IgG3Fc, CXCL13(3-87K/R→A)-IgG3Fc, CXCL13-IgG4Fc, CXCL13(3-87)-IgG4Fc, and CXCL13(3-87K/R→A)-IgG4Fc.

A further aspect of the present application is directed to a pharmaceutical composition comprising (1) a chemokine-immunoglobulin fusion polypeptide of the present application or an expression vector encoding a chemokine-immunoglobulin fusion polypeptide of the present application, and (2) a pharmaceutically acceptable carrier.

A further aspect of the present application is directed to a method for treating a chemokine receptor-mediated disorder in a subject, comprising administering to said subject an effective amount of the pharmaceutical composition of the present application.

Another aspect of the present application relates to a method for modulating inflammation in a subject, comprising administering to said subject an effective amount of the pharmaceutical composition of the present application.

Another aspect of the present application relates to a method for treating a chemokine receptor-mediated disorder in a subject, comprising administering to said subject an effective amount of a pegylated chemokine, wherein the chemokine is selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof.

In a further embodiment, the pegylated chemokine is selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

BRIEF DESCRIPTION OF THE DRAWINGS

FIG. 1A depicts the expression vector pCCL2.hIgG1Fc. The Fc region comprises the CH2 and CH3 domains of the IgG heavy chain and the hinge region. The hinge serves as a flexible spacer between the two parts of the Fc-fusion protein, allowing each part of the molecule to function independently. hEF1-HTLV prom is a composite promoter comprising the Elongation Factor-1α (EF-1α) core promoter1 and the R segment and part of the U5 sequence (R-U5') of the Human T-Cell Leukemia Virus (HTLV) Type 1 Long Terminal Repeat2. The EF-1α promoter exhibits a strong activity and yields long lasting expression of a transgene in vivo. The R-U5' has been coupled to the EF-1α core promoter to enhance stability of RNA. MCS: The multiple cloning site. SV40 pAn: the Simian Virus 40 late polyadenylation signal. ori: a minimal *E. coli* origin of replication. CMV enh/hFerL prom: This composite promoter combines the human cytomegalovirus immediate-early gene 1 enhancer and the core promoter of the human ferritin light chain gene. This ubiquitous promoter drives the expression of the Zeocin™-resistance gene in mammalian cells. EM2KC is a bacterial promoter that enables the constitutive expression of the antibiotic resistance gene in *E. coli*. EM2KC is located within an intron and is spliced out in mammalian cells. Zeo: Resistance to Zeocin™ is conferred by the Sh ble gene from *Streptoalloteichus hindustanus* The same resistance gene confers selection in both mammalian cells and *E. coli*. βG10 pAn: The human beta-globin 3'UTR and polyadenylation sequence allows efficient arrest of the transgene transcription4

FIG. 1B depicts the expression vector pCCL2(5-76).hIgG1Fc.

Figure 1C:
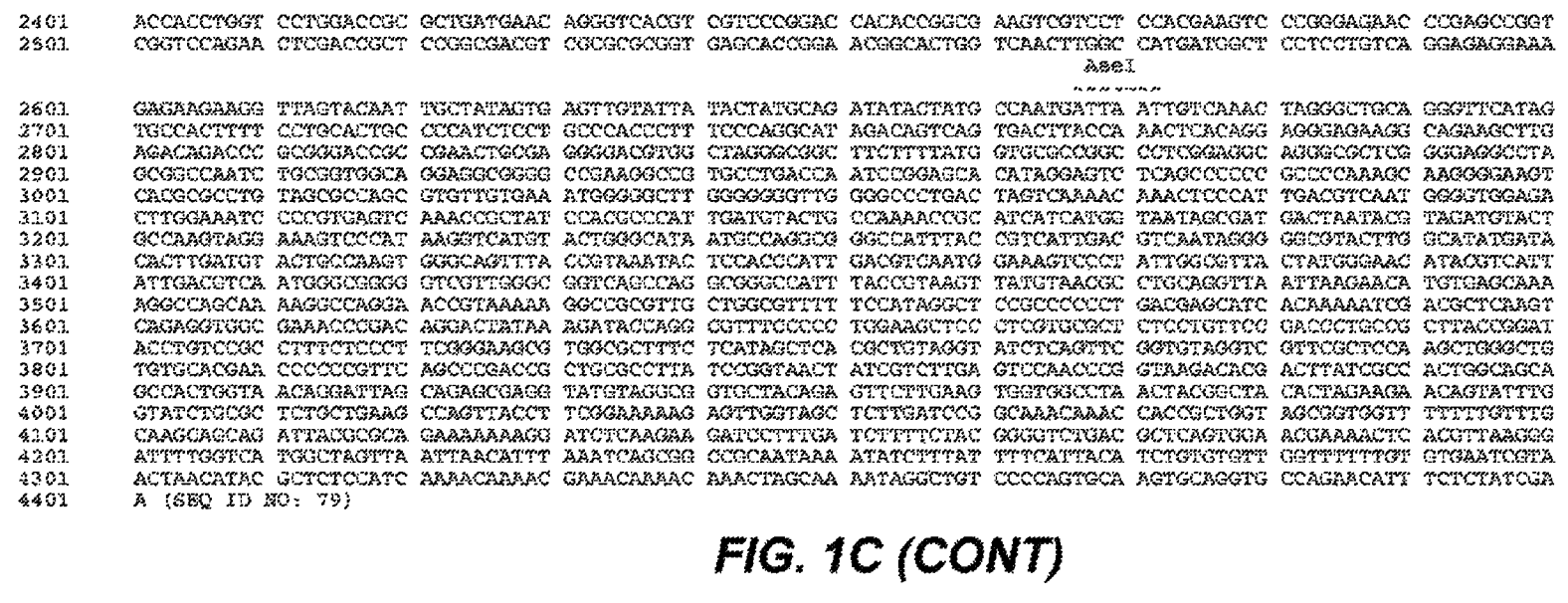

FIG. 1C shows the nuceotide sequence of the expression vector pCCL2.hIgG1Fc.

Figure 1D:
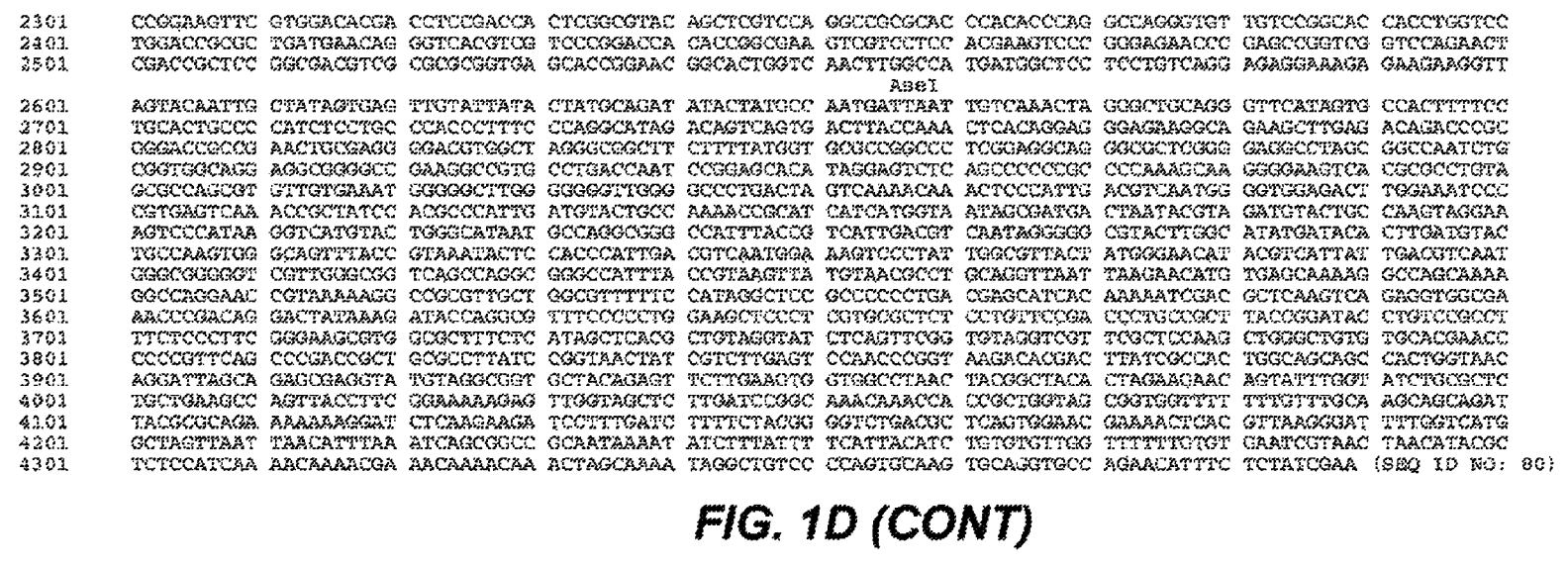

FIG. 1D shows the nuceotide sequence of the expression vector pCCL2(5-76).hIgG1Fc.

Figure 1E:
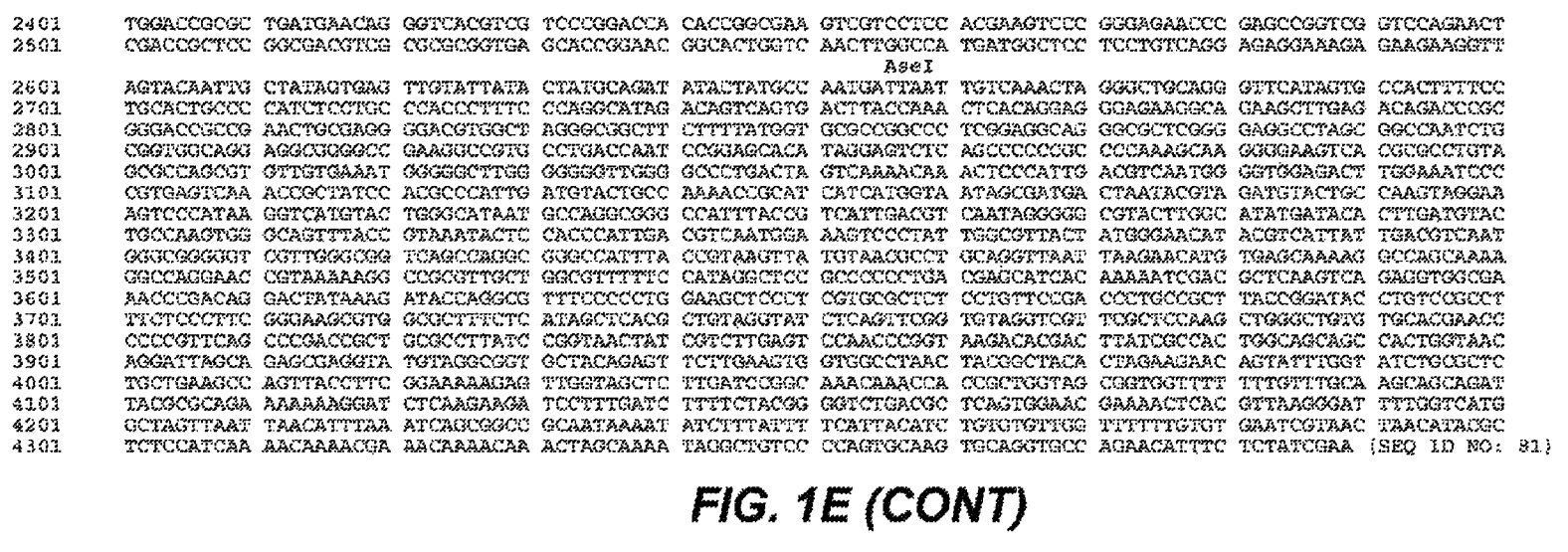

FIG. 1E shows the nuceotide sequence of the expression vector pCCL2(5-76).hIgG1Fc with alanine substitutions for removal of GAG binding sites—lys and his.

Figure 2A:
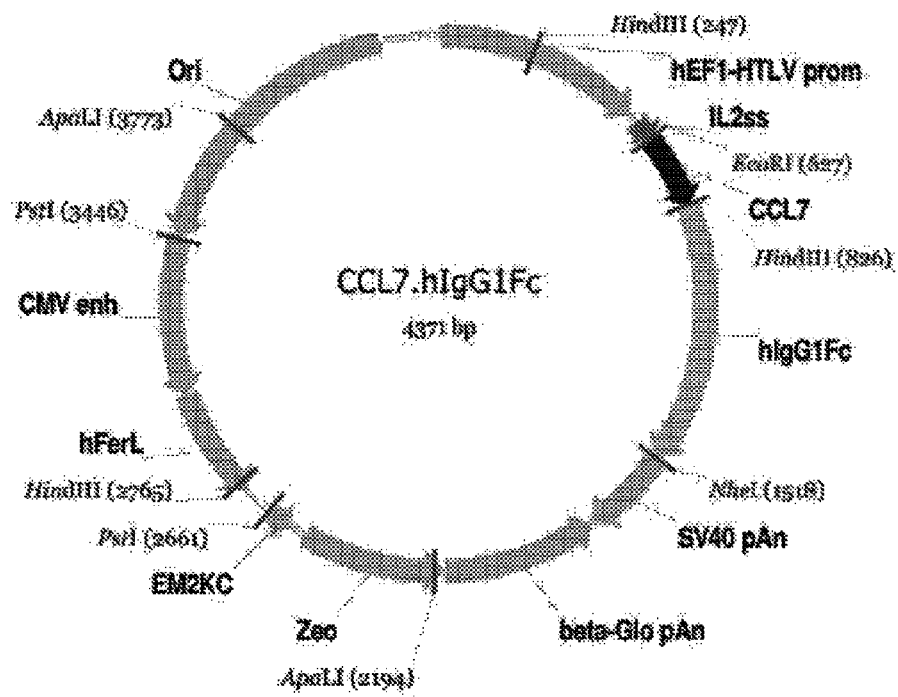

FIG. 2A depicts the expression vector pCCL7.hIgG1Fc.

Figure 2B:
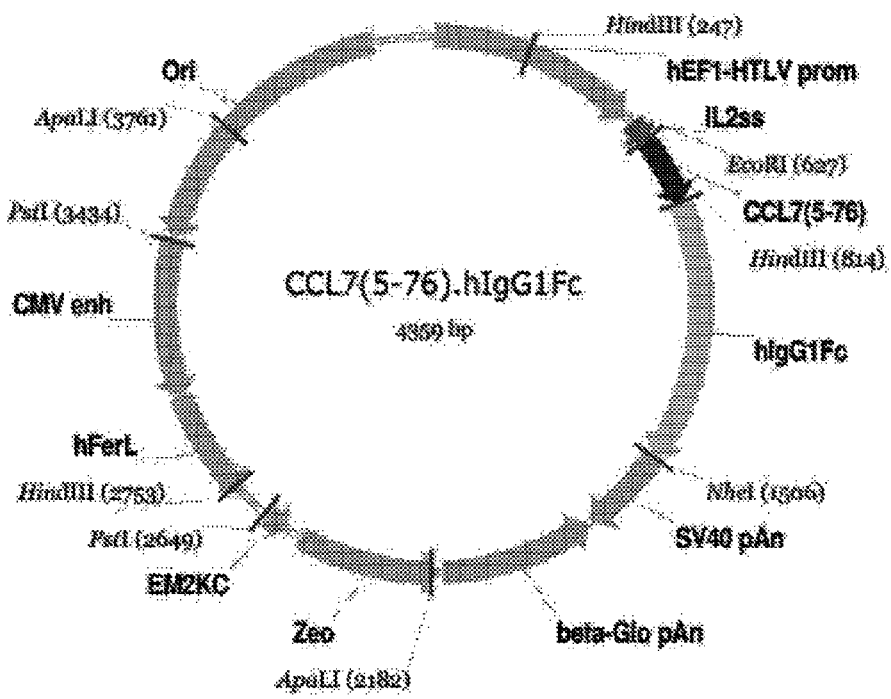

FIG. 2B depicts the expression vector pCCL7(5-76).hIgG1Fc.

FIG. 2C shows the nuceotide sequence of the expression vector pCCL7.hIgG1Fc.

Figure 2D:
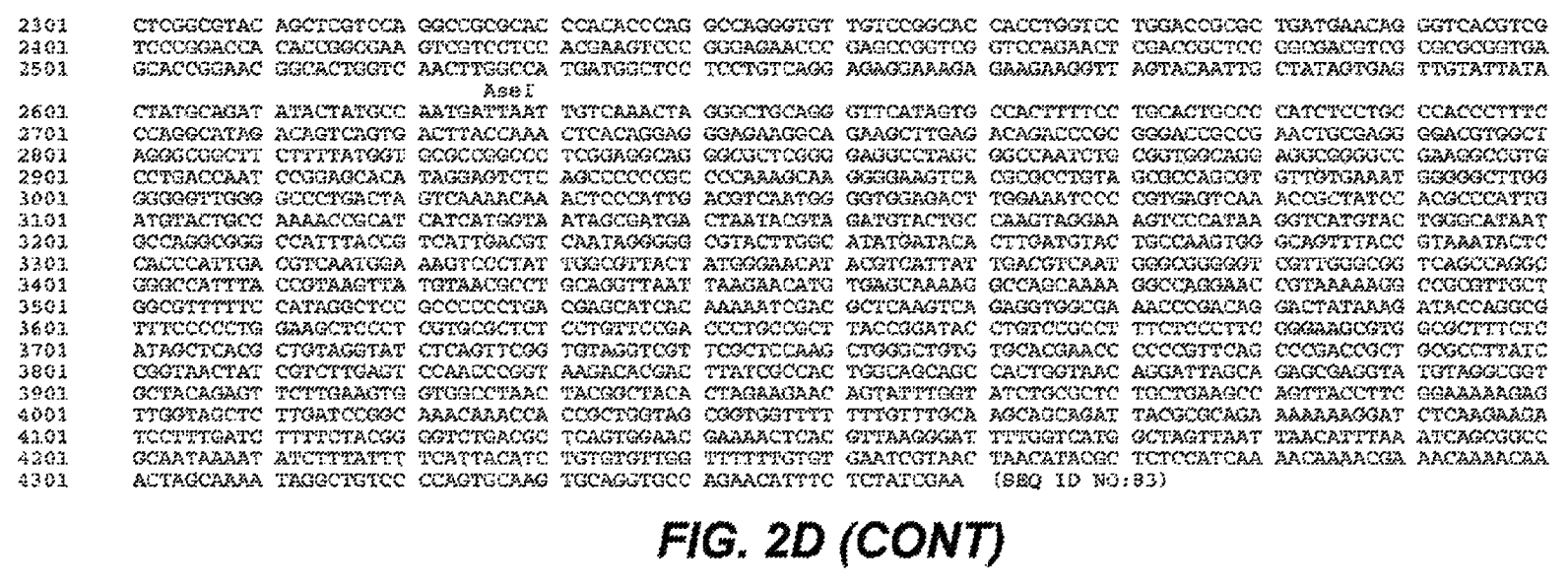

FIG. 2D shows the nuceotide sequence of the expression vector pCCL7(5-76).hIgG1Fc.

Figure 2E:
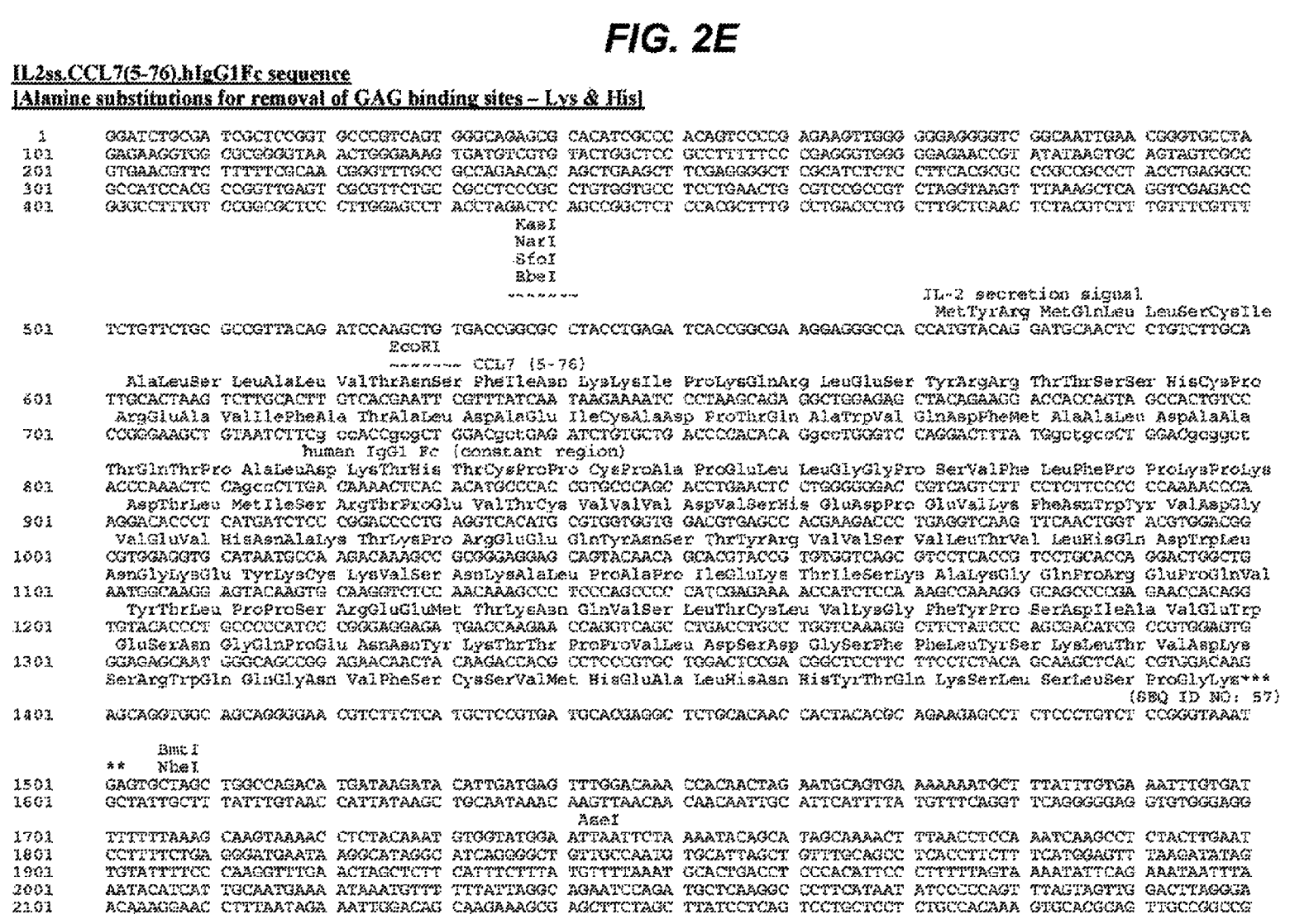
Figure 2E:
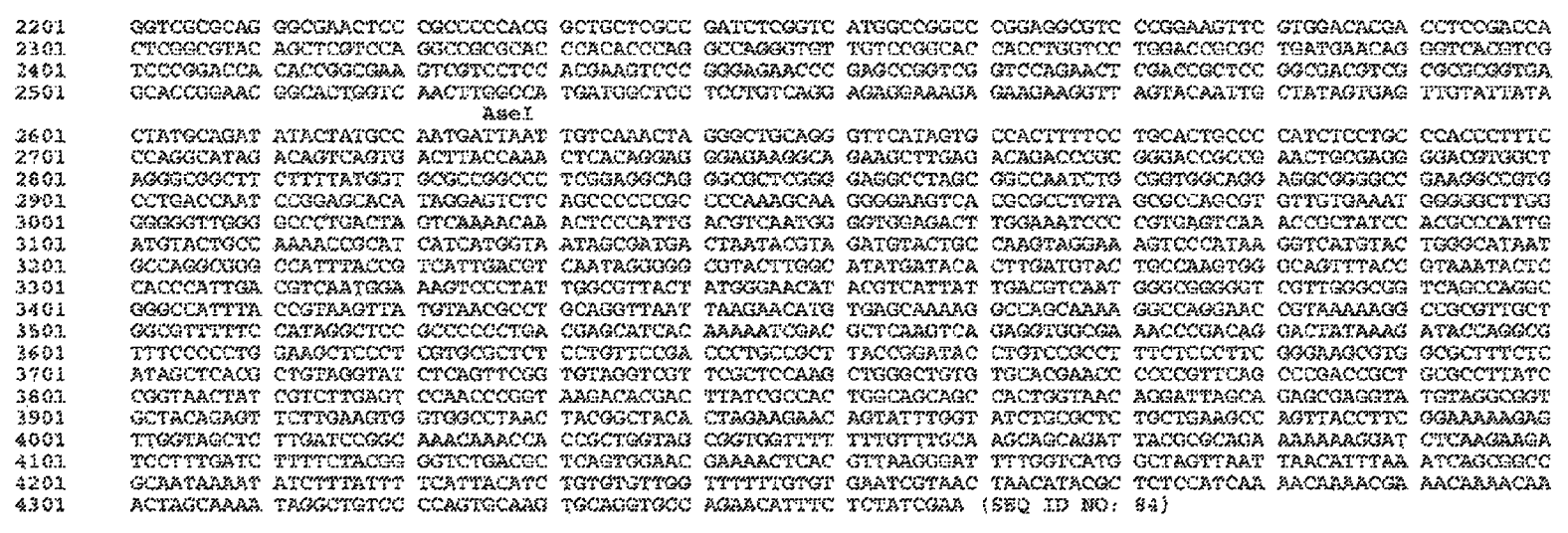

FIG. 2E shows the nuceotide sequence of the expression vector pCCL7(5-76).hIgG1Fc with alanine substitutions for removal of GAG binding sites—lys and his.

Figure 3A:
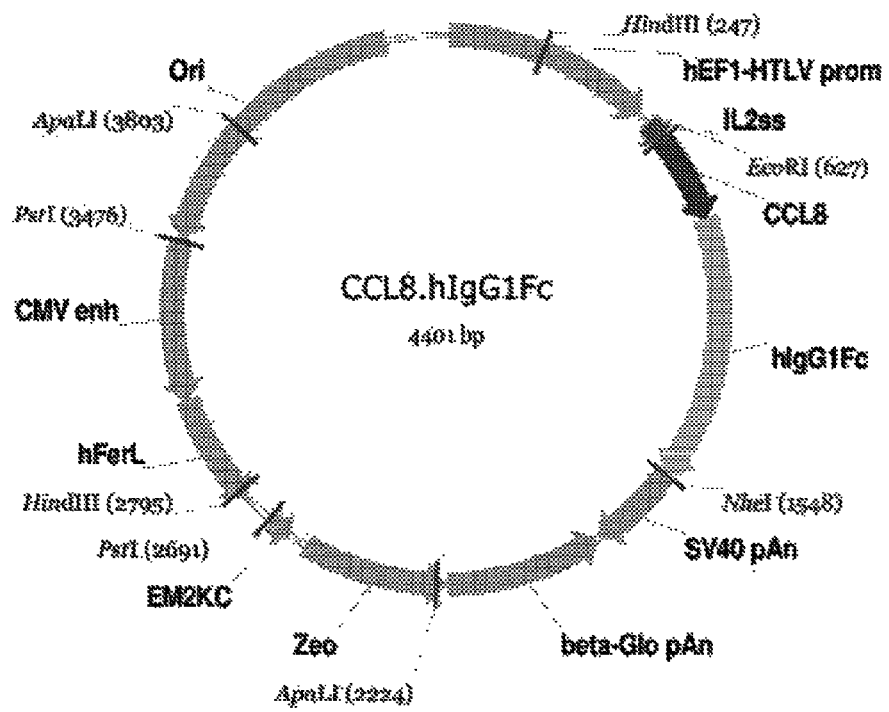

FIG. 3A depicts the expression vector pCCL8.hIgG1Fc.

Figure 3B:
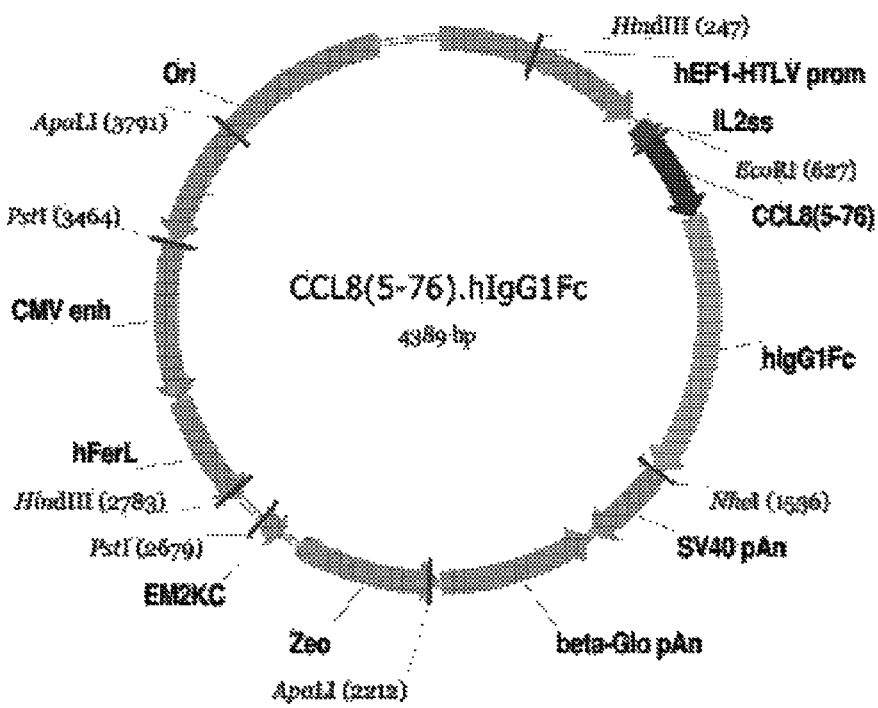

FIG. 3B depicts the expression vector pCCL8(5-76).hIgG1Fc.

Figure 3C:
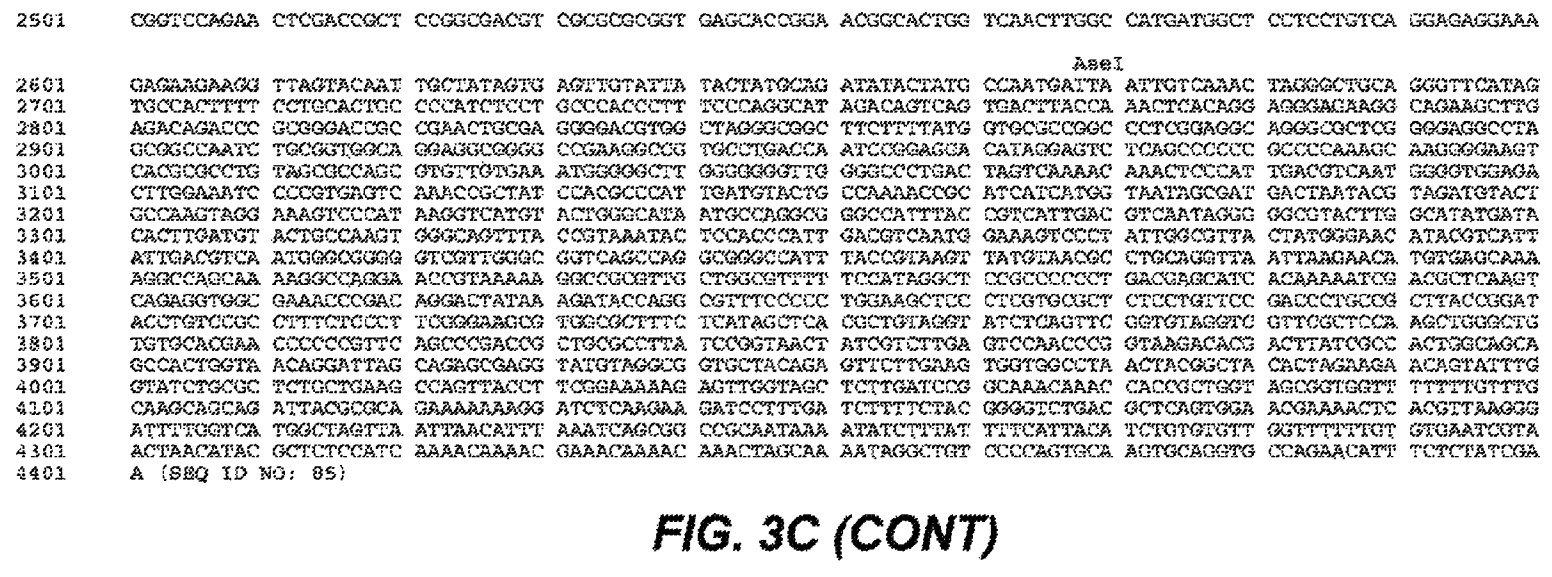

FIG. 3C shows the nuceotide sequence of the expression vector pCCL8.hIgG1Fc.

Figure 3D:
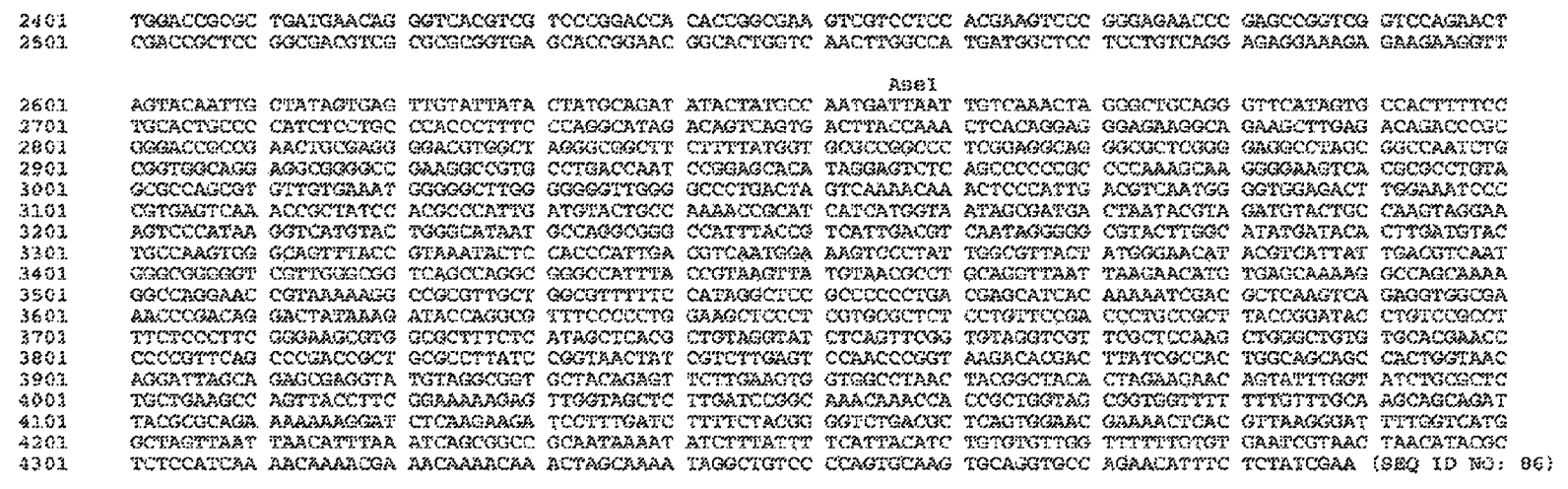

FIG. 3D shows the nuceotide sequence of the expression vector pCCL8(5-76).hIgG1Fc.

Figure 3E:
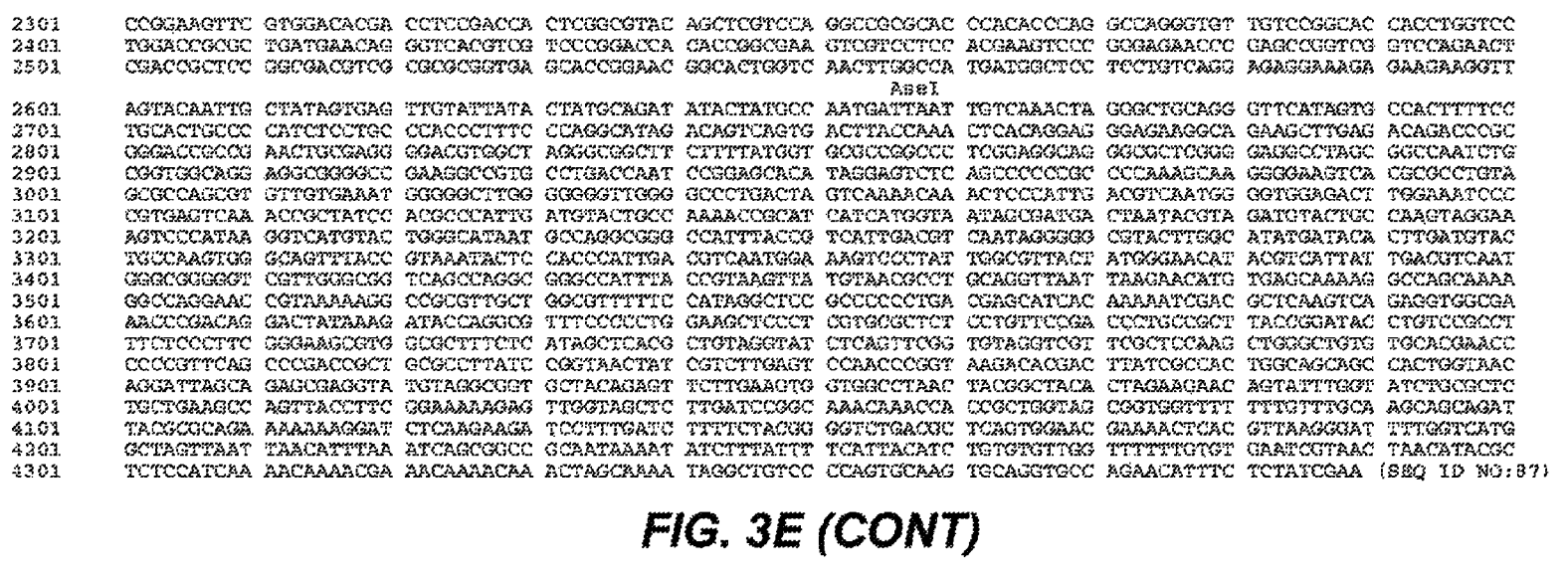
Figure 4A:
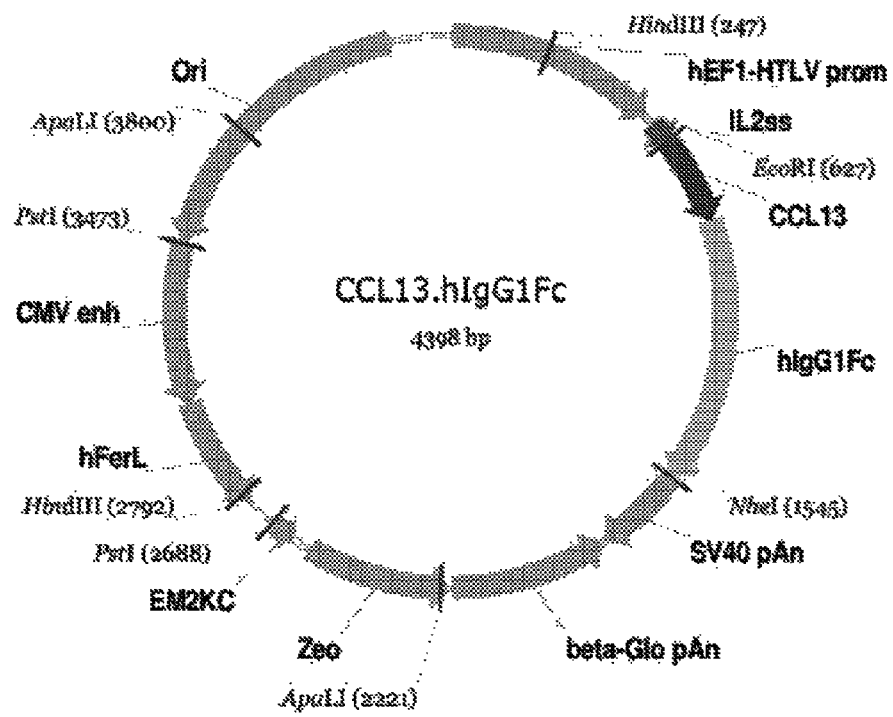

FIG. 3E shows the nuceotide sequence of the expression vector pCCL8(5-76).hIgG1Fc with alanine substitution FIG. 4A depicts the expression vector pCCL13.hIgG1Fc.

Figure 4B:
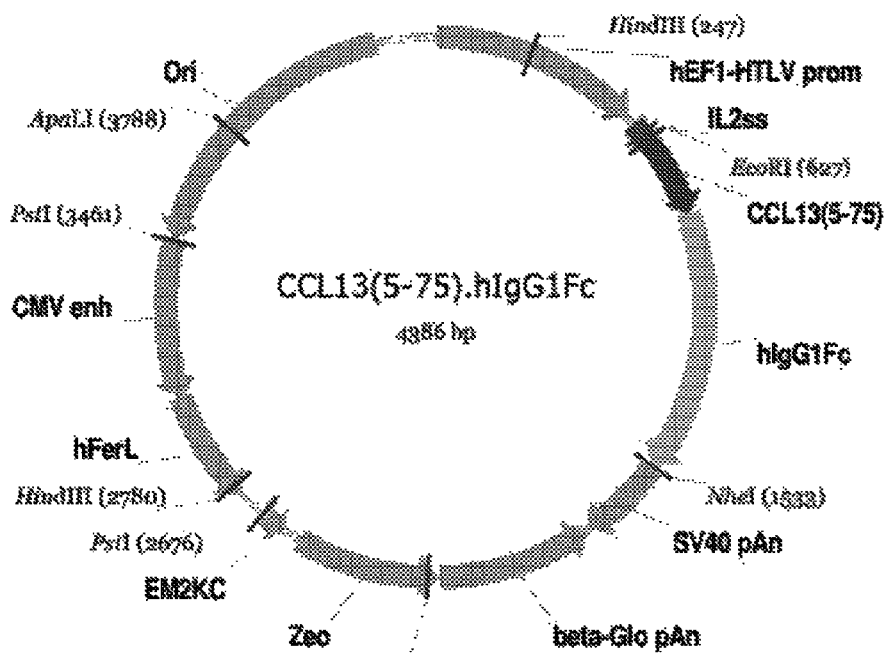

FIG. 4B depicts the expression vector pCCL13(5-75).hIgG1Fc.

Figure 4C:
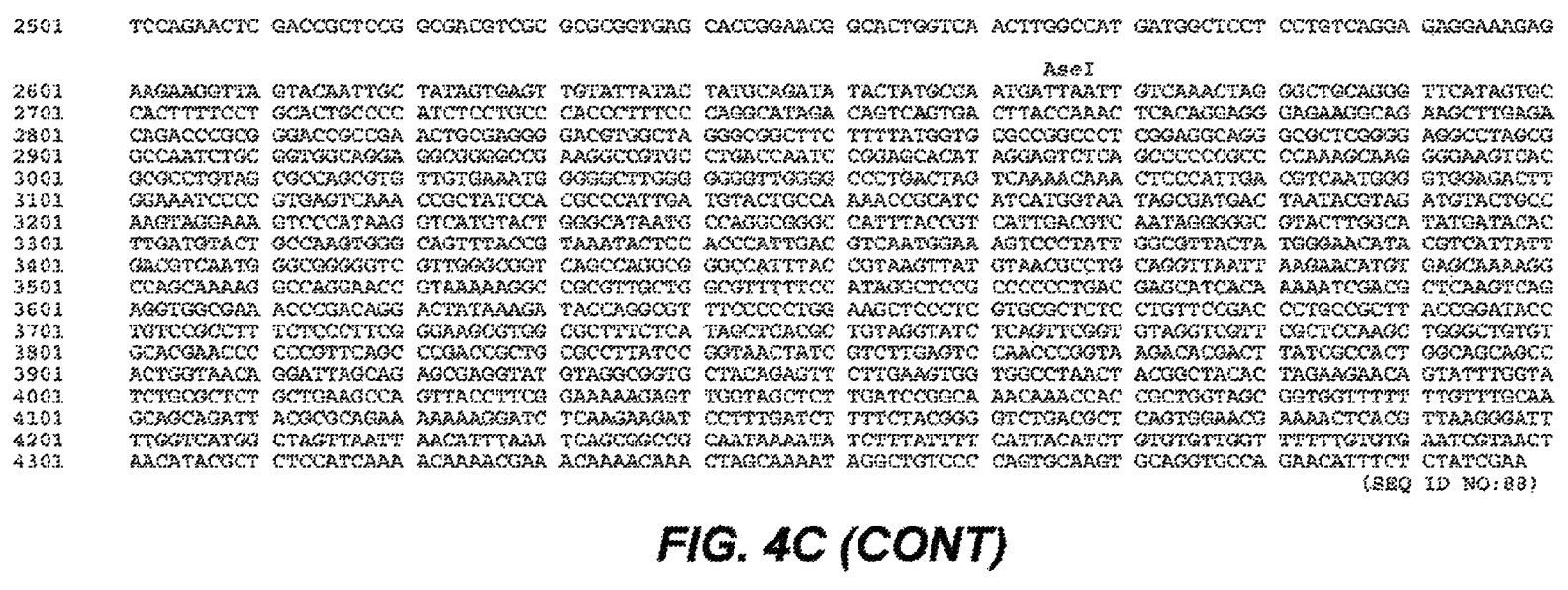

FIG. 4C shows the nuceotide sequence of the expression vector pCCL13.hIgG1Fc.

Figure 4D:
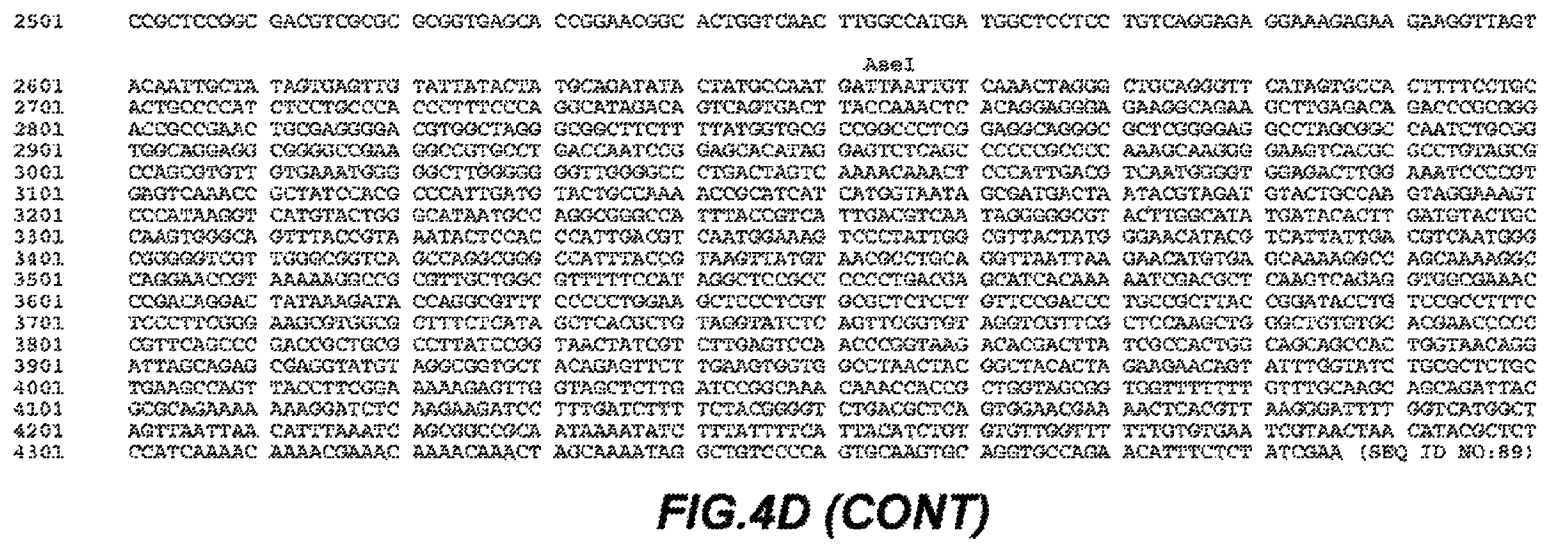

FIG. 4D shows the nuceotide sequence of the expression vector pCCL13(5-75).hIgG1Fc.

Figure 4E:
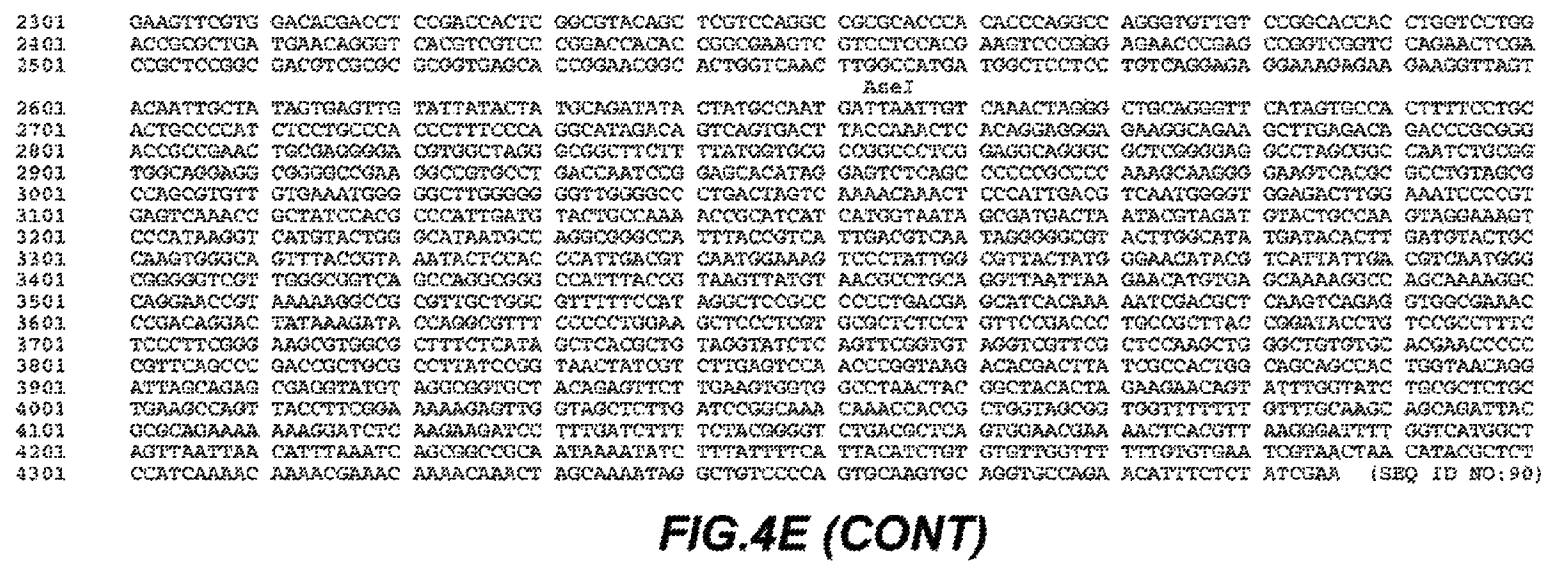

FIG. 4E shows the nuceotide sequence of the expression vector pCCL13(5-76).hIgG1Fc with alanine substitutions for removal of GAG binding sites—lys and his.

Figure 5A:
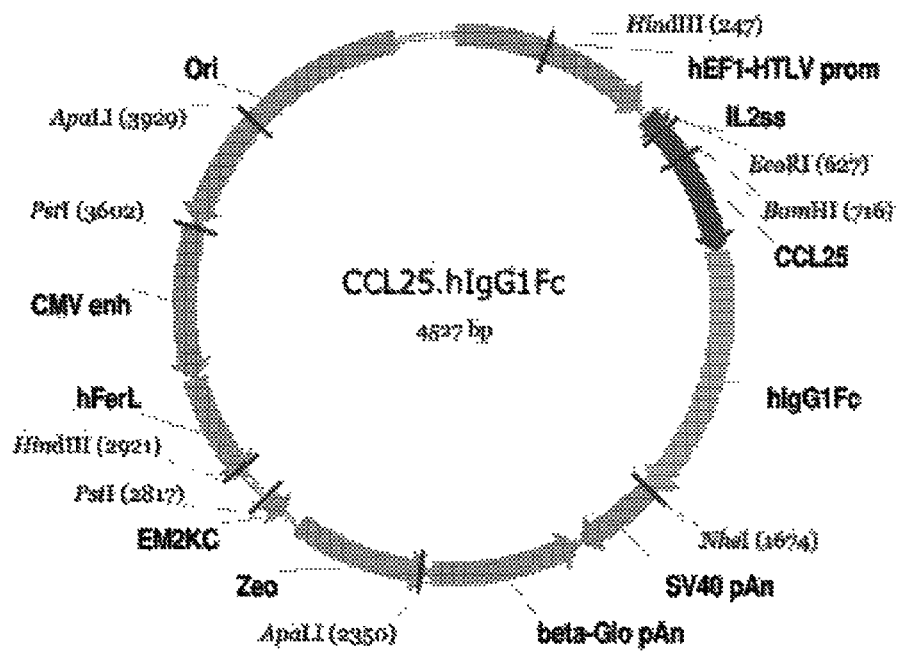

FIG. 5A depicts the expression vector pCCL25.hIgG1Fc.

Figure 5B:
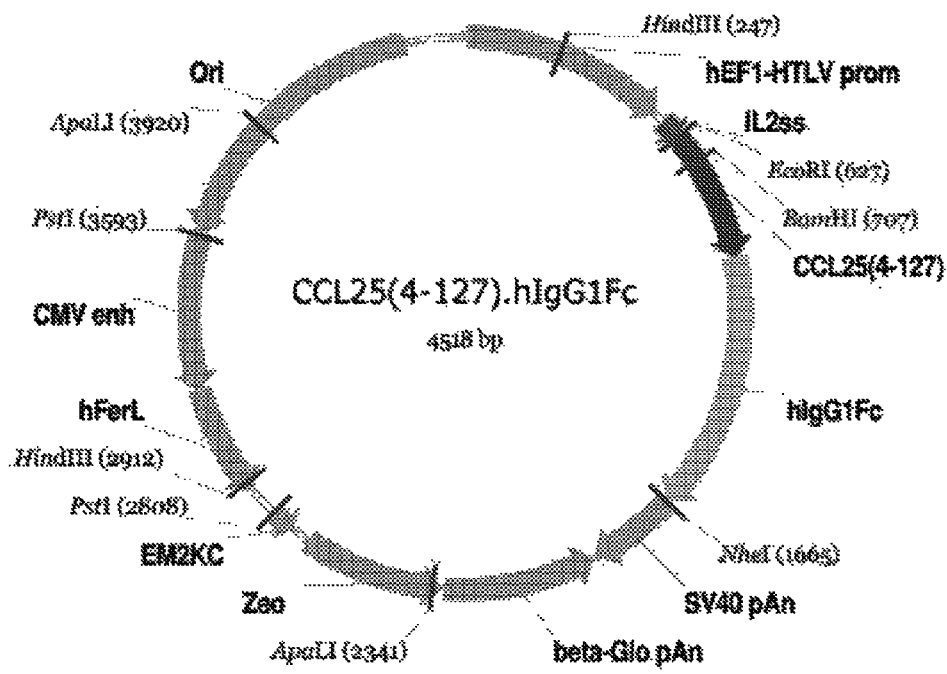

FIG. 5B depicts the expression vector pCCL25(4-127).hIgG1Fc.

Figure 5C:
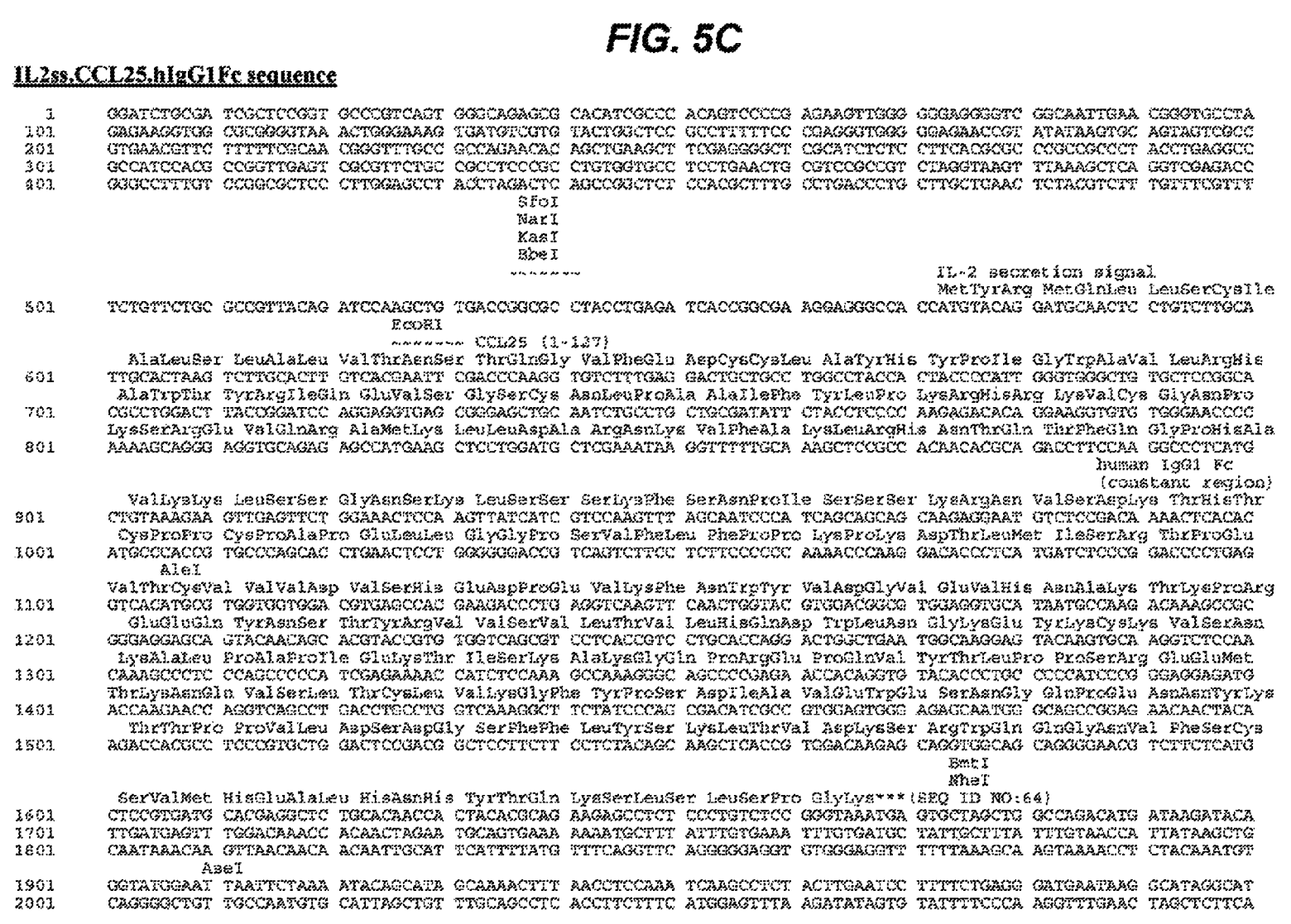

FIG. 5C shows the nuceotide sequence of the expression vector pCCL25.hIgG1Fc.

Figure 5D:
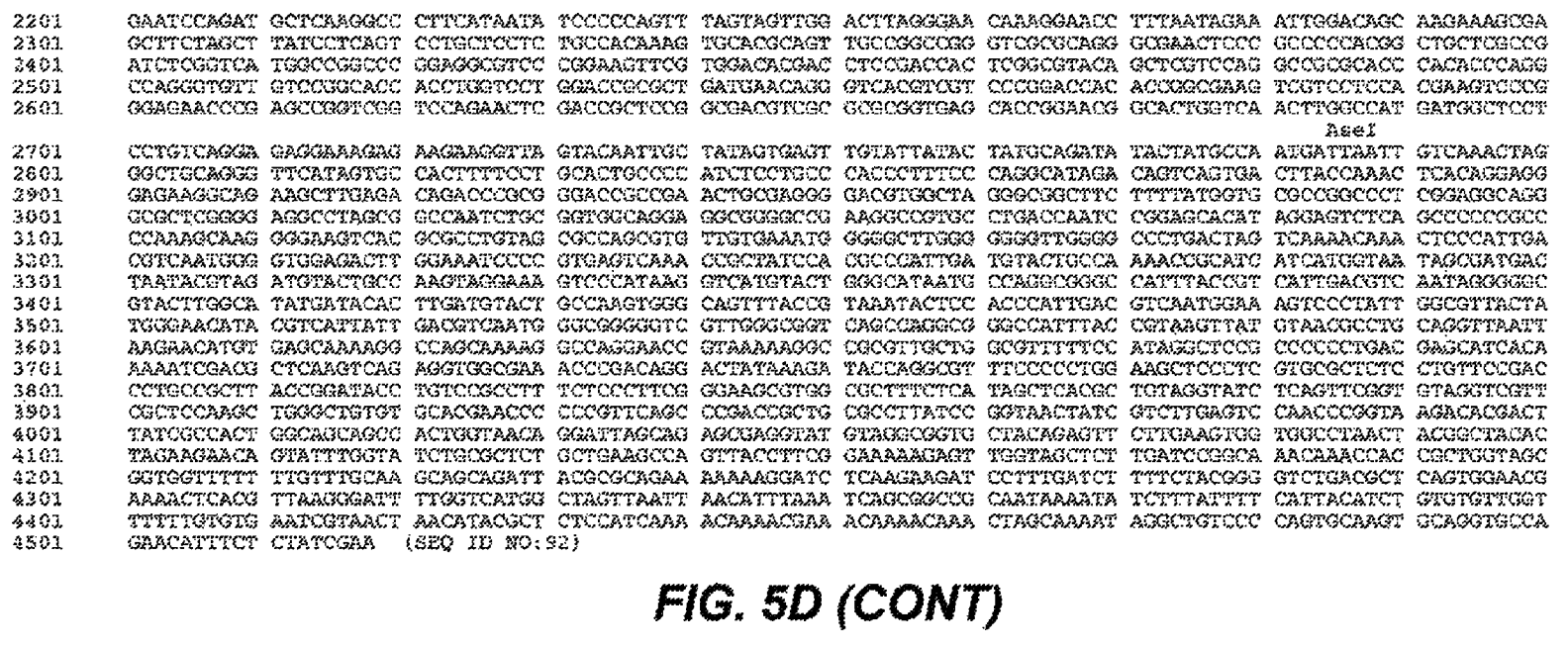

FIG. 5D shows the nuceotide sequence of the expression vector pCCL25(4-127).hIgG1Fc.

Figure 5E:
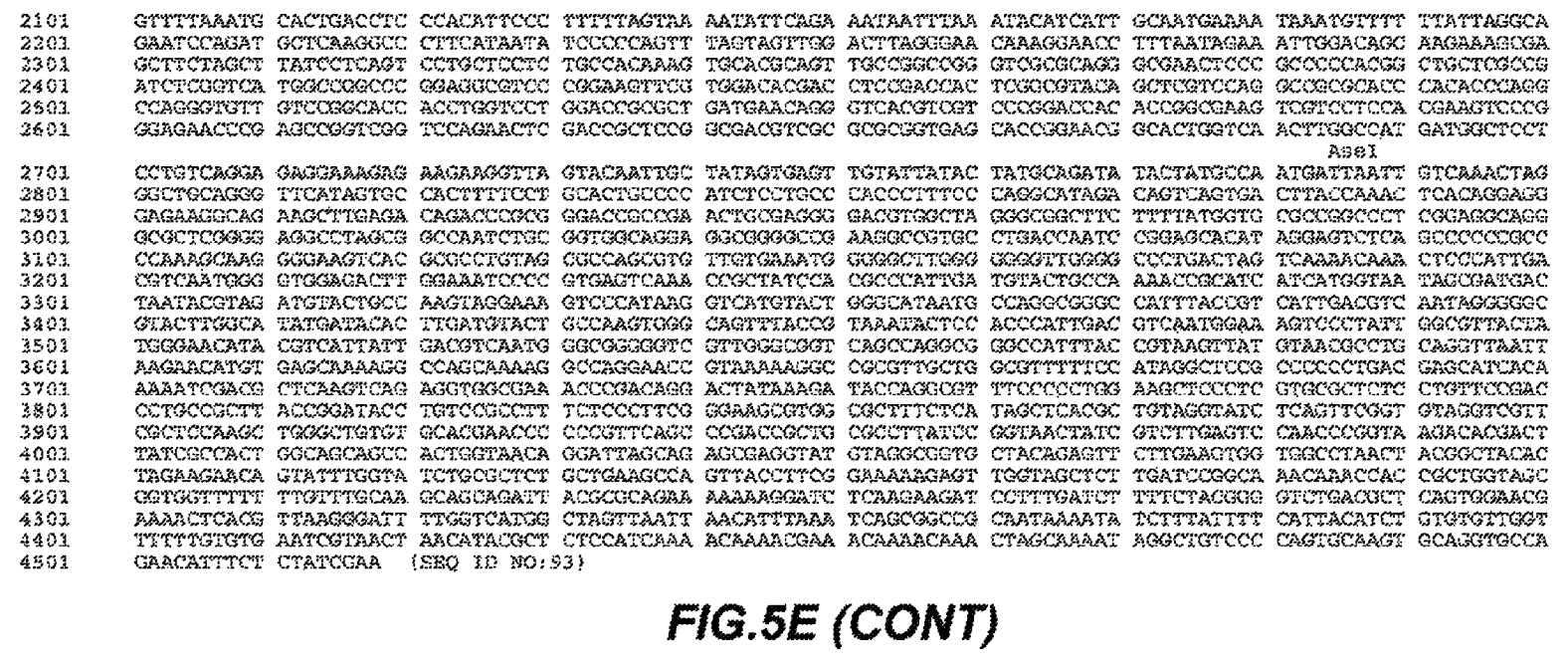

FIG. 5E shows the nuceotide sequence of the expression vector pCCL25(4-127).hIgG1Fc with alanine substitutions for removal of GAG binding sites—lys and his.

Figure 6A:
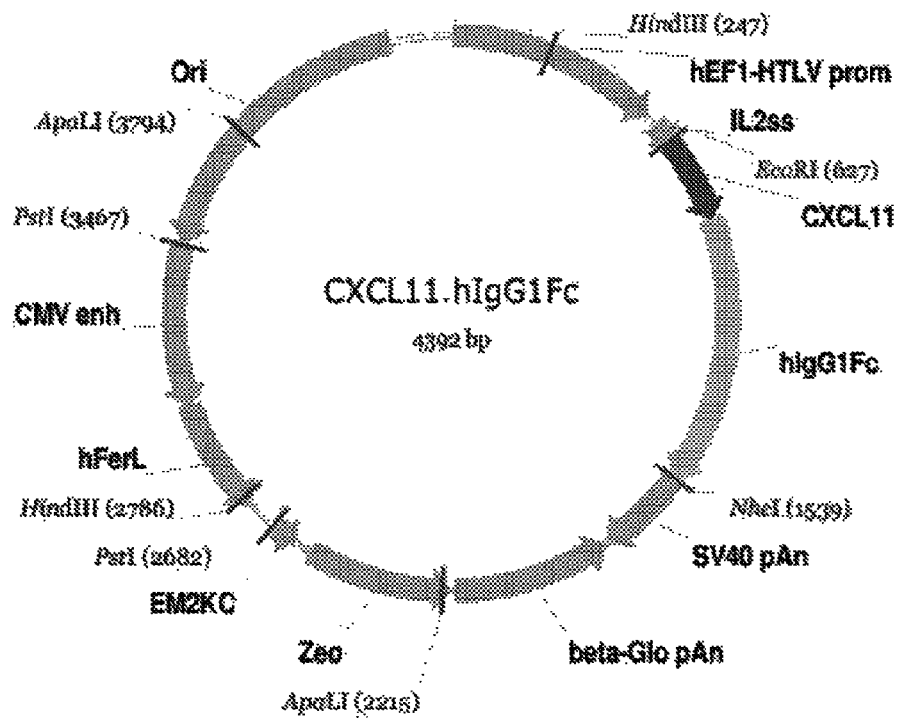

FIG. 6A depicts the expression vector pCXCL11.hIgG1Fc.

Figure 6B:
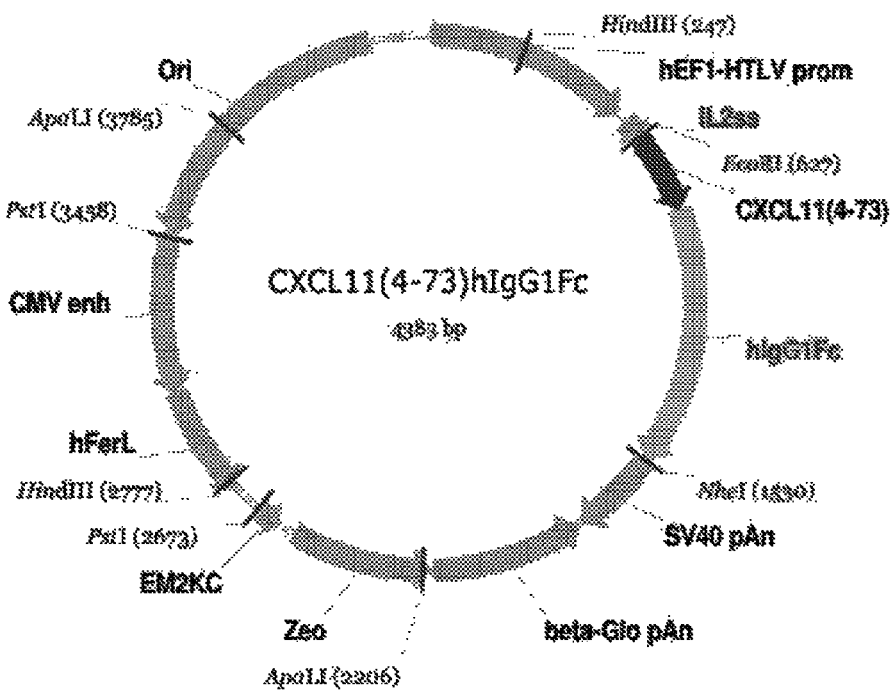

FIG. 6B depicts the expression vector pCXCL11(4-73).hIgG1Fc.

Figure 6C:
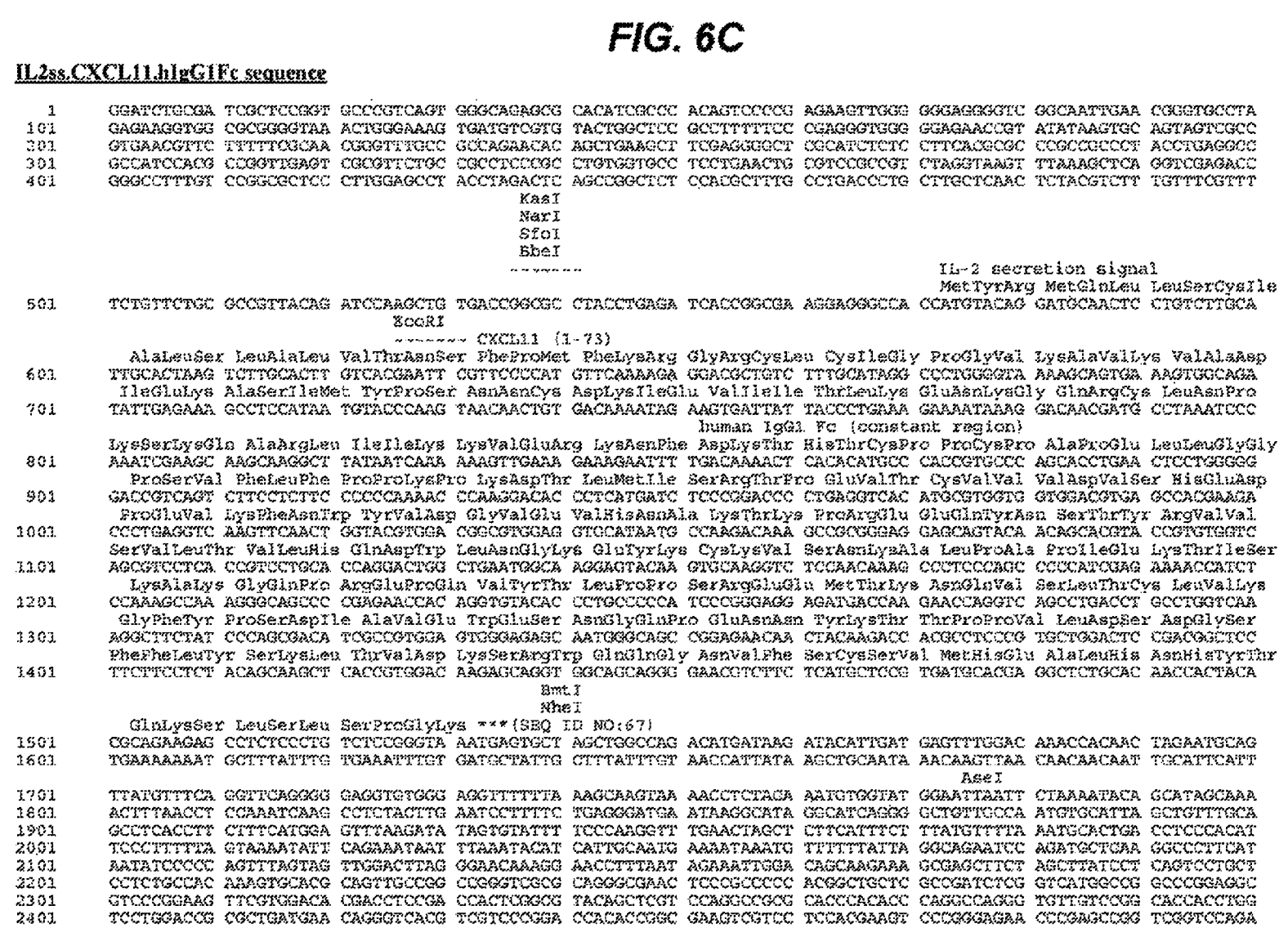
Figure 6C:
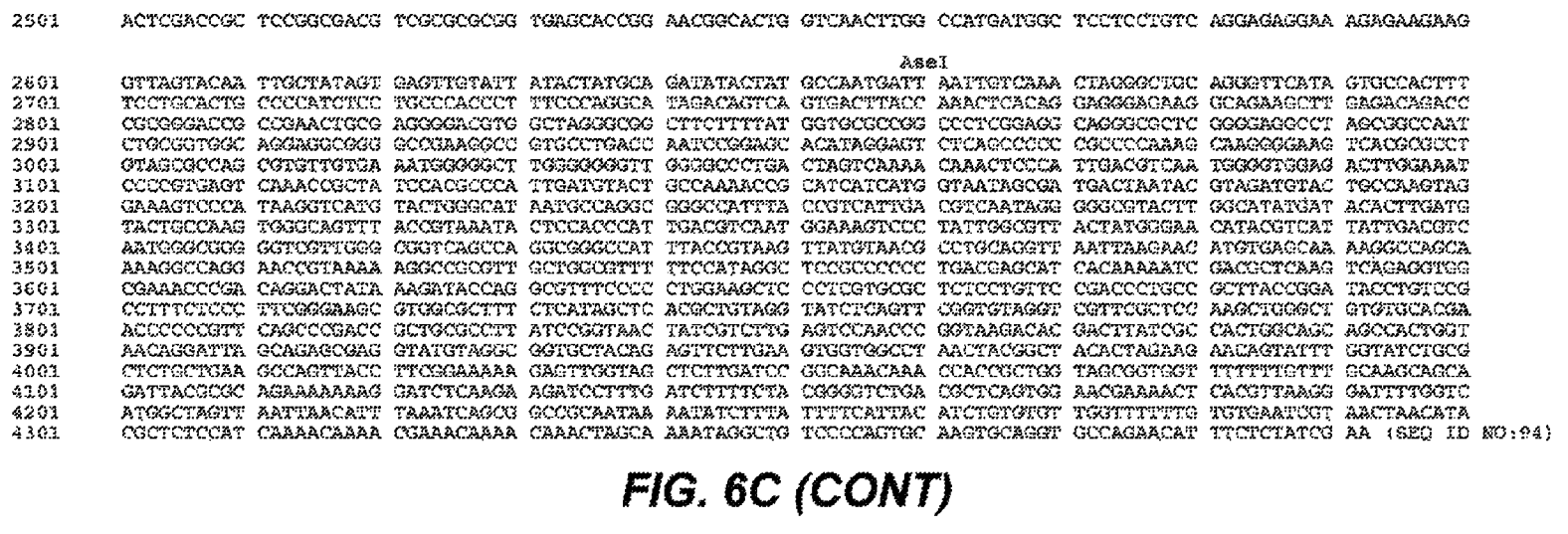

FIG. 6C shows the nuceotide sequence of the expression vector pCXCL11.hIgG1Fc.

FIG. 6D shows the nuceotide sequence of the expression vector pCXCL11(4-73).hIgG1Fc.

Figure 6E:
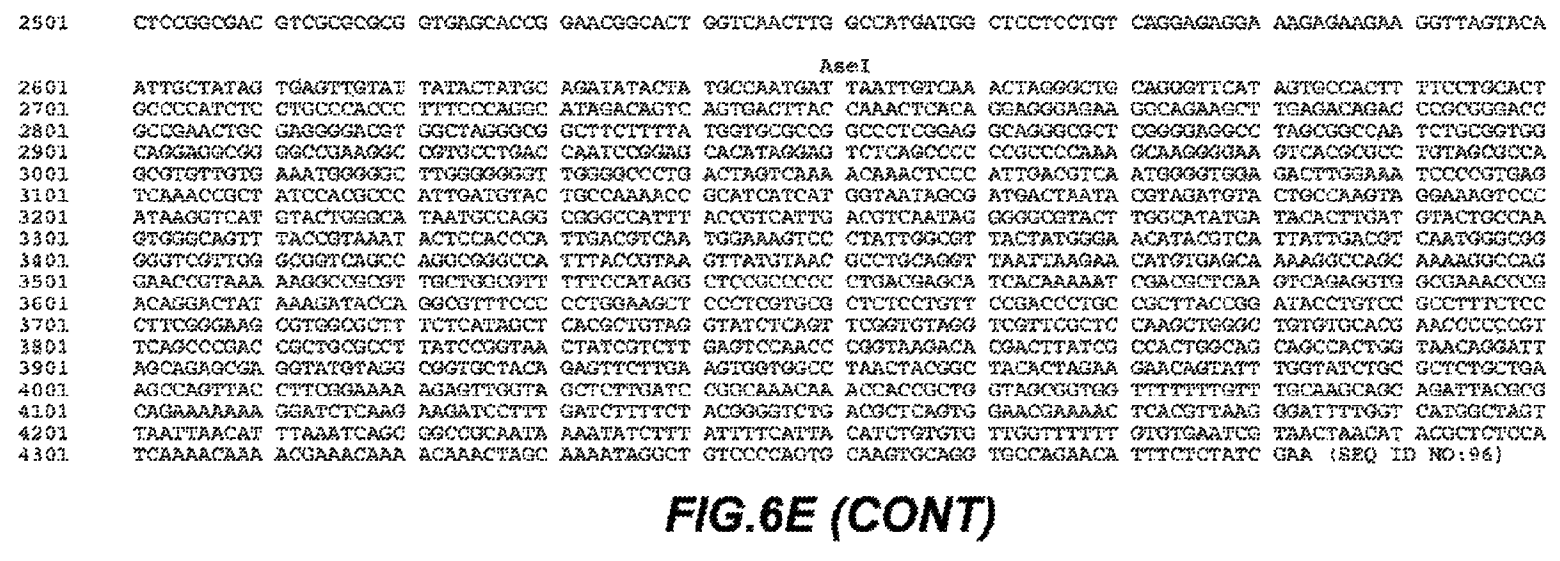

FIG. 6E shows the nuceotide sequence of the expression vector pCXCL11(4-127).hIgG1Fc with alanine substitutions for removal of GAG binding sites—lys and his.

Figure 7A:
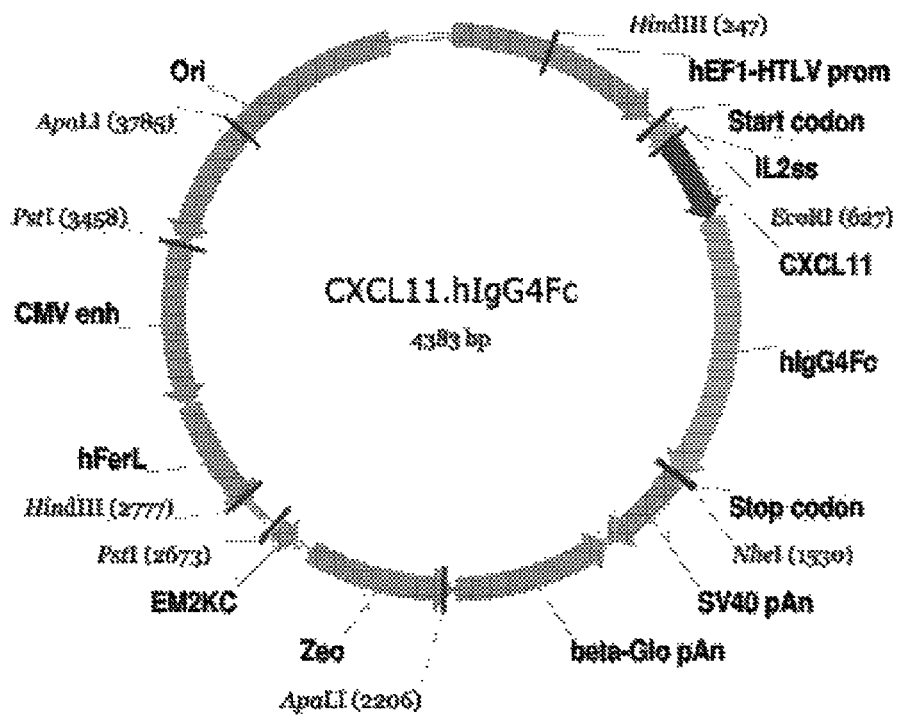

FIG. 7A depicts the expression vector pCXCL11.hIgG4Fc.

Figure 7B:
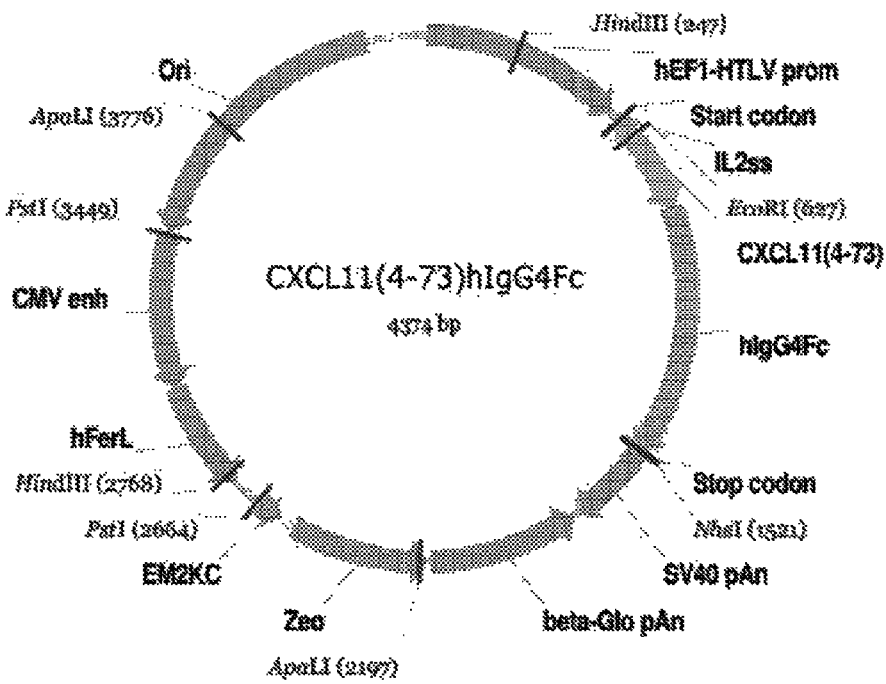

FIG. 7B depicts the expression vector pCXCL11(4-73).hIgG4Fc.

FIG. 7C shows the nuceotide sequence of the expression vector pCXCL11.hIgG4Fc.

Figure 7D:
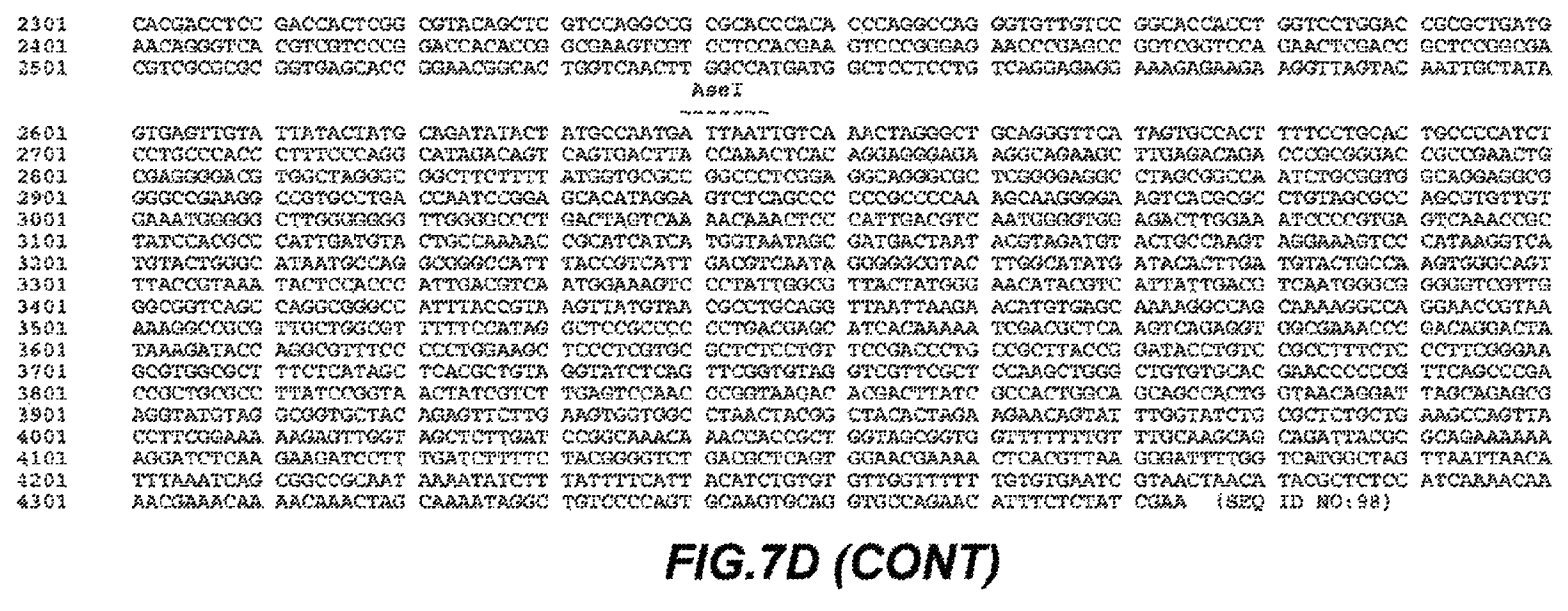

FIG. 7D shows the nuceotide sequence of the expression vector pCXCL11(4-73).hIgG4Fc.

Figure 7E:
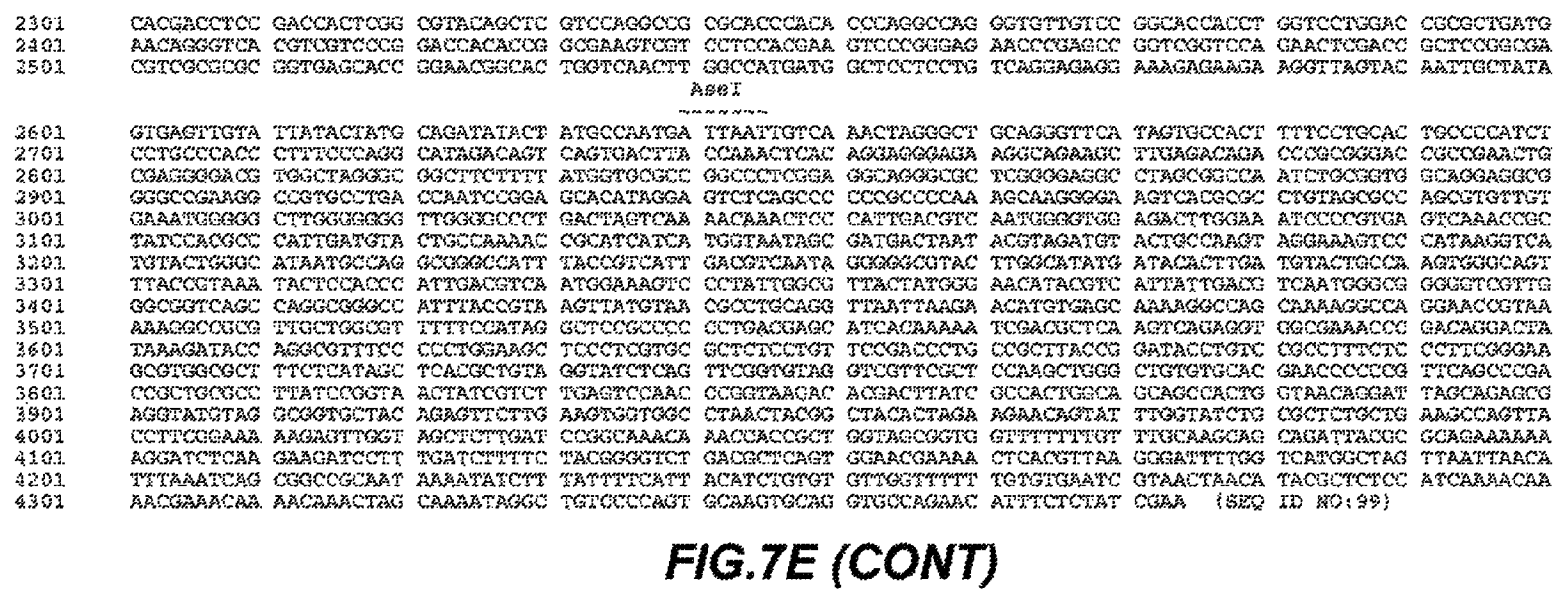

FIG. 7E shows the nuceotide sequence of the expression vector pCXCL11(4-127).hIgG4Fc with alanine substitutions for removal of GAG binding sites—lys and his.

FIG. 8A depicts the expression vector pCXCL13.hIgG1Fc.

FIG. 8B depicts the expression vector pCXCL13(3-87).hIgG1Fc.

Figure 8C:
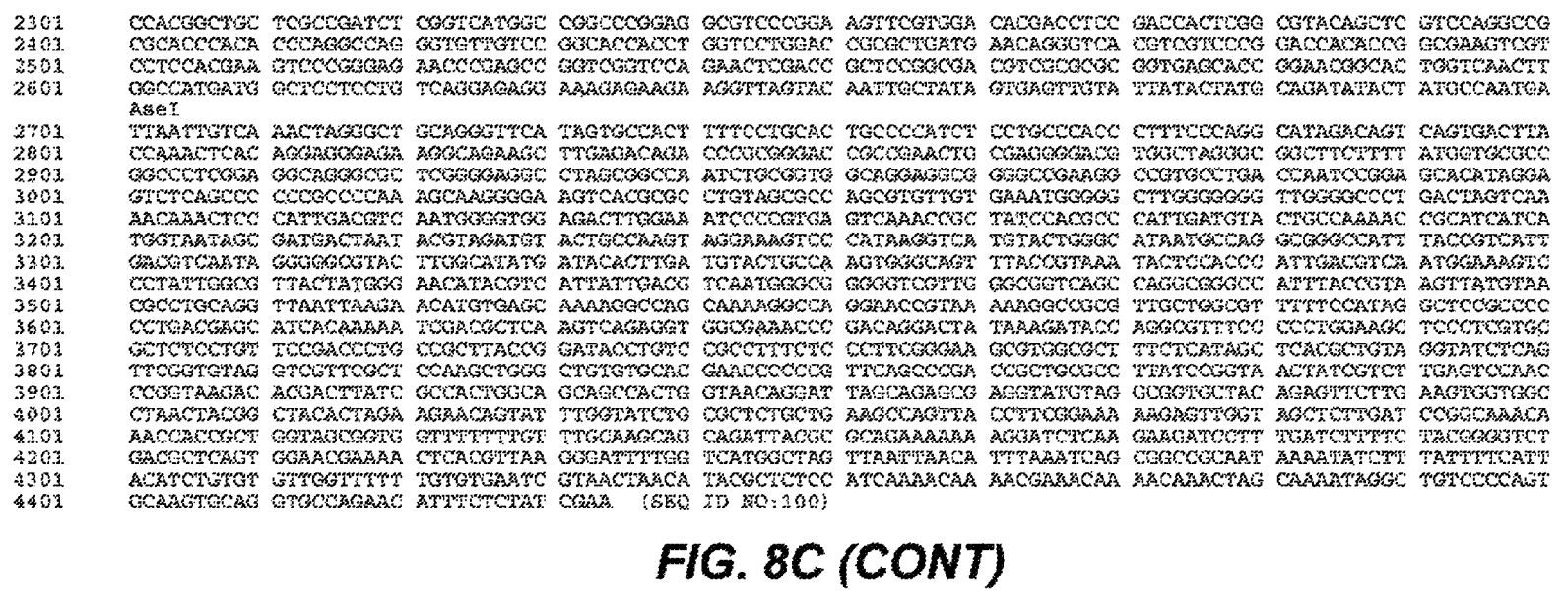

FIG. 8C shows the nuceotide sequence of the expression vector pCXCL13.hIgG1Fc.

Figure 8D:
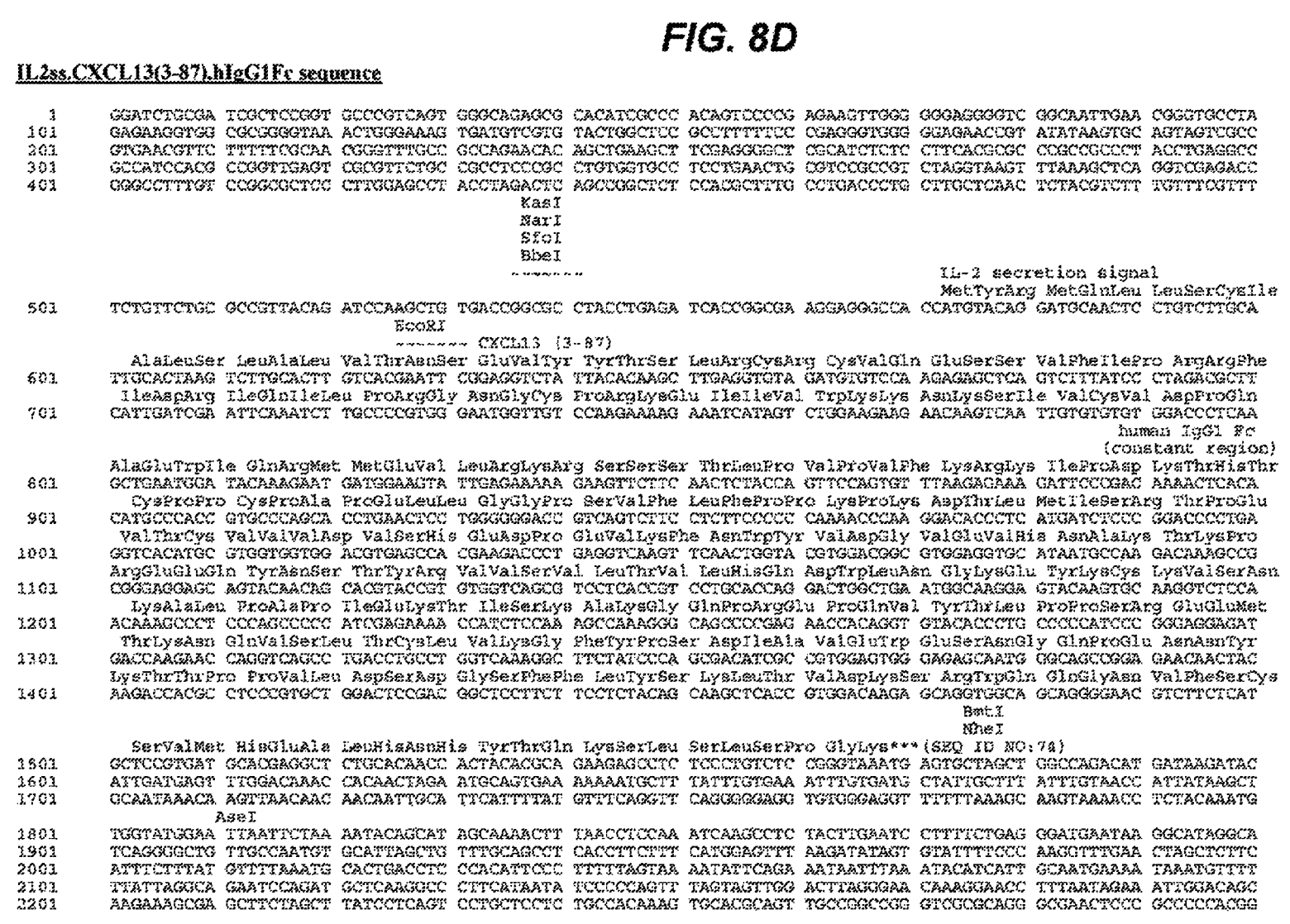
Figure 8D:
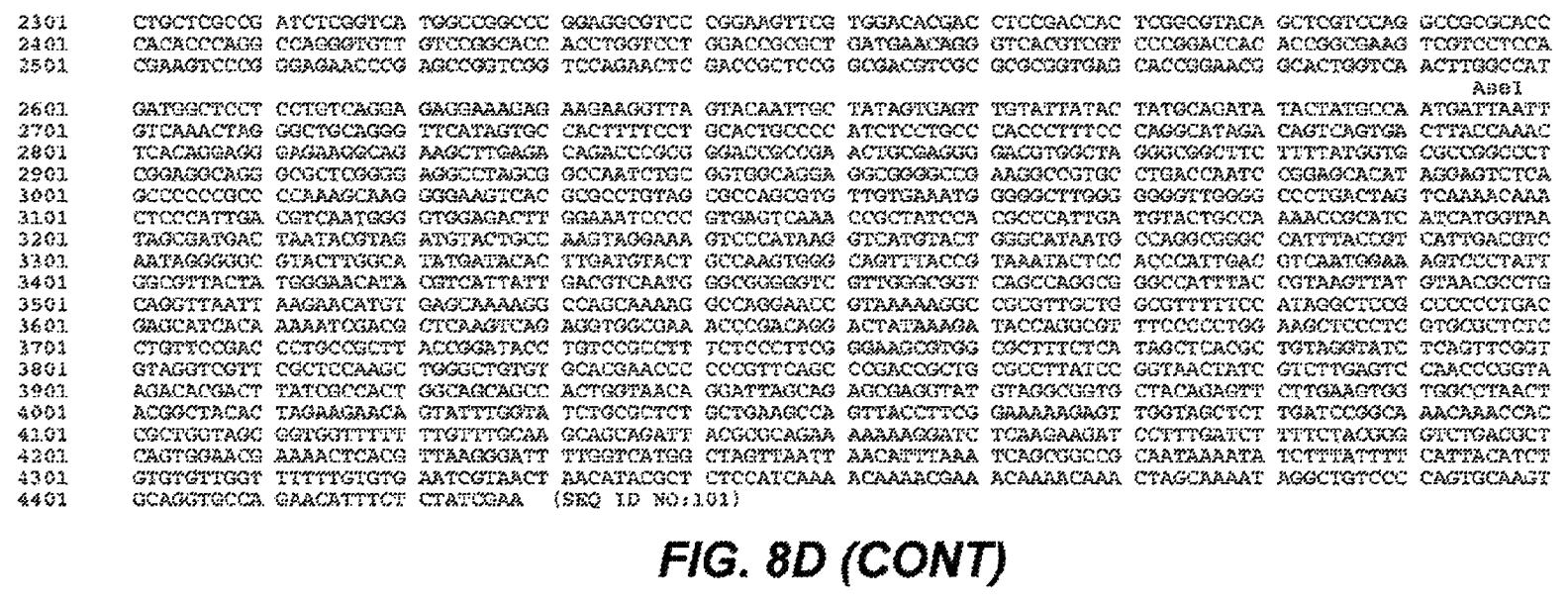

FIG. 8D shows the nuceotide sequence of the expression vector pCXCL13(4-73).hIgG1Fc.

Figure 8E:
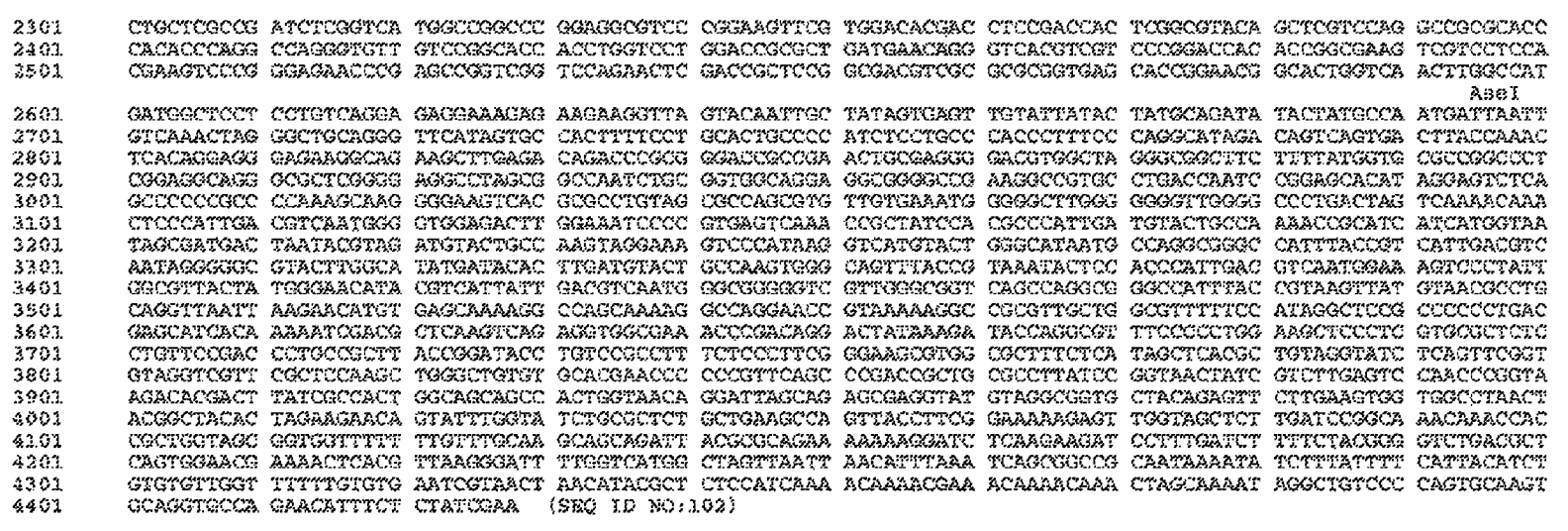

FIG. 8E shows the nuceotide sequence of the expression vector pCXCL13(4-127).hIgG1Fc with alanine substitutions for removal of GAG binding sites—lys and his.

Figure 9A:
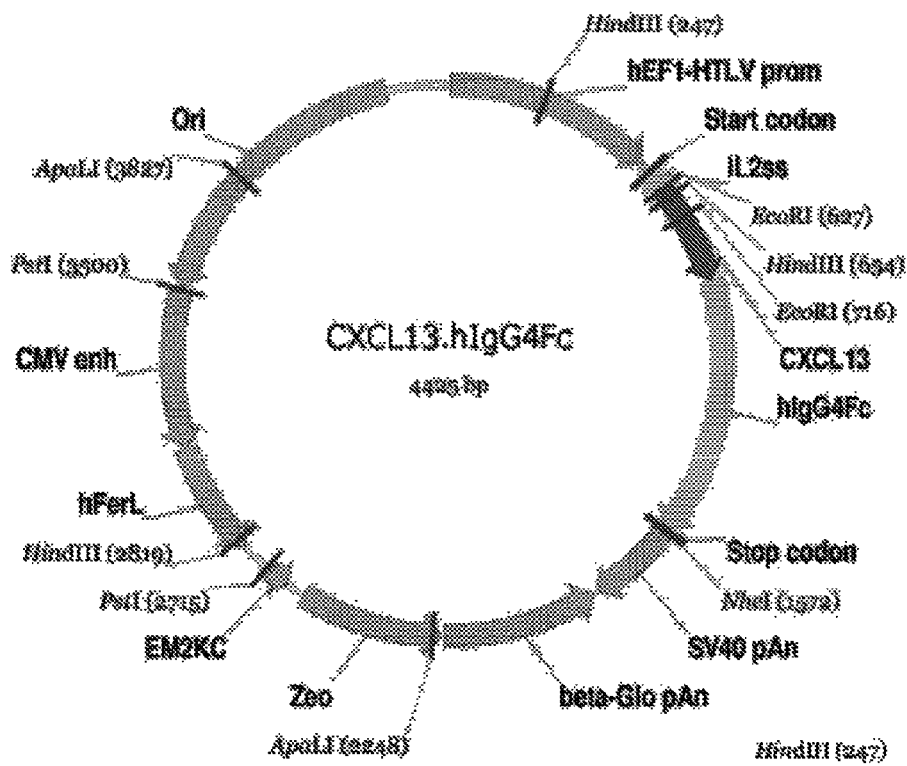

FIG. 9A depicts the expression vector pCXCL13.hIgG4Fc.

Figure 9B:
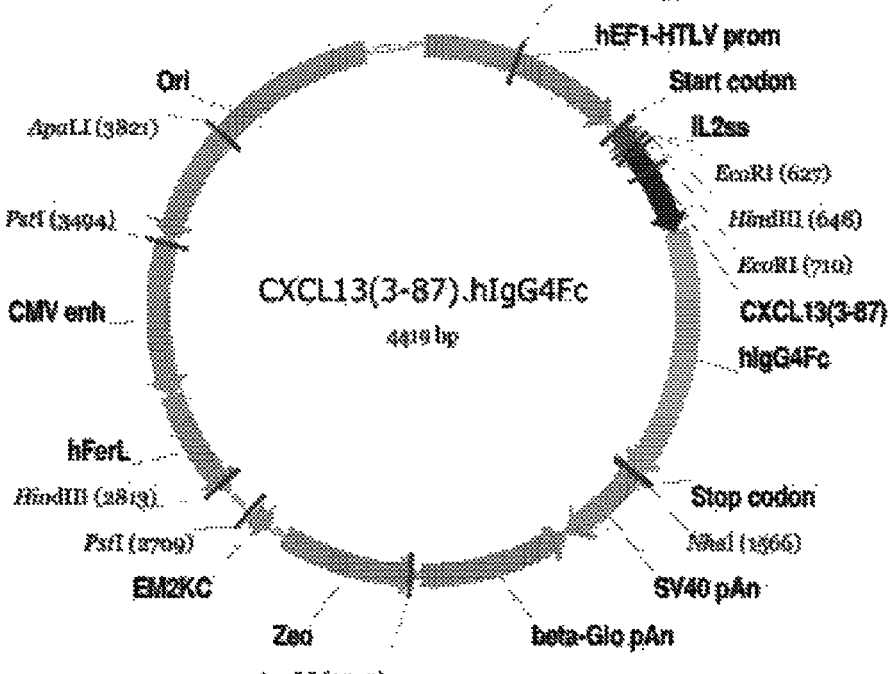

FIG. 9B depicts the expression vector pCXCL13(3-87).hIgG4Fc.

Figure 9C:
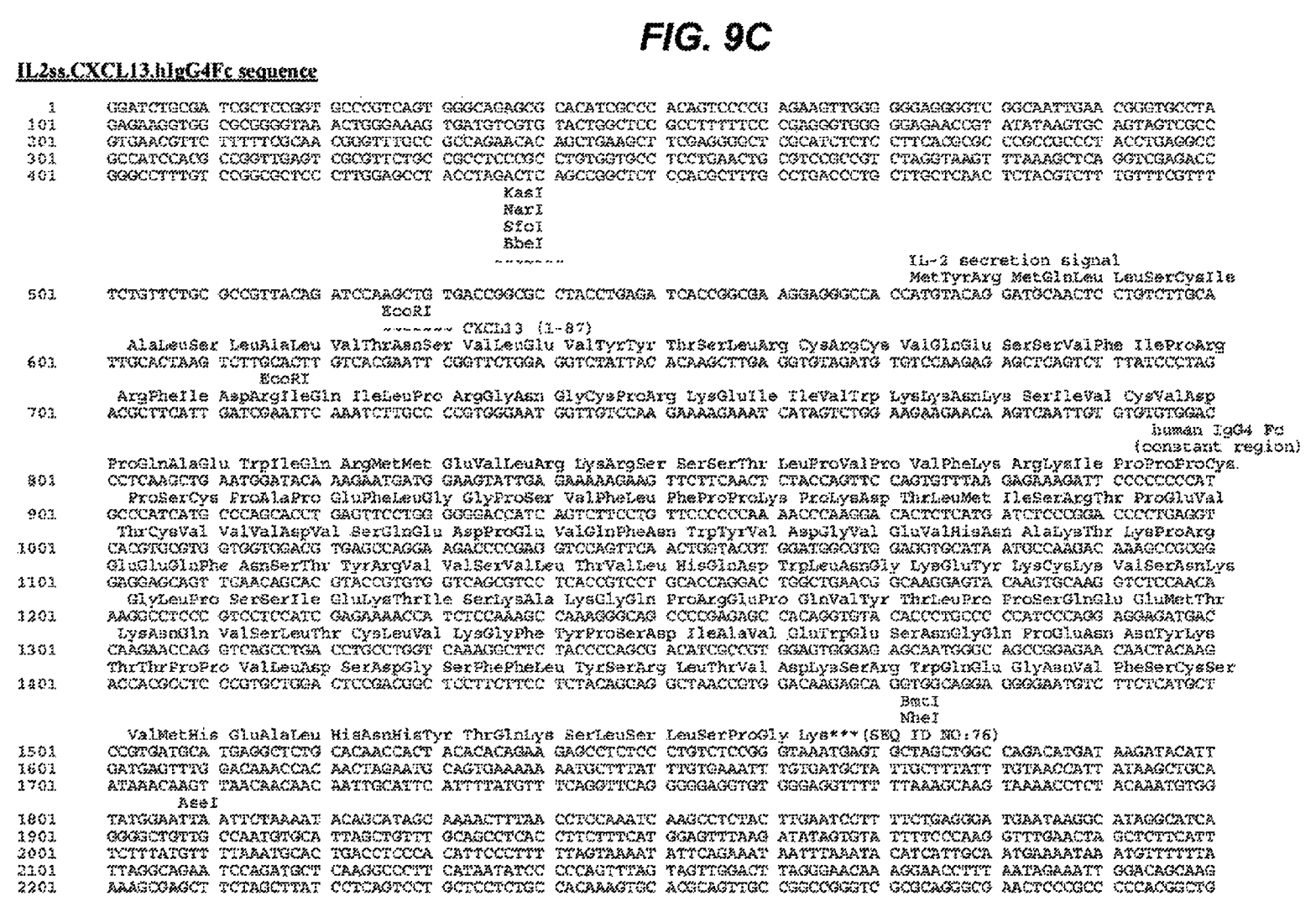
Figure 9C:
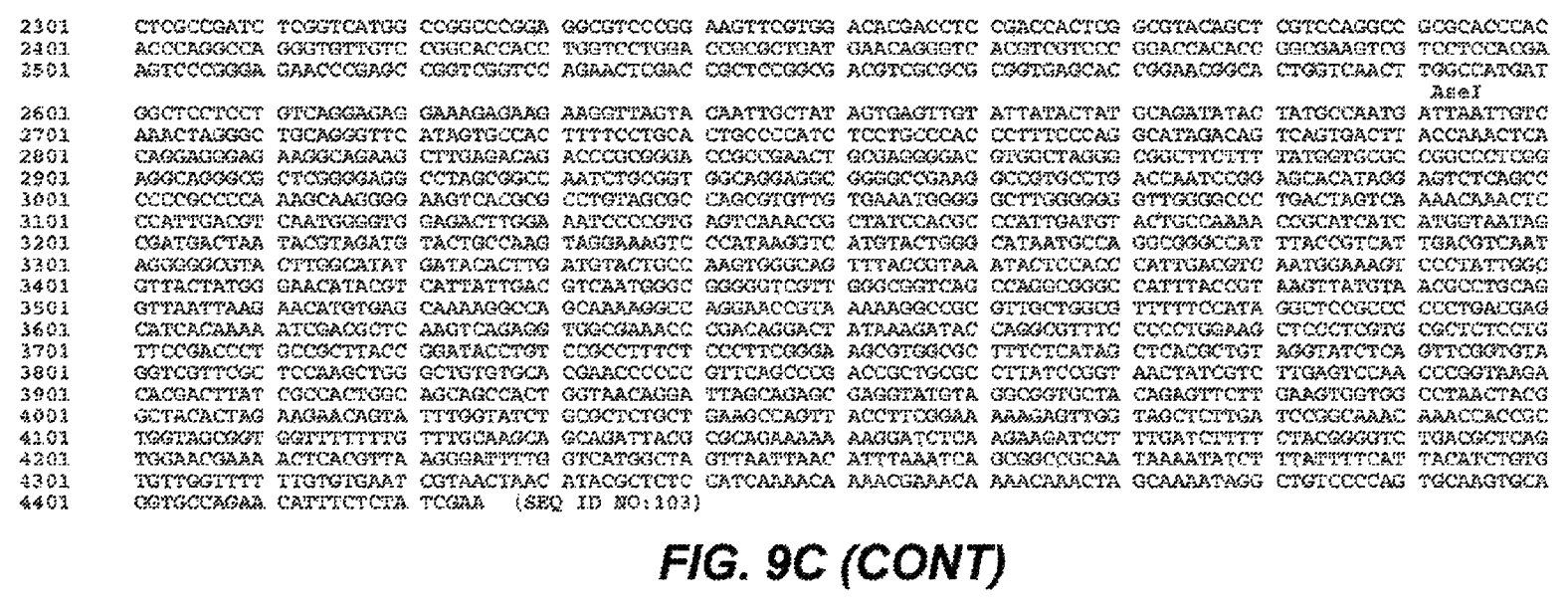

FIG. 9C shows the nuceotide sequence of the expression vector pCXCL13.hIgG4Fc.

Figure 9D:
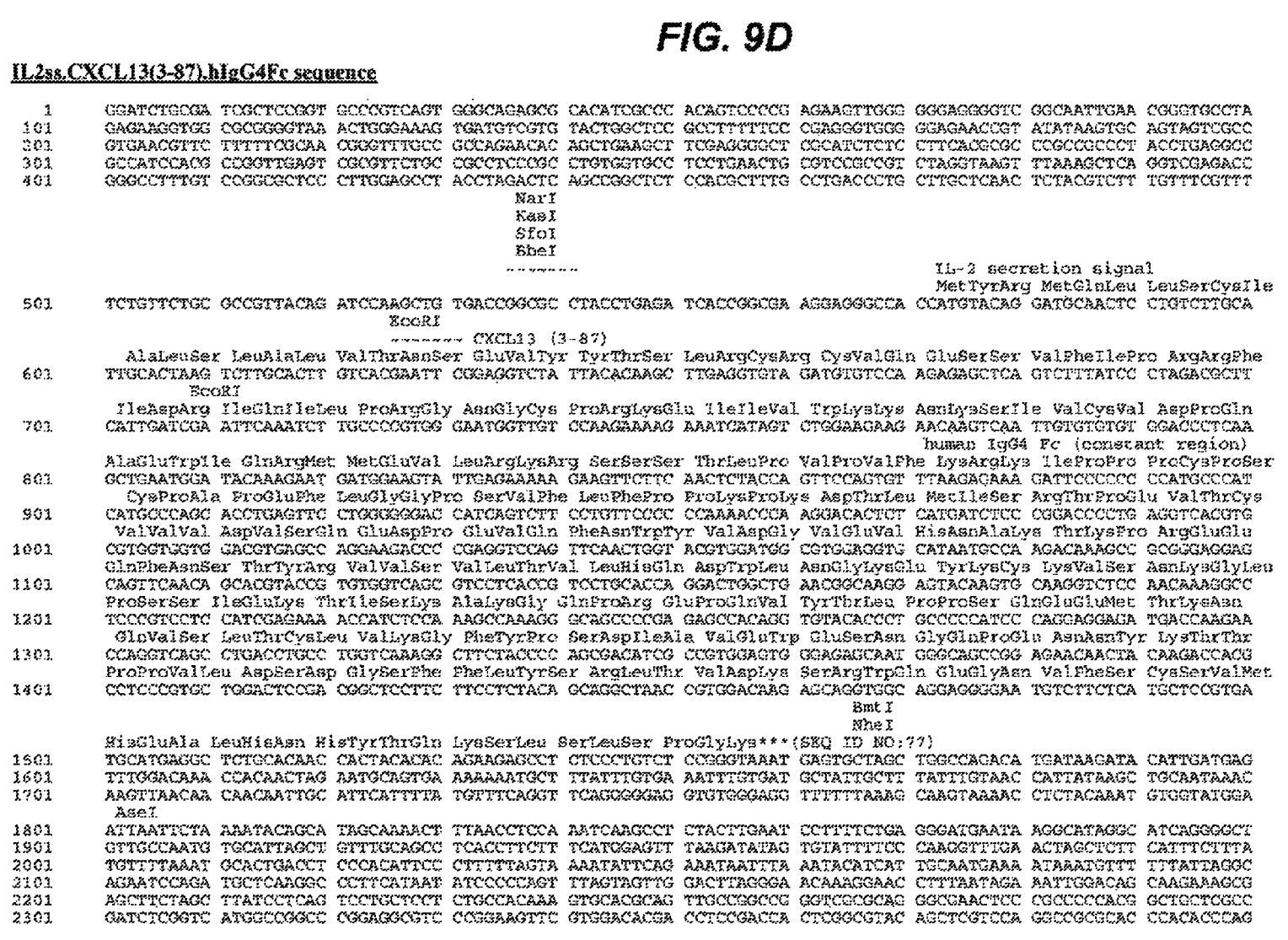
Figure 9D:
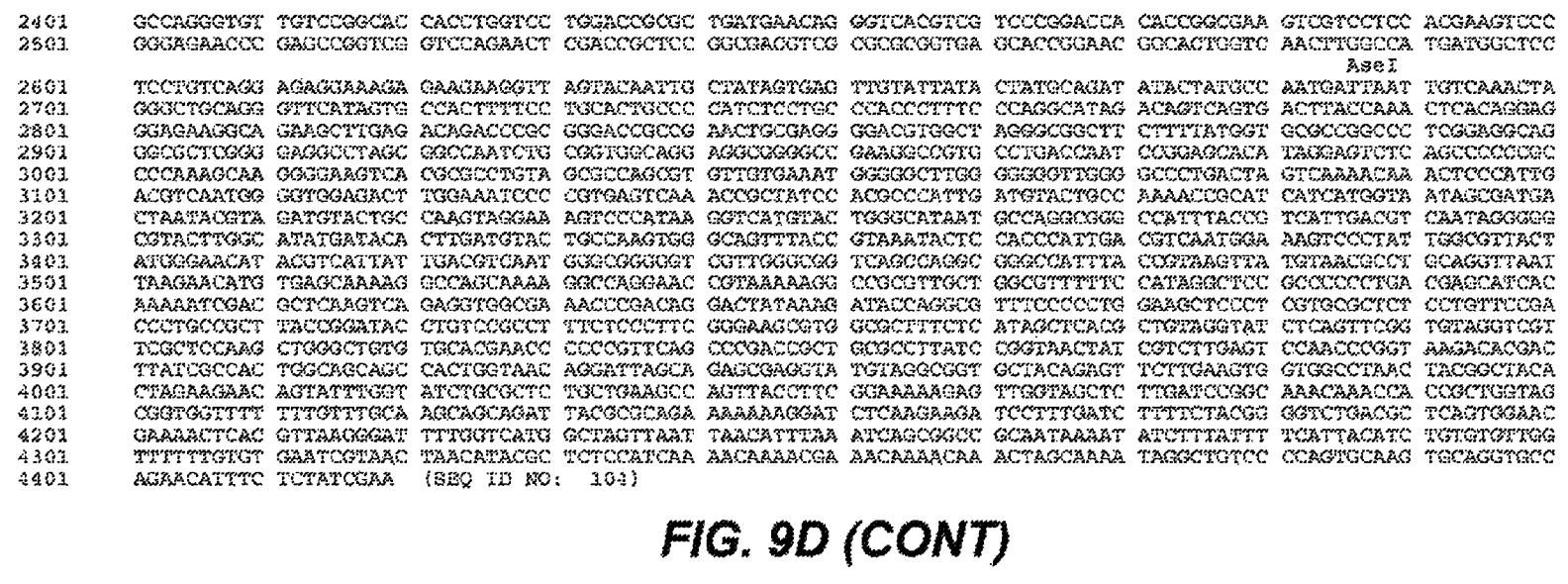

FIG. 9D shows the nuceotide sequence of the expression vector pCXCL13(3-87).hIgG4Fc.

FIG. 9E shows the nuceotide sequence of the expression vector pCXCL11(4-127).hIgG4Fc with alanine substitutions for removal of GAG binding sites—lys and his.

Figure 10A:
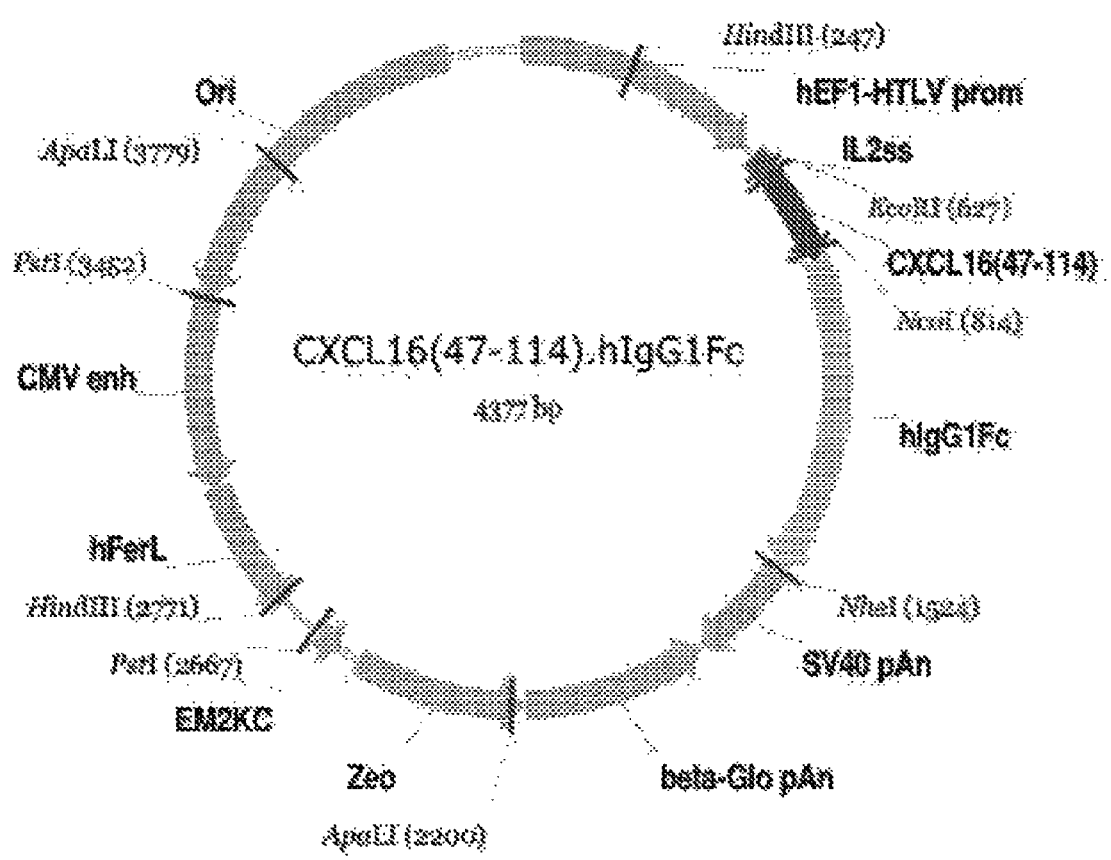

FIG. 10A depicts the expression vector pCXCL16(47-114).hIgG1Fc.

Figure 11:
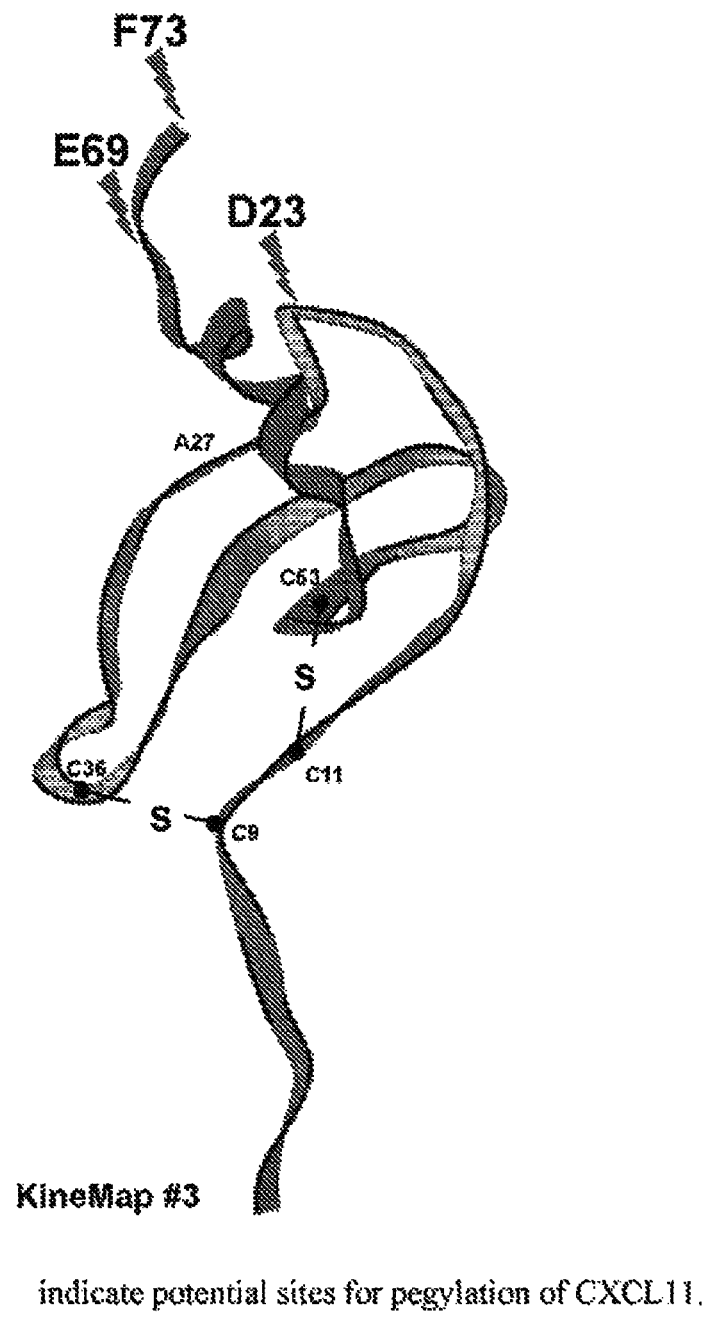

FIG. 11 depicts a cartoon of the structure of CXCL11 indication potential pegylation sites.

FIG. 12 shows the amino acid sequences of the chemokines and human IgG Fc fragments listed in Table 1.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless otherwise defined, scientific and technical terms used in connection with the present invention shall have the meanings that are commonly understood by those of ordinary skill in the art. Although any methods, devices, and materials similar or equivalent to those described herein can be used in the practice or testing of the presently disclosed subject matter, representative methods, devices, and materials are now described. Further, unless otherwise required by context, singular terms shall include pluralities and plural terms shall include the singular.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

The present application generally relates to compositions and methods for treating chemokine receptor-mediated disorders and modulating inflammation. Particularly, the present application relates to chemokine-immunoglobulin fusion polypeptides, chemokine-polymer conjugates, and uses thereof to modulate immunity, cancer progression, and inflammation as well as treat chemokine receptor-mediated disorders, including tissue regeneration, wound repair, stem cell homeostasis, cell proliferative disorders, and inflammatory.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "treat," "treating" or "treatment" as used herein, refers to a method of alleviating or abrogating a disorder and/or its attendant symptoms. The terms "prevent", "preventing" or "prevention," as used herein, refer to a method of barring a subject from acquiring a disorder and/or its attendant symptoms. In certain embodiments, the terms "prevent," "preventing" or "prevention" refer to a method of reducing the risk of acquiring a disorder and/or its attendant symptoms.

In a pharmacological sense, in the context of the present invention, an "effective amount" of a composition refers to an amount effective in the prevention or treatment of a disorder for the treatment of which the composition is effective. A "disorder" is any condition that would benefit from treatment with the composition.

"Mammal" for purposes of treatment refers to any animal classified as a mammal, including humans, non-human primates, domestic and farm animals, and zoo, sports, or pet animals, such as dogs, horses, cats, cows, etc. Preferably, the mammal is human.

The term "inhibits" is a relative term, an agent inhibits a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, a composition that reduces or prevents an infection or a response, such as a pathological response, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

Chemokine-Immunoglobulin Fusion Polypeptides

Chemokines have been demonstrated to mediate a number of cellular functions involving motility, invasion, adherence, proliferation, and survival. At the appropriate levels and expression, these chemotactic cytokines promote proper wound healing, neovascularization or immunity. If inappropriately expressed, these factors can dictate chronic diseases like keloid formation, angiogenesis, metastasis/drug resistance of cancer cells, autoimmunity, graft rejection, inflammation (e.g., arthritis, ulcerative colitis, Crohn's disease, multiple sclerosis, COPD, etc.), diabetes. Both beneficial and deleterious functions are mediated by binding and activation of chemokine receptors, which are class A, G protein coupled receptors.

A number of small molecule antagonists have been constructed to block the action of these receptors. Remarkably, many of these compounds have high affinities (5-50 nM) and specificities for their target. However, these inhibitors have two major limitations: (i) hydrophobicity and possible liver retention/toxicity and (ii) relative short serum-half life or bioavailability (<6 hours).

The present application provides isolated chemokine-immunoglobulin fusion polypeptides for clinical use. The fusion polypeptides comprise a wild-type human chemokine or a variant thereof fused to the constant region (i.e., CH2 and CH3) of a human immunoglobulin (Ig) G or a variant thereof. The chemokine-immunoglobulin fusion polypeptide can bind with specificity to one or more particular chemokine receptors and thereby modulate one or more biological activities (e.g., receptor activation) of the receptor(s).

One aspect of the present invention relates to an isolated chemokine-immunoglobulin fusion polypeptide having a chemokine moiety and an immunoglobulin moiety. In some embodiments, the chemokine moiety comprises a chemokine selected from the group consisting of human CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof. In some embodiments, the chemokine moiety comprises CCL2 and functional variants thereof. In other embodiments, the chemokine moiety comprises CCL25 and functional variants thereof. In other embodiments, the chemokine moiety comprises CXCL12 and functional variants thereof. In other embodiments, the chemokine moiety comprises CXCL13 and functional variants thereof. In other embodiments, the chemokine moiety comprises CXCL16 and functional variants thereof. As used herein, each chemokine noted above refers to all isoforms of the chemokine. The immunoglobulin moiety comprises a human immunoglobulin fragment, such as a constant region of a human immunoglobulin, a Fc fragment of a human immunoglobulin, or a functional variant thereof. In certain embodiments, human immunoglobulin fragment is selected from the group consisting of the constant region (Fc) of human IgG1 (IgG1Fc), the constant region of human IgG2 (IgG2Fc), the constant region of human IgG3 (IgG3Fc), the constant region of human IgG4 (IgG4Fc), and functional variants thereof. The complete amino acid sequences of the above-described chemokines and the Fc regions of human IgG1, IgG2, IgG3 and IgG4 are listed in Table 1 below and shown in FIG. 12.

TABLE 1

| Chemokine/Receptor | Protein Accession No. | SEQ ID NO: |
|---|---|---|
| CCL1 | NP_002972 | 1 |
| CCL2 | NP_002973 | 2 |
| CCL3 | NP_002974 | 3 |
| CCL4 | NP_002975 | 4 |
| CCL4L1 | NP_001001435 | 5 |
| CCL5 | NP_002976 | 6 |
| CCL7 | NP_006264 | 7 |
| CCL8 | NP_005614 | 8 |
| CCL11 | CAG33702 | 9 |
| CCL13 | NP_005399 | 10 |
| CCL14-1 | NP_116739 | 11 |
| CCL14-2 | NP_116738 | 12 |
| CCL15 | NP_116741 | 13 |
| CCL16 | NP_004581 | 14 |
| CCL17 | NP_002978 | 15 |
| CCL18 | NP_002979 | 16 |
| CCL19 | NP_006265 | 17 |
| CCL20-1 | NP_004582 | 18 |
| CCL20-2 | NP_001123518 | 19 |
| CCL21 | NP_002980 | 20 |
| CCL22 | NP_002981 | 21 |
| CCL23-1 | NP_665905 | 22 |
| CCL23-2 | NP_005055 | 23 |
| CCL24 | NP_002982 | 24 |
| CCL25-1 | NP_005615 | 25 |
| CCL25-2 | NP_683686 | 26 |
| CCL25-3 | EAW68951 | 27 |
| CCL26 | NP_006063 | 28 |
| CCL27 | NP_006655 | 29 |
| CCL28 | NP_683513 | 30 |
| CXCL1 | NP_001502 | 31 |
| CXCL2 | NP_002080 | 32 |
| CXCL3 | NP_002081 | 33 |
| CXCL4 | NP_002610 | 34 |
| CXCL5 | NP_002985 | 35 |
| CXCL6 | NP_002984 | 36 |
| CXCL7 | NP_002695 | 37 |
| CXCL8 | NP_000575 | 38 |
| CXCL9 | NP_002407 | 39 |
| CXCL10 | NP_001556 | 40 |
| CXCL11 | NP_005400 | 41 |
| CXCL12 | NP_000600 | 42 |
| CXCL13 | NP_006410 | 43 |
| CXCL16 | NP_071342 | 44 |
| XCL1 | AAH69817 | 45 |
| XCL2 | NP_003166 | 46 |
| CX3CL1 | NP_002987 | 47 |
| IgG1Fc | CBX54381.1 | 48 |
| IgG2Fc | CBX54382.1 | 49 |
| IgG3Fc | CBX54383.1 | 50 |
| IgG4Fc | CBX54384.1 | 51 |

Without wishing to be bound by any particular theory of operation, the immunoglobulin region can increase serum-half life or bioavailability of the fusion polypeptide and the precise polypeptide sequences of the Fc portion can be selected to maximize serum-half life and/or bioavailability. In addition, Fc regions from different IgG subclasses (e.g., IgG1, IgG2, IgG3, and IgG4) exhibit different immunological activities, and therefore the IgG Fc region can be selected based on a desired immunological activity. For example, the Fc region of IgG1 can activate complement, while the Fc region of IgG4 has reduced complement activity.

Thus, a particular Fc region can be selected for a particular application based on the desired immunological activities manifested by each region. In some particular embodiments, the Fc region can be the Fc region of human IgG1, IgG2, IgG3 or IgG4. As such, the chemokine-immunoglobulin fusion polypeptide find utility in enhancing immunity, suppressing autoimmunity, suppressing inflammation, and/or inhibiting growth/metastasis of proliferative disorder cells.

The present application further provides isolated polynucleotide which encode the chemokine-immunoglobulin fusion polypeptide disclosed herein and expression vectors capable of expressing the chemokine-immunoglobulin fusion polypeptide in vivo.

The term "isolated", when applied to a protein or polynucleotide, denotes that the protein or polynucleotide is essentially free of other cellular components with which it is associated in the natural state. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A protein that is the predominant species present in a preparation is substantially isolated. The term "isolated" denotes that a protein or polynucleotide gives rise to essentially one band in an electrophoretic gel. Particularly, it means that the protein or polynucleotide is in some embodiments at least about 50% pure, in some embodiments at least about 85% pure, and in some embodiments at least about 99% pure.

The term "polynucleotide" refers to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues. The term "polynucleotide" or "polynucleotide sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The chemokine portion of the chemokine-immunoglobulin fusion polypeptide can be selected based on the chemokine receptor or receptors to which it exhibits binding specificity. This provides for the selective targeting of the chemokine-immunoglobulin fusion polypeptide to one or more specific chemokine receptors to thereby modulate activation and subsequent biological activities of the receptor(s). Table 1 (adapted from Allen et al. (2007) Annu. Rev. Immunol. 25:787-820) provides an exemplary list of receptors that can be targeted by one or more chemokines, which can be incorporated into the chemokine-immunoglobulin fusion polypeptide of the presently-disclosed subject matter.

As disclosed in Table 2, certain chemokines can specifically bind more than one chemokine receptor. For example, CXCL11 can bind with specificity to chemokine receptors CXCR3-A, CXCR3-B, CXCR7, and DARC/Duffy. As such, if it is desirable to target more than one chemokine receptor, a particular chemokine, such as CXC11, can be selected for incorporation into the chemokine-immunoglobulin fusion polypeptide of the presently-disclosed subject matter. In some embodiments of the presently disclosed subject matter, the chemokine-immunoglobulin fusion polypeptide can comprise of a chemokine portion selected from the group consisting of CCL2, CCL7, CCL8, CCL13, CCL25, CXCL11, CXCL13, and mutations thereof. "Mutations" of the polypeptides include variants and fragments of the reference polypeptides.

TABLE 2

Chemokine receptors and their ligands

| Receptor | Ligands |
| --- | --- |
| CCR1 | CCL3, CCL5, CCL7, CCL13, CCL14, CCL15, CCL16, CCL23 |
| CCR2 | CCL2, CCL7, CCL8, CCL13, CCL16 |
| CCR3 | CCL5, CCL7, CCL8, CCL11, CCL13, CCL15, CCL16, CCL24, CCL26, CCL28 |
| CCR4 | CCL17, CCL22 |
| CCR5 | CCL3, CCL4, CCL5, CCL8, CCL11, CCL14, CCL16 |
| CCR6 | CCL20 |
| CCR7 | CCL19, CCL21 |
| CCR8 | CCL1 |
| CCR9 | CCL25 |
| CCR10 | CCL27, CCL28 |
| CXCR1 | CXCL6, CXCL7, CXCL8 |
| CXCR2 | CXCL1, CXCL2, CXCL3, CXCL5, CXCL6, CXCL7, CXCL8 |
| CXCR3-A | CXCL9, CXCL10, CXCL11, CCL11 |
| CXCR3-B | CXCL4, CXCL9, CXCL10, CXCL11, CCL11 |
| CXCR4 | CXCL12 |
| CXCR5 | CXCL13 |
| CXCR6 | CXCL16 |
| CXCR7 | CXCL12, CXCL11 |
| XCR1 | XCL1, XCL2 |
| CX$_3$CR1 | CX$_3$CL1 |
| CCX-CKR | CCL19, CCL21, CCL25 |
| D6 | CCL2, CCL3L1, CCL4, CCL5, CCL7, CCL8, CCL11, CCL13, CCL14, CCL17, CCL22 |
| DARC/Duffy | CCL2, CCL7, CCL8, CCL11, CCL13, CCL14, CCL16, CCL17, CXCL1, CXCL5, CXCL6, CXCL7, CXCL8, CXCL9, CXCL11, CXCL13 |

The term "functional variant" refers to protein or polypeptide that is different from the reference protein or polypeptide by one or more amino acids, e.g., one or more amino acid substitutions, but substantially maintains the biological function of the reference protein or polypeptide. As used herein, a functional variant of a chemokine is a variant that maintains the receptor binding function of the original chemokine and a functional variant of the Fc region of IgG is a variant that maintains the immunoglivla activities of the original Fc region.

A functional variant of a polypeptide may be a fragment of the original polypeptide. The term "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 3, 5, 6, 8 or 10 amino acids long, at least 14 amino acids long, at least 20, 30, 40 or 50 amino acids long, at least 75 amino acids long, or at least 100, 150, 200, or more amino acids long.

The term "functional variant" further includes conservatively substituted variants. The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another, such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein. In some embodiments, the functional variant of a peptide shares a sequence identity of 70%, 75%, 80%, 85%, 90%, 91%, 92%, 93%, 94%, 95%, 96%, 97%, 98% or 99% with the reference peptide. For example, a functional variant of a chemokine may shares a sequence identity of 70%, 75%, 80%, 85%, 90%, 91%, 92%, 93%, 94%, 95%, 96%, 97%, 98% and 99% with the reference chemokine; a functional variant of an immunoglobin Fc fragment may shares a sequence identity of 70%, 75%, 80%, 85%, 90%, 91%, 92%, 93%, 94%, 95%, 96%, 97%, 98% and 99% with the reference immunoglobin Fc fragment; and a functional variant of a chemokine-immunoglobin fusion protein may shares a sequence identity of 70%, 75%, 80%, 85%, 90%, 91%, 92%, 93%, 94%, 95%, 96%, 97%, 98% and 99% with the reference chemokine-immunoglobin fusion protein.

The term "sequence identity," as used herein, means that two peptide sequences are identical (i.e., on an amino acid-by-amino acid basis) over the window of comparison. The term "percentage of sequence identity" is calculated by comparing two optimally aligned sequences over the window of comparison, determining the number of positions at which the identical amino acid residue occurs in both sequences to yield the number of matched positions, dividing the number of matched positions by the total number of positions in the window of comparison (i.e., the window size), and multiplying the result by 100 to yield the percentage of sequence identity. The reference sequence may be a subset of a larger sequence, for example, as a segment of the full-length sequences of the compositions claimed in the present invention.

In some particular embodiments, the chemokine-immunoglobulin fusion polypeptides disclosed herein include functional variants to the chemokine portion that introduce amino acid substitutions to eliminate glycosaminoglycan (e.g., heparin, laminin, GAG)-binding, which can thereby increase the serum half-life of the polypeptide. For example, in some embodiments one or more alanines can be substituted for lysines, arginines and/or histidines within GAG binding sites of the chemokine portions.

Specific chemokine-immunoglobulin fusion polypeptides disclosed herein that include a chemokine variant having one or more mutations in the chemokine sequence are named accordingly to indicate the particular mutation. For example "var-" before the chemokine name (e.g., var-CCL2) is indicative of a functional variant having an engineered mutation to the chemokine portion that results in a polypeptide sequence that differs from the reference chemokine sequence (e.g., CCL2). A fragment mutation resulting from a truncation is notated be the sequence remaining after truncation. For example, a truncation of the N-terminal 4 amino acids of the 76 amino acid CCL2 chemokine would be notated as "var-CCL2" or "CCL2(5-76)". A variant mutation resulting from one or more amino acid substitutions would be notated as a parenthetical after the chemokine name in the form "X#Y" or "X→Y", wherein the amino acid X (in standard one letter amino acid code, as is known in the art) in the reference polypeptide is substituted with the amino acid Y either at a particular residue (#) or throughout the polypeptide, or a particular region of the polypeptide (X→Y), such as for example a GAG-binding region of the chemokine polypeptide. In some embodiments, a mutation can include both a variant and a fragment of the reference chemokine polypeptide. These mutants are indicated in the named polypeptide in succession in a parenthetical following the chemokine name. For example, "CCL2(5-76K/H→A)" indicates a chemokine-immunoglobulin fusion polypeptide including in the chemokine portion a mutant CCL2 polypeptide that has been truncated at the N-terminus to remove residues 1-4 and also mutated to substitute alanines (A) for lysines (K) and histidines (H) within the sequence. In some embodiments, a chemokine variant (e.g., var-CXCL13) shares a sequence identity of 70%, 75%, 80%, 85%, 90%, 91%, 92%, 93%, 94%, 95%, 96%, 97%, 98% and 99% with the reference chemokine (i.e., CXCL13). Finally, in reference to nomenclature, the chemokine-immunoglobulin fusion polypeptides disclosed herein are named according to the chemokine portion (A) and the immunoglobulin portion (B) fused together (i.e. A-B). Thus, for example, CCL2-IgG1Fc refers to a chemokine-immunoglobulin fusion polypeptide comprising a wild-type CCL2 chemokine portion fused with an Fc constant region of an IgG class 1 immunoglobulin.

In some embodiments, the present application provides a human chemokine polypeptide fused to a human immunoglobulin polypeptide. In some embodiments, the present application provides the following novel isolated chemokine-immunoglobulin fusion polypeptides: CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fc.

In particular embodiments, the present application provides the following novel isolated chemokine-immunoglobulin fusion polypeptides: CCL2-IgG1Fc (SEQ ID NO:52), CCL2(5-76)-IgG1Fc (SEQ ID NO:53), CCL2(5-76K/H→A)-IgG1Fc (SEQ ID NO:54), CCL7-IgG1Fc (SEQ ID NO:55), CCL7(5-76)-IgG1Fc (SEQ ID NO:56), CCL7(5-76K/H→A)-IgG1Fc (SEQ ID NO:57), CCL8-IgG1Fc (SEQ ID NO:58), CCL8(5-76)-IgG1Fc (SEQ ID NO:59), CCL8(5-76K/H→A)-IgG1Fc (SEQ ID NO:60), CCL13-IgG1Fc (SEQ ID NO:61), CCL13(5-75)-IgG1Fc (SEQ ID NO:62), CCL13(5-75K/H→A)-IgG1Fc (SEQ ID NO:63), CCL25-IgG1Fc (SEQ ID NO:64), CCL25(4-127)-IgG1Fc (SEQ ID NO:65), CCL25(4-127K/H→A)-IgG1Fc (SEQ ID NO:66), CXCL11-IgG1Fc (SEQ ID NO:67), CXCL11(4-73)-IgG1Fc (SEQ ID NO:68), CXCL11(4-73K/H→A)-IgG1Fc (SEQ ID NO:69), CXCL11-IgG4Fc (SEQ ID NO:70), CXCL11(4-73)-IgG4Fc (SEQ ID NO:71), CXCL11(4-73K/H→A)-IgG4Fc (SEQ ID NO:72), CXCL13-IgG1Fc (SEQ ID NO:73), CXCL13(3-87)-IgG1Fc (SEQ ID NO:74), CXCL13(3-87K/H→A)-IgG1Fc (SEQ ID NO:75), CXCL13-IgG4Fc (SEQ ID NO:76), CXCL13(3-87)-IgG4Fc (SEQ ID NO:77), and CXCL13(3-87K/H→A)-IgG4Fc (SEQ ID NO:78).

The novel chemokine-immunoglobulin fusion polypeptides disclosed herein can be produced using any of a variety of peptide production techniques generally known in the art. For example, recombinant genetic techniques can be utilized to produce the fusion polypeptides disclosed herein. As such, in some embodiments, an isolated nucleic acid molecule which encodes a chemokine-immunoglobulin fusion polypeptide selected from the group consisting of CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fc is provided.

In particular embodiments, the isolated nucleic acid molecule encodes a chemokine-immunoglobulin fusion polypeptide selected from the group consisting of CCL2-IgG1Fc, CCL2(5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H→A)-IgG1Fc, CCL8-IgG2Fc, CCL8(5-76)-IgG2Fc, CCL8(5-76K/H→A)-IgG2Fc, CCL8-IgG3Fc, CCL8(5-76)-IgG3Fc, CCL8(5-76K/H→A)-IgG3Fc, CCL8-IgG4Fc, CCL8(5-76)-IgG4Fc, CCL8(5-76K/H→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/

H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H→A)-IgG1Fc, CCL25-IgG2Fc, CCL25(4-127)-IgG2Fc, CCL25(4-127K/H→A)-IgG2Fc, CCL25-IgG3Fc, CCL25(4-127)-IgG3Fc, CCL25 (4-127K/H→A)-IgG3Fc, CCL25-IgG4Fc, CCL25(4-127)-IgG4Fc, CCL25(4-127K/H→A)-IgG4Fc, CXCL11-IgG1Fc, CXCL11(4-73)-IgG1Fc, CXCL11(4-73K/H→A)-IgG1Fc, CXCL11-IgG2Fc, CXCL11(4-73)-IgG2Fc, CXCL11(4-73K/H→A)-IgG2Fc, CXCL11-IgG3Fc, CXCL11(4-73)-IgG3Fc, CXCL11(4-73K/H→A)-IgG3Fc, CXCL11-IgG4Fc, CXCL11(4-73)-IgG4Fc, CXCL11(4-73K/H→A)-IgG4Fc, CXCL13-IgG1Fc, CXCL13(3-87)-IgG1Fc, CXCL13(3-87K/H→A)-IgG1Fc, CXCL13-IgG2Fc, CXCL13(3-87)-IgG2Fc, CXCL13(3-87K/H→A)-IgG2Fc, CXCL13-IgG3Fc, CXCL13(3-87)-IgG3Fc, CXCL13(3-87K/H→A)-IgG3Fc, CXCL13-IgG4Fc, CXCL13(3-87)-IgG4Fc, and CXCL13(3-87K/H→A)-IgG4Fc. Recombinant cloning techniques may also be used to construct the heterologous gene sequences that encode for the fusion polypeptide gene product, as is known in the art.

Expression Vectors

Recombinant expression vectors comprising nucleic acid molecules which encode the polypeptides disclosed herein are also provided. Particularly useful vectors are contemplated to be those vectors in which the coding portion of the DNA segment is positioned under the control of a promoter. The promoter may be in the form of the promoter which is naturally associated with the chemokine or immunoglobulin gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a chemokine or immunoglobulin gene in its natural environment. Such promoters may include promoters isolated from plant, insect, bacterial, viral, eukaryotic, fish, avian or mammalian cells. Naturally, it will be important to employ a promoter that effectively directs the expression of the DNA segment in the cell type chosen for expression. The use of promoter and cell type combinations for protein expression is generally known to those of skill in the art of molecular biology. The promoters employed may be constitutive, or inducible, and can be used under the appropriate conditions to direct high level expression of the introduced DNA segment, such as is advantageous in the large-scale production of recombinant proteins or peptides.

Expression vectors generally contain sequences for transcriptional termination, and may additionally contain one or more elements positively affecting mRNA stability. An expression vector may further include an internal ribosome entry site (IRES) between adjacent protein coding regions to facilitate expression two or more proteins from a common mRNA in an infected or transfected cell. Additionally, the expression vectors may further include nucleic acid sequence encoding a marker product. This marker product may be used to determine if the gene has been delivered to the cell and is being expressed. Preferred marker genes are the E. coli lacZ gene, which encodes β-galactosidase, and green fluorescent protein (GFP).

In some embodiments, the expression vectors of the present application are plasmid expression vectors that are capable of expressing the chemokine-immunoglobulin fusion polypeptides of the present application in an in vitro setting. The expressed fusion polypeptide is then isolated and purified using methods well known to a person skilled in the art.

In other embodiments, the expression vectors of the present application are plasmid expression vectors that are capable of expressing the chemokine-immunoglobulin fusion polypeptides of the present application in an in vivo setting. These expression vectors may be introduced into a subject using delivery systems such as liposomes, including cationic liposomes (e.g., DOTMA, DOPE, DC-cholesterol) and anionic liposomes, microcapsules, nanoparticles and electroporation. In some embodiments, the expression vectors are targeted to a particular cell type via antibodies, receptors, or receptor ligands. Vehicles such as "stealth" and other antibody conjugated liposomes (including lipid mediated drug targeting to cells of interest), receptor mediated targeting of DNA through cell specific ligands or viral vectors targeting e.g., lymphoid, epithelial or endothelial cells. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor level regulation. Many receptors follow more than one intracellular pathway, depending on the cell type, receptor concentration, type of ligand, ligand valency, and ligand concentration.

In yet other embodiments, the expression vectors of the present application are virus-based expression vectors that are capable of expressing the chemokine-immunoglobulin fusion polypeptides of the present application in an in vivo setting. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses, and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers, and can be delivered in aerosol formulation, and can transfect non-dividing cells. Poxviral vectors are large and have several sites for inserting genes, they are thermostable and can be stored at room temperature. Viral delivery systems typically utilize viral vectors having one or more genes removed and with and an exogenous gene and/or gene/promotor cassette being inserted into the viral genome in place of the removed viral DNA. The necessary functions of the removed gene(s) may be supplied by cell lines which have been engineered to express the gene products of the early genes in trans.

In other embodiments, the expression vectors are phage DNA, yeast plasmids or baculovirus.

Exemplary expression vector constructs comprising polynucleotides which encode chemokine-immunoglobulin fusion polypeptides disclosed herein are shown in FIGS. 1-10. These expression vectors include pCCL2-IgG1Fc (SEQ ID NO:79), pCCL2(5-76)-IgG1Fc (SEQ ID NO:80), pCCL2(5-76K/H→A)-IgG1Fc (SEQ ID NO:81), pCCL7-IgG1Fc (SEQ ID NO:82), pCCL7(5-76)-IgG1Fc (SEQ ID NO:83), pCCL7(5-76K/H→A)-IgG1Fc (SEQ ID NO:84), pCCL8-IgG1Fc (SEQ ID NO:85), pCCL8(5-76)-IgG1Fc (SEQ ID NO:86), pCCL8(5-76K/H→A)-IgG1Fc (SEQ ID NO:87), pCCL13-IgG1Fc (SEQ ID NO:88), pCCL13(5-75)-IgG1Fc (SEQ ID NO:89), pCCL13(5-75K/H→A)-IgG1Fc (SEQ ID NO:90), pCCL25-IgG1Fc (SEQ ID NO:91), pCCL25(4-127)-IgG1Fc (SEQ ID NO:92), pCCL25(4-127K/H→A)-IgG1Fc (SEQ ID NO:93), pCXCL11-IgG1Fc (SEQ ID NO:94), pCXCL11(4-73)-IgG1Fc (SEQ ID NO:95), pCXCL11(4-73K/H→A)-IgG1Fc (SEQ ID NO:96), pCXCL11-IgG4Fc (SEQ ID NO:97), pCXCL11(4-73)-IgG4Fc (SEQ ID NO:98), pCXCL11(4-73K/H→A)-IgG4Fc (SEQ ID NO:99), pCXCL13-IgG1Fc (SEQ ID NO:100), pCXCL13(3-87)-IgG1Fc (SEQ ID NO:101), pCXCL13(3-87K/H→A)-IgG1Fc (SEQ ID NO:102), pCXCL13-IgG4Fc (SEQ ID NO:103), pCXCL13(3-87)-IgG4Fc (SEQ ID NO:104), and CXCL13(3-87K/H→A)-IgG4Fc (SEQ ID NO:105). It is understood that additional combinations of vectors and genes than those specifically disclosed above are contemplated by the presently-disclosed subject matter, as would be understood by one of ordinary skill in the art.

Protein Conjugates

In some embodiments, the chemokine-immunoglobulin fusion polypeptides of the present application, as well as certain chemokines and variants thereof, are conjugated to a non-protein polymer to form protein-polymer conjugates. Unless specifically indicated to the contrary, the term "non-protein polymer" is defined as a molecule formed by covalent linkage of two or more monomers, wherein none of the monomers is contained in the group consisting of alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), and tyrosine (Tyr) residues. Serum soluble non-protein polymers, such as polyethylene glycol, and tissue or fat soluble polymers, such as polycaprolactone, can be used for delivery, release, and/or retention of polypeptides. In some embodiments, the protein-polymer conjugate is a pegylated chemokine-immunoglobulin fusion polypeptide, chemokine or a variant thereof.

In one aspect, the present application encompass a conjugate having any molar ratio of polymer to chemokine or fragment thereof that endows the conjugate with an apparent size in the desired range as taught herein. The apparent size of the conjugate will depend in part upon the size and shape of the polymer used, the size and shape of the chemokine or fragment thereof used, the number of polymer molecules attached to the chemokine or fragment thereof, and the location of such attachment site(s) on the chemokine or fragment thereof. These parameters can easily be identified and maximized to obtain the conjugate with the desired apparent size for any type of chemokine or fragment thereof, polymer and linkage system.

In some embodiments, the protein-polymer conjugate of the present application has an effective size of at least about 500,000 D, or at least about 800,000 D, or at least about 900,000 D, or at least about 1,000,000 D, or at least about 1,200,000 D, or at least about 1,400,000 D, or at least about 1,500,000 D, or at least about 1,800,000 D, or at least about 2,000,000 D, or at least about 2,500,000 D. In one embodiment, the polymer is PEG.

In other embodiments, the protein-polymer conjugate of the present application has an effective size of at or about 500,000 D to at or about 10,000,000 D, or an effective size of at or about 500,000 D to at or about 8,000,000 D, or an effective size of at or about 500,000 D to at or about 5,000,000 D, or an effective size of at or about 500,000 D to at or about 4,000,000 D, or an effective size of at or about 500,000 D to at or about 3,000,000 D, or an effective size of at or about 500,000 D to at or about 2,500,000 D, or an effective size of at or about 500,000 D to at or about 2,000,000 D, or an effective size of at or about 500,000 D to at or about 1,800,000 D, or an effective size of at or about 500,000 D to at or about 1,600,000 D, or an effective size of at or about 500,000 D to at or about 1,500,000 D, or an effective size of at or about 500,000 D to at or about 1,000,000 D. In one embodiment, the polymer is PEG.

In a further embodiment, the protein-polymer conjugate has an effective size that is at least about 8 fold greater, or at least about 10 fold greater, or at least about 12 fold greater, or at least about 15 fold greater, or at least about 18 fold greater, or at least about 20 fold greater, or at least about 25 fold greater, or at least about 28 fold greater, or at least about 30 fold greater, or at least about 40 fold greater, than the effective size of the unconjugated chemokine-immunoglobulin fusion polypeptide, chemokine or variant thereof. In one embodiment, the polymer is PEG.

In another embodiment, the protein-polymer conjugate has an effective size that is about 8 fold to about 100 fold greater, or is about 8 fold to about 80 fold greater, or is about 8 fold to about 50 fold greater, or is about 8 fold to about 40 fold greater, or is about 8 fold to about 30 fold greater, or is about 8 fold to about 28 fold greater, or is about 8 fold to about 25 fold greater, or is about 8 fold to about 20 fold greater, or is about 8 fold to about 18 fold greater, or is about 8 fold to about 15 fold greater, than the effective size of the unconjugated chemokine-immunoglobulin fusion polypeptide, chemokine or variant thereof. In one embodiment, the polymer is PEG.

In another embodiment, the protein-polymer conjugate has an effective size that is about 25 fold to about 100 fold greater, or is about 25 fold to about 80 fold greater, or is about 25 fold to about 50 fold greater, or is about 25 fold to about 40 fold greater, or is about 25 fold to about 30 fold greater, or is about 25 fold to about 28 fold greater, than the effective size of the unconjugated chemokine-immunoglobulin fusion polypeptide, chemokine or variant thereof. In one embodiment, the polymer is PEG.

In another embodiment, the protein-polymer conjugate has a polymer-to-protein molar ratio of no more than about 10:1, or no more than about 5:1, or no more than about 4:1, or no more than about 3:1, or no more than about 2:1, or no more than 1:1. In one embodiment, the polymer is PEG.

In still another embodiment, the protein-polymer conjugate is a chemokine-immunoglobulin fusion polypeptide, chemokine or variant thereof covalently attached to at least one polymer having an actual MW of at least about 20,000 D. In one embodiment, the polymer is PEG.

In a further embodiment, the conjugate is a chemokine-immunoglobulin fusion polypeptide, chemokine or variant thereof covalently attached to at least one polymer having an actual MW of at least about 30,000 D. In one embodiment, the polymer is PEG.

In yet another embodiment, the conjugate is a chemokine-immunoglobulin fusion polypeptide, chemokine or variant thereof covalently attached to at least one polymer having an actual MW of at least about 40,000 D. In one embodiment, the polymer is PEG.

In another embodiment, the conjugate is a chemokine-immunoglobulin fusion polypeptide, chemokine or variant thereof covalently attached to at least one polymer having an actual MW that is at or about 20,000 D to at or about 300,000 D, or is at or about 30,000 D to at or about 300,000 D, or is at or about 40,000 D to at or about 300,000 D. In one embodiment, the polymer is PEG.

The conjugates of the present application can be made using any suitable technique now known or hereafter developed for derivatizing chemokines or fragments thereof with polymers. It will be appreciated that the invention is not limited to conjugates utilizing any particular type of linkage between a chemokine or fragment thereof and a polymer.

The conjugates of the present application include species wherein a polymer is covalently attached to a non-specific site or non-specific sites on a chemokine-immunoglobulin fusion polypeptide, a chemokine or a variant thereof (i.e. the polymer attachment is not targeted to a particular region or a particular amino acid residue in the unconjugated chemokine or fragment thereof). In such embodiments, the coupling chemistry can, for example, utilize the free epsilon amino groups of lysine residues in the unconjugated antibody as attachment sites for the polymer, wherein such lysine residue amino groups are randomly derivatized with polymer.

In addition, the conjugates of the invention include species wherein a polymer is covalently attached to a specific site or specific sites on the unconjugated chemokine or fragment thereof (i.e. a polymer attachment is targeted to a particular region or a particular amino acid residue or residues in the unconjugated chemokine or fragment thereof). FIG. 11 depicts a cartoon of the structure of CXCL11 indication potential pegylation sites. In such embodiments, the coupling chemistry can, for example, utilize the free sulfhydryl group of a cysteine residue not in a disulfide bridge in the unconjugated chemokine or fragment thereof. In one embodiment, one or more cysteine residue(s) is (are) engineered into a selected site or sites in the unconjugated chemokine or fragment thereof for the purpose of providing a specific attachment site or sites for polymer. The polymer can be activated with any functional group that is capable of reacting specifically with the free sulfhydryl or thiol group(s) on the unconjugated antibody, such as maleimide, sulfhydryl, thiol, triflate, tesylate, aziridine, exirane, and 5-pyridyl functional groups. The polymer can be coupled to the unconjugated chemokine or fragment thereof using any protocol suitable for the chemistry of the coupling system selected.

In another embodiment, polymer attachment is targeted to the receptor binding site of the unconjugated chemokine or fragment thereof. In another embodiment, polymer attachment is targeted to a site on the chemokine or fragment thereof away from the receptor binding site of the unconjugated chemokine or fragment thereof.

In certain embodiments, the protein portion of the protein-polymer conjugate is selected from the group consisting of human CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the polymer portion of the protein-polymer conjugate is PEG. FIG. 11 depicts a cartoon of the structure of CXCL11 indication potential pegylation sites.

In other embodiments, the protein portion of the protein-polymer conjugate is a chemokine-immunoglobulin fusion polypeptide wherein the chemokine moiety is selected from the group consisting of a human CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the immunoglobulin moiety is selected from the group consisting of the Fc region of human IgG1, the Fc region of human IgG2, the Fc region of human IgG3, the Fc region of human IgG4 and variants thereof.

In some embodiments, the protein-polymer conjugate is a serum labile polypeptide selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

In particular embodiments, the protein-polymer conjugate is a serum labile polypeptide selected from the group consisting of CCL2-PEG, CCL2(5-76)-PEG, CCL2(5-76K/H→A)-PEG, CCL7-PEG, CCL7(5-76)-PEG, CCL7(5-76K/H→A)-PEG, CCL8-PEG, CCL8(5-76)-PEG, CCL8(5-76K/H→A)-PEG, CCL13-PEG, CCL13(5-75)-PEG, CCL13(5-75K/H→A)-PEG, CCL25-PEG, CCL25(4-127)-PEG, CCL25(4-127K/H→A)-PEG, CXCL11-PEG, CXCL11(4-73)-PEG, CXCL11(4-73K/H→A)-PEG, CXCL11-IgG4Fc, CXCL11(4-73)-IgG4Fc, CXCL11(4-73K/H→A)-IgG4Fc, CXCL13-PEG, CXCL13(3-87)-PEG, CXCL13(3-87K/H→A)-PEG, CXCL16-PEG, CXCL16(3-87)-PEG, and CXCL16(3-87K/H→A)-PEG.

It is believed that the serum half-life, MRT and/or serum clearance rate of any chemokine or fragment thereof can be greatly improved by derivatizing the chemokine or fragment thereof with polymer as taught herein. In a preferred embodiment, the conjugate contains a chemokine or fragment thereof selected from the group consisting of CCL2, CCL7, CCL8, CCL13, CCL25, CXCL11, CXCL12α, CXCL13, and mutations, variants and fragments thereof.

Methods of Producing Chemokine-Immunoglobulin Fusion Polypeptides

The chemokine-immunoglobulin fusion polypeptides or variants thereof may be produced using methods well known in the art. In certain embodiments, the chemokine-immunoglobulin fusion polypeptide or variants thereof are produced by chemical synthesis. Briefly, a chemokine-immunoglobulin fusion polypeptide may be synthesized by coupling the carboxyl group or C-terminus of one amino acid to the amino group or N-terminus of another. Due to the possibility of unintended reactions, protecting groups are usually necessary. Chemical peptide synthesis starts at the C-terminal end of the peptide and ends at the N-terminus. This is the opposite of protein biosynthesis, which starts at the N-terminal end.

In some embodiments, the chemokine-immunoglobulin fusion polypeptide may be synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is pegylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction.

In other embodiments, the chemokine-immunoglobulin fusion polypeptides or variants thereof are produced using recombinant DNA technologies. Procedures for the expression and purification of recombinant proteins are well established.

In certain embodiments, the chemokine-immunoglobulin fusion polypeptides are expressed using the expression vectors such as bacterial plasmids; phage DNA; baculovirus; yeast plasmids; vectors derived from combinations of plasmids and phage DNA, and viral vectors ushc as vaccinia, adenovirus, fowl pox virus, pseudorabies, adenovirus, adeno-associated virus, retroviruses and many others viruses.

Expression vectors carrying the chemokine-immunoglobulin fusion polypeptides can be introduced into host cells by any of a variety of well-known procedures, such as electroporation, liposome mediated transfection, calcium phosphate precipitation, infection, transfection and the like, depending on the selection of vectors and host cells.

Host cells that contain expression vectors of chemokine-immunoglobulin fusion polypeptides are, thus, also a feature of this disclosure. Favorable host cells include prokaryotic (i.e., bacterial) host cells, such as *E. coli*, as well as numerous eukaryotic host cells, including fungal (e.g., yeast, such as *Saccharomyces cerevisiae* and *Picchia pastoris*) cells, insect cells, plant cells, and mammalian cells (such as CHO cells). Examples of appropriate expression hosts include: bacterial cells, such as *E. coli*, *Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein. The chemokine-immunoglobulin fusion polypeptides can also be produced in non-animal cells such as plants, yeast, fungi, bacteria and the like. In bacterial systems, a number of expression vectors can be selected depending upon the use intended for the expressed product. For example, when large quantities of a polypeptide or fragments thereof are needed for the production of antibodies, vectors which direct high level expression of fusion polypeptides that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion polypeptide; pIN vectors (Van Heeke & Schuster (1989) J Biol Chem 264:5503-5509); pET vectors (Novagen, Madison Wis.), in which the amino-terminal methionine is ligated in frame with a histidine tag; and the like.

Similarly, in yeast, such as *Saccharomyces cerevisiae*, a number of vectors containing constitutive or inducible promoters such as alpha factor, alcohol oxidase and PGH can be used for production of the desired expression products. In mammalian host cells, a number expression systems, including both plasmids and viral-based systems, can be utilized.

For long-term, high-yield production of the chemokine-immunoglobulin fusion polypeptides, stable expression systems are typically used. For example, polynucleotides encoding a the chemokine-immunglobulin fusion polypeptide are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells, which successfully express the introduced sequences. For example, resistant groups or colonies of stably transformed cells can be proliferated using tissue culture techniques appropriate to the cell type. Host cells transformed with a nucleic acid encoding a c the chemokine-immunoglobulin fusion polypeptide are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed the chemokine-immunoglobulin fusion polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art.

In another example, a polynucleotide sequence that encodes the chemokine-immunoglobulin fusion polypeptide is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the chemokine-immunoglobulin fusion polypeptide is inserted into the pAcSG2 transfer vector. Then, host cells SF9 (*Spodoptera frugiperda*) are co-transfected by pAcSG2-chimer plasmid and BD BaculoGold, containing the linearized genomic DNA of the baculovirus *Autographa californica* nuclear polyhedrosis virus (AcNPV). Following transfection, homologous recombination occurs between the pACSG2 plasmid and the Baculovirus genome to generate the recombinant virus. In one example, the chemokine-immunoglobulin fusion polypeptide is expressed under the regulatory control of the polyhedrin promoter (pH). Similar transfer vectors can be produced using other promoters, such as the basic (Ba) and p10 promoters. Similarly, alternative insect cells can be employed, such as SF21, which is closely related to the Sf9, and the High Five (Hi5) cell line derived from a cabbage looper, *Trichoplusia ni*. Following transfection and induction of expression (according to the selected promoter and/or enhancers or other regulatory elements), the expressed the chemokine-immunoglobulin fusion polypeptides are recovered (e.g., purified or enriched) and renatured to ensure folding into a biologically active conformation.

In yet other embodiments, the chemokine-immunoglobulin fusion polypeptides are expressed in vivo by a plasmid vector or a viral vector.

Treatment Methods

The present application further provides methods of using the chemokine-immunoglobulin fusion polypeptides disclosed herein to modulate inflammation and/or treat chemokine receptor-mediated disorders. In some embodiments, a method for treating a chemokine receptor-mediated disorder in a subject is provided. In some embodiments, the method comprises administering an effective amount of a chemokine-immunoglobulin fusion polypeptide disclosed herein to a subject in need thereof.

As used herein, the terms "treatment" or "treating" relate to any treatment of a chemokine receptor-mediated disorder, including but not limited to prophylactic treatment and therapeutic treatment. As such, the terms "treatment" or "treating" include, but are not limited to: preventing a chemokine receptor-mediated disorder or the development of a chemokine receptor-mediated disorder; inhibiting the progression of a chemokine receptor-mediated disorder; arresting or preventing the development of a chemokine receptor-mediated disorder; reducing the severity of a chemokine receptor-mediated disorder; ameliorating or relieving symptoms associated with a chemokine receptor-mediated disorder; and causing a regression of the chemokine receptor-mediated disorder or one or more of the symptoms associated with the chemokine receptor-mediated disorder.

The embodiments of the therapeutic compounds exhibit activity in the treatment of chemokine receptor-mediated disorders and inflammation, when administered in effective amounts. An effective amount of a composition disclosed herein is a nontoxic, but sufficient amount of the composition, such that the desired prophylactic or therapeutic effect is produced. The exact amount of the composition that is required will vary from subject to subject, depending on the species, age, condition of the animal, severity of the inflammation or chemokine receptor-mediated disorder in the animal, the particular carrier or adjuvant being used, its mode of administration, and the like. Accordingly, the effective amount of any particular therapeutic composition disclosed herein will vary based on the particular circumstances, and an appropriate effective amount can be determined in each case of application by one of ordinary skill in the art using only routine experimentation. The compositions disclosed herein can be administered in amounts ranging from about 0.1 µg to about 100 mg per kilogram of body weight. For example, the dosage regimen could be from about 1 µg to about 10 mg per kilogram of body weight, and such dosage units could be employed so that a total of from about 7 µg to about 700 mg of the composition is administered to a subject of about 70 kg of body weight.

A dosage regimen can be adjusted to provide an optimum therapeutic response and can be administered daily, biweekly, weekly, bimonthly, monthly, or at other appropriate time intervals. For example, compositions disclosed herein can be administered from once a day to once a week in dosages of about 5-250 mg per administration. For another example, several divided doses can be administered daily or the dose can be proportionally reduced as indicated by the exigencies of the therapeutic situation. One practical advantage is that the compound can be administered in a convenient manner such as intravenously, intratumorally, subcutaneously, transdermally, intraperitoneally or orally.

In some embodiments, the active composition is administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The form should be sterile and fluid to the extent that easy syringability exists. It should be stable under the conditions of manufacture and storage and should be preserved against the contaminating action of microorganisms, such as bacteria and fungi. The pharmaceutical carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, the inclusion of isotonic agents can be desirable, for example, sugars or sodium chloride. Prolonged absorption of the injectable compositions can be brought about by the use in the compositions of agents, delaying absorption, for example, aluminum monostearate and gelatin.

Sterile injectable solutions can be prepared by incorporating the composition in the required amount in the appropriate solvent with various of the other ingredients enumerated above, followed by filtered sterilization. Generally, dispersions can be prepared by incorporating the various sterilized active ingredient into a sterile vehicle containing the basic dispersion medium and the required other ingredients from those enumerated above. In the case of sterile powders for the preparation of sterile injectable solutions, methods of preparation include vacuum drying and freeze drying techniques, which yield a powder of the active ingredient plus any additional desired ingredient from previously sterile filtered solution thereof.

As used herein, "pharmaceutically acceptable carrier" and "pharmaceutical carrier" are used interchangeably and include solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Parenteral compositions may be formulated in dosage-unit form for ease of administration and uniformity of dosage. Dosage-unit form, as used herein, refers to physically discrete units suited as unitary dosages for the subjects to be treated, each unit containing a predetermined quantity of active material calculated to produce the desired therapeutic effect in association with the required pharmaceutical carrier. The specification for the dosage-unit forms of the present application can be chosen based upon: (a) the unique characteristics of the active material and the particular therapeutic effect to be achieved, and (b) the limitations inherent in the art of compounding such an active material for the treatment of conditions in living subjects having a condition in which bodily health is impaired as described herein.

The active ingredient can be compounded for convenient and effective administration in effective amounts with a suitable pharmaceutically acceptable carrier in dosage unit form as described herein. A unit dosage form can, for example, contain the principle active compound in amounts ranging from, for example, about 0.1 to about 1000 mg or, for another example, from about 5 to about 500 mg. Expressed in proportions, the compound is generally present in from about 1 to about 100 mg/ml of carrier. In the case of compositions containing supplementary active ingredients, the dosages can be determined by reference to the usual dose and manner of administration of the ingredients.

Further, with respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos.

Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments of the presently-disclosed subject matter, the chemokine receptor-mediated disorder treated is a cell proliferative disorder, such as tumor or cancer. The present application provides chemokine-immunoglobulin fusion polypeptides that can target specific chemokine receptors expressed on cells of proliferative disorders disclosed herein. Cancer cells express functionally active chemokine receptors that may support adhesion, invasion, and cell survival. Chemokine receptor signaling and aggregation following binding of chemokines is coupled to integrin clustering, which enhances cell survival and firm cell adhesion. Without wishing to be bound by theory, the novel chemokine-immunoglobulin fusion polypeptides disclosed herein can bind chemokine receptors on these diseased cells and inhibit cellular events, including cell survival, migration, invasion, adhesion, or combinations thereof, and thereby treat the cell proliferative disorder. Table 3 lists various cancers and associations of the listed cancers with particular chemokines and chemokine receptors.

TABLE 3

Chemokine, Chemokine Receptor and Cancer Association (dependent of stage of disease)

| Cancer | Chemokine | Chemokine Receptor |
| --- | --- | --- |
| Carcinoma | CCL1, CCL4, CCL17, CCL19, CCL21, CCL22, CCL25, CXCL1, CXCL2, CXCL5, CXCL8, CXCL11, CXCL12, CXCL13, CXCL16 | CCR7, CCR8, CCR9, CXCR1, CXCR2, CXCR3, CXCR4, CXCR5, CXCR6, CXCR7, CX3CR1 |
| Leukemia | CCL1, CCL4, CCL17, CCL19, CCL21, CCL22, CCL25, CXCL12 | CCR7, CCR8, CCR9, CXCR4 |
| Lymphoma | CXCL12, CXCL13 | CXCR4, CXCR5 |
| Melanoma | CCL25, CCL27, CXCL1, CXCL2, CXCL3, CXCL5, CXCL6, CXCL7, CXCL8, CXCL12, CXCL13, CXCL16 CX3CL1 | CCR9, CCR10, CXCR1, CXCR2, CXCR4, CXCR5, CXCR6, CX3CR1 |
| Sarcoma | CCL1, CCL3, CCL4, CCL5, CCL7, CCL8, CCL11, CCL13, CCL17, CCL19, CCL22, CCL24, CXCL12, CX3CL1 | CCR3, CCR5, CCR8, CXCR4 CX3CR1, CCXCKR |

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. "Cancer" refers to any of various malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Examples of cancers are cancer of the brain, bladder, breast, cervix, colon, head and neck, kidney, lung, non-small cell lung, mesothelioma, ovary, prostate, stomach and uterus, leukemia, and medulloblastoma.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

In some embodiments, a chemokine-immunoglobulin fusion polypeptide of the present application is used for the treatment of cancer. The chemokine-immunoglobulin fusion polypeptide comprises a chemokine moiety selected from the group consisting of CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and an immunoglobulin moiety selected from the group consisting of the constant region of human IgG1 and functional variants thereof.

In other embodiments, the chemokine receptor-mediated disorder treated is an inflammatory disorder. Without wishing to be bound by theory, the novel chemokine-immunoglobulin fusion polypeptides disclosed herein can bind chemokine receptors on these cells and inhibit cellular events that can result in inflammation and inflammatory disorders. Table 4 lists various exemplary inflammatory disorders and associations of the listed disorders with particular chemokines and chemokine receptors. Targeting of the listed chemokine receptors with chemokine-immunoglobulin fusion polypeptides disclosed herein that act as specific ligands of the receptors can be useful for treating the listed inflammatory disorders.

In some embodiments, a chemokine-immunoglobulin fusion polypeptide of the present application is used for the treatment of an inflammatory disorder. The chemokine-immunoglobulin fusion polypeptide comprises a chemokine moiety selected from the group consisting of CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and an immunoglobulin moiety selected from the group consisting of the constant region of human IgG4 and functional variants thereof.

TABLE 4

Chemokine, Chemokine Receptor and Inflammatory Disorder Association (dependent of stage of disease)

| Inflammatory Disorder | Chemokine | Chemokine Receptor |
|---|---|---|
| Allergies (Skin, Food & Respiratory) | CCL1, CCL2, CCL5, CCL7, CCL8, CCL11, CCL13, CCL17, CCL22, CCL24, CCL25, CCL26 | CCR3, CCR4, CCR8, CCR9 |
| Asthma | CCL3, CCL4, CCL5, CCL7, CCL8, CCL11, CCL15, CCL17, CCL22, CCL24, CCL26 | CCR3, CCR4, CCR5 |
| Septic Shock, Anaphylaxis | CXCL1, CXCL2, CXCL3, CXCL5, CXCL6, CXCL7, CXCL8, CXCL9, CXCL10, CXCL11, CCL5 | CXCR1, CXCR2, CXCR3 |
| Arthritis (septic, rheumatoid, psoriatic) | CXCL9, CXCL10, CXCL11, CXCL12, CXCL13 CCL20 XCL1 CX3CL1 | CXCR3, CXCR4, CXCR5 CCR6 XCR1 CX3CR1 |
| Osteoarthritis | CXCL1, CXCL2, CXCL3, CXCL5, CXCL6, CXCL7, CXCL8, CXCL12, CXCL13 CCL2, CCL3, CCL4, CCL7, CCL8, CCL13, CCL5, CCL18 | CXCR1, CXCR2 CCR2, CCR5 |
| Atherosclerosis | CXCL1, CXCL2, CXCL3, CXCL4, CXCL5, CXCL8 CCL2, CCL3, CCL4, CCL8, CCL12, CCL13, CCL17, CCL22 CX3CL1 | CXCR1, CXCR2 CCR2, CCR8 CX3CR1 |
| Dermatitis & Delayed-Typed Hypersensitivity | CXCL9, CXCL10, CXCL11 CCL2, CCL3, CCL4, CCL5, CCL17, CCL20, CCL22, CCL27 | CXCR3 CCR4, CCR5, CCR6, CCR10 |
| Diabetes | CXCL9, CXCL10, CXCL11 CCL2, CCL9 CX3CL1 | CXCR3 CCR2, CCR4 CX3CR1 |
| Graft rejection | CXCL9, CXCL10, CXCL11 CCL3, CCL4, CCL5 XCL1, XCL2 | CXCR3 CCR5 XCR1 |
| Inflammatory Bowel Disorders | CXCL9, CXCL10, CXCL11 CCL3, CCL4, CCL5, CCL25 | CXCR3 CCR5 |
| Interstitial Cystitis | CXCL9, CXCL10, CXCL11 CCL3, CCL4, CCL5 | CXCR3 CCR5 |
| Multiple Sclerosis | CXCL9, CXCL10, CXCL11 CCL3, CCL4, CCL5, CCL7, CCL14, CCL15, CCL23 | CXCR3 CCR1, CCR5 |
| Myasthemia gravis, Grave's disease, & Hashimoto thyroiditis | CXCL9, CXCL10, CXCL11 CCL3, CCL4, CCL5 XCL1, XCL2 | CXCR3 CCR5 XCR1 |
| Nephritis & Systemic Lupus Erthematosus | CXCL9, CXCL10, CXCL11, CXCL13 CCL2, CCL3, CCL4, CCL5, CCL8, CCL12, CCL13 CX3CL1 | CXCR3, CXCR5 CCR2, CCR4 CX3CR1 |
| Pneumonitis, Chronic Obstructive Pulmonary Disease, & Chronic Bronchitis | CXCL1, CXCL2, CXCL3, CXCL5, CXCL7, CXCL8 CCL3, CCL5, CCL7, CCL8, CCL11, CCL13, CCL24, CCL26 | CXCR2, CXCR3 CCR3 |

As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cell proliferative disorders, or other agents Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to, inflammatory disorders of the central or peripheral nervous system (e.g., abscess, AIDS related infections, Alzheimer's disease, chronic fatigue syndrome, congenital infections, encephalitis, ischemia, meningitis, multiple sclerosis, traumatic brain injury, etc.); inflammatory disorders of the urogenital system (e.g., endometriosis, glomerulosclerosis, infections of the vagina and cervix, intra-amniotic infection, pelvic inflammatory disease, renal inflammation/nephritis, sexually transmitted diseases, urethritis, urinary tract infections, yeast infection, etc.); inflammatory disorders of the digestive system (e.g., colon cancer, hepatitis, inflammatory bowel disease, interstitial cystitis, irritable bowel syndrome, ulcers, etc.); inflammatory disorders of the respiratory system (e.g., chronic lung disease, asthma, tuberculosis, pneumonia, etc.); inflammatory disorders of the skin, integument and musculoskeletal system (e.g., Behçet's disease, Crohn's disease, dermatitis, gingivitis, gout, myalgias, osteoarthritis, periodontitis, psoriasis, rheumatoid arthritis, spondyloarthropathies, skin sunburn, etc.); inflammatory disorders of the cardiovascular system (e.g., atherosclerosis, pericarditis, endocarditis, Kawasaki's disease, myocarditis, rheumatic fever, vasculitis); autoimmune disorders; cat scratch disease; infections of the eye; Lyme disease; lymphadenopathy; lymphatic inflammation; radiation-induced inflammation; sarcoidosis; Sjogren's syndrome; systemic lupus erythematosus and related disorders; and inflammatory disorders resulting from infections by microorganisms and inflammatory molecules. As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As noted, an inflammatory disorder is often caused, at least in part, or exacerbated by, inflammation, which may be characterized by symptoms and/or manifestations of the inflammatory disorder which may include, but are not limited to, increased blood flow, edema, activation of immune cells (e.g., proliferation, cytokine production, or enhanced phagocytosis), heat, redness, swelling, pain and loss of function in the affected tissue and organ. As such, the present application further provides methods of modulating inflammation. The term "modulating inflammation" refers to either inducement of inflammation or alleviating inflammation where inflammation is pathological, as occurs in inflammatory disorders. The term "alleviating" as used herein refers to preventing the symptoms and/or manifestations of inflammation or the development of the symptoms and/or manifestations of inflammation; inhibiting the progression of the symptoms and/or manifestations of inflammation; arresting or preventing the development of the symptoms and/or manifestations of inflammation; reducing the severity of symptoms and/or manifestations inflammation; ameliorating or relieving the symptoms and/or manifestations associated with inflammation; and/or causing a regression of the symptoms and/or manifestations of inflammation. The present invention is further illustrated by the following examples that should not be construed as limiting. The following examples may include compilations of data that are representative of data gathered at various times during the course of development and experimentation related to the present subject matter.

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1: Generation of Plasmid Expression Vectors

Expression vectors capable of expressing a chemokine-immunoglobulin fusion polypeptide are generated from pFUSE-hIgG1-Fc1, pFUSE-hIgG2-Fc1, pFUSE-hIgG3-Fc1 and pFUSE-hIgG4-Fc1 vectors from InvivoGen (San Diego, Calif.) using standard molecular biology procedures. Examples of the expression vectors are shown in FIGS. 1-10.

Example 2: Expression of Chemokine Receptors in Breast Cancer Cell Lines

Experiments are conducted to compare expression levels of CXCR7 and CXCR3 in breast cancer tissue of various stages, in non-neoplastic breast tissue. Non-neoplastic breast tissue does not express detectable levels of CXCR7. CXCR7 expression is significantly higher in tissues with advanced breast cancer, comparing to non-neoplastic breast tissue. CXCR7 and CXCR3 mRNAs are also elevated in breast cancer cell lines (MDA-MB-231), compared to normal breast cells (MCF-10A).

Example 3: Var-CXCL11-IgG Fusion Polypeptide Inhibits CXCR7 and CXCR3 Activation in Breast Cancer Cells Using Amnis ImageStream analysis, we found that CXCL11 stimulates CXCR3 and CXCR7 aggregation and rapid desensitization, that CXCL12 modulates modest CXCR7 clustering, and that adrenomedullin (AM) stimulates CXCR3 and CXCR7 clustering. CXCL11-IgG fusion polypeptide abrogates CXCR3 and CXCR7, but not CXCR4, clustering and desensitization by CXCL11, CXCL12 and AM.

The above description is for the purpose of teaching the person of ordinary skill in the art how to practice the present invention, and is not intended to detail all those obvious modifications and variations of it that will become apparent to the skilled worker upon reading the description. It is intended, however, that all such obvious modifications and variations be included within the scope of the present invention, which is defined by the following embodiments. The embodiments are intended to cover the components and steps in any sequence that is effective to meet the objectives there intended, unless the context specifically indicates the contrary. All the references cited in the specification are herein incorporated by reference in their entirely.

---

What is claimed is:

1. A composition comprising a chemokine-immunoglobulin fusion polypeptide, the fusion polypeptide comprising:
a chemokine moiety and an immunoglobulin moiety,
wherein the chemokine moiety consists of CXCL12α(3-67) or CXCL12α(3-67K/R→A), and
wherein the immunoglobulin moiety is selected from the group consisting of the constant region of human IgG1 (IgG1Fc), the constant region of human IgG2 (IgG2Fc), the constant region of human IgG3 (IgG3Fc), and the constant region of human IgG4 (IgG4Fc).

2. The composition of claim 1, wherein said composition comprises a pegylated fusion polypeptide.

3. The composition of claim 2, wherein said pegylated fusion polypeptide comprises a polyethyelene glycol (PEG) having a molecular weight of at least about 500,000 dalton.

4. The composition of claim 2, wherein said pegylated fusion polypeptide has a PEG-to-fusion polypeptide molar ratio of no more than about 10:1.

5. The composition of claim 2, wherein said pegylated fusion polypeptide has a PEG-to-fusion polypeptide molar ratio of no more than about 2:1.

6. An isolated polynucleotide, encoding the chemokine-immunoglobulin fusion polypeptide of claim 1.

7. An expression vector, comprising:
a regulatory element; and
a polynucleotide operatively linked to said regulatory element,
wherein said polynucleotide encodes the chemokine-immunoglobulin fusion polypeptide of claim 1.

8. The expression vector of claim 7, wherein said vector is a plasmid-based expression vector or a virus-based expression vector.

9. A pharmaceutical composition, comprising:
the chemokine-immunoglobulin fusion polypeptide of claim 1; and
a pharmaceutically acceptable carrier.

10. A pharmaceutical composition, comprising:
the expression vector of claim 7; and
a pharmaceutically acceptable carrier.

11. A method for treating a chemokine receptor-mediated disorder, wherein treatment comprises inhibiting growth and/or metastasis of proliferative disorder cells in a subject in need thereof, comprising administering to said subject an effective amount of the chemokine-immunoglobulin fusion polypeptide of claim 1.

12. The method of claim 11, wherein said chemokine receptor-mediated disorder is selected from the group consisting of leukemia, carcinoma, melanoma, sarcoma and lymphoma.

13. A method for treating an inflammatory disorder in a subject in need thereof, wherein the inflammatory disorder is selected from the group consisting of osteoarthritis, rheumatoid arthritis, psoriatic arthritis and septic arthritis, comprising: administering to said subject an effective amount of the composition of claim 1.

* * * * *

SEQUENCE LISTING

```
<160> NUMBER OF SEQ ID NOS: 106

<210> SEQ ID NO 1
<211> LENGTH: 96
<212> TYPE: PRT
<213> ORGANISM: Homo sapiens

<400> SEQUENCE: 1

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
        35                  40                  45

Cys Tyr Arg Asn Thr Ser Ser Ile Cys Ser Asn Glu Gly Leu Ile Phe
    50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95
```

```
<210> SEQ ID NO 2
<211> LENGTH: 99
<212> TYPE: PRT
<213> ORGANISM: Homo sapiens

<400> SEQUENCE: 2

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 3
<211> LENGTH: 92
<212> TYPE: PRT
<213> ORGANISM: Homo sapiens

<400> SEQUENCE: 3

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
        50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 4
<211> LENGTH: 92
<212> TYPE: PRT
<213> ORGANISM: Homo sapiens

<400> SEQUENCE: 4

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
        50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90
```

<210> SEQ ID NO 5
<211> LENGTH: 92
<212> TYPE: PRT
<213> ORGANISM: Homo sapiens

<400> SEQUENCE: 5

Met Lys Leu Cys Val Thr Val Leu Ser Leu Val Leu Val Ala Ala
1               5                   10                  15

Phe Cys Ser Leu Ala Leu Ser Ala Pro Met Gly Ser Asp Pro Pro Thr
            20                  25                  30

Ala Cys Cys Phe Ser Tyr Thr Ala Arg Lys Leu Pro Arg Asn Phe Val
        35                  40                  45

Val Asp Tyr Tyr Glu Thr Ser Ser Leu Cys Ser Gln Pro Ala Val Val
    50                  55                  60

Phe Gln Thr Lys Arg Gly Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 6
<211> LENGTH: 91
<212> TYPE: PRT
<213> ORGANISM: Homo sapiens

<400> SEQUENCE: 6

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
            20                  25                  30

Cys Cys Phe Ala Tyr Ile Ala Arg Pro Leu Pro Arg Ala His Ile Lys
        35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 7
<211> LENGTH: 99
<212> TYPE: PRT
<213> ORGANISM: Homo sapiens

<400> SEQUENCE: 7

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
            20                  25                  30

Thr Cys Cys Tyr Arg Phe Ile Asn Lys Lys Ile Pro Lys Gln Arg Leu
        35                  40                  45

Glu Ser Tyr Arg Arg Thr Thr Ser Ser His Cys Pro Arg Glu Ala Val
    50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
                85                  90                  95

Pro Lys Leu

```
<210> SEQ ID NO 8
<211> LENGTH: 99
<212> TYPE: PRT
<213> ORGANISM: Homo sapiens

<400> SEQUENCE: 8
```

Met Lys Val Ser Ala Ala Leu Leu Cys Leu Leu Met Ala Ala Thr
1               5                   10                  15

Phe Ser Pro Gln Gly Leu Ala Gln Pro Asp Ser Val Ser Ile Pro Ile
                20                  25                  30

Thr Cys Cys Phe Asn Val Ile Asn Arg Lys Ile Pro Ile Gln Arg Leu
            35                  40                  45

Glu Ser Tyr Thr Arg Ile Thr Asn Ile Gln Cys Pro Lys Glu Ala Val
50                  55                  60

Ile Phe Lys Thr Lys Arg Gly Lys Glu Val Cys Ala Asp Pro Lys Glu
65                  70                  75                  80

Arg Trp Val Arg Asp Ser Met Lys His Leu Asp Gln Ile Phe Gln Asn
                85                  90                  95

Leu Lys Pro

```
<210> SEQ ID NO 9
<211> LENGTH: 97
<212> TYPE: PRT
<213> ORGANISM: Homo sapiens

<400> SEQUENCE: 9
```

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro

```
<210> SEQ ID NO 10
<211> LENGTH: 98
<212> TYPE: PRT
<213> ORGANISM: Homo sapiens

<400> SEQUENCE: 10
```

Met Lys Val Ser Ala Val Leu Leu Cys Leu Leu Leu Met Thr Ala Ala
1               5                   10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr

<210> SEQ ID NO 11
<211> LENGTH: 93
<212> TYPE: PRT
<213> ORGANISM: Homo sapiens

<400> SEQUENCE: 11

Met Lys Ile Ser Val Ala Ala Ile Pro Phe Phe Leu Leu Ile Thr Ile
1               5                   10                  15

Ala Leu Gly Thr Lys Thr Glu Ser Ser Ser Arg Gly Pro Tyr His Pro
                20                  25                  30

Ser Glu Cys Cys Phe Thr Tyr Thr Thr Tyr Lys Ile Pro Arg Gln Arg
            35                  40                  45

Ile Met Asp Tyr Tyr Glu Thr Asn Ser Gln Cys Ser Lys Pro Gly Ile
        50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90

<210> SEQ ID NO 12
<211> LENGTH: 109
<212> TYPE: PRT
<213> ORGANISM: Homo sapiens

<400> SEQUENCE: 12

Met Lys Ile Ser Val Ala Ala Ile Pro Phe Phe Leu Leu Ile Thr Ile
1               5                   10                  15

Ala Leu Gly Thr Lys Thr Glu Ser Ser Ser Gln Thr Gly Gly Lys Pro
                20                  25                  30

Lys Val Val Lys Ile Gln Leu Lys Leu Val Gly Gly Pro Tyr His Pro
            35                  40                  45

Ser Glu Cys Cys Phe Thr Tyr Thr Thr Tyr Lys Ile Pro Arg Gln Arg
            50                  55                  60

Ile Met Asp Tyr Tyr Glu Thr Asn Ser Gln Cys Ser Lys Pro Gly Ile
65                  70                  75                  80

Val Phe Ile Thr Lys Arg Gly His Ser Val Cys Thr Asn Pro Ser Asp
                85                  90                  95

Lys Trp Val Gln Asp Tyr Ile Lys Asp Met Lys Glu Asn
                100                 105

<210> SEQ ID NO 13
<211> LENGTH: 113
<212> TYPE: PRT
<213> ORGANISM: Homo sapiens

<400> SEQUENCE: 13

Met Lys Val Ser Val Ala Ala Leu Ser Cys Leu Met Leu Val Ala Val
1               5                   10                  15

Leu Gly Ser Gln Ala Gln Phe Ile Asn Asp Ala Glu Thr Glu Leu Met
                20                  25                  30

Met Ser Lys Leu Pro Leu Glu Asn Pro Val Val Leu Asn Ser Phe His
            35                  40                  45

Phe Ala Ala Asp Cys Cys Thr Ser Tyr Ile Ser Gln Ser Ile Pro Cys

```
                    50                  55                  60

Ser Leu Met Lys Ser Tyr Phe Glu Thr Ser Ser Glu Cys Ser Lys Pro
 65                  70                  75                  80

Gly Val Ile Phe Leu Thr Lys Lys Gly Arg Gln Val Cys Ala Lys Pro
                     85                  90                  95

Ser Gly Pro Gly Val Gln Asp Cys Met Lys Lys Leu Lys Pro Tyr Ser
                100                 105                 110

Ile

<210> SEQ ID NO 14
<211> LENGTH: 120
<212> TYPE: PRT
<213> ORGANISM: Homo sapiens

<400> SEQUENCE: 14

Met Lys Val Ser Glu Ala Ala Leu Ser Leu Leu Val Leu Ile Leu Ile
  1               5                  10                  15

Ile Thr Ser Ala Ser Arg Ser Gln Pro Lys Val Pro Glu Trp Val Asn
                 20                  25                  30

Thr Pro Ser Thr Cys Cys Leu Lys Tyr Tyr Glu Lys Val Leu Pro Arg
             35                  40                  45

Arg Leu Val Val Gly Tyr Arg Lys Ala Leu Asn Cys His Leu Pro Ala
 50                  55                  60

Ile Ile Phe Val Thr Lys Arg Asn Arg Glu Val Cys Thr Asn Pro Asn
 65                  70                  75                  80

Asp Asp Trp Val Gln Glu Tyr Ile Lys Asp Pro Asn Leu Pro Leu Leu
                 85                  90                  95

Pro Thr Arg Asn Leu Ser Thr Val Lys Ile Ile Thr Ala Lys Asn Gly
                100                 105                 110

Gln Pro Gln Leu Leu Asn Ser Gln
                115                 120

<210> SEQ ID NO 15
<211> LENGTH: 94
<212> TYPE: PRT
<213> ORGANISM: Homo sapiens

<400> SEQUENCE: 15

Met Ala Pro Leu Lys Met Leu Ala Leu Val Thr Leu Leu Leu Gly Ala
  1               5                  10                  15

Ser Leu Gln His Ile His Ala Ala Arg Gly Thr Asn Val Gly Arg Glu
                 20                  25                  30

Cys Cys Leu Glu Tyr Phe Lys Gly Ala Ile Pro Leu Arg Lys Leu Lys
             35                  40                  45

Thr Trp Tyr Gln Thr Ser Glu Asp Cys Ser Arg Asp Ala Ile Val Phe
 50                  55                  60

Val Thr Val Gln Gly Arg Ala Ile Cys Ser Asp Pro Asn Asn Lys Arg
 65                  70                  75                  80

Val Lys Asn Ala Val Lys Tyr Leu Gln Ser Leu Glu Arg Ser
                 85                  90

<210> SEQ ID NO 16
<211> LENGTH: 89
<212> TYPE: PRT
<213> ORGANISM: Homo sapiens

<400> SEQUENCE: 16
```

Met Lys Gly Leu Ala Ala Leu Leu Val Leu Cys Thr Met Ala
1               5                   10                  15

Leu Cys Ser Cys Ala Gln Val Gly Thr Asn Lys Glu Cys Cys Leu
            20                  25                  30

Val Tyr Thr Ser Trp Gln Ile Pro Gln Lys Phe Ile Val Asp Tyr Ser
            35                  40                  45

Glu Thr Ser Pro Gln Cys Pro Lys Pro Gly Val Ile Leu Leu Thr Lys
        50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85

<210> SEQ ID NO 17
<211> LENGTH: 98
<212> TYPE: PRT
<213> ORGANISM: Homo sapiens

<400> SEQUENCE: 17

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
            35                  40                  45

Leu Leu Ile Lys Asp Gly Cys Arg Val Pro Ala Val Val Phe Thr Thr
        50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 18
<211> LENGTH: 96
<212> TYPE: PRT
<213> ORGANISM: Homo sapiens

<400> SEQUENCE: 18

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
            35                  40                  45

Phe Thr Arg Gln Leu Ala Asn Glu Gly Cys Asp Ile Asn Ala Ile Ile
        50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 19
<211> LENGTH: 95
<212> TYPE: PRT
<213> ORGANISM: Homo sapiens

<400> SEQUENCE: 19

Met Cys Cys Thr Lys Ser Leu Leu Ala Ala Leu Met Ser Val Leu
1               5                   10                  15

Leu Leu His Leu Cys Gly Glu Ser Glu Ala Ser Asn Phe Asp Cys Cys
                20                  25                  30

Leu Gly Tyr Thr Asp Arg Ile Leu His Pro Lys Phe Ile Val Gly Phe
            35                  40                  45

Thr Arg Gln Leu Ala Asn Glu Gly Cys Asp Ile Asn Ala Ile Ile Phe
    50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Val Lys Asn Met
                85                  90                  95

<210> SEQ ID NO 20
<211> LENGTH: 134
<212> TYPE: PRT
<213> ORGANISM: Homo sapiens

<400> SEQUENCE: 20

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
                20                  25                  30

Leu Lys Tyr Ser Gln Arg Lys Ile Pro Ala Lys Val Val Arg Ser Tyr
            35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
            115                 120                 125

Gln Thr Pro Lys Gly Pro
    130

<210> SEQ ID NO 21
<211> LENGTH: 93
<212> TYPE: PRT
<213> ORGANISM: Homo sapiens

<400> SEQUENCE: 21

Met Asp Arg Leu Gln Thr Ala Leu Leu Val Val Leu Val Leu Leu Ala
1               5                   10                  15

Val Ala Leu Gln Ala Thr Glu Ala Gly Pro Tyr Gly Ala Asn Met Glu
                20                  25                  30

Asp Ser Val Cys Cys Arg Asp Tyr Val Arg Tyr Arg Leu Pro Leu Arg
            35                  40                  45

Val Val Lys His Phe Tyr Trp Thr Ser Asp Ser Cys Pro Arg Pro Gly
    50                  55                  60

Val Val Leu Leu Thr Phe Arg Asp Lys Glu Ile Cys Ala Asp Pro Arg
65                  70                  75                  80

Val Pro Trp Val Lys Met Ile Leu Asn Lys Leu Ser Gln
                85                  90

<210> SEQ ID NO 22
<211> LENGTH: 120
<212> TYPE: PRT
<213> ORGANISM: Homo sapiens

<400> SEQUENCE: 22

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Arg Phe His
            35                  40                  45

Ala Thr Ser Ala Asp Cys Cys Ile Ser Tyr Thr Pro Arg Ser Ile Pro
    50                  55                  60

Cys Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Val Arg Met Leu Lys Leu Asp
            100                 105                 110

Thr Arg Ile Lys Thr Arg Lys Asn
        115                 120

<210> SEQ ID NO 23
<211> LENGTH: 137
<212> TYPE: PRT
<213> ORGANISM: Homo sapiens

<400> SEQUENCE: 23

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Met Leu Trp
            35                  40                  45

Arg Arg Lys Ile Gly Pro Gln Met Thr Leu Ser His Ala Ala Gly Phe
    50                  55                  60

His Ala Thr Ser Ala Asp Cys Cys Ile Ser Tyr Thr Pro Arg Ser Ile
65                  70                  75                  80

Pro Cys Ser Leu Leu Glu Ser Tyr Phe Glu Thr Asn Ser Glu Cys Ser
                85                  90                  95

Lys Pro Gly Val Ile Phe Leu Thr Lys Lys Gly Arg Arg Phe Cys Ala
            100                 105                 110

Asn Pro Ser Asp Lys Gln Val Gln Val Cys Val Arg Met Leu Lys Leu
        115                 120                 125

Asp Thr Arg Ile Lys Thr Arg Lys Asn
    130                 135

<210> SEQ ID NO 24
<211> LENGTH: 119
<212> TYPE: PRT
<213> ORGANISM: Homo sapiens

<400> SEQUENCE: 24

Met Ala Gly Leu Met Thr Ile Val Thr Ser Leu Leu Phe Leu Gly Val
1               5                   10                  15

```
Cys Ala His His Ile Ile Pro Thr Gly Ser Val Val Ile Pro Ser Pro
             20                  25                  30

Cys Cys Met Phe Phe Val Ser Lys Arg Ile Pro Glu Asn Arg Val Val
         35                  40                  45

Ser Tyr Gln Leu Ser Ser Arg Ser Thr Cys Leu Lys Ala Gly Val Ile
 50                  55                  60

Phe Thr Thr Lys Lys Gly Gln Gln Phe Cys Gly Asp Pro Lys Gln Glu
 65                  70                  75                  80

Trp Val Gln Arg Tyr Met Lys Asn Leu Asp Ala Lys Gln Lys Lys Ala
                 85                  90                  95

Ser Pro Arg Ala Arg Ala Val Ala Val Lys Gly Pro Val Gln Arg Tyr
            100                 105                 110

Pro Gly Asn Gln Thr Thr Cys
            115

<210> SEQ ID NO 25
<211> LENGTH: 150
<212> TYPE: PRT
<213> ORGANISM: Homo sapiens

<400> SEQUENCE: 25

Met Asn Leu Trp Leu Leu Ala Cys Leu Val Ala Gly Phe Leu Gly Ala
 1               5                  10                  15

Trp Ala Pro Ala Val His Thr Gln Gly Val Phe Glu Asp Cys Cys Leu
             20                  25                  30

Ala Tyr His Tyr Pro Ile Gly Trp Ala Val Leu Arg Arg Ala Trp Thr
         35                  40                  45

Tyr Arg Ile Gln Glu Val Ser Gly Ser Cys Asn Leu Pro Ala Ala Ile
 50                  55                  60

Phe Tyr Leu Pro Lys Arg His Arg Lys Val Cys Gly Asn Pro Lys Ser
 65                  70                  75                  80

Arg Glu Val Gln Arg Ala Met Lys Leu Leu Asp Ala Arg Asn Lys Val
                 85                  90                  95

Phe Ala Lys Leu His His Asn Thr Gln Thr Phe Gln Ala Gly Pro His
            100                 105                 110

Ala Val Lys Lys Leu Ser Ser Gly Asn Ser Lys Leu Ser Ser Ser Lys
            115                 120                 125

Phe Ser Asn Pro Ile Ser Ser Lys Arg Asn Val Ser Leu Leu Ile
            130                 135                 140

Ser Ala Asn Ser Gly Leu
145                 150

<210> SEQ ID NO 26
<211> LENGTH: 84
<212> TYPE: PRT
<213> ORGANISM: Homo sapiens

<400> SEQUENCE: 26

Met Asn Leu Trp Leu Leu Ala Cys Leu Val Ala Gly Phe Leu Gly Ala
 1               5                  10                  15

Trp Ala Pro Ala Val His Thr Gln Gly Val Phe Glu Asp Cys Cys Leu
             20                  25                  30

Ala Tyr His Tyr Pro Ile Gly Trp Ala Val Leu Arg Arg Ala Trp Thr
         35                  40                  45

Tyr Arg Ile Gln Glu Val Ser Gly Ser Cys Asn Leu Pro Ala Ala Ile
 50                  55                  60
```

```
Arg Pro Ser Cys Cys Lys Glu Val Glu Phe Trp Lys Leu Gln Val Ile
 65                  70                  75                  80

Ile Val Gln Val

<210> SEQ ID NO 27
<211> LENGTH: 84
<212> TYPE: PRT
<213> ORGANISM: Homo sapiens

<400> SEQUENCE: 27

Met Asn Leu Trp Leu Leu Ala Cys Leu Val Ala Gly Phe Leu Gly Ala
 1               5                  10                  15

Trp Ala Pro Ala Val His Thr Gln Gly Val Phe Glu Asp Cys Cys Leu
                20                  25                  30

Ala Tyr His Tyr Pro Ile Gly Trp Ala Val Leu Arg Arg Ala Trp Thr
            35                  40                  45

Tyr Arg Ile Gln Glu Val Ser Gly Ser Cys Asn Leu Pro Ala Ala Ile
        50                  55                  60

Arg Pro Ser Cys Cys Lys Glu Val Glu Phe Trp Lys Leu Gln Val Ile
 65                  70                  75                  80

Ile Ile Gln Val

<210> SEQ ID NO 28
<211> LENGTH: 94
<212> TYPE: PRT
<213> ORGANISM: Homo sapiens

<400> SEQUENCE: 28

Met Met Gly Leu Ser Leu Ala Ser Ala Val Leu Leu Ala Ser Leu Leu
 1               5                  10                  15

Ser Leu His Leu Gly Thr Ala Thr Arg Gly Ser Asp Ile Ser Lys Thr
                20                  25                  30

Cys Cys Phe Gln Tyr Ser His Lys Pro Leu Pro Trp Thr Trp Val Arg
            35                  40                  45

Ser Tyr Glu Phe Thr Ser Asn Ser Cys Ser Gln Arg Ala Val Ile Phe
        50                  55                  60

Thr Thr Lys Arg Gly Lys Lys Val Cys Thr His Pro Arg Lys Lys Trp
 65                  70                  75                  80

Val Gln Lys Tyr Ile Ser Leu Leu Lys Thr Pro Lys Gln Leu
                85                  90

<210> SEQ ID NO 29
<211> LENGTH: 112
<212> TYPE: PRT
<213> ORGANISM: Homo sapiens

<400> SEQUENCE: 29

Met Lys Gly Pro Pro Thr Phe Cys Ser Leu Leu Leu Ser Leu Leu
 1               5                  10                  15

Leu Ser Pro Asp Pro Thr Ala Ala Phe Leu Leu Pro Pro Ser Thr Ala
                20                  25                  30

Cys Cys Thr Gln Leu Tyr Arg Lys Pro Leu Ser Asp Lys Leu Leu Arg
            35                  40                  45

Lys Val Ile Gln Val Glu Leu Gln Glu Ala Asp Gly Asp Cys His Leu
        50                  55                  60

Gln Ala Phe Val Leu His Leu Ala Gln Arg Ser Ile Cys Ile His Pro
 65                  70                  75                  80
```

```
Gln Asn Pro Ser Leu Ser Gln Trp Phe Glu His Gln Glu Arg Lys Leu
             85                  90                  95

His Gly Thr Leu Pro Lys Leu Asn Phe Gly Met Leu Arg Lys Met Gly
            100                 105                 110
```

<210> SEQ ID NO 30
<211> LENGTH: 127
<212> TYPE: PRT
<213> ORGANISM: Homo sapiens

<400> SEQUENCE: 30

```
Met Gln Gln Arg Gly Leu Ala Ile Val Ala Leu Ala Val Cys Ala Ala
1               5                   10                  15

Leu His Ala Ser Glu Ala Ile Leu Pro Ile Ala Ser Ser Cys Cys Thr
                20                  25                  30

Glu Val Ser His His Ile Ser Arg Arg Leu Leu Glu Arg Val Asn Met
            35                  40                  45

Cys Arg Ile Gln Arg Ala Asp Gly Asp Cys Asp Leu Ala Ala Val Ile
50                  55                  60

Leu His Val Lys Arg Arg Arg Ile Cys Val Ser Pro His Asn His Thr
65                  70                  75                  80

Val Lys Gln Trp Met Lys Val Gln Ala Ala Lys Lys Asn Gly Lys Gly
                85                  90                  95

Asn Val Cys His Arg Lys Lys His His Gly Lys Arg Asn Ser Asn Arg
            100                 105                 110

Ala His Gln Gly Lys His Glu Thr Tyr Gly His Lys Thr Pro Tyr
        115                 120                 125
```

<210> SEQ ID NO 31
<211> LENGTH: 107
<212> TYPE: PRT
<213> ORGANISM: Homo sapiens

<400> SEQUENCE: 31

```
Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
                20                  25                  30

Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105
```

<210> SEQ ID NO 32
<211> LENGTH: 107
<212> TYPE: PRT
<213> ORGANISM: Homo sapiens

<400> SEQUENCE: 32

```
Met Ala Arg Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
```

```
            20                  25                  30

Ala Gly Ala Pro Leu Ala Thr Glu Leu Arg Cys Gln Cys Leu Gln Thr
            35                  40                  45

Leu Gln Gly Ile His Leu Lys Asn Ile Gln Ser Val Lys Val Lys Ser
        50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
            100                 105

<210> SEQ ID NO 33
<211> LENGTH: 107
<212> TYPE: PRT
<213> ORGANISM: Homo sapiens

<400> SEQUENCE: 33

Met Ala His Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
            20                  25                  30

Ala Gly Ala Ser Val Val Thr Glu Leu Arg Cys Gln Cys Leu Gln Thr
            35                  40                  45

Leu Gln Gly Ile His Leu Lys Asn Ile Gln Ser Val Asn Val Arg Ser
        50                  55                  60

Pro Gly Pro His Cys Ala Gln Thr Glu Val Ile Ala Thr Leu Lys Asn
65                  70                  75                  80

Gly Lys Lys Ala Cys Leu Asn Pro Ala Ser Pro Met Val Gln Lys Ile
                85                  90                  95

Ile Glu Lys Ile Leu Asn Lys Gly Ser Thr Asn
            100                 105

<210> SEQ ID NO 34
<211> LENGTH: 101
<212> TYPE: PRT
<213> ORGANISM: Homo sapiens

<400> SEQUENCE: 34

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
            35                  40                  45

Gln Val Arg Pro Arg His Ile Thr Ser Leu Glu Val Ile Lys Ala Gly
        50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100

<210> SEQ ID NO 35
<211> LENGTH: 114
<212> TYPE: PRT
```

<213> ORGANISM: Homo sapiens

<400> SEQUENCE: 35

Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Thr Gln Pro Gly
            20                  25                  30

Pro Ile Ala Ser Ala Gly Pro Ala Ala Val Leu Arg Glu Leu Arg
            35                  40                  45

Cys Val Cys Leu Gln Thr Thr Gln Gly Val His Pro Lys Met Ile Ser
        50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn

<210> SEQ ID NO 36
<211> LENGTH: 114
<212> TYPE: PRT
<213> ORGANISM: Homo sapiens

<400> SEQUENCE: 36

Met Ser Leu Pro Ser Ser Arg Ala Ala Arg Val Pro Gly Pro Ser Gly
1               5                   10                  15

Ser Leu Cys Ala Leu Leu Ala Leu Leu Leu Leu Thr Pro Pro Gly
            20                  25                  30

Pro Leu Ala Ser Ala Gly Pro Val Ser Ala Val Leu Thr Glu Leu Arg
            35                  40                  45

Cys Thr Cys Leu Arg Val Thr Leu Arg Val Asn Pro Lys Thr Ile Gly
        50                  55                  60

Lys Leu Gln Val Phe Pro Ala Gly Pro Gln Cys Ser Lys Val Glu Val
65                  70                  75                  80

Val Ala Ser Leu Lys Asn Gly Lys Gln Val Cys Leu Asp Pro Glu Ala
                85                  90                  95

Pro Phe Leu Lys Lys Val Ile Gln Lys Ile Leu Asp Ser Gly Asn Lys
            100                 105                 110

Lys Asn

<210> SEQ ID NO 37
<211> LENGTH: 128
<212> TYPE: PRT
<213> ORGANISM: Homo sapiens

<400> SEQUENCE: 37

Met Ser Leu Arg Leu Asp Thr Thr Pro Ser Cys Asn Ser Ala Arg Pro
1               5                   10                  15

Leu His Ala Leu Gln Val Leu Leu Leu Ser Leu Leu Leu Thr Ala
            20                  25                  30

Leu Ala Ser Ser Thr Lys Gly Gln Thr Lys Arg Asn Leu Ala Lys Gly
            35                  40                  45

Lys Glu Glu Ser Leu Asp Ser Asp Leu Tyr Ala Glu Leu Arg Cys Met
        50                  55                  60

Cys Ile Lys Thr Thr Ser Gly Ile His Pro Lys Asn Ile Gln Ser Leu

```
                 65                  70                  75                  80
Glu Val Ile Gly Lys Gly Thr His Cys Asn Gln Val Glu Val Ile Ala
                     85                  90                  95

Thr Leu Lys Asp Gly Arg Lys Ile Cys Leu Asp Pro Asp Ala Pro Arg
                100                 105                 110

Ile Lys Lys Ile Val Gln Lys Leu Ala Gly Asp Glu Ser Ala Asp
                115                 120                 125

<210> SEQ ID NO 38
<211> LENGTH: 99
<212> TYPE: PRT
<213> ORGANISM: Homo sapiens

<400> SEQUENCE: 38

Met Thr Ser Lys Leu Ala Val Ala Leu Leu Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
                35                  40                  45

Ile Lys Glu Leu Arg Val Ile Glu Ser Gly Pro His Cys Ala Asn Thr
                50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                    85                  90                  95

Glu Asn Ser

<210> SEQ ID NO 39
<211> LENGTH: 125
<212> TYPE: PRT
<213> ORGANISM: Homo sapiens

<400> SEQUENCE: 39

Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
                20                  25                  30

Cys Ile Ser Thr Asn Gln Gly Thr Ile His Leu Gln Ser Leu Lys Asp
                35                  40                  45

Leu Lys Gln Phe Ala Pro Ser Pro Ser Cys Glu Lys Ile Glu Ile Ile
                50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Gln Val Ser Gln Lys
                    85                  90                  95

Lys Lys Gln Lys Asn Gly Lys Lys His Gln Lys Lys Val Leu Lys
                100                 105                 110

Val Arg Lys Ser Gln Arg Ser Arg Gln Lys Lys Thr Thr
                115                 120                 125

<210> SEQ ID NO 40
<211> LENGTH: 98
<212> TYPE: PRT
<213> ORGANISM: Homo sapiens

<400> SEQUENCE: 40
```

```
Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 41
<211> LENGTH: 94
<212> TYPE: PRT
<213> ORGANISM: Homo sapiens

<400> SEQUENCE: 41

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90

<210> SEQ ID NO 42
<211> LENGTH: 93
<212> TYPE: PRT
<213> ORGANISM: Homo sapiens

<400> SEQUENCE: 42

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 43
<211> LENGTH: 109
<212> TYPE: PRT
<213> ORGANISM: Homo sapiens

<400> SEQUENCE: 43
```

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
                20                  25                  30

Cys Arg Cys Val Gln Glu Ser Ser Val Phe Ile Pro Arg Arg Phe Ile
            35                  40                  45

Asp Arg Ile Gln Ile Leu Pro Arg Gly Asn Gly Cys Pro Arg Lys Glu
        50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
                100                 105

<210> SEQ ID NO 44
<211> LENGTH: 273
<212> TYPE: PRT
<213> ORGANISM: Homo sapiens

<400> SEQUENCE: 44

Met Ser Gly Ser Gln Ser Glu Val Ala Pro Ser Pro Gln Ser Pro Arg
1               5                   10                  15

Ser Pro Glu Met Gly Arg Asp Leu Arg Pro Gly Ser Arg Val Leu Leu
                20                  25                  30

Leu Leu Leu Leu Leu Leu Leu Val Tyr Leu Thr Gln Pro Gly Asn Gly
            35                  40                  45

Asn Glu Gly Ser Val Thr Gly Ser Cys Tyr Cys Gly Lys Arg Ile Ser
        50                  55                  60

Ser Asp Ser Pro Pro Ser Val Gln Phe Met Asn Arg Leu Arg Lys His
65                  70                  75                  80

Leu Arg Ala Tyr His Arg Cys Leu Tyr Tyr Thr Arg Phe Gln Leu Leu
                85                  90                  95

Ser Trp Ser Val Cys Gly Gly Asn Lys Asp Pro Trp Val Gln Glu Leu
                100                 105                 110

Met Ser Cys Leu Asp Leu Lys Glu Cys Gly His Ala Tyr Ser Gly Ile
            115                 120                 125

Val Ala His Gln Lys His Leu Leu Pro Thr Ser Pro Pro Ile Ser Gln
        130                 135                 140

Ala Ser Glu Gly Ala Ser Ser Asp Ile His Thr Pro Ala Gln Met Leu
145                 150                 155                 160

Leu Ser Thr Leu Gln Ser Thr Gln Arg Pro Thr Leu Pro Val Gly Ser
                165                 170                 175

Leu Ser Ser Asp Lys Glu Leu Thr Arg Pro Asn Glu Thr Thr Ile His
                180                 185                 190

Thr Ala Gly His Ser Leu Ala Ala Gly Pro Glu Ala Gly Glu Asn Gln
            195                 200                 205

Lys Gln Pro Glu Lys Asn Ala Gly Pro Thr Ala Arg Thr Ser Ala Thr
        210                 215                 220

Val Pro Val Leu Cys Leu Leu Ala Ile Ile Phe Ile Leu Thr Ala Ala
225                 230                 235                 240

Leu Ser Tyr Val Leu Cys Lys Arg Arg Arg Gly Gln Ser Pro Gln Ser
                245                 250                 255

Ser Pro Asp Leu Pro Val His Tyr Ile Pro Val Ala Pro Asp Ser Asn

<210> SEQ ID NO 45
<211> LENGTH: 114
<212> TYPE: PRT
<213> ORGANISM: Homo sapiens

<400> SEQUENCE: 45

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 46
<211> LENGTH: 114
<212> TYPE: PRT
<213> ORGANISM: Homo sapiens

<400> SEQUENCE: 46

Met Arg Leu Leu Ile Leu Ala Leu Leu Gly Ile Cys Ser Leu Thr Ala
1               5                   10                  15

Tyr Ile Val Glu Gly Val Gly Ser Glu Val Ser His Arg Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly

<210> SEQ ID NO 47
<211> LENGTH: 397
<212> TYPE: PRT
<213> ORGANISM: Homo sapiens

<400> SEQUENCE: 47

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
                35                  40                  45

Ile His Tyr Gln Gln Asn Gln Ala Ser Cys Gly Lys Arg Ala Ile Ile
 50                  55                  60

Leu Glu Thr Arg Gln His Arg Leu Phe Cys Ala Asp Pro Lys Glu Gln
 65                  70                  75                  80

Trp Val Lys Asp Ala Met Gln His Leu Asp Arg Gln Ala Ala Leu
                 85                  90                  95

Thr Arg Asn Gly Gly Thr Phe Glu Lys Gln Ile Gly Glu Val Lys Pro
                100                 105                 110

Arg Thr Thr Pro Ala Ala Gly Gly Met Asp Glu Ser Val Val Leu Glu
                115                 120                 125

Pro Glu Ala Thr Gly Glu Ser Ser Ser Leu Glu Pro Thr Pro Ser Ser
            130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
                180                 185                 190

Thr Ala Ala Thr Trp Gln Ser Ser Ala Pro His Gln Pro Gly Pro Ser
                195                 200                 205

Leu Trp Ala Glu Ala Lys Thr Ser Glu Ala Pro Ser Thr Gln Asp Pro
210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
                260                 265                 270

Asp Ala Phe Gln Asp Trp Gly Pro Gly Ser Met Ala His Val Ser Val
                275                 280                 285

Val Pro Val Ser Ser Glu Gly Thr Pro Ser Arg Glu Pro Val Ala Ser
                290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
                340                 345                 350

Phe Cys Leu Gly Val Ala Met Phe Thr Tyr Gln Ser Leu Gln Gly Cys
                355                 360                 365

Pro Arg Lys Met Ala Gly Glu Met Ala Glu Gly Leu Arg Tyr Ile Pro
370                 375                 380

Arg Ser Cys Gly Ser Asn Ser Tyr Val Leu Val Pro Val
385                 390                 395

<210> SEQ ID NO 48
<211> LENGTH: 233
<212> TYPE: PRT
<213> ORGANISM: Homo sapiens

<400> SEQUENCE: 48

Ser Glu Pro Lys Ser Cys Asp Lys Thr His Thr Cys Pro Pro Cys Pro

```
            1               5                  10                 15
         Ala Pro Glu Leu Leu Gly Gly Pro Ser Val Phe Leu Phe Pro Pro Lys
                          20                 25                 30

Pro Lys Asp Thr Leu Met Ile Ser Arg Thr Pro Glu Val Thr Cys Val
                          35                 40                 45

Val Val Asp Val Ser His Glu Asp Pro Glu Val Lys Phe Asn Trp Tyr
         50                        55                 60

Val Asp Gly Val Glu Val His Asn Ala Lys Thr Lys Pro Arg Glu Glu
         65                        70                 75                 80

Gln Tyr Asn Ser Thr Tyr Arg Val Val Ser Val Leu Thr Val Leu His
                          85                 90                 95

Gln Asp Trp Leu Asn Gly Lys Glu Tyr Lys Cys Lys Val Ser Asn Lys
                          100                105                110

Ala Leu Pro Ala Pro Ile Glu Lys Thr Ile Ser Lys Ala Lys Gly Gln
                          115                120                125

Pro Arg Glu Pro Gln Val Tyr Thr Leu Pro Pro Ser Arg Asp Glu Leu
         130                       135                140

Thr Lys Asn Gln Val Ser Leu Thr Cys Leu Val Lys Gly Phe Tyr Pro
         145                       150                155                160

Ser Asp Ile Ala Val Glu Trp Glu Ser Asn Gly Gln Pro Glu Asn Asn
                          165                170                175

Tyr Lys Thr Thr Pro Pro Val Leu Asp Ser Asp Gly Ser Phe Phe Leu
                          180                185                190

Tyr Ser Lys Leu Thr Val Asp Lys Ser Arg Trp Gln Gln Gly Asn Val
                          195                200                205

Phe Ser Cys Ser Val Met His Glu Ala Leu His Asn His Tyr Thr Gln
         210                       215                220

Lys Ser Leu Ser Leu Ser Pro Gly Lys
         225                       230

<210> SEQ ID NO 49
<211> LENGTH: 228
<212> TYPE: PRT
<213> ORGANISM: Homo sapiens

<400> SEQUENCE: 49

Glu Arg Lys Cys Cys Val Glu Cys Pro Pro Cys Pro Ala Pro Pro Val
         1               5                  10                 15

Ala Gly Pro Ser Val Phe Leu Phe Pro Pro Lys Pro Lys Asp Thr Leu
                          20                 25                 30

Met Ile Ser Arg Thr Pro Glu Val Thr Cys Val Val Val Asp Val Ser
                          35                 40                 45

His Glu Asp Pro Glu Val Gln Phe Asn Trp Tyr Val Asp Gly Val Glu
         50                        55                 60

Val His Asn Ala Lys Thr Lys Pro Arg Glu Glu Gln Phe Asn Ser Thr
         65                        70                 75                 80

Phe Arg Val Val Ser Val Leu Thr Val Val His Gln Asp Trp Leu Asn
                          85                 90                 95

Gly Lys Glu Tyr Lys Cys Lys Val Ser Asn Lys Gly Leu Pro Ala Pro
                          100                105                110

Ile Glu Lys Thr Ile Ser Lys Thr Lys Gly Gln Pro Arg Glu Pro Gln
                          115                120                125

Val Tyr Thr Leu Pro Pro Ser Arg Glu Glu Met Thr Lys Asn Gln Val
         130                       135                140
```

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 50
<211> LENGTH: 279
<212> TYPE: PRT
<213> ORGANISM: Homo sapiens

<400> SEQUENCE: 50

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Phe
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275
```

<210> SEQ ID NO 51
<211> LENGTH: 229
<212> TYPE: PRT
<213> ORGANISM: Homo sapiens

<400> SEQUENCE: 51

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 52
<211> LENGTH: 303
<212> TYPE: PRT
<213> ORGANISM: Artificial Sequence
<220> FEATURE:
<223> OTHER INFORMATION: CCL2-IgG1Fc

<400> SEQUENCE: 52

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr Asp Lys Thr His
65                  70                  75                  80
```

```
Thr Cys Pro Pro Cys Pro Ala Pro Glu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
            115                 120                 125

Val Lys Phe Asn Trp Tyr Val Asp Gly Val Glu Val His Asn Ala Lys
    130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
    195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
    275                 280                 285

His Asn His Tyr Thr Gln Lys Ser Leu Ser Leu Ser Pro Gly Lys
    290                 295                 300

<210> SEQ ID NO 53
<211> LENGTH: 309
<212> TYPE: PRT
<213> ORGANISM: Artificial Sequence
<220> FEATURE:
<223> OTHER INFORMATION: CCL2(5-76)-IgG1Fc

<400> SEQUENCE: 53

Ala Leu Ser Leu Ala Leu Val Thr Asn Ser Ile Asn Ala Pro Val Thr
1               5                   10                  15

Cys Cys Tyr Asn Phe Thr Asn Arg Lys Ile Ser Val Gln Arg Leu Ala
            20                  25                  30

Ser Tyr Arg Arg Ile Thr Ser Ser Lys Cys Pro Lys Glu Ala Val Ile
        35                  40                  45

Phe Lys Thr Ile Val Ala Lys Glu Ile Cys Ala Asp Pro Lys Gln Lys
    50                  55                  60

Trp Val Gln Asp Ser Met Asp His Leu Asp Lys Gln Thr Gln Thr Pro
65                  70                  75                  80

Lys Thr Asp Lys Thr His Thr Cys Pro Pro Cys Pro Ala Pro Glu Leu
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140
```

```
Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
            165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
            195                 200                 205

Gln Val Tyr Thr Leu Pro Pro Ser Arg Glu Glu Met Thr Lys Asn Gln
            210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
            245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
            275                 280                 285

Val Met His Glu Ala Leu His Asn His Tyr Thr Gln Lys Ser Leu Ser
290                 295                 300

Leu Ser Pro Gly Lys
305

<210> SEQ ID NO 54
<211> LENGTH: 299
<212> TYPE: PRT
<213> ORGANISM: Artificial Sequence
<220> FEATURE:
<223> OTHER INFORMATION: CCL2(5-76K/H-A)-IgG1Fc

<400> SEQUENCE: 54

Ile Asn Ala Pro Val Thr Cys Cys Tyr Asn Phe Thr Asn Arg Lys Ile
1               5                   10                  15

Ser Val Gln Arg Leu Ala Ser Tyr Arg Arg Ile Thr Ser Ser Lys Cys
            20                  25                  30

Pro Lys Glu Ala Val Ile Phe Lys Thr Ile Val Ala Ala Glu Ile Cys
            35                  40                  45

Ala Asp Pro Ala Gln Ala Trp Val Gln Asp Ser Met Asp Ala Leu Asp
50                  55                  60

Ala Gln Thr Gln Thr Pro Ala Thr Asp Lys Thr His Thr Cys Pro Pro
65                  70                  75                  80

Cys Pro Ala Pro Glu Leu Leu Gly Gly Pro Ser Val Phe Leu Phe Pro
            85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
            115                 120                 125

Trp Tyr Val Asp Gly Val Glu Val His Asn Ala Lys Thr Lys Pro Arg
            130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
            165                 170                 175

Asn Lys Ala Leu Pro Ala Pro Ile Glu Lys Thr Ile Ser Lys Ala Lys
            180                 185                 190
```

```
Gly Gln Pro Arg Glu Pro Gln Val Tyr Thr Leu Pro Pro Ser Arg Glu
            195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
            275                 280                 285

Thr Gln Lys Ser Leu Ser Leu Ser Pro Gly Lys
    290                 295

<210> SEQ ID NO 55
<211> LENGTH: 289
<212> TYPE: PRT
<213> ORGANISM: Artificial Sequence
<220> FEATURE:
<223> OTHER INFORMATION: CCL7-IgG1Fc

<400> SEQUENCE: 55

Phe Ile Asn Lys Lys Ile Pro Lys Gln Arg Leu Glu Ser Tyr Arg Arg
1               5                   10                  15

Thr Thr Ser Ser His Cys Pro Arg Glu Ala Val Ile Phe Lys Thr Lys
            20                  25                  30

Leu Asp Lys Glu Ile Cys Ala Asp Pro Thr Gln Lys Trp Val Gln Asp
        35                  40                  45

Phe Met Lys His Leu Asp Lys Lys Thr Gln Thr Pro Lys Leu Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Glu Glu Met Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255
```

```
Ser Arg Trp Gln Gln Gly Asn Val Phe Ser Cys Ser Val Met His Glu
        260                 265                 270

Ala Leu His Asn His Tyr Thr Gln Lys Ser Leu Ser Leu Ser Pro Gly
        275                 280                 285

Lys

<210> SEQ ID NO 56
<211> LENGTH: 293
<212> TYPE: PRT
<213> ORGANISM: Artificial Sequence
<220> FEATURE:
<223> OTHER INFORMATION: CCL7(5-76)-IgGFc

<400> SEQUENCE: 56

Cys Cys Tyr Arg Phe Ile Asn Lys Lys Ile Pro Lys Gln Arg Leu Glu
1               5                   10                  15

Ser Tyr Arg Arg Thr Thr Ser Ser His Cys Pro Arg Glu Ala Val Ile
            20                  25                  30

Phe Lys Thr Lys Leu Asp Lys Glu Ile Cys Ala Asp Pro Thr Gln Lys
        35                  40                  45

Trp Val Gln Asp Phe Met Lys His Leu Asp Lys Lys Thr Gln Thr Pro
    50                  55                  60

Lys Leu Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
    130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Glu Glu Met Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
            290

<210> SEQ ID NO 57
<211> LENGTH: 289
<212> TYPE: PRT
```

<213> ORGANISM: Artificial Sequence
<220> FEATURE:
<223> OTHER INFORMATION: CCL7(5-76K/H-A)-IgGFc

<400> SEQUENCE: 57

Phe Ile Asn Lys Lys Ile Pro Lys Gln Arg Leu Glu Ser Tyr Arg Arg
1               5                   10                  15

Thr Thr Ser Ser His Cys Pro Arg Glu Ala Val Ile Phe Ala Thr Ala
            20                  25                  30

Leu Asp Ala Glu Ile Cys Ala Asp Pro Thr Gln Ala Trp Val Gln Asp
        35                  40                  45

Phe Met Ala Ala Leu Asp Ala Ala Thr Gln Thr Pro Ala Leu Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Glu Glu Met Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
        275                 280                 285

Lys

<210> SEQ ID NO 58
<211> LENGTH: 303
<212> TYPE: PRT
<213> ORGANISM: Artificial Sequence
<220> FEATURE:
<223> OTHER INFORMATION: CCL8-IgG1Fc

<400> SEQUENCE: 58

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly

```
            35                  40                  45
Lys Glu Val Cys Ala Asp Pro Lys Glu Arg Trp Val Arg Asp Ser Met
 50                  55                  60

Lys His Leu Asp Gln Ile Phe Gln Asn Leu Lys Pro Asp Lys Thr His
 65                  70                  75                  80

Thr Cys Pro Pro Cys Pro Ala Pro Glu Leu Gly Gly Pro Ser Val
                 85                  90                  95

Phe Leu Phe Pro Pro Lys Pro Lys Asp Thr Leu Met Ile Ser Arg Thr
                100                 105                 110

Pro Glu Val Thr Cys Val Val Val Asp Val Ser His Glu Asp Pro Glu
                115                 120                 125

Val Lys Phe Asn Trp Tyr Val Asp Gly Val Glu Val His Asn Ala Lys
            130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
                180                 185                 190

Ser Lys Ala Lys Gly Gln Pro Arg Glu Pro Gln Val Tyr Thr Leu Pro
            195                 200                 205

Pro Ser Arg Glu Glu Met Thr Lys Asn Gln Val Ser Leu Thr Cys Leu
210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
                260                 265                 270

Trp Gln Gln Gly Asn Val Phe Ser Cys Ser Val Met His Glu Ala Leu
            275                 280                 285

His Asn His Tyr Thr Gln Lys Ser Leu Ser Leu Ser Pro Gly Lys
        290                 295                 300

<210> SEQ ID NO 59
<211> LENGTH: 299
<212> TYPE: PRT
<213> ORGANISM: Artificial Sequence
<220> FEATURE:
<223> OTHER INFORMATION: CCL8(5-76)-IgG1Fc

<400> SEQUENCE: 59

Val Ser Ile Pro Ile Thr Cys Cys Phe Asn Val Ile Asn Arg Lys Ile
 1               5                  10                  15

Pro Ile Gln Arg Leu Glu Ser Tyr Thr Arg Ile Thr Asn Ile Gln Cys
                20                  25                  30

Pro Lys Glu Ala Val Ile Phe Lys Thr Lys Arg Gly Lys Glu Val Cys
            35                  40                  45

Ala Asp Pro Lys Glu Arg Trp Val Arg Asp Ser Met Lys His Leu Asp
 50                  55                  60

Gln Ile Phe Gln Asn Leu Lys Pro Asp Lys Thr His Thr Cys Pro Pro
 65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
```

```
                    100                 105                 110
        Cys Val Val Val Asp Val Ser His Glu Asp Pro Glu Val Lys Phe Asn
                        115                 120                 125

Trp Tyr Val Asp Gly Val Glu Val His Asn Ala Lys Thr Lys Pro Arg
                        130                 135                 140

Glu Glu Gln Tyr Asn Ser Thr Tyr Arg Val Val Ser Val Leu Thr Val
        145                 150                 155                 160

Leu His Gln Asp Trp Leu Asn Gly Lys Glu Tyr Lys Cys Lys Val Ser
                            165                 170                 175

Asn Lys Ala Leu Pro Ala Pro Ile Glu Lys Thr Ile Ser Lys Ala Lys
                        180                 185                 190

Gly Gln Pro Arg Glu Pro Gln Val Tyr Thr Leu Pro Pro Ser Arg Glu
                        195                 200                 205

Glu Met Thr Lys Asn Gln Val Ser Leu Thr Cys Leu Val Lys Gly Phe
                210                 215                 220

Tyr Pro Ser Asp Ile Ala Val Glu Trp Glu Ser Asn Gly Gln Pro Glu
        225                 230                 235                 240

Asn Asn Tyr Lys Thr Thr Pro Pro Val Leu Asp Ser Asp Gly Ser Phe
                            245                 250                 255

Phe Leu Tyr Ser Lys Leu Thr Val Asp Lys Ser Arg Trp Gln Gln Gly
                        260                 265                 270

Asn Val Phe Ser Cys Ser Val Met His Glu Ala Leu His Asn His Tyr
                        275                 280                 285

Thr Gln Lys Ser Leu Ser Leu Ser Pro Gly Lys
            290                 295

<210> SEQ ID NO 60
<211> LENGTH: 265
<212> TYPE: PRT
<213> ORGANISM: Artificial Sequence
<220> FEATURE:
<223> OTHER INFORMATION: CCL8(5-76K/H-A)-IgG1Fc

<400> SEQUENCE: 60

Val Ser Ile Pro Ile Thr Cys Cys Phe Asn Val Ile Asn Arg Lys Ile
        1               5                   10                  15

Pro Ile Gln Arg Leu Glu Ser Tyr Thr Arg Ile Thr Asn Ile Gln Cys
                        20                  25                  30

Pro Lys Glu Ala Val Ile Phe Lys Thr Ala Ala Gly Ala Glu Val Cys
                    35                  40                  45

Ala Asp Pro Ala Glu Ala Trp Val Ala Asp Ser Met Ala Ala Leu Asp
        50                  55                  60

Gln Ile Phe Gln Asn Leu Ala Pro Asp Lys Thr His Thr Cys Pro Pro
        65                  70                  75                  80

Cys Pro Ala Pro Glu Leu Leu Gly Gly Pro Ser Val Phe Leu Phe Pro
                        85                  90                  95

Pro Lys Pro Lys Asp Thr Leu Met Ile Ser Arg Thr Pro Glu Val Thr
                        100                 105                 110

Cys Val Val Val Asp Val Ser His Glu Asp Pro Glu Val Lys Phe Asn
                        115                 120                 125

Trp Tyr Val Asp Gly Val Glu Val His Asn Ala Lys Thr Lys Pro Arg
                        130                 135                 140

Glu Glu Gln Tyr Asn Ser Thr Tyr Arg Val Val Ser Val Leu Thr Val
        145                 150                 155                 160

Leu His Gln Asp Trp Leu Asn Gly Lys Glu Tyr Lys Cys Lys Val Ser
```

```
                  165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Lys Ser Leu Ser Leu Ser Pro Gly Lys
            260                 265

<210> SEQ ID NO 61
<211> LENGTH: 302
<212> TYPE: PRT
<213> ORGANISM: Artificial Sequence
<220> FEATURE:
<223> OTHER INFORMATION: CCL13-IgG1Fc

<400> SEQUENCE: 61

Gln Pro Asp Ala Leu Asn Val Pro Ser Thr Cys Cys Phe Thr Phe Ser
1               5                   10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
        35                  40                  45

Glu Ile Cys Ala Asp Pro Lys Glu Lys Trp Val Gln Asn Tyr Met Lys
    50                  55                  60

His Leu Gly Arg Lys Ala His Thr Leu Lys Thr Asp Lys Thr His Thr
65                  70                  75                  80

Cys Pro Pro Cys Pro Ala Pro Glu Leu Leu Gly Gly Pro Ser Val Phe
                85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
        115                 120                 125

Lys Phe Asn Trp Tyr Val Asp Gly Val Glu Val His Asn Ala Lys Thr
    130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
        195                 200                 205

Ser Arg Glu Glu Met Thr Lys Asn Gln Val Ser Leu Thr Cys Leu Val
    210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
```

```
                        260                 265                 270
Gln Gln Gly Asn Val Phe Ser Cys Ser Val Met His Glu Ala Leu His
            275                 280                 285
Asn His Tyr Thr Gln Lys Ser Leu Ser Leu Ser Pro Gly Lys
            290                 295                 300

<210> SEQ ID NO 62
<211> LENGTH: 298
<212> TYPE: PRT
<213> ORGANISM: Artificial Sequence
<220> FEATURE:
<223> OTHER INFORMATION: CCL13(5-75)-IgG1Fc

<400> SEQUENCE: 62

Leu Asn Val Pro Ser Thr Cys Cys Phe Thr Phe Ser Ser Lys Lys Ile
1               5                   10                  15
Ser Leu Gln Arg Leu Lys Ser Tyr Val Ile Thr Thr Ser Arg Cys Pro
            20                  25                  30
Gln Lys Ala Val Ile Phe Arg Thr Lys Leu Gly Lys Glu Ile Cys Ala
        35                  40                  45
Asp Pro Lys Glu Lys Trp Val Gln Asn Tyr Met Lys His Leu Gly Arg
    50                  55                  60
Lys Ala His Thr Leu Lys Thr Asp Lys Thr His Thr Cys Pro Pro Cys
65                  70                  75                  80
Pro Ala Pro Glu Leu Leu Gly Gly Pro Ser Val Phe Leu Phe Pro Pro
                85                  90                  95
Lys Pro Lys Asp Thr Leu Met Ile Ser Arg Thr Pro Glu Val Thr Cys
            100                 105                 110
Val Val Val Asp Val Ser His Glu Asp Pro Glu Val Lys Phe Asn Trp
        115                 120                 125
Tyr Val Asp Gly Val Glu Val His Asn Ala Lys Thr Lys Pro Arg Glu
    130                 135                 140
Glu Gln Tyr Asn Ser Thr Tyr Arg Val Val Ser Val Leu Thr Val Leu
145                 150                 155                 160
His Gln Asp Trp Leu Asn Gly Lys Glu Tyr Lys Cys Lys Val Ser Asn
                165                 170                 175
Lys Ala Leu Pro Ala Pro Ile Glu Lys Thr Ile Ser Lys Ala Lys Gly
            180                 185                 190
Gln Pro Arg Glu Pro Gln Val Tyr Thr Leu Pro Pro Ser Arg Glu Glu
        195                 200                 205
Met Thr Lys Asn Gln Val Ser Leu Thr Cys Leu Val Lys Gly Phe Tyr
    210                 215                 220
Pro Ser Asp Ile Ala Val Glu Trp Glu Ser Asn Gly Gln Pro Glu Asn
225                 230                 235                 240
Asn Tyr Lys Thr Thr Pro Pro Val Leu Asp Ser Asp Gly Ser Phe Phe
                245                 250                 255
Leu Tyr Ser Lys Leu Thr Val Asp Lys Ser Arg Trp Gln Gln Gly Asn
            260                 265                 270
Val Phe Ser Cys Ser Val Met His Glu Ala Leu His Asn His Tyr Thr
        275                 280                 285
Gln Lys Ser Leu Ser Leu Ser Pro Gly Lys
    290                 295

<210> SEQ ID NO 63
<211> LENGTH: 298
<212> TYPE: PRT
```

<213> ORGANISM: Artificial Sequence
<220> FEATURE:
<223> OTHER INFORMATION: CCL13(5-75K/H-A)-IgG1Fc

<400> SEQUENCE: 63

```
Leu Asn Val Pro Ser Thr Cys Cys Phe Thr Phe Ser Ser Lys Lys Ile
1               5                   10                  15

Ser Leu Gln Arg Leu Lys Ser Tyr Val Ile Thr Thr Ser Arg Cys Pro
            20                  25                  30

Gln Lys Ala Val Ile Phe Arg Thr Ala Leu Gly Ala Glu Ile Cys Ala
        35                  40                  45

Asp Pro Ala Glu Ala Trp Val Gln Asn Tyr Met Ala Ala Leu Gly Arg
    50                  55                  60

Lys Ala Ala Thr Leu Ala Thr Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295
```

<210> SEQ ID NO 64
<211> LENGTH: 345
<212> TYPE: PRT
<213> ORGANISM: Artificial Sequence
<220> FEATURE:
<223> OTHER INFORMATION: CCL25-IgG1Fc

<400> SEQUENCE: 64

```
Thr Gln Gly Val Phe Glu Asp Cys Cys Leu Ala Tyr His Tyr Pro Ile
1               5                   10                  15

Gly Trp Ala Val Leu Arg Arg Ala Trp Thr Tyr Arg Ile Gln Glu Val
            20                  25                  30
```

Ser Gly Ser Cys Asn Leu Pro Ala Ala Ile Phe Tyr Leu Pro Lys Arg
            35                  40                  45

His Arg Lys Val Cys Gly Asn Pro Lys Ser Arg Glu Val Gln Arg Ala
 50                  55                  60

Met Lys Leu Leu Asp Ala Arg Asn Lys Val Phe Ala Lys Leu Arg His
65                  70                  75                  80

Asn Thr Gln Thr Phe Gln Gly Pro His Ala Val Lys Lys Leu Ser Ser
                85                  90                  95

Gly Asn Ser Lys Leu Ser Ser Lys Phe Ser Asn Pro Ile Ser Ser
            100                 105                 110

Ser Lys Arg Asn Val Ser Asp Lys Thr His Thr Cys Pro Pro Cys Pro
            115                 120                 125

Ala Pro Glu Leu Leu Gly Gly Pro Ser Val Phe Leu Phe Pro Pro Lys
            130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
            195                 200                 205

Gln Asp Trp Leu Asn Gly Lys Glu Tyr Lys Cys Lys Val Ser Asn Lys
            210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
            275                 280                 285

Tyr Lys Thr Thr Pro Pro Val Leu Asp Ser Asp Gly Ser Phe Phe Leu
            290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 65
<211> LENGTH: 342
<212> TYPE: PRT
<213> ORGANISM: Artificial Sequence
<220> FEATURE:
<223> OTHER INFORMATION: CCL25(4-127)-IgG1Fc

<400> SEQUENCE: 65

Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
                20                  25                  30

Cys Asn Leu Pro Ala Ala Ile Phe Tyr Leu Pro Lys Arg His Arg Lys
            35                  40                  45

Val Cys Gly Asn Pro Lys Ser Arg Glu Val Gln Arg Ala Met Lys Leu
    50                  55                  60

Leu Asp Ala Arg Asn Lys Val Phe Ala Lys Leu Arg His Asn Thr Gln
65                  70                  75                  80

Thr Phe Gln Gly Pro His Ala Val Lys Lys Leu Ser Ser Gly Asn Ser
                85                  90                  95

Lys Leu Ser Ser Ser Lys Phe Ser Asn Pro Ile Ser Ser Ser Lys Arg
                100                 105                 110

Asn Val Ser Asp Lys Thr His Thr Cys Pro Pro Cys Pro Ala Pro Glu
            115                 120                 125

Leu Leu Gly Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 66
<211> LENGTH: 342
<212> TYPE: PRT
<213> ORGANISM: Artificial Sequence
<220> FEATURE:
<223> OTHER INFORMATION: CCL25(4-127K/H-A)-IgG1Fc

<400> SEQUENCE: 66

Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
            20                  25                  30

Cys Asn Leu Pro Ala Ala Ile Phe Tyr Leu Pro Ala Ala Ala Ala Ala
        35                  40                  45

Val Cys Gly Asn Pro Ala Ser Ala Glu Val Gln Ala Ala Met Ala Leu
    50                  55                  60

```
Leu Asp Ala Ala Asn Ala Val Phe Ala Ala Leu Ala Ala Asn Thr Gln
 65                  70                  75                  80

Thr Phe Gln Gly Pro Ala Ala Val Ala Ala Leu Ser Ser Gly Asn Ser
                 85                  90                  95

Ala Leu Ser Ser Ser Ala Phe Ser Asn Pro Ile Ser Ser Ser Ala Ala
            100                 105                 110

Asn Val Ser Asp Lys Thr His Thr Cys Pro Pro Cys Pro Ala Pro Glu
            115                 120                 125

Leu Leu Gly Gly Pro Ser Val Phe Leu Phe Pro Pro Lys Pro Lys Asp
        130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 67
<211> LENGTH: 300
<212> TYPE: PRT
<213> ORGANISM: Artificial Sequence
<220> FEATURE:
<223> OTHER INFORMATION: CXCL11-IgG1Fc

<400> SEQUENCE: 67

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Gln Ala Arg Leu Ile
    50                  55                  60

Ile Lys Lys Val Glu Arg Lys Asn Phe Asp Lys Thr His Thr Cys Pro
65                  70                  75                  80
```

```
Pro Cys Pro Ala Pro Glu Leu Leu Gly Gly Pro Ser Val Phe Leu Phe
            85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
            115                 120                 125

Asn Trp Tyr Val Asp Gly Val Glu Val His Asn Ala Lys Thr Lys Pro
            130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
            165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
            195                 200                 205

Glu Glu Met Thr Lys Asn Gln Val Ser Leu Thr Cys Leu Val Lys Gly
            210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
            245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
            275                 280                 285

Tyr Thr Gln Lys Ser Leu Ser Leu Ser Pro Gly Lys
            290                 295                 300

<210> SEQ ID NO 68
<211> LENGTH: 297
<212> TYPE: PRT
<213> ORGANISM: Artificial Sequence
<220> FEATURE:
<223> OTHER INFORMATION: CXCL11(4-73)-IgG1Fc

<400> SEQUENCE: 68

Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30

Cys Asp Lys Ile Glu Val Ile Ile Thr Leu Lys Glu Asn Lys Gly Gln
            35                  40                  45

Arg Cys Leu Asn Pro Lys Ser Lys Gln Ala Arg Leu Ile Ile Lys Lys
50                  55                  60

Val Glu Arg Lys Asn Phe Asp Lys Thr His Thr Cys Pro Pro Cys Pro
65                  70                  75                  80

Ala Pro Glu Leu Leu Gly Gly Pro Ser Val Phe Leu Phe Pro Pro Lys
            85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
            115                 120                 125

Val Asp Gly Val Glu Val His Asn Ala Lys Thr Lys Pro Arg Glu Glu
            130                 135                 140
```

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 69
<211> LENGTH: 297
<212> TYPE: PRT
<213> ORGANISM: Artificial Sequence
<220> FEATURE:
<223> OTHER INFORMATION: CXCL11(4-73K/H-A)-IgG1Fc

<400> SEQUENCE: 69

Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
            20                  25                  30

Cys Asp Lys Ile Glu Val Ile Ile Thr Leu Ala Glu Asn Ala Gly Gln
        35                  40                  45

Ala Cys Leu Asn Pro Ala Ser Ala Gln Ala Ala Leu Ile Ile Ala Ala
    50                  55                  60

Val Glu Ala Ala Asn Phe Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Glu Glu Met
        195                 200                 205

```
Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295
```

<210> SEQ ID NO 70
<211> LENGTH: 297
<212> TYPE: PRT
<213> ORGANISM: Artificial Sequence
<220> FEATURE:
<223> OTHER INFORMATION: CXCL11-IgG4Fc

<400> SEQUENCE: 70

```
Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe Pro Pro Cys Pro Ser Cys Pro
65                  70                  75                  80

Ala Pro Glu Phe Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser Gln Glu Asp Pro Glu Val Gln Phe Asn Trp Tyr
        115                 120                 125

Val Asp Gly Val Glu Val His Asn Ala Lys Thr Lys Pro Arg Glu Glu
    130                 135                 140

Gln Phe Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Gly Leu Pro Ser Ser Ile Glu Lys Thr Ile Ser Lys Ala Lys Gly Gln
            180                 185                 190

Pro Arg Glu Pro Gln Val Tyr Thr Leu Pro Pro Ser Gln Glu Glu Met
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Arg Leu Thr Val Asp Lys Ser Arg Trp Gln Glu Gly Asn Val
            260                 265                 270
```

Phe Ser Cys Ser Val Met His Glu Ala Leu His Asn His Tyr Thr Gln
            275                 280                 285

Lys Ser Leu Ser Leu Ser Pro Gly Lys
    290                 295

<210> SEQ ID NO 71
<211> LENGTH: 294
<212> TYPE: PRT
<213> ORGANISM: Artificial Sequence
<220> FEATURE:
<223> OTHER INFORMATION: CXCL11(4-73)-IgG4Fc

<400> SEQUENCE: 71

Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30

Cys Asp Lys Ile Glu Val Ile Ile Thr Leu Lys Glu Asn Lys Gly Gln
        35                  40                  45

Arg Cys Leu Asn Pro Lys Ser Lys Gln Ala Arg Leu Ile Ile Lys Lys
    50                  55                  60

Val Glu Arg Lys Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
            180                 185                 190

Pro Gln Val Tyr Thr Leu Pro Pro Ser Gln Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290

<210> SEQ ID NO 72
<211> LENGTH: 294
<212> TYPE: PRT
<213> ORGANISM: Artificial Sequence
<220> FEATURE:

<223> OTHER INFORMATION: CXCL11(4-73K/H-A)-IgG4Fc

<400> SEQUENCE: 72

```
Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
            20                  25                  30

Cys Asp Lys Ile Glu Val Ile Ile Thr Leu Ala Glu Asn Ala Gly Gln
        35                  40                  45

Ala Cys Leu Asn Pro Ala Ser Ala Gln Ala Ala Leu Ile Ile Ala Ala
    50                  55                  60

Val Glu Ala Ala Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
            180                 185                 190

Pro Gln Val Tyr Thr Leu Pro Pro Ser Gln Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
        290
```

<210> SEQ ID NO 73
<211> LENGTH: 314
<212> TYPE: PRT
<213> ORGANISM: Artificial Sequence
<220> FEATURE:
<223> OTHER INFORMATION: CXCL13-IgG1Fc

<400> SEQUENCE: 73

```
Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
        35                  40                  45
```

-continued

```
Asn Lys Ser Ile Val Cys Val Asp Pro Gln Ala Glu Trp Ile Gln Arg
 50                  55                  60

Met Met Glu Val Leu Arg Lys Arg Ser Ser Thr Leu Pro Val Pro
 65                  70                  75                  80

Val Phe Lys Arg Lys Ile Pro Asp Lys Thr His Thr Cys Pro Pro Cys
                 85                  90                  95

Pro Ala Pro Glu Leu Leu Gly Gly Pro Ser Val Phe Leu Phe Pro Pro
                100                 105                 110

Lys Pro Lys Asp Thr Leu Met Ile Ser Arg Thr Pro Glu Val Thr Cys
            115                 120                 125

Val Val Val Asp Val Ser His Glu Asp Pro Glu Val Lys Phe Asn Trp
130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
            180                 185                 190

Lys Ala Leu Pro Ala Pro Ile Glu Lys Thr Ile Ser Lys Ala Lys Gly
        195                 200                 205

Gln Pro Arg Glu Pro Gln Val Tyr Thr Leu Pro Pro Ser Arg Glu Glu
    210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310

<210> SEQ ID NO 74
<211> LENGTH: 312
<212> TYPE: PRT
<213> ORGANISM: Artificial Sequence
<220> FEATURE:
<223> OTHER INFORMATION: CXCL13(3-87)-IgG1Fc

<400> SEQUENCE: 74

Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
                20                  25                  30

Gly Asn Gly Cys Pro Arg Lys Glu Ile Ile Val Trp Lys Lys Asn Lys
            35                  40                  45

Ser Ile Val Cys Val Asp Pro Gln Ala Glu Trp Ile Gln Arg Met Met
        50                  55                  60

Glu Val Leu Arg Lys Arg Ser Ser Thr Leu Pro Val Pro Val Phe
65                  70                  75                  80

Lys Arg Lys Ile Pro Asp Lys Thr His Thr Cys Pro Pro Cys Pro Ala
                85                  90                  95
```

```
Pro Glu Leu Leu Gly Gly Pro Ser Val Phe Leu Phe Pro Pro Lys Pro
            100                 105                 110

Lys Asp Thr Leu Met Ile Ser Arg Thr Pro Glu Val Thr Cys Val Val
            115                 120                 125

Val Asp Val Ser His Glu Asp Pro Glu Val Lys Phe Asn Trp Tyr Val
            130                 135                 140

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
            180                 185                 190

Leu Pro Ala Pro Ile Glu Lys Thr Ile Ser Lys Ala Lys Gly Gln Pro
            195                 200                 205

Arg Glu Pro Gln Val Tyr Thr Leu Pro Pro Ser Arg Glu Glu Met Thr
210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
            275                 280                 285

Ser Cys Ser Val Met His Glu Ala Leu His Asn His Tyr Thr Gln Lys
            290                 295                 300

Ser Leu Ser Leu Ser Pro Gly Lys
305                 310

<210> SEQ ID NO 75
<211> LENGTH: 312
<212> TYPE: PRT
<213> ORGANISM: Artificial Sequence
<220> FEATURE:
<223> OTHER INFORMATION: CXCL13(3-87K/H-A)-IgG1Fc

<400> SEQUENCE: 75

Glu Val Tyr Tyr Thr Ser Leu Arg Cys Arg Cys Val Gln Glu Ser Ser
1               5                   10                  15

Val Phe Ile Pro Arg Arg Phe Ile Asp Ala Ile Gln Ile Leu Pro Arg
            20                  25                  30

Gly Asn Gly Cys Pro Arg Lys Glu Ile Ile Val Trp Ala Ala Asn Ala
        35                  40                  45

Ser Ile Val Cys Val Asp Pro Gln Ala Glu Trp Ile Gln Ala Met Met
    50                  55                  60

Glu Val Leu Ala Ala Ala Ser Ser Ser Thr Leu Pro Val Pro Val Phe
65                  70                  75                  80

Ala Ala Ala Ile Pro Asp Lys Thr His Thr Cys Pro Pro Cys Pro Ala
                85                  90                  95

Pro Glu Leu Leu Gly Gly Pro Ser Val Phe Leu Phe Pro Pro Lys Pro
            100                 105                 110

Lys Asp Thr Leu Met Ile Ser Arg Thr Pro Glu Val Thr Cys Val Val
            115                 120                 125

Val Asp Val Ser His Glu Asp Pro Glu Val Lys Phe Asn Trp Tyr Val
            130                 135                 140
```

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
            180                 185                 190

Leu Pro Ala Pro Ile Glu Lys Thr Ile Ser Lys Ala Lys Gly Gln Pro
        195                 200                 205

Arg Glu Pro Gln Val Tyr Thr Leu Pro Pro Ser Arg Glu Glu Met Thr
    210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
    290                 295                 300

Ser Leu Ser Leu Ser Pro Gly Lys
305                 310

<210> SEQ ID NO 76
<211> LENGTH: 311
<212> TYPE: PRT
<213> ORGANISM: Artificial Sequence
<220> FEATURE:
<223> OTHER INFORMATION: CXCL13-IgG4Fc

<400> SEQUENCE: 76

Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30

Pro Arg Gly Asn Gly Cys Pro Arg Lys Glu Ile Ile Val Trp Lys Lys
        35                  40                  45

Asn Lys Ser Ile Val Cys Val Asp Pro Gln Ala Glu Trp Ile Gln Arg
    50                  55                  60

Met Met Glu Val Leu Arg Lys Arg Ser Ser Ser Thr Leu Pro Val Pro
65                  70                  75                  80

Val Phe Lys Arg Lys Ile Pro Pro Pro Cys Pro Ser Cys Pro Ala Pro
                85                  90                  95

Glu Phe Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Asp Val Ser Gln Glu Asp Pro Glu Val Gln Phe Asn Trp Tyr Val Asp
    130                 135                 140

Gly Val Glu Val His Asn Ala Lys Thr Lys Pro Arg Glu Glu Gln Phe
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Gly Leu
            180                 185                 190

Pro Ser Ser Ile Glu Lys Thr Ile Ser Lys Ala Lys Gly Gln Pro Arg
            195                 200                 205

Glu Pro Gln Val Tyr Thr Leu Pro Pro Ser Gln Glu Glu Met Thr Lys
210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
            245                 250                 255

Thr Thr Pro Pro Val Leu Asp Ser Asp Gly Ser Phe Phe Leu Tyr Ser
            260                 265                 270

Arg Leu Thr Val Asp Lys Ser Arg Trp Gln Glu Gly Asn Val Phe Ser
            275                 280                 285

Cys Ser Val Met His Glu Ala Leu His Asn His Tyr Thr Gln Lys Ser
            290                 295                 300

Leu Ser Leu Ser Pro Gly Lys
305                 310

<210> SEQ ID NO 77
<211> LENGTH: 309
<212> TYPE: PRT
<213> ORGANISM: Artificial Sequence
<220> FEATURE:
<223> OTHER INFORMATION: CXCL13(3-87)-IgG4Fc

<400> SEQUENCE: 77

Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
            20                  25                  30

Gly Asn Gly Cys Pro Arg Lys Glu Ile Ile Val Trp Lys Lys Asn Lys
        35                  40                  45

Ser Ile Val Cys Val Asp Pro Gln Ala Glu Trp Ile Gln Arg Met Met
50                  55                  60

Glu Val Leu Arg Lys Arg Ser Ser Ser Thr Leu Pro Val Pro Val Phe
65                  70                  75                  80

Lys Arg Lys Ile Pro Pro Cys Pro Ser Cys Pro Ala Pro Glu Phe
            85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser Gln Glu Asp Pro Glu Val Gln Phe Asn Trp Tyr Val Asp Gly Val
130                 135                 140

Glu Val His Asn Ala Lys Thr Lys Pro Arg Glu Gln Phe Asn Ser
145                 150                 155                 160

Thr Tyr Arg Val Val Ser Val Leu Thr Val Leu His Gln Asp Trp Leu
            165                 170                 175

Asn Gly Lys Glu Tyr Lys Cys Lys Val Ser Asn Lys Gly Leu Pro Ser
            180                 185                 190

Ser Ile Glu Lys Thr Ile Ser Lys Ala Lys Gly Gln Pro Arg Glu Pro
        195                 200                 205

Gln Val Tyr Thr Leu Pro Pro Ser Gln Glu Glu Met Thr Lys Asn Gln
210                 215                 220

Val Ser Leu Thr Cys Leu Val Lys Gly Phe Tyr Pro Ser Asp Ile Ala
225                 230                 235                 240

```
Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Arg Leu
            260                 265                 270

Thr Val Asp Lys Ser Arg Trp Gln Glu Gly Asn Val Phe Ser Cys Ser
        275                 280                 285

Val Met His Glu Ala Leu His Asn His Tyr Thr Gln Lys Ser Leu Ser
290                 295                 300

Leu Ser Pro Gly Lys
305

<210> SEQ ID NO 78
<211> LENGTH: 309
<212> TYPE: PRT
<213> ORGANISM: Artificial Sequence
<220> FEATURE:
<223> OTHER INFORMATION: CXCL13(3-87K/H-A)-IgG4Fc

<400> SEQUENCE: 78

Glu Val Tyr Tyr Thr Ser Leu Arg Cys Arg Cys Val Gln Glu Ser Ser
1               5                   10                  15

Val Phe Ile Pro Arg Arg Phe Ile Asp Ala Ile Gln Ile Leu Pro Arg
            20                  25                  30

Gly Asn Gly Cys Pro Arg Lys Glu Ile Ile Val Trp Ala Ala Asn Ala
        35                  40                  45

Ser Ile Val Cys Val Asp Pro Gln Ala Glu Trp Ile Gln Ala Met Met
    50                  55                  60

Glu Val Leu Ala Ala Ala Ser Ser Ser Thr Leu Pro Val Pro Val Phe
65                  70                  75                  80

Ala Ala Ala Ile Pro Pro Cys Pro Ser Cys Pro Ala Pro Glu Phe
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser Gln Glu Asp Pro Glu Val Gln Phe Asn Trp Tyr Val Asp Gly Val
    130                 135                 140

Glu Val His Asn Ala Lys Thr Lys Pro Arg Glu Glu Gln Phe Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Gly Leu Pro Ser
            180                 185                 190

Ser Ile Glu Lys Thr Ile Ser Lys Ala Lys Gly Gln Pro Arg Glu Pro
        195                 200                 205

Gln Val Tyr Thr Leu Pro Pro Ser Gln Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Arg Leu
            260                 265                 270

Thr Val Asp Lys Ser Arg Trp Gln Glu Gly Asn Val Phe Ser Cys Ser
        275                 280                 285
```

Val Met His Glu Ala Leu His Asn His Tyr Thr Gln Lys Ser Leu Ser
    290                 295                 300

Leu Ser Pro Gly Lys
305

<210> SEQ ID NO 79
<211> LENGTH: 4401
<212> TYPE: DNA
<213> ORGANISM: Artificial Sequence
<220> FEATURE:
<223> OTHER INFORMATION: pCCL2-IgG1Fc

<400> SEQUENCE: 79

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gcctttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgaggggct | cgcatctctc | cttcacgcgc | ccgccgccct | acctgaggcc | 300 |
| gccatccacg | ccgttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgcagccaga | tgcaatcaat | gccccagtca | 660 |
| cctgctgtta | taacttcacc | aataggaaga | tctcagtgca | gaggctcgcg | agctatagaa | 720 |
| gaatcaccag | cagcaagtgt | cccaaagaag | ctgtgatctt | caagaccatt | gtggccaagg | 780 |
| agatctgtgc | tgaccccaag | cagaagtggg | ttcaggattc | catggaccac | ctggacaagc | 840 |
| aaacccaaac | tccgaagact | gacaaaactc | acacatgccc | accgtgccca | gcacctgaac | 900 |
| tcctgggggg | accgtcagtc | ttcctcttcc | cccaaaacc | caaggacacc | ctcatgatct | 960 |
| cccggacccc | tgaggtcaca | tgcgtggtgg | tggacgtgag | ccacgaagac | cctgaggtca | 1020 |
| agttcaactg | gtacgtggac | ggcgtggagg | tgcataatgc | caagacaaag | ccgcgggagg | 1080 |
| agcagtacaa | cagcacgtac | cgtgtggtca | gcgtcctcac | cgtcctgcac | caggactggc | 1140 |
| tgaatggcaa | ggagtacaag | tgcaaggtct | ccaacaaagc | cctcccagcc | cccatcgaga | 1200 |
| aaaccatctc | caaagccaaa | gggcagcccc | gagaaccaca | ggtgtacacc | ctgccccat | 1260 |
| cccgggagga | gatgaccaag | aaccaggtca | gcctgacctg | cctggtcaaa | ggcttctatc | 1320 |
| ccagcgacat | cgccgtggag | tgggagagca | atgggcagcc | ggagaacaac | tacaagacca | 1380 |
| cgcctcccgt | gctggactcc | gacggctcct | tcttcctcta | cagcaagctc | accgtggaca | 1440 |
| agagcaggtg | gcagcagggg | aacgtcttct | catgctccgt | gatgcacgag | gctctgcaca | 1500 |
| accactacac | gcagaagagc | ctctccctgt | ctccgggtaa | atgagtgcta | gctggccaga | 1560 |
| catgataaga | tacattgatg | agtttggaca | aaccacaact | agaatgcagt | gaaaaaaatg | 1620 |
| ctttatttgt | gaaatttgtg | atgctattgc | tttatttgta | accattataa | gctgcaataa | 1680 |
| acaagttaac | aacaacaatt | gcattcattt | tatgtttcag | gttcaggggg | aggtgtggga | 1740 |
| ggttttttaa | agcaagtaaa | acctctacaa | atgtggtatg | gaattaattc | taaaatacag | 1800 |
| catagcaaaa | ctttaacctc | caaatcaagc | ctctacttga | atccttttct | gagggatgaa | 1860 |

```
taaggcatag gcatcagggg ctgttgccaa tgtgcattag ctgtttgcag cctcaccttc  1920
tttcatggag tttaagatat agtgtatttt cccaaggttt gaactagctc ttcatttctt  1980
tatgttttaa atgcactgac ctcccacatt ccctttttag taaaatattc agaaataatt  2040
taaatacatc attgcaatga aaataaatgt tttttattag gcagaatcca gatgctcaag  2100
gcccttcata atatccccca gtttagtagt tggacttagg gaacaaagga acctttaata  2160
gaaattggac agcaagaaag cgagcttcta gcttatcctc agtcctgctc ctctgccaca  2220
aagtgcacgc agttgccggc cgggtcgcgc agggcgaact cccgccccca cggctgctcg  2280
ccgatctcgg tcatggccgg cccggaggcg tcccggaagt tcgtggacac gacctccgac  2340
cactcggcgt acagctcgtc caggccgcgc acccacaccc aggccagggt gttgtccggc  2400
accacctggt cctggaccgc gctgatgaac agggtcacgt cgtcccggac cacaccggcg  2460
aagtcgtcct ccacgaagtc ccgggagaac ccgagccggt cggtccagaa ctcgaccgct  2520
ccggcgacgt cgcgcgcggt gagcaccgga acggcactgg tcaacttggc catgatggct  2580
cctcctgtca ggagaggaaa gagaagaagg ttagtacaat tgctatagtg agttgtatta  2640
tactatgcag atatactatg ccaatgatta attgtcaaac tagggctgca gggttcatag  2700
tgccactttt cctgcactgc cccatctcct gcccacccett tcccaggcat agacagtcag  2760
tgacttacca aactcacagg agggagaagg cagaagcttg agacagaccc gcgggaccgc  2820
cgaactgcga gggacgtgg ctagggcgg ttctttatg gtgcgccggc cctcggaggc  2880
agggcgctcg ggaggccta gcggccaatc tgcggtggca ggaggcgggg ccgaaggccg  2940
tgcctgacca atccggagca cataggagtc tcagcccccc gccccaaagc aaggggaagt  3000
cacgcgcctg tagcgccagc gtgttgtgaa atgggggctt ggggggggttg gggccctgac  3060
tagtcaaaac aaactcccat tgacgtcaat ggggtggaga cttggaaatc cccgtgagtc  3120
aaaccgctat ccacgcccat tgatgtactg ccaaaaccgc atcatcatgg taatagcgat  3180
gactaatacg tagatgtact gccaagtagg aaagtcccat aaggtcatgt actgggcata  3240
atgccaggcg ggccatttac cgtcattgac gtcaataggg ggcgtacttg gcatatgata  3300
cacttgatgt actgccaagt gggcagttta ccgtaaatac tccacccatt gacgtcaatg  3360
gaaagtccct attggcgtta ctatgggaac atacgtcatt attgacgtca atgggcgggg  3420
gtcgttgggc ggtcagccag gcgggccatt taccgtaagt tatgtaacgc ctgcaggtta  3480
attaagaaca tgtgagcaaa aggccagcaa aaggccagga accgtaaaaa ggccgcgttg  3540
ctggcgtttt tccataggct ccgcccccct gacgagcatc acaaaaatcg acgctcaagt  3600
cagaggtggc gaaacccgac aggactataa agataccagg cgtttccccc tggaagctcc  3660
ctcgtgcgct ctcctgttcc gaccctgccg cttaccggat acctgtccgc ctttctccct  3720
tcgggaagcg tggcgctttc tcatagctca cgctgtaggt atctcagttc ggtgtaggtc  3780
gttcgctcca agctgggctg tgtgcacgaa ccccccgttc agcccgaccg ctgcgcctta  3840
tccggtaact atcgtcttga gtccaacccg gtaagacacg acttatcgcc actggcagca  3900
gccactggta acaggattag cagagcgagg tatgtaggcg gtgctacaga gttcttgaag  3960
tggtggccta actacggcta cactagaaga acagtatttg gtatctgcgc tctgctgaag  4020
ccagttacct tcggaaaaag agttggtagc tcttgatccg gcaaacaaac caccgctggt  4080
agcggtggtt tttttgtttg caagcagcag attacgcgca gaaaaaaagg atctcaagaa  4140
gatcctttga tcttttctac ggggtctgac gctcagtgga acgaaaactc acgttaaggg  4200
attttggtca tggctagtta attaacattt aaatcagcgg ccgcaataaa atatctttat  4260
```

| | |
|---|---|
| tttcattaca tctgtgtgtt ggttttttgt gtgaatcgta actaacatac gctctccatc | 4320 |
| aaaacaaaac gaaacaaaac aaactagcaa ataggctgt ccccagtgca agtgcaggtg | 4380 |
| ccagaacatt tctctatcga a | 4401 |

<210> SEQ ID NO 80
<211> LENGTH: 4389
<212> TYPE: DNA
<213> ORGANISM: Artificial Sequence
<220> FEATURE:
<223> OTHER INFORMATION: pCCL2(5-76)-IgG1Fc

<400> SEQUENCE: 80

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct cgagggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgatcaatgc cccagtcacc tgctgttata | 660 |
| acttcaccaa taggaagatc tcagtgcaga ggctcgcgag ctatagaaga atcaccagca | 720 |
| gcaagtgtcc caaagaagct gtgatcttca agaccattgt ggccaaggag atctgtgctg | 780 |
| accccaagca agtgtgggtt caggattcca tggaccacct ggacaagcaa acccaaaactc | 840 |
| cgaagactga caaaactcac acatgcccac cgtgcccagc acctgaactc ctggggggac | 900 |
| cgtcagtctt cctcttcccc ccaaaaccca aggacaccct catgatctcc cggacccctg | 960 |
| aggtcacatg cgtggtggtg gacgtgagcc acgaagaccc tgaggtcaag ttcaactggt | 1020 |
| acgtggacgg cgtggaggtg cataatgcca agacaaagcc gcgggaggag cagtacaaca | 1080 |
| gcacgtaccg tgtggtcagc gtcctcaccg tcctgcacca ggactggctg aatggcaagg | 1140 |
| agtacaagtg caaggtctcc aacaaagccc tcccagcccc catcgagaaa accatctcca | 1200 |
| aagccaaagg gcagccccga gaaccacagg tgtacaccct gcccccatcc cgggaggaga | 1260 |
| tgaccaagaa ccaggtcagc ctgacctgcc tggtcaaagg cttctatccc agcgacatcg | 1320 |
| ccgtggagtg ggagagcaat gggcagccgg agaacaacta caagaccacg cctcccgtgc | 1380 |
| tggactccga cggctccttc ttcctctaca gcaagctcac cgtggacaag agcaggtggc | 1440 |
| agcaggggaa cgtcttctca tgctccgtga tgcacgaggc tctgcacaac cactacacgc | 1500 |
| agaagagcct ctccctgtct ccgggtaaat gagtgctagc tggccagaca tgataagata | 1560 |
| cattgatgag tttggacaaa ccacaactag aatgcagtga aaaaaatgct ttatttgtga | 1620 |
| aatttgtgat gctattgctt tatttgtaac cattataagc tgcaataaac aagttaacaa | 1680 |
| caacaattgc attcatttta tgtttcaggt tcaggggag gtgtgggagg ttttttaaag | 1740 |
| caagtaaaac tctacaaat gtggtatgga attaattcta aaatacagca tagcaaaact | 1800 |
| ttaacctcca aatcaagcct ctacttgaat ccttttctga gggatgaata aggcataggc | 1860 |

```
atcaggggct gttgccaatg tgcattagct gtttgcagcc tcaccttctt tcatggagtt   1920
taagatatag tgtatttcc caaggtttga actagctctt catttcttta tgttttaaat    1980
gcactgacct cccacattcc cttttagta aaatattcag aaataattta aatacatcat    2040
tgcaatgaaa ataaatgttt tttattaggc agaatccaga tgctcaaggc ccttcataat   2100
atcccccagt ttagtagttg gacttaggga acaaaggaac ctttaataga aattggacag   2160
caagaaagcg agcttctagc ttatcctcag tcctgctcct ctgccacaaa gtgcacgcag   2220
ttgccggccg ggtcgcgcag ggcgaactcc cgccccacg gctgctcgcc gatctcggtc    2280
atggccggcc cggaggcgtc ccggaagttc gtggacacga cctccgacca ctcggcgtac   2340
agctcgtcca ggccgcgcac ccacacccag gccagggtgt tgtccggcac cacctggtcc   2400
tggaccgcgc tgatgaacag ggtcacgtcg tcccggacca caccggcgaa gtcgtcctcc   2460
acgaagtccc gggagaaccc gagccggtcg gtccagaact cgaccgctcc ggcgacgtcg   2520
cgcgcggtga gcaccggaac ggcactggtc aacttggcca tgatggctcc tcctgtcagg   2580
agaggaaaga gaagaaggtt agtacaattg ctatagtgag ttgtattata ctatgcagat   2640
atactatgcc aatgattaat tgtcaaacta gggctgcagg gttcatagtg ccactttcc    2700 tgcactgccc catctcctgc ccacccttc ccaggcatag acagtcagtg acttaccaaa    2760
ctcacaggag ggagaaggca gaagcttgag acagacccgc gggaccgccg aactgcgagg   2820
ggacgtggct agggcggctt cttttatggt gcgccggccc tcggaggcag ggcgctcggg   2880
gaggcctagc ggccaatctg cggtggcagg aggcggggcc gaaggccgtg cctgaccaat   2940
ccggagcaca taggagtctc agccccccgc cccaaagcaa ggggaagtca cgcgcctgta   3000
gcgccagcgt gttgtgaaat ggggggcttgg ggggttggg gccctgacta gtcaaaacaa   3060
actcccattg acgtcaatgg ggtggagact tggaaatccc cgtgagtcaa accgctatcc   3120
acgcccattg atgtactgcc aaaaccgcat catcatggta atagcgatga ctaatacgta   3180
gatgtactgc caagtaggaa agtcccataa ggtcatgtac tgggcataat gccaggcggg   3240
ccatttaccg tcattgacgt caataggggg cgtacttggc atatgataca cttgatgtac   3300
tgccaagtgg gcagtttacc gtaaatactc cacccattga cgtcaatgga aagtccctat   3360
tggcgttact atgggaacat acgtcattat tgacgtcaat gggcggggt cgttgggcgg    3420 tcagccaggc gggccattta ccgtaagtta tgtaacgcct gcaggttaat taagaacatg   3480
tgagcaaaag gccagcaaaa ggccaggaac cgtaaaaagg ccgcgttgct ggcgtttttc   3540
cataggctcc gccccctga cgagcatcac aaaaatcgac gctcaagtca gaggtggcga   3600
aacccgacag gactataaag ataccaggcg tttccccctg gaagctccct cgtgcgctct   3660
cctgttccga ccctgccgct taccggatac ctgtccgcct ttctcccttc gggaagcgtg   3720
gcgctttctc atagctcacg ctgtaggtat ctcagttcgg tgtaggtcgt tcgctccaag   3780
ctgggctgtg tgcacgaacc ccccgttcag cccgaccgct cgccttatc cggtaactat    3840 cgtcttgagt ccaacccggt aagacacgac ttatcgccac tggcagcagc cactggtaac   3900
aggattagca gagcgaggta tgtaggcggt gctacagagt tcttgaagtg gtggcctaac   3960
tacggctaca ctagaagaac agtatttggt atctgcgctc tgctgaagcc agttaccttc   4020
ggaaaaagag ttggtagctc ttgatccggc aaacaaacca ccgctggtag cggtggtttt   4080
tttgtttgca agcagcagat tacgcgcaga aaaaaaggat ctcaagaaga tcctttgatc   4140
ttttctacgg ggtctgacgc tcagtggaac gaaaactcac gttaagggat tttggtcatg   4200
gctagttaat taacatttaa atcagcggcc gcaataaaat atctttattt tcattacatc   4260
```

```
tgtgtgttgg ttttttgtgt gaatcgtaac taacatacgc tctccatcaa acaaaacga    4320 aacaaaacaa actagcaaaa taggctgtcc ccagtgcaag tgcaggtgcc agaacatttc    4380
tctatcgaa                                                            4389
```

<210> SEQ ID NO 81
<211> LENGTH: 4389
<212> TYPE: DNA
<213> ORGANISM: Artificial Sequence
<220> FEATURE:
<223> OTHER INFORMATION: pCCL2(5-76K/H-A)-IgG1Fc

<400> SEQUENCE: 81

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc ttttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgatcaatgc cccagtcacc tgctgttata    660
acttcaccaa taggaagatc tcagtgcaga ggctcgcgag ctatagaaga atcaccagca    720
gcaagtgtcc caaagaagct gtgatcttca agaccattgt ggccgcggag atctgtgctg    780
accccgctca ggcctgggtt caggattcca tggacgctct ggacgcccaa acccaaactc    840
cggcgactga caaaactcac acatgcccac cgtgcccagc acctgaactc ctggggggac    900
cgtcagtctt cctcttcccc ccaaaaccca aggacaccct catgatctcc cggacccctg    960
aggtcacatg cgtggtggtg gacgtgagcc acgaagaccc tgaggtcaag ttcaactggt   1020
acgtggacgg cgtggaggtg cataatgcca agacaaagcc gcgggaggag cagtacaaca   1080
gcacgtaccg tgtggtcagc gtcctcaccg tcctgcacca ggactggctg aatggcaagg   1140
agtacaagtg caaggtctcc aacaaagccc tcccagcccc catcgagaaa accatctcca   1200
aagccaaagg gcagccccga gaaccacagg tgtacaccct gcccccatcc cgggaggaga   1260
tgaccaagaa ccaggtcagc ctgacctgcc tggtcaaagg cttctatccc agcgacatcg   1320
ccgtggagtg ggagagcaat gggcagccgg agaacaacta caagaccacg cctcccgtgc   1380
tggactccga cggctccttc ttcctctaca gcaagctcac cgtggacaag agcaggtggc   1440
agcaggggaa cgtcttctca tgctccgtga tgcacgaggc tctgcacaac cactacacgc   1500
agaagagcct ctccctgtct ccgggtaaat gagtgctagc tggccagaca tgataagata   1560
cattgatgag tttggacaaa ccacaactag aatgcagtga aaaaaatgct ttatttgtga   1620
aatttgtgat gctattgctt tatttgtaac cattataagc tgcaataaac aagttaacaa   1680
caacaattgc attcatttta tgtttcaggt tcaggggag gtgtgggagg ttttttaaag   1740
caagtaaaac ctctacaaat gtggtatgga attaattcta aaatacagca tagcaaaact   1800
ttaacctcca aatcaagcct ctacttgaat ccttttctga gggatgaata aggcataggc   1860
```

```
atcagggct  gttgccaatg  tgcattagct  gtttgcagcc  tcaccttctt  tcatggagtt   1920
taagatatag  tgtattttcc  caaggtttga  actagctctt  catttcttta  tgttttaaat   1980
gcactgacct  cccacattcc  cttttagta   aaatattcag  aaataattta  aatacatcat   2040
tgcaatgaaa  ataaatgttt  tttattaggc  agaatccaga  tgctcaaggc  ccttcataat   2100
atcccccagt  ttagtagttg  gactaggga   acaaaggaac  ctttaataga  aattggacag   2160
caagaaagcg  agcttctagc  ttatcctcag  tcctgctcct  ctgccacaaa  gtgcacgcag   2220
ttgccggccg  ggtcgcgcag  ggcgaactcc  cgccccacg   gctgctcgcc  gatctcggtc   2280
atggccggcc  cggaggcgtc  ccggaagttc  gtggacacga  cctccgacca  ctcggcgtac   2340
agctcgtcca  ggccgcgcac  ccacacccag  gccagggtgt  tgtccggcac  cacctggtcc   2400
tggaccgcgc  tgatgaacag  ggtcacgtcg  tcccggacca  caccggcgaa  gtcgtcctcc   2460
acgaagtccc  gggagaaccc  gagccggtcg  gtccagaact  cgaccgctcc  ggcgacgtcg   2520
cgcgcggtga  gcaccggaac  ggcactggtc  aacttggcca  tgatggctcc  tcctgtcagg   2580
agaggaaaga  gaagaaggtt  agtacaattg  ctatagtgag  ttgtattata  ctatgcagat   2640
atactatgcc  aatgattaat  tgtcaaacta  gggctgcagg  gttcatagtg  ccactttcc   2700 tgcactgccc  catctcctgc  ccacccttc   ccaggcatag  acagtcagtg  acttaccaaa   2760
ctcacaggag  ggagaaggca  gaagcttgag  acagacccgc  gggaccgccg  aactgcgagg   2820
ggacgtggct  agggcggctt  cttttatggt  gcgccggccc  tcggaggcag  ggcgctcggg   2880
gaggcctagc  ggccaatctg  cggtggcagg  aggcggggcc  gaaggccgtg  cctgaccaat   2940
ccggagcaca  taggagtctc  agccccccgc  cccaaagcaa  ggggaagtca  cgcgcctgta   3000
gcgccagcgt  gttgtgaaat  ggggggcttgg gggggttggg  gccctgacta  gtcaaaacaa   3060
actcccattg  acgtcaatgg  ggtggagact  tggaaatccc  cgtgagtcaa  accgctatcc   3120
acgcccattg  atgtactgcc  aaaaccgcat  catcatggta  atagcgatga  ctaatacgta   3180
gatgtactgc  caagtaggaa  agtcccataa  ggtcatgtac  tgggcataat  gccaggcggg   3240
ccatttaccg  tcattgacgt  caatagggg   cgtacttggc  atatgataca  cttgatgtac   3300
tgccaagtgg  gcagtttacc  gtaaatactc  cacccattga  cgtcaatgga  aagtccctat   3360
tggcgttact  atgggaacat  acgtcattat  tgacgtcaat  gggcggggt   cgttgggcgg   3420 tcagccaggc  gggccattta  ccgtaagtta  tgtaacgcct  gcaggttaat  taagaacatg   3480
tgagcaaaag  gccagcaaaa  ggccaggaac  cgtaaaaagg  ccgcgttgct  ggcgtttttc   3540
cataggctcc  gccccctga   cgagcatcac  aaaatcgac   gctcaagtca  gaggtggcga   3600
aacccgacag  gactataaag  ataccaggcg  tttccctg    gaagctccct  cgtgcgctct   3660
cctgttccga  ccctgccgct  taccggatac  ctgtccgcct  ttctccttc   gggaagcgtg   3720 gcgctttctc  atagctcacg  ctgtaggtat  ctcagttcgg  tgtaggtcgt  tcgctccaag   3780
ctgggctgtg  tgcacgaacc  ccccgttcag  cccgaccgct  gcgccttatc  cggtaactat   3840
cgtcttgagt  ccaacccggt  aagacacgac  ttatcgccac  tggcagcagc  cactggtaac   3900
aggattagca  gagcgaggta  tgtaggcggt  gctacagagt  tcttgaagtg  gtggcctaac   3960
tacggctaca  ctagaagaac  agtatttggt  atctgcgctc  tgctgaagcc  agttaccttc   4020
ggaaaaagag  ttggtagctc  ttgatccggc  aaacaaacca  ccgctggtag  cggtggtttt   4080
tttgtttgca  agcagcagat  tacgcgcaga  aaaaaggat   ctcaagaaga  tcctttgatc   4140
ttttctacgg  ggtctgacgc  tcagtggaac  gaaaactcac  gttaagggat  tttggtcatg   4200
gctagttaat  taacatttaa  atcagcggcc  gcaataaaat  atctttatttt tcattacatc   4260
```

```
tgtgtgttgg ttttttgtgt gaatcgtaac taacatacgc tctccatcaa acaaaacga    4320 aacaaaacaa actagcaaaa taggctgtcc ccagtgcaag tgcaggtgcc agaacatttc    4380
tctatcgaa                                                            4389
```

<210> SEQ ID NO 82
<211> LENGTH: 4371
<212> TYPE: DNA
<213> ORGANISM: Artificial Sequence
<220> FEATURE:
<223> OTHER INFORMATION: pCCL7-IgG1Fc

<400> SEQUENCE: 82

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac      240
agctgaagct tcgaggggct cgcatctctc cttcacgcgc ccgccgccct acctgaggcc     300
gccatccacg ccgttgagt cgcgttctgc cgcctcccgc ctgtggtgcc tcctgaactg      360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgtgctgcta cagatttatc aataagaaaa     660
tccctaagca gaggctggag agctacgaaa ggaccaccag tagccactgt ccccgggaag     720
ctgtaatctt caagaccaaa ctggacaagg agatctgtgc tgaccccaca cagaagtggg     780
tccaggactt tatgaagcac ctggacaaga aacccaaaac tccaaagctt gacaaaactc     840
acacatgccc accgtgccca gcacctgaac tcctgggggg accgtcagtc ttcctcttcc     900
ccccaaaacc caaggacacc ctcatgatct cccggacccc tgaggtcaca tgcgtggtgg     960
tggacgtgag ccacgaagac cctgaggtca agttcaactg gtacgtggac ggcgtggagg    1020
tgcataatgc caagacaaag ccgcgggagg agcagtacaa cagcacgtac cgtgtggtca    1080
gcgtcctcac cgtcctgcac caggactggc tgaatggcaa ggagtacaag tgcaaggtct    1140
ccaacaaagc cctcccagcc cccatcgaga aaaccatctc caaagccaaa gggcagcccc    1200
gagaaccaca ggtgtacacc ctgcccccat cccgggagga tgaccaagaa ccaggtca     1260 gcctgacctg cctggtcaaa ggcttctatc ccagcgacat cgccgtggag tgggagagca    1320
atgggcagcc ggagaacaac tacaagacca cgcctcccgt gctggactcc gacggctcct    1380
tcttcctcta cagcaagctc accgtggaca agagcaggtg gcagcagggg aacgtcttct    1440
catgctccgt gatgcacgag gctctgcaca accactacac gcagaagagc ctctcccctgt    1500 ctccgggtaa atgagtgcta gctggccaga catgataaga tacattgatg agtttggaca    1560
aaccacaact agaatgcagt gaaaaaaatg ctttatttgt gaaatttgtg atgctattgc    1620
tttatttgta accattataa gctgcaataa acaagttaac aacaacaatt gcattcattt    1680
tatgtttcag gttcagggggg aggtgtggga ggttttttaa agcaagtaaa acctctacaa    1740
atgtggtatg gaattaattc taaaatacag catagcaaaa ctttaacctc caaatcaagc    1800
ctctacttga atccttttct gagggatgaa taaggcatag gcatcagggg ctgttgccaa    1860
```

```
tgtgcattag ctgtttgcag cctcaccttc tttcatggag tttaagatat agtgtatttt    1920
cccaaggttt gaactagctc ttcatttctt tatgttttaa atgcactgac ctcccacatt    1980
ccctttttag taaaatattc agaaataatt taaatacatc attgcaatga aaataaatgt    2040
tttttattag gcagaatcca gatgctcaag gcccttcata atatccccca gtttagtagt    2100
tggacttagg gaacaaagga acctttaata gaaattggac agcaagaaag cgagcttcta    2160
gcttatcctc agtcctgctc ctctgccaca aagtgcacgc agttgccggc cgggtcgcgc    2220
agggcgaact cccgccccca cggctgctcg ccgatctcgg tcatggccgg cccggaggcg    2280
tcccggaagt tcgtggacac gacctccgac cactcggcgt acagctcgtc caggccgcgc    2340
acccacaccc aggccagggt gttgtccggc accacctggt cctggaccgc gctgatgaac    2400 aggtcacgt cgtcccggac cacaccggcg aagtcgtcct ccacgaagtc ccgggagaac    2460
ccgagccggt cggtccagaa ctcgaccgct ccggcgacgt cgcgcgcggt gagcaccgga    2520
acggcactgg tcaacttggc catgatggct cctcctgtca ggagaggaaa gagaagaagg    2580
ttagtacaat tgctatagtg agttgtatta tactatgcag atatactatg ccaatgatta    2640
attgtcaaac tagggctgca gggttcatag tgccactttt cctgcactgc cccatctcct    2700 gcccacccctt tcccaggcat agacagtcag tgacttacca aactcacagg agggagaagg    2760
cagaagcttg agacagaccc gcgggaccgc cgaactgcga ggggacgtgg ctagggcggc    2820
ttcttttatg gtgcgccggc cctcggaggc agggcgctcg ggaggccta gcggccaatc    2880 tgcggtggca ggaggcgggg ccgaaggccg tgcctgacca atccggagca cataggagtc    2940 tcagccccc gccccaaagc aagggggaagt cacgcgcctg tagcgccagc gtgttgtgaa    3000
atgggggctt gggggggttg gggccctgac tagtcaaaac aaactcccat tgacgtcaat    3060
ggggtggaga cttggaaatc cccgtgagtc aaaccgctat ccacgcccat tgatgtactg    3120
ccaaaaccgc atcatcatgg taatagcgat gactaatacg tagatgtact gccaagtagg    3180
aaagtcccat aaggtcatgt actgggcata atgccaggcg ggccatttac cgtcattgac    3240
gtcaataggg ggcgtacttg gcatatgata cacttgatgt actgccaagt gggcagttta    3300
ccgtaaatac tccacccatt gacgtcaatg gaaagtccct attggcgtta ctatgggaac    3360
atacgtcatt attgacgtca atgggcgggg gtcgttgggc ggtcagccag gcgggccatt    3420
taccgtaagt tatgtaacgc ctgcaggtta attaagaaca tgtgagcaaa aggccagcaa    3480
aaggccagga accgtaaaaa ggccgcgttg ctggcgtttt tccataggct ccgccccct    3540 gacgagcatc acaaaaatcg acgctcaagt cagaggtggc gaaacccgac aggactataa    3600
agataccagg cgtttccccc tggaagctcc ctcgtgcgct ctcctgttcc gaccctgccg    3660
cttaccggat acctgtccgc ctttctccct tcgggaagcg tggcgctttc tcatagctca    3720
cgctgtaggt atctcagttc ggtgtaggtc gttcgctcca agctgggctg tgtgcacgaa    3780
ccccccgttc agcccgaccg ctgcgcctta tccggtaact atcgtcttga gtccaacccg    3840
gtaagacacg acttatcgcc actggcagca gccactggta acaggattag cagagcgagg    3900
tatgtaggcg gtgctacaga gttcttgaag tggtggccta actacggcta cactagaaga    3960
acagtatttg gtatctgcgc tctgctgaag ccagttacct tcggaaaaag agttggtagc    4020
tcttgatccg gcaaacaaac caccgctggt agcggtggtt ttttgtttg caagcagcag    4080 attacgcgca gaaaaaaagg atctcaagaa gatcctttga tcttttctac ggggtctgac    4140
gctcagtgga acgaaaactc acgttaaggg attttggtca tggctagtta attaacattt    4200
aaatcagcgg ccgcaataaa atatctttat tttcattaca tctgtgtgtt ggttttttgt    4260
```

-continued

```
gtgaatcgta actaacatac gctctccatc aaaacaaaac gaaacaaaac aaactagcaa    4320
aataggctgt ccccagtgca agtgcaggtg ccagaacatt tctctatcga a             4371
```

<210> SEQ ID NO 83
<211> LENGTH: 4359
<212> TYPE: DNA
<213> ORGANISM: Artificial Sequence
<220> FEATURE:
<223> OTHER INFORMATION: pCCL7(5-76)-IgG1Fc

<400> SEQUENCE: 83

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa    120
actgggaaag tgatgtcgtg tactggctcc gccttttttcc cgagggtggg ggagaaccgt   180
atataagtgc agtagtcgcc gtgaacgttc tttttcgcaa cgggtttgcc gccagaacac    240
agctgaagct cgaggggct cgcatctctc cttcacgcgc ccgccgccct acctgaggcc     300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgtttatcaa taagaaaatc cctaagcaga    660
ggctggagag ctacagaagg accaccagta gccactgtcc ccgggaagct gtaatcttca    720
agaccaaact ggacaaggag atctgtgctg acccccacaca gaagtgggtc caggactttta    780 tgaagcacct ggacaagaaa acccaaactc caaagcttga caaaactcac acatgcccac    840
cgtgcccagc acctgaactc ctggggggac cgtcagtctt cctcttcccc ccaaaaccca    900
aggacaccct catgatctcc cggacccctg aggtcacatg cgtggtggtg gacgtgagcc    960
acgaagaccc tgaggtcaag ttcaactggt acgtggacgg cgtggaggtg cataatgcca   1020
agacaaagcc gcgggaggag cagtacaaca gcacgtaccg tgtggtcagc gtcctcaccg   1080
tcctgcacca ggactggctg aatggcaagg agtacaagtg caaggtctcc aacaaagccc   1140
tcccagcccc catcgagaaa accatctcca agccaaagg gcagcccga gaaccacagg    1200 tgtacaccct gcccccatcc cgggaggaga tgaccaagaa ccaggtcagc ctgacctgcc   1260
tggtcaaagg cttctatccc agcgacatcg ccgtggagtg ggagagcaat gggcagccgg   1320
agaacaacta caagaccacg cctcccgtgc tggactccga cggctccttc ttcctctaca   1380
gcaagctcac cgtggacaag agcaggtggc agcaggggaa cgtcttctca tgctccgtga   1440
tgcacgaggc tctgcacaac cactacacgc agaagagcct ctccctgtct ccgggtaaat   1500
gagtgctagc tggccagaca tgataagata cattgatgag tttggacaaa ccacaactag   1560
aatgcagtga aaaaaatgct ttatttgtga atttgtgat gctattgctt tatttgtaac   1620
cattataagc tgcaataaac aagttaacaa caacaattgc attcatttta tgtttcaggt   1680 tcaggggag gtgtgggagg ttttttaaag caagtaaaac ctctacaaat gtggtatgga   1740
attaattcta aaatacagca tagcaaaact ttaacctcca aatcaagcct ctacttgaat   1800 cctttttctga gggatgaata aggcataggc atcaggggct gttgccaatg tgcattagct   1860
gtttgcagcc tcaccttctt tcatggagtt taagatatag tgtattttcc caaggtttga   1920
```

```
actagctctt catttcttta tgttttaaat gcactgacct cccacattcc cttttttagta    1980 aaatattcag aaataattta aatacatcat tgcaatgaaa ataaatgttt tttattaggc    2040
agaatccaga tgctcaaggc ccttcataat atcccccagt ttagtagttg gacttaggga    2100
acaaaggaac ctttaataga aattggacag caagaaagcg agcttctagc ttatcctcag    2160
tcctgctcct ctgccacaaa gtgcacgcag ttgccggccg ggtcgcgcag ggcgaactcc    2220 cgccccacg gctgctcgcc gatctcggtc atggccggcc cggaggcgtc ccggaagttc    2280
gtggacacga cctccgacca ctcggcgtac agctcgtcca ggccgcgcac ccacacccag    2340
gccagggtgt tgtccggcac cacctggtcc tggaccgcgc tgatgaacag ggtcacgtcg    2400
tcccggacca caccggcgaa gtcgtcctcc acgaagtccc gggagaaccc gagccggtcg    2460
gtccagaact cgaccgctcc ggcgacgtcg cgcgcggtga gcaccggaac ggcactggtc    2520
aacttggcca tgatggctcc tcctgtcagg agaggaaaga gaagaaggtt agtacaattg    2580
ctatagtgag ttgtattata ctatgcagat atactatgcc aatgattaat tgtcaaacta    2640
gggctgcagg gttcatagtg ccacttttcc tgcactgccc catctcctgc ccacccttt    2700 ccaggcatag acagtcagtg acttaccaaa ctcacaggag ggagaaggca gaagcttgag    2760
acagacccgc gggaccgccg aactgcgagg ggacgtggct agggcggctt cttttatggt    2820
gcgccggccc tcggaggcag ggcgctcggg gaggcctagc ggccaatctg cggtggcagg    2880
aggcggggcc gaaggccgtg cctgaccaat ccggagcaca taggagtctc agcccccgc    2940 cccaaagcaa ggggaagtca cgcgcctgta gcgccagcgt gttgtgaaat gggggcttgg    3000
gggggttggg gccctgacta gtcaaaacaa actcccattg acgtcaatgg ggtggagact    3060
tggaaatccc cgtgagtcaa accgctatcc acgcccattg atgtactgcc aaaaccgcat    3120
catcatggta atagcgatga ctaatacgta gatgtactgc caagtaggaa agtcccataa    3180
ggtcatgtac tgggcataat gccaggcggg ccatttaccg tcattgacgt caataggggg    3240
cgtacttggc atatgataca cttgatgtac tgccaagtgg gcagtttacc gtaaatactc    3300
cacccattga cgtcaatgga aagtccctat tggcgttact atgggaacat acgtcattat    3360
tgacgtcaat gggcgggggt cgttgggcgg tcagccaggc gggccattta ccgtaagtta    3420
tgtaacgcct gcaggttaat taagaacatg tgagcaaaag gccagcaaaa ggccaggaac    3480
cgtaaaaagg ccgcgttgct ggcgtttttc cataggctcc gccccctga cgagcatcac    3540 aaaaatcgac gctcaagtca gaggtggcga aacccgacag gactataaag ataccaggcg    3600
tttccccctg gaagctccct cgtgcgctct cctgttccga ccctgccgct taccggatac    3660
ctgtccgcct ttctcccttc gggaagcgtg gcgctttctc atagctcacg ctgtaggtat    3720
ctcagttcgg tgtaggtcgt tcgctccaag ctgggctgtg tgcacgaacc ccccgttcag    3780
cccgaccgct gcgccttatc cggtaactat cgtcttgagt ccaacccggt aagacacgac    3840
ttatcgccac tggcagcagc cactggtaac aggattagca gagcgaggta tgtaggcggt    3900
gctacagagt tcttgaagtg gtggcctaac tacggctaca ctagaagaac agtatttggt    3960
atctgcgctc tgctgaagcc agttaccttc ggaaaaagag ttggtagctc ttgatccggc    4020
aaacaaacca ccgctggtag cggtggtttt tttgtttgca agcagcagat tacgcgcaga    4080 aaaaaggat ctcaagaaga tcctttgatc ttttctacgg ggtctgacgc tcagtggaac    4140
gaaaactcac gttaagggat tttggtcatg ctagttaat taacatttaa atcagcggcc    4200
gcaataaaat atctttattt tcattacatc tgtgtgttgg ttttttgtgt gaatcgtaac    4260
taacatacgc tctccatcaa aacaaaacga aacaaaacaa actagcaaaa taggctgtcc    4320
```

```
                                                           -continued ccagtgcaag tgcaggtgcc agaacatttc tctatcgaa                      4359

<210> SEQ ID NO 84
<211> LENGTH: 4359
<212> TYPE: DNA
<213> ORGANISM: Artificial Sequence
<220> FEATURE:
<223> OTHER INFORMATION: pCCL7(5-76K/H-A)-IgG1Fc

<400> SEQUENCE: 84
ggatctgcga tcgctccggt gcccgtcagt gggcagagcg cacatcgccc acagtccccg      60
agaagttggg gggagggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct cgaggggct cgcatctctc cttcacgcgc ccgccgccct acctgaggcc      300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgtttatcaa taagaaaatc cctaagcaga    660
ggctggagag ctacagaagg accaccagta gccactgtcc ccgggaagct gtaatcttcg    720
ccaccgcgct ggacgctgag atctgtgctg accccacaca ggcctgggtc caggacttta    780
tggctgccct ggacgcggct acccaaactc cagcccttga caaaactcac acatgcccac    840
cgtgcccagc acctgaactc ctggggggac cgtcagtctt cctcttcccc ccaaaaccca    900
aggacaccct catgatctcc cggacccctg aggtcacatg cgtggtggtg gacgtgagcc    960
acgaagaccc tgaggtcaag ttcaactggt acgtggacgg cgtggaggtg cataatgcca   1020
agacaaagcc gcgggaggag cagtacaaca gcacgtaccg tgtggtcagc gtcctcaccg   1080
tcctgcacca ggactggctg aatggcaagg agtacaagtg caaggtctcc aacaaagccc   1140
tcccagcccc catcgagaaa accatctcca aagccaaagg gcagccccga gaaccacagg   1200
tgtacaccct gcccccatcc cgggaggaga tgaccaagaa ccaggtcagc ctgacctgcc   1260
tggtcaaagg cttctatccc agcgacatcg ccgtggagtg ggagagcaat gggcagccgg   1320
agaacaacta caagaccacg cctcccgtgc tggactccga cggctccttc ttcctctaca   1380
gcaagctcac cgtggacaag agcaggtggc agcaggggaa cgtcttctca tgctccgtga   1440
tgcacgaggc tctgcacaac cactacacgc agaagagcct ctccctgtct ccgggtaaat   1500
gagtgctagc tggccagaca tgataagata cattgatgag tttggacaaa ccacaactag   1560
aatgcagtga aaaaaatgct ttatttgtga aatttgtgat gctattgctt tatttgtaac   1620
cattataagc tgcaataaac aagttaacaa caacaattgc attcatttta tgtttcaggt   1680
tcaggggggag gtgtgggagg ttttttaaag caagtaaaac ctctacaaat gtggtatgga   1740
attaattcta aaatacagca tagcaaaact ttaacctcca aatcaagcct ctacttgaat   1800
ccttttctga gggatgaata aggcataggc atcagggct gttgccaatg tgcattagct   1860
gtttgcagcc tcaccttctt tcatggagtt aagatatag tgtattttcc caaggtttga   1920
actagctctt catttcttta tgtttaaat gcactgacct cccacattcc cttttagta    1980
```

```
aaatattcag aaataattta aatacatcat tgcaatgaaa ataaatgttt tttattaggc   2040
agaatccaga tgctcaaggc ccttcataat atcccccagt ttagtagttg gacttaggga   2100
acaaaggaac ctttaataga aattggacag caagaaagcg agcttctagc ttatcctcag   2160
tcctgctcct ctgccacaaa gtgcacgcag ttgccggccg ggtcgcgcag ggcgaactcc   2220
cgcccccacg gctgctcgcc gatctcggtc atggccggcc cggaggcgtc ccggaagttc   2280
gtggacacga cctccgacca ctcggcgtac agctcgtcca ggccgcgcac ccacacccag   2340
gccagggtgt tgtccggcac cacctggtcc tggaccgcgc tgatgaacag ggtcacgtcg   2400
tcccggacca caccggcgaa gtcgtcctcc acgaagtccc gggagaaccc gagccggtcg   2460
gtccagaact cgaccgctcc ggcgacgtcg cgcgcggtga gcaccggaac ggcactggtc   2520
aacttggcca tgatggctcc tcctgtcagg agaggaaaga gaagaaggtt agtacaattg   2580
ctatagtgag ttgtattata ctatgcagat atactatgcc aatgattaat tgtcaaacta   2640
gggctgcagg gttcatagtg ccacttttcc tgcactgccc catctcctgc ccacccttc    2700 ccaggcatag acagtcagtg acttaccaaa ctcacaggag ggagaaggca gaagcttgag   2760
acagacccgc gggaccgccg aactgcgagg ggacgtggct agggcggctt cttttatggt   2820
gcgccggccc tcgaggcag ggcgctcggg gaggcctagc ggccaatctg cggtggcagg    2880
aggcggggcc gaaggccgtg cctgaccaat ccggagcaca taggagtctc agccccccgc   2940
cccaaagcaa ggggaagtca cgcgcctgta gcgccagcgt gttgtgaaat gggggcttgg   3000
gggggttggg gccctgacta gtcaaaacaa actcccattg acgtcaatgg ggtggagact   3060
tggaaatccc cgtgagtcaa accgctatcc acgcccattg atgtactgcc aaaaccgcat   3120
catcatggta atagcgatga ctaatacgta gatgtactgc caagtaggaa agtcccataa   3180
ggtcatgtac tgggcataat gccaggcggg ccatttaccg tcattgacgt caataggggg   3240
cgtacttggc atatgataca cttgatgtac tgccaagtgg gcagtttacc gtaaatactc   3300
cacccattga cgtcaatgga aagtccctat tggcgttact atgggaacat acgtcattat   3360
tgacgtcaat gggcgggggt cgttgggcgg tcagccaggc gggccattta ccgtaagtta   3420
tgtaacgcct gcaggttaat taagaacatg tgagcaaaag gccagcaaaa ggccaggaac   3480
cgtaaaaagg ccgcgttgct ggcgtttttc cataggctcc gcccccctga cgagcatcac   3540
aaaaatcgac gctcaagtca gaggtggcga aacccgacag gactataaag ataccaggcg   3600
tttccccctg gaagctccct cgtgcgctct cctgttccga cctgccgct taccggatac    3660 ctgtccgcct ttctcccttc gggaagcgtg gcgctttctc atagctcacg ctgtaggtat   3720
ctcagttcgg tgtaggtcgt tcgctccaag ctgggctgtg tgcacgaacc ccccgttcag   3780
cccgaccgct gcgccttatc cggtaactat cgtcttgagt ccaacccggt aagacacgac   3840
ttatcgccac tggcagcagc cactggtaac aggattagca gagcgaggta tgtaggcggt   3900
gctacagagt tcttgaagtg gtggcctaac tacggctaca ctagaagaac agtatttggt   3960
atctgcgctc tgctgaagcc agttaccttc ggaaaaagag ttggtagctc ttgatccggc   4020
aaacaaacca ccgctggtag cggtggtttt tttgtttgca agcagcagat tacgcgcaga   4080
aaaaaaggat ctcaagaaga tcctttgatc ttttctacgg ggtctgacgc tcagtggaac   4140
gaaaactcac gttaagggat tttggtcatg ctagttaat taacatttaa atcagcggcc    4200
gcaataaaat atctttattt tcattacatc tgtgtgttgg tttttgtgt gaatcgtaac     4260 taacatacgc tctccatcaa aacaaaacga aacaaaacaa actagcaaaa taggctgtcc   4320
ccagtgcaag tgcaggtgcc agaacatttc tctatcgaa                          4359
```

<210> SEQ ID NO 85
<211> LENGTH: 4401
<212> TYPE: DNA
<213> ORGANISM: Artificial Sequence
<220> FEATURE:
<223> OTHER INFORMATION: pCCL8-IgG1Fc

<400> SEQUENCE: 85

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgcagccaga ttcagtttcc attccaatca     660
cctgctgctt taacgtgatc aataggaaaa ttcctatcca gaggctggag agctacacaa     720
gaatcaccaa catccaatgt cccaaggaag ctgtgatctt caagaccaaa cggggcaagg     780
aggtctgtgc tgaccccaag gagagatggg tcagggattc catgaagcat ctggaccaaa     840
tatttcaaaa tctgaagcca gacaaaactc acacatgccc accgtgccca gcacctgaac     900
tcctgggggg accgtcagtc ttcctcttcc ccccaaaacc caaggacacc ctcatgatct     960
cccggacccc tgaggtcaca tgcgtggtgg tggacgtgag ccacgaagac cctgaggtca    1020
agttcaactg gtacgtggac ggcgtggagg tgcataatgc caagacaaag ccgcgggagg    1080
agcagtacaa cagcacgtac cgtgtggtca gcgtcctcac cgtcctgcac caggactggc    1140
tgaatggcaa ggagtacaag tgcaaggtct ccaacaaagc cctcccagcc cccatcgaga    1200
aaaccatctc caaagccaaa gggcagcccc gagaaccaca ggtgtacacc ctgcccccat    1260
cccgggagga tgaccaagaa ccaggtca gcctgacctg cctggtcaaa ggcttctatc      1320
ccagcgacat cgccgtggag tgggagagca atgggcagcc ggagaacaac tacaagacca    1380
cgcctcccgt gctggactcc gacggctcct tcttcctcta cagcaagctc accgtggaca    1440
agagcaggtg gcagcagggg aacgtcttct catgctccgt gatgcacgag gctctgcaca    1500
accactacac gcagaagagc ctctccctgt ctccgggtaa atgagtgcta gctgccaga    1560
catgataaga tacattgatg agtttggaca accacaact agaatgcagt gaaaaaaatg     1620
ctttatttgt gaaatttgtg atgctattgc tttatttgta accattataa gctgcaataa    1680
acaagttaac aacaacaatt gcattcattt tatgtttcag gttcagggg aggtgtggga    1740
ggttttttaa agcaagtaaa acctctacaa atgtggtatg gaattaattc taaaatacag    1800
catagcaaaa ctttaacctc caaatcaagc ctctacttga atccttttct gagggatgaa    1860
taaggcatag gcatcagggg ctgttgccaa tgtgcattag ctgtttgcag cctcaccttc    1920
tttcatggag tttaagatat agtgtatttt cccaaggttt gaactagctc ttcatttctt    1980
tatgttttaa atgcactgac ctcccacatt cccttttag taaaatattc agaaataatt    2040
```

```
taaatacatc attgcaatga aaataaatgt ttttttattag gcagaatcca gatgctcaag    2100
gcccttcata atatccccca gtttagtagt tggacttagg gaacaaagga acctttaata    2160
gaaattggac agcaagaaag cgagcttcta gcttatcctc agtcctgctc ctctgccaca    2220
aagtgcacgc agttgccggc cgggtcgcgc agggcgaact cccgccccca cggctgctcg    2280
ccgatctcgg tcatggccgg cccggaggcg tcccggaagt tcgtggacac gacctccgac    2340
cactcggcgt acagctcgtc caggccgcgc acccacaccc aggccagggt gttgtccggc    2400
accacctggt cctggaccgc gctgatgaac agggtcacgt cgtcccggac cacaccggcg    2460
aagtcgtcct ccacgaagtc ccgggagaac ccgagccggt cggtccagaa ctcgaccgct    2520
ccggcgacgt cgcgcgcggt gagcaccgga acggcactgg tcaacttggc catgatggct    2580
cctcctgtca ggagaggaaa gagaagaagg ttagtacaat tgctatagtg agttgtatta    2640
tactatgcag atatactatg ccaatgatta attgtcaaac tagggctgca gggttcatag    2700
tgccactttt cctgcactgc cccatctcct gcccacccctt tcccaggcat agacagtcag    2760
tgacttacca aactcacagg agggagaagg cagaagcttg agacagaccc gcgggaccgc    2820
cgaactgcga ggggacgtgg ctagggcggc ttctttatg gtgcgccggc cctcggaggc    2880
agggcgctcg ggaggcccta gcggccaatc tgcggtggca ggaggcgggg ccgaaggccg    2940
tgcctgacca atccggagca cataggagtc tcagcccccc gccccaaagc aaggggaagt    3000
cacgcgcctg tagcgccagc gtgttgtgaa atggggggctt ggggggggttg gggccctgac    3060
tagtcaaaac aaactcccat tgacgtcaat ggggtggaga cttggaaatc cccgtgagtc    3120
aaaccgctat ccacgcccat tgatgtactg ccaaaaccgc atcatcatgg taatagcgat    3180
gactaatacg tagatgtact gccaagtagg aaagtcccat aaggtcatgt actgggcata    3240
atgccaggcg ggccatttac cgtcattgac gtcaataggg ggcgtacttg gcatatgata    3300
cacttgatgt actgccaagt gggcagttta ccgtaaatac tccacccatt gacgtcaatg    3360
gaaagtccct attggcgtta ctatgggaac atacgtcatt attgacgtca atgggcgggg    3420
gtcgttgggc ggtcagccag gcgggccatt taccgtaagt tatgtaacgc ctgcaggtta    3480
attaagaaca tgtgagcaaa aggccagcaa aaggccagga accgtaaaaa ggccgcgttg    3540
ctggcgtttt tccataggct ccgcccccct gacgagcatc acaaaaatcg acgctcaagt    3600
cagaggtggc gaaacccgac aggactataa agataccagg cgtttccccc tggaagctcc    3660
ctcgtgcgct ctcctgttcc gaccctgccg cttaccggat acctgtccgc ctttctccct    3720
tcggaagcg tggcgctttc tcatagctca cgctgtaggt atctcagttc ggtgtaggtc    3780
gttcgctcca agctgggctg tgtgcacgaa ccccccgttc agcccgaccg ctgcgcctta    3840
tccggtaact atcgtcttga gtccaacccg gtaagacacg acttatcgcc actggcagca    3900
gccactggta acaggattag cagagcgagg tatgtaggcg gtgctacaga gttcttgaag    3960
tggtggccta actacggcta cactagaaga acagtatttg gtatctgcgc tctgctgaag    4020
ccagttacct tcggaaaaag agttggtagc tcttgatccg gcaaacaaac caccgctggt    4080
agcggtggtt ttttgtttg caagcagcag attacgcgca gaaaaaaagg atctcaagaa    4140
gatcctttga tcttttctac ggggtctgac gctcagtgga acgaaaactc acgttaaggg    4200
attttggtca tggctagtta attaacattt aaatcagcgg ccgcaataaa atatctttat    4260
tttcattaca tctgtgtgtt ggttttttgt gtgaatcgta actaacatac gctctccatc    4320
aaaacaaaac gaaacaaaac aaactagcaa aataggctgt ccccagtgca agtgcaggtg    4380
ccagaacatt tctctatcga a                                              4401
```

<210> SEQ ID NO 86
<211> LENGTH: 4389
<212> TYPE: DNA
<213> ORGANISM: Artificial Sequence
<220> FEATURE:
<223> OTHER INFORMATION: pCCL8(5-76)-IgG1Fc

<400> SEQUENCE: 86

```
ggatctgcga tcgctccggt gcccgtcagt gggcagagcg cacatcgccc acagtccccg      60
agaagttggg gggagggtc ggcaattgaa cgggtgccta gagaaggtgg cgcggggtaa     120
actgggaaag tgatgtcgtg tactggctcc gccttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggtttccat tccaatcacc tgctgcttta     660
acgtgatcaa taggaaaatt cctatccaga ggctggagag ctacacaaga atcaccaaca     720
tccaatgtcc caaggaagct gtgatcttca agaccaaacg gggcaaggag gtctgtgctg     780
accccaagga gagatgggtc agggattcca tgaagcatct ggaccaaata tttcaaaatc     840
tgaagccaga caaaactcac acatgcccac cgtgcccagc acctgaactc ctggggggac     900
cgtcagtctt cctcttcccc ccaaaaccca aggacaccct catgatctcc cggacccctg     960
aggtcacatg cgtggtggtg gacgtgagcc acgaagaccc tgaggtcaag ttcaactggt    1020
acgtggacgg cgtggaggtg cataatgcca agacaaagcc gcgggaggag cagtacaaca    1080
gcacgtaccg tgtggtcagc gtcctcaccg tcctgcacca ggactggctg aatggcaagg    1140
agtacaagtg caaggtctcc aacaaagccc tcccagcccc catcgagaaa accatctcca    1200
aagccaaagg gcagccccga gaaccacagg tgtacaccct gcccccatcc cgggaggaga    1260
tgaccaagaa ccaggtcagc ctgacctgcc tggtcaaagg cttctatccc agcgacatcg    1320
ccgtggagtg ggagagcaat gggcagccgg agaacaacta caagaccacg cctcccgtgc    1380
tggactccga cggctccttc ttcctctaca gcaagctcac cgtggacaag agcaggtggc    1440
agcaggggaa cgtcttctca tgctccgtga tgcacgaggc tctgcacaac cactacacgc    1500
agaagagcct ctccctgtct ccgggtaaat gagtgctagc tggccagaca tgataagata    1560
cattgatgag tttggacaaa ccacaactag aatgcagtga aaaaaatgct ttatttgtga    1620
aatttgtgat gctattgctt tatttgtaac cattataagc tgcaataaac aagttaacaa    1680
caacaattgc attcatttta tgtttcaggt tcagggggag gtgtgggagg ttttttaaag    1740
caagtaaaac tctctacaaat gtggtatgga attaattcta aaatacagca tagcaaaact    1800
ttaacctcca aatcaagcct ctacttgaat ccttttctga gggatgaata aggcataggc    1860
atcagggggct gttgccaatg tgcattagct gtttgcagcc tcaccttctt tcatggagtt    1920
taagatatag tgtattttcc caaggtttga actagctctt catttcttta tgttttaaat    1980
gcactgacct cccacattcc cttttttagta aaatattcag aaataattta aatacatcat    2040
```

```
tgcaatgaaa ataaatgttt tttattaggc agaatccaga tgctcaaggc ccttcataat    2100
atcccccagt ttagtagttg gacttaggga acaaaggaac ctttaataga aattggacag    2160
caagaaagcg agcttctagc ttatcctcag tcctgctcct ctgccacaaa gtgcacgcag    2220
ttgccggccg ggtcgcgcag ggcgaactcc cgccccacg gctgctcgcc gatctcggtc     2280
atggccggcc cggaggcgtc ccggaagttc gtggacacga cctccgacca ctcggcgtac    2340
agctcgtcca ggccgcgcac ccacacccag gccagggtgt tgtccggcac cacctggtcc    2400
tggaccgcgc tgatgaacag ggtcacgtcg tcccggacca caccggcgaa gtcgtcctcc    2460
acgaagtccc gggagaaccc gagccggtcg gtccagaact cgaccgctcc ggcgacgtcg    2520
cgcgcggtga gcaccggaac ggcactggtc aacttggcca tgatggctcc tcctgtcagg    2580
agaggaaaga gaagaaggtt agtacaattg ctatagtgag ttgtattata ctatgcagat    2640
atactatgcc aatgattaat tgtcaaacta gggctgcagg gttcatagtg ccacttttcc    2700
tgcactgccc catctcctgc ccaccctttc ccaggcatag acagtcagtg acttaccaaa    2760
ctcacaggag ggagaaggca gaagcttgag acagacccgc gggaccgccg aactgcgagg    2820
ggacgtggct agggcggctt cttttatggt gcgccggccc tcggaggcag ggcgctcggg    2880
gaggcctagc ggccaatctg cggtggcagg aggcggggcc gaaggccgtg cctgaccaat    2940
ccggagcaca taggagtctc agccccccgc cccaaagcaa ggggaagtca cgcgcctgta    3000
gcgccagcgt gttgtgaaat gggggcttgg ggggttggg gccctgacta gtcaaaacaa     3060
actcccattg acgtcaatgg ggtggagact tggaaatccc cgtgagtcaa accgctatcc    3120
acgcccattg atgtactgcc aaaaccgcat catcatggta atagcgatga ctaatacgta    3180
gatgtactgc caagtaggaa agtcccataa ggtcatgtac tgggcataat gccaggcggg    3240
ccatttaccg tcattgacgt caatagggg cgtacttggc atatgataca cttgatgtac     3300
tgccaagtgg gcagtttacc gtaaatactc cacccattga cgtcaatgga aagtccctat    3360
tggcgttact atgggaacat acgtcattat tgacgtcaat gggcggggt cgttgggcgg     3420 tcagccaggc gggccattta ccgtaagtta tgtaacgcct gcaggttaat taagaacatg    3480
tgagcaaaag gccagcaaaa ggccaggaac cgtaaaaagg ccgcgttgct ggcgtttttc    3540
cataggctcc gcccccctga cgagcatcac aaaaatcgac gctcaagtca gaggtggcga    3600
aacccgacag gactataaag ataccaggcg tttccccctg gaagctccct cgtgcgctct    3660
cctgttccga ccctgccgct taccggatac ctgtccgcct ttctcccttc gggaagcgtg    3720
gcgctttctc atagctcacg ctgtaggtat ctcagttcgg tgtaggtcgt tcgctccaag    3780
ctgggctgtg tgcacgaacc ccccgttcag cccgaccgct gcgccttatc cggtaactat    3840
cgtcttgagt ccaacccggt aagacacgac ttatcgccac tggcagcagc cactggtaac    3900
aggattagca gagcgaggta tgtaggcggt gctacagagt tcttgaagtg gtggcctaac    3960
tacggctaca ctagaagaac agtatttggt atctgcgctc tgctgaagcc agttaccttc    4020
ggaaaaagag ttggtagctc ttgatccggc aaacaaacca ccgctggtag cggtggtttt    4080
tttgtttgca agcagcagat tacgcgcaga aaaaaggat ctcaagaaga tcctttgatc      4140
ttttctacgg ggtctgacgc tcagtggaac gaaaactcac gttaagggat tttggtcatg    4200
gctagttaat taacatttaa atcagcggcc gcaataaaat atctttatttt tcattacatc    4260 tgtgtgttgg tttttgtgt gaatcgtaac taacatacgc tctccatcaa aacaaaacga     4320
aacaaaacaa actagcaaaa taggctgtcc ccagtgcaag tgcaggtgcc agaacatttc    4380
tctatcgaa                                                           4389
```

<210> SEQ ID NO 87
<211> LENGTH: 4389
<212> TYPE: DNA
<213> ORGANISM: Artificial Sequence
<220> FEATURE:
<223> OTHER INFORMATION: pCCL8(5-76K/H-A)-IgG1Fc

<400> SEQUENCE: 87

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttcc cgagggtggg ggagaaccgt      180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggtttccat tccaatcacc tgctgcttta     660
acgtgatcaa taggaaaatt cctatccaga ggctggagag ctacacaaga atcaccaaca     720
tccaatgtcc caaggaagct gtgatcttca agaccgccgc gggcgctgag gtctgtgctg     780
accccgccga ggcgtgggtc gctgattcca tggccgcgct ggaccaaata tttcaaaatc     840
tggctccaga caaaactcac acatgcccac cgtgcccagc acctgaactc ctggggggac     900
cgtcagtctt cctcttcccc ccaaaaccca aggacaccct catgatctcc cggacccctg     960
aggtcacatg cgtggtggtg gacgtgagcc acgaagaccc tgaggtcaag ttcaactggt    1020
acgtggacgg cgtggaggtg cataatgcca agacaaagcc gcgggaggag cagtacaaca    1080
gcacgtaccg tgtggtcagc gtcctcaccg tcctgcacca ggactggctg aatggcaagg    1140
agtacaagtg caaggtctcc aacaaagccc tcccagcccc catcgagaaa accatctcca    1200
aagccaaagg gcagccccga gaaccacagg tgtacaccct gcccccatcc cgggaggaga    1260
tgaccaagaa ccaggtcagc ctgacctgcc tggtcaaagg cttctatccc agcgacatcg    1320
ccgtggagtg ggagagcaat gggcagccgg agaacaacta caagaccacg cctcccgtgc    1380
tggactccga cggctccttc ttcctctaca gcaagctcac cgtggacaag agcaggtggc    1440
agcaggggaa cgtcttctca tgctccgtga tgcacgaggc tctgcacaac cactacacgc    1500
agaagagcct ctccctgtct ccgggtaaat gagtgctagc tggccagaca tgataagata    1560
cattgatgag tttggacaaa ccacaactag aatgcagtga aaaaaatgct ttatttgtga    1620
aatttgtgat gctattgctt tatttgtaac cattataagc tgcaataaac aagttaacaa    1680
caacaattgc attcatttta tgtttcaggt tcagggggag gtgtgggagg ttttttaaag    1740
caagtaaaac tctacaaatg tggtatgga attaattcta aaatacagca tagcaaaact    1800
ttaacctcca atcaagcct ctacttgaat ccttttctga gggatgaata aggcataggc    1860
atcaggggct gttgccaatg tgcattagct gtttgcagcc tcaccttctt tcatggagtt    1920
taagatatag tgtattttcc caaggtttga actagctctt catttcttta tgttttaaat    1980
gcactgacct cccacattcc ctttttagta aaatattcag aaataattta aatacatcat    2040
```

```
tgcaatgaaa ataaatgttt tttattaggc agaatccaga tgctcaaggc ccttcataat    2100
atcccccagt ttagtagttg gacttaggga acaaaggaac ctttaataga aattggacag    2160
caagaaagcg agcttctagc ttatcctcag tcctgctcct ctgccacaaa gtgcacgcag    2220
ttgccggccg ggtcgcgcag ggcgaactcc cgccccacg gctgctcgcc gatctcggtc     2280
atggccggcc cggaggcgtc ccggaagttc gtggacacga cctccgacca ctcggcgtac    2340
agctcgtcca ggccgcgcac ccacacccag gccagggtgt tgtccggcac cacctggtcc    2400
tggaccgcgc tgatgaacag ggtcacgtcg tcccggacca caccggcgaa gtcgtcctcc    2460
acgaagtccc gggagaaccc gagccggtcg gtccagaact cgaccgctcc ggcgacgtcg    2520
cgcgcggtga gcaccggaac ggcactggtc aacttggcca tgatggctcc tcctgtcagg    2580
agaggaaaga gaagaaggtt agtacaattg ctatagtgag ttgtattata ctatgcagat    2640
atactatgcc aatgattaat tgtcaaacta gggctgcagg gttcatagtg ccacttttcc    2700
tgcactgccc catctcctgc ccaccctttc ccaggcatag acagtcagtg acttaccaaa    2760
ctcacaggag ggagaaggca gaagcttgag acagacccgc gggaccgccg aactgcgagg    2820
ggacgtggct agggcggctt cttttatggt gcgccggccc tcggaggcag ggcgctcggg    2880
gaggcctagc ggccaatctg cggtggcagg aggcggggcc gaaggccgtg cctgaccaat    2940
ccggagcaca taggagtctc agccccccgc cccaaagcaa ggggaagtca cgcgcctgta    3000
gcgccagcgt gttgtgaaat gggggcttgg gggggttggg gccctgacta gtcaaaacaa    3060
actcccattg acgtcaatgg ggtggagact tggaaatccc cgtgagtcaa accgctatcc    3120
acgcccattg atgtactgcc aaaaccgcat catcatggta atagcgatga ctaatacgta    3180
gatgtactgc caagtaggaa agtcccataa ggtcatgtac tgggcataat gccaggcggg    3240
ccatttaccg tcattgacgt caataggggg cgtacttggc atatgataca cttgatgtac    3300
tgccaagtgg gcagtttacc gtaaatactc cacccattga cgtcaatgga aagtccctat    3360
tggcgttact atgggaacat acgtcattat tgacgtcaat gggcggggt cgttgggcgg    3420 tcagccaggc gggccatttta ccgtaagtta tgtaacgcct gcaggttaat taagaacatg    3480
tgagcaaaag gccagcaaaa ggccaggaac cgtaaaaagg ccgcgttgct ggcgtttttc    3540
cataggctcc gcccccctga cgagcatcac aaaaatcgac gctcaagtca gaggtggcga    3600
aacccgacag gactataaag ataccaggcg tttccccctg gaagctccct cgtgcgctct    3660
cctgttccga ccctgccgct taccggatac ctgtccgcct ttctcccttc gggaagcgtg    3720
gcgctttctc atagctcacg ctgtaggtat tcagttcgg tgtaggtcgt tcgctccaag    3780
ctgggctgtg tgcacgaacc ccccgttcag cccgaccgct gcgccttatc cggtaactat    3840
cgtcttgagt ccaacccggt aagacacgac ttatcgccac tggcagcagc cactggtaac    3900
aggattagca gagcgaggta tgtaggcggt gctacagagt tcttgaagtg gtggcctaac    3960
tacggctaca ctagaagaac agtatttggt atctgcgctc tgctgaagcc agttaccttc    4020
ggaaaaagag ttggtagctc ttgatccggc aaacaaacca ccgctggtag cggtggtttt    4080
tttgtttgca agcagcagat tacgcgcaga aaaaaggat ctcaagaaga tcctttgatc    4140
ttttctacgg ggtctgacgc tcagtggaac gaaaactcac gttaagggat tttggtcatg    4200
gctagttaat taacatttaa atcagcggcc gcaataaaat atctttattt tcattacatc    4260
tgtgtgttgg ttttttgtgt gaatcgtaac taacatacgc tctccatcaa aacaaaacga    4320
aacaaaacaa actagcaaaa taggctgtcc ccagtgcaag tgcaggtgcc agaacatttc    4380
tctatcgaa                                                            4389
```

<210> SEQ ID NO 88
<211> LENGTH: 4398
<212> TYPE: DNA
<213> ORGANISM: Artificial Sequence
<220> FEATURE:
<223> OTHER INFORMATION: pCCL13-IgG1Fc

<400> SEQUENCE: 88

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttcc  cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgcagccaga tgcactcaac gtcccatcta     660
cttgctgctt cacatttagc agtaagaaga tctccttgca gaggctgaag agctatgtga     720
tcaccaccag caggtgtccc cagaaggctg tcatcttcag aaccaaactg ggcaaggaga     780
tctgtgctga cccaaaggag aagtgggtcc agaattatat gaaacacctg gccggaaag      840
ctcacaccct gaagactgac aaaactcaca catgcccacc gtgcccagca cctgaactcc     900
tggggggacc gtcagtcttc ctcttccccc caaaacccaa ggacaccctc atgatctccc     960
ggacccctga ggtcacatgc gtggtggtgg acgtgagcca cgaagaccct gaggtcaagt    1020
tcaactggta cgtggacggc gtggaggtgc ataatgccaa gacaaagccg cgggaggagc    1080
agtacaacag cacgtaccgt gtggtcagcg tcctcaccgt cctgcaccag gactggctga    1140
atggcaagga gtacaagtgc aaggtctcca acaaagcccc cagccccc  atcgagaaaa    1200
ccatctccaa agccaagggg cagccccgag aaccacaggt gtacaccctg cccccatccc    1260
gggaggagat gaccaagaac caggtcagcc tgacctgcct ggtcaaaggc ttctatccca    1320
gcgacatcgc cgtggagtgg gagagcaatg ggcagccgga gaacaactac aagaccacgc    1380
ctcccgtgct ggactccgac ggctccttct tcctctacag caagctcacc gtggacaaga    1440
gcaggtggca gcagggggaac gtcttctcat gctccgtgat gcacgaggct ctgcacaacc    1500
actacacgca gaagagcctc tccctgtctc cgggtaaatg agtgctagct ggccagacat    1560
gataagatac attgatgagt ttggacaaac cacaactaga atgcagtgaa aaaaatgctt    1620
tatttgtgaa atttgtgatg ctattgcttt atttgtaacc attataagct gcaataaaca    1680
agttaacaac aacaattgca ttcatttat gtttcaggtt caggggggagg tgtgggaggt    1740
ttttaaagc  aagtaaaacc tctacaaatg tggtatggaa ttaattctaa aatacagcat    1800
agcaaaactt taacctccaa atcaagcctc tacttgaatc cttttctgag ggatgaataa    1860
ggcataggca tcaggggctg ttgccaatgt gcattagctg tttgcagcct caccttcttt    1920
catggagttt aagatatagt gtattttccc aaggtttgaa ctagctcttc atttcttat    1980
gttttaaatg cactgacctc ccacattccc tttttagtaa aatattcaga ataatttaa    2040
```

```
atacatcatt gcaatgaaaa taaatgtttt ttattaggca gaatccagat gctcaaggcc      2100
cttcataata tcccccagtt tagtagttgg acttagggaa caaggaacc tttaatagaa       2160
attggacagc aagaaagcga gcttctagct tatcctcagt cctgctcctc tgccacaaag      2220
tgcacgcagt tgccgccgg gtcgcgcagg gcgaactccc gccccacgg ctgctcgccg        2280
atctcggtca tggccggccc ggaggcgtcc cggaagttcg tggacacgac ctccgaccac      2340
tcggcgtaca gctcgtccag gccgcgcacc cacacccagg ccagggtgtt gtccggcacc     2400
acctggtcct ggaccgcgct gatgaacagg gtcacgtcgt cccggaccac accggcgaag    2460
tcgtcctcca cgaagtcccg ggagaacccg agccggtcgg tccagaactc gaccgctccg    2520
gcgacgtcgc gcgcggtgag caccggaacg gcactggtca acttggccat gatggctcct    2580
cctgtcagga gaggaaagag aagaaggtta gtacaattgc tatagtgagt tgtattatac   2640
tatgcagata tactatgcca atgattaatt gtcaaactag ggctgcaggg ttcatagtgc    2700
cacttttcct gcactgcccc atctcctgcc caccctttcc caggcataga cagtcagtga    2760
cttaccaaac tcacaggagg gagaaggcag aagcttgaga cagacccgcg ggaccgccga    2820
actgcgaggg gacgtggcta gggcggcttc ttttatggtg cgccggccct cggaggcagg    2880
gcgctcgggg aggcctagcg gccaatctgc ggtggcagga ggcggggccg aaggccgtgc    2940
ctgaccaatc cggagcacat aggagtctca gccccccgcc ccaaagcaag gggaagtcac    3000
gcgcctgtag cgccagcgtg ttgtgaaatg ggggcttggg ggggttgggg ccctgactag    3060
tcaaaacaaa ctcccattga cgtcaatggg gtggagactt ggaaatcccc gtgagtcaaa    3120
ccgctatcca cgcccattga tgtactgcca aaaccgcatc atcatggtaa tagcgatgac    3180
taatacgtag atgtactgcc aagtaggaaa gtcccataag gtcatgtact gggcataatg    3240
ccaggcgggc catttaccgt cattgacgtc aataggggc gtacttggca tatgatacac     3300
ttgatgtact gccaagtggg cagtttaccg taaatactcc acccattgac gtcaatggaa    3360
agtccctatt ggcgttacta tgggaacata cgtcattatt gacgtcaatg ggcggggtc    3420
gttgggcggt cagccaggcg ggccatttac cgtaagttat gtaacgcctg caggttaatt    3480
aagaacatgt gagcaaaagg ccagcaaaag gccaggaacc gtaaaaaggc cgcgttgctg    3540
gcgttttttcc ataggctccg cccccctgac gagcatcaca aaaatcgacg ctcaagtcag    3600
aggtggcgaa acccgacagg actataaaga taccaggcgt ttccccctgg aagctccctc    3660
gtgcgctctc ctgttccgac cctgccgctt accggatacc tgtccgcctt tctcccttcg    3720
ggaagcgtgg cgctttctca tagctcacgc tgtaggtatc tcagttcggt gtaggtcgtt    3780
cgctccaagc tgggctgtgt gcacgaaccc cccgttcagc ccgaccgctg cgccttatcc    3840
ggtaactatc gtcttgagtc aacccggta agacacgact tatcgccact ggcagcagcc    3900
actggtaaca ggattagcag agcgaggtat gtaggcggtg ctacagagtt cttgaagtgg    3960
tggcctaact acggctacac tagaagaaca gtatttggta tctgcgctct gctgaagcca    4020
gttaccttcg gaaaaagagt tggtagctct tgatccggca acaaaccac cgctggtagc     4080
ggtggttttt ttgtttgcaa gcagcagatt acgcgcagaa aaaaggatc tcaagaagat    4140
cctttgatct tttctacggg gtctgacgct cagtggaacg aaaactcacg ttaagggatt    4200
ttggtcatgg ctagttaatt aacatttaaa tcagcggccg caataaaata tctttatttt    4260
cattacatct gtgtgttggt tttttgtgtg aatcgtaact aacatacgct ctccatcaaa    4320
acaaaacgaa acaaaacaaa ctagcaaaat aggctgtccc cagtgcaagt gcaggtgcca    4380
gaacatttct ctatcgaa                                                   4398
```

<210> SEQ ID NO 89
<211> LENGTH: 4386
<212> TYPE: DNA
<213> ORGANISM: Artificial Sequence
<220> FEATURE:
<223> OTHER INFORMATION: pCCL13(5-75)-IgG1Fc

<400> SEQUENCE: 89

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gcctttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | tcgaggggct | cgcatctctc | cttcacgcgc | ccgccgccct | acctgaggcc | 300 |
| gccatccacg | ccggttgagt | cgcgttctgc | cgcctcccgc | tgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgctcaacgt | cccatctact | tgctgcttca | 660 |
| catttagcag | taagaagatc | tccttgcaga | ggctgaagag | ctatgtgatc | accaccagca | 720 |
| ggtgtcccca | gaaggctgtc | atcttcagaa | ccaaactggg | caaggagatc | tgtgctgacc | 780 |
| caaaggagaa | gtgggtccag | aattatatga | aacacctggg | ccggaaagct | cacacctga | 840 |
| agactgacaa | aactcacaca | tgcccaccgt | gcccagcacc | tgaactcctg | ggggaccgt | 900 |
| cagtcttcct | cttccccca | aaacccaagg | acaccctcat | gatctcccgg | accctgagg | 960 |
| tcacatgcgt | ggtggtggac | gtgagccacg | aagaccctga | ggtcaagttc | aactggtacg | 1020 |
| tggacggcgt | ggaggtgcat | aatgccaaga | caaagccgcg | ggaggagcag | tacaacagca | 1080 |
| cgtaccgtgt | ggtcagcgtc | ctcaccgtcc | tgcaccagga | ctggctgaat | ggcaaggagt | 1140 |
| acaagtgcaa | ggtctccaac | aaagccctcc | cagcccccat | cgagaaaacc | atctccaaag | 1200 |
| ccaaagggca | gccccgagaa | ccacaggtgt | acaccctgcc | cccatcccgg | gaggagatga | 1260 |
| ccaagaacca | ggtcagcctg | acctgcctgg | tcaaaggctt | ctatcccagc | gacatcgccg | 1320 |
| tggagtggga | gagcaatggg | cagccggaga | acaactacaa | gaccacgcct | cccgtgctgg | 1380 |
| actccgacgg | ctccttcttc | ctctacagca | agctcaccgt | ggacaagagc | aggtggcagc | 1440 |
| aggggaacgt | cttctcatgc | tccgtgatgc | acgaggctct | gcacaaccac | tacacgcaga | 1500 |
| agagcctctc | cctgtctccg | ggtaaatgag | tgctagctgg | ccagacatga | taagatacat | 1560 |
| tgatgagttt | ggacaaacca | caactagaat | gcagtgaaaa | aaatgcttta | tttgtgaaat | 1620 |
| ttgtgatgct | attgctttat | ttgtaaccat | tataagctgc | aataaacaag | ttaacaacaa | 1680 |
| caattgcatt | cattttatgt | ttcaggttca | ggggaggtg | tgggaggttt | tttaaagcaa | 1740 |
| gtaaaacctc | tacaaatgtg | gtatggaatt | aattctaaaa | tacagcatag | caaaactta | 1800 |
| acctccaaat | caagcctcta | cttgaatcct | tttctgaggg | atgaataagg | cataggcatc | 1860 |
| aggggctgtt | gccaatgtgc | attagctgtt | tgcagcctca | ccttctttca | tggagtttaa | 1920 |
| gatatagtgt | attttcccaa | ggtttgaact | agctcttcat | ttctttatgt | tttaaatgca | 1980 |
| ctgacctccc | acattccctt | tttagtaaaa | tattcagaaa | taatttaaat | acatcattgc | 2040 |

```
aatgaaaata aatgttttt attaggcaga atccagatgc tcaaggccct tcataatatc    2100
ccccagttta gtagttggac ttagggaaca aaggaacctt taatagaaat tggacagcaa    2160
gaaagcgagc ttctagctta tcctcagtcc tgctcctctg ccacaaagtg cacgcagttg    2220
ccggccgggt cgcgcagggc gaactcccgc ccccacggct gctcgccgat ctcggtcatg    2280
gccggcccgg aggcgtcccg gaagttcgtg gacacgacct ccgaccactc ggcgtacagc    2340
tcgtccaggc cgcgcaccca cacccaggcc agggtgttgt ccggcaccac ctggtcctgg    2400
accgcgctga tgaacagggt cacgtcgtcc cggaccacac cggcgaagtc gtcctccacg    2460
aagtcccggg agaacccgag ccggtcggtc cagaactcga ccgctccggc gacgtcgcgc    2520
gcggtgagca ccggaacggc actggtcaac ttggccatga tggctcctcc tgtcaggaga    2580
ggaaagagaa gaaggttagt acaattgcta tagtgagttg tattatacta tgcagatata    2640
ctatgccaat gattaattgt caaactaggg ctgcagggtt catagtgcca cttttcctgc    2700
actgccccat ctcctgccca cccttcccca ggcatagaca gtcagtgact taccaaactc    2760
acaggaggga gaaggcagaa gcttgagaca gacccgcggg accgccgaac tgcgagggga    2820
cgtggctagg gcggcttctt ttatggtgcg ccggccctcg gaggcagggc gctcggggag    2880
gcctagcgga caatctgcgg tggcaggagg cggggccgaa ggccgtgcct gaccaatccg    2940
gagcacatag gagtctcagc cccccgcccc aaagcaaggg gaagtcacgc gcctgtagcg    3000
ccagcgtgtt gtgaaatggg ggcttggggg ggttggggcc ctgactagtc aaaacaaact    3060
cccattgacg tcaatggggt ggagacttgg aaatccccgt gagtcaaacc gctatccacg    3120
cccattgatg tactgccaaa accgcatcat catggtaata gcgatgacta atacgtagat    3180
gtactgccaa gtaggaaagt cccataaggt catgtactgg gcataatgcc aggcgggcca    3240
tttaccgtca ttgacgtcaa tagggggcgt acttggcata tgatacactt gatgtactgc    3300
caagtgggca gtttaccgta atactccacc ccattgacgt caatggaaag tccctattgg    3360
cgttactatg ggaacatacg tcattattga cgtcaatggg cggggtcgt tgggcggtca    3420
gccaggcggg ccatttaccg taagttatgt aacgcctgca ggttaattaa gaacatgtga    3480
gcaaaaggcc agcaaaaggc caggaaccgt aaaaaggccg cgttgctggc gttttcccat    3540
aggctccgcc cccctgacga gcatcacaaa aatcgacgct caagtcagag gtggcgaaac    3600
ccgacaggac tataaagata ccaggcgttt ccccctggaa gctccctcgt gcgctctcct    3660
gttccgaccc tgccgcttac cggatacctg tccgcctttc tcccttcggg aagcgtggcg    3720
ctttctcata gctcacgctg taggtatctc agttcggtgt aggtcgttcg ctccaagctg    3780
ggctgtgtgc acgaaccccc cgttcagccc gaccgctgcg ccttatccgg taactatcgt    3840
cttgagtcca acccggtaag acacgactta tcgccactgg cagcagccac tggtaacagg    3900
attagcagag cgaggtatgt aggcggtgct acagagttct tgaagtggtg gcctaactac    3960
ggctacacta agaacagt atttggtatc tgcgctctgc tgaagccagt taccttcgga    4020
aaaagagttg gtagctcttg atccggcaaa caaaccaccg ctggtagcgg tggttttttt    4080
gtttgcaagc agcagattac gcgcagaaaa aaggatctc aagaagatcc tttgatcttt    4140
tctacggggt ctgacgctca gtggaacgaa aactcacgtt aagggatttt ggtcatggct    4200
agttaattaa catttaaatc agcggccgca ataaatatc tttattttca ttacatctgt    4260
gtgttggttt tttgtgtgaa tcgtaactaa catacgctct ccatcaaaac aaaacgaaac    4320
aaaacaaact agcaaaatag gctgtcccca gtgcaagtgc aggtgccaga acatttctct    4380
atcgaa                                                               4386
```

<210> SEQ ID NO 90
<211> LENGTH: 4386
<212> TYPE: DNA
<213> ORGANISM: Artificial Sequence
<220> FEATURE:
<223> OTHER INFORMATION: pCCL13(5-75K/H-A)-IgG1Fc

<400> SEQUENCE: 90

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt     180
atataagtgc agtagtcgcc gtgaacgttc ttttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc tgtggtgcc tcctgaactg      360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgctcaacgt cccatctact tgctgcttca     660
catttagcag taagaagatc tccttgcaga ggctgaagag ctatgtgatc accaccagca     720
ggtgtcccca gaaggctgtc atcttcagaa ccgccctggg cgcggagatc tgtgctgacc     780
cagccgaggc ctgggtccag aattatatgg cggctctggg ccggaaagct gccaccctgg     840
ctactgacaa aactcacaca tgcccaccgt gcccagcacc tgaactcctg ggggaccgt      900
cagtcttcct cttcccccca aaacccaagg acaccctcat gatctcccgg acccctgagg     960
tcacatgcgt ggtggtggac gtgagccacg aagaccctga ggtcaagttc aactggtacg    1020
tggacggcgt ggaggtgcat aatgccaaga caaagccgcg ggaggagcag tacaacagca    1080
cgtaccgtgt ggtcagcgtc ctcaccgtcc tgcaccagga ctggctgaat ggcaaggagt    1140
acaagtgcaa ggtctccaac aaagccctcc cagcccccat cgagaaaacc atctccaaag    1200
ccaaagggca gccccgagaa ccacaggtgt acaccctgcc cccatcccgg gaggagatga    1260
ccaagaacca ggtcagcctg acctgcctgg tcaaaggctt ctatcccagc gacatcgccg    1320
tggagtggga gagcaatggg cagccggaga caactacaa gaccacgcct cccgtgctgg     1380
actccgacgg ctccttcttc ctctacagca agctcaccgt ggacaagagc aggtggcagc    1440
aggggaacgt cttctcatgc tccgtgatgc acgaggctct gcacaaccac tacacgcaga    1500
agagcctctc cctgtctccg ggtaaatgag tgctagctgg ccagacatga taagatacat    1560
tgatgagttt ggacaaacca actagaat gcagtgaaaa aaatgcttta tttgtgaaat     1620
ttgtgatgct attgctttat ttgtaaccat tataagctgc aataaacaag ttaacaacaa    1680
caattgcatt cattttatgt ttcaggttca ggggaggtg tgggaggttt tttaaagcaa     1740
gtaaacctc tacaaatgtg gtatggaatt aattctaaaa tacagcatag caaaactttta   1800
acctccaaat caagcctcta cttgaatcct ttctgagggg atgaataagg cataggcatc    1860
aggggctgtt gccaatgtgc attagctgtt tgcagcctca ccttctttca tggagtttaa    1920
gatatagtgt attttcccaa ggtttgaact agctcttcat ttctttatgt tttaaatgca    1980
ctgacctccc acattccctt tttagtaaaa tattcagaaa taatttaaat acatcattgc    2040
```

```
aatgaaaata aatgttttt attaggcaga atccagatgc tcaaggccct tcataatatc    2100
ccccagttta gtagttggac ttagggaaca aaggaaccttt taatagaaat tggacagcaa  2160
gaaagcgagc ttctagctta tcctcagtcc tgctcctctg ccacaaagtg cacgcagttg   2220
ccggccgggt cgcgcagggc gaactcccgc ccccacggct gctcgccgat ctcggtcatg   2280
gccggcccgg aggcgtcccg gaagttcgtg gacacgacct ccgaccactc ggcgtacagc   2340
tcgtccaggc cgcgcaccca cacccaggcc agggtgttgt ccggcaccac ctggtcctgg   2400
accgcgctga tgaacagggt cacgtcgtcc cggaccacac cggcgaagtc gtcctccacg   2460
aagtcccggg agaacccgag ccggtcggtc cagaactcga ccgctccggc gacgtcgcgc   2520
gcggtgagca ccggaacggc actggtcaac ttggccatga tggctcctcc tgtcaggaga   2580
ggaaagagaa gaaggttagt acaattgcta tagtgagttg tattatacta tgcagatata   2640
ctatgccaat gattaattgt caaactaggg ctgcagggtt catagtgcca cttttcctgc   2700
actgccccat ctcctgccca cccttttccca ggcatagaca gtcagtgact taccaaactc  2760
acaggaggga gaaggcagaa gcttgagaca gacccgcggg accgccgaac tgcgagggga   2820
cgtggctagg gcggcttctt ttatggtgcg ccggccctcg gaggcagggc gctcggggag   2880
gcctagcgga caatctgcgg tggcaggagg cggggccgaa ggccgtgcct gaccaatccg   2940
gagcacatag gagtctcagc cccccgcccc aaagcaaggg gaagtcacgc gcctgtagcg   3000
ccagcgtgtt gtgaaatggg ggcttgggg ggttggggcc ctgactagtc aaaacaaact    3060
cccattgacg tcaatggggt ggagacttgg aaatccccgt gagtcaaacc gctatccacg   3120
cccattgatg tactgccaaa accgcatcat catggtaata gcgatgacta atacgtagat   3180
gtactgccaa gtaggaaagt cccataaggt catgtactgg gcataatgcc aggcgggcca   3240
tttaccgtca ttgacgtcaa tagggggcgt acttggcata tgatacactt gatgtactgc   3300
caagtgggca gtttaccgta atactccac ccattgacgt caatggaaag tccctattgg    3360
cgttactatg ggaacatacg tcattattga cgtcaatggg cggggtcgt tgggcggtca    3420
gccaggcggg ccatttaccg taagttatgt aacgcctgca ggttaattaa gaacatgtga   3480
gcaaaaggcc agcaaaggc caggaaccgt aaaaaggccg cgttgctggc gttttttccat   3540
aggctccgcc cccctgacga gcatcacaaa aatcgacgct caagtcagag gtggcgaaac   3600
ccgacaggac tataaagata ccaggcgttt cccctggaa gctccctcgt gcgctctcct    3660
gttccgaccc tgccgcttac cggatacctg tccgcctttc tccccttcggg aagcgtggcg  3720
ctttctcata gctcacgctg taggtatctc agttcggtgt aggtcgttcg ctccaagctg   3780
ggctgtgtgc acgaaccccc cgttcagccc gaccgctgcg ccttatccgg taactatcgt   3840
cttgagtcca acccggtaag acacgactta tcgccactgg cagcagccac tggtaacagg   3900
attagcagag cgaggtatgt aggcggtgct acagagttct tgaagtggtg gcctaactac   3960
ggctacacta gaagaacagt atttggtatc tgcgctctgc tgaagccagt taccttcgga   4020
aaaagagttg gtagctcttg atccggcaaa caaaccaccg ctggtagcgg tggtttttt    4080
gtttgcaagc agcagattac gcgcagaaaa aaggatctc aagaagatcc tttgatcttt   4140
tctacggggt ctgacgctca gtggaacgaa aactcacgtt aagggatttt ggtcatggct  4200
agttaattaa catttaaatc agcggccgca ataaatatc tttattttca ttacatctgt    4260
gtgttggttt tttgtgtgaa tcgtaactaa catacgctct ccatcaaaac aaaacgaaac    4320
aaaacaaact agcaaaatag gctgtcccca gtgcaagtgc aggtgccaga acatttctct   4380
atcgaa                                                              4386
```

<210> SEQ ID NO 91
<211> LENGTH: 4527
<212> TYPE: DNA
<213> ORGANISM: Artificial Sequence
<220> FEATURE:
<223> OTHER INFORMATION: pCCL25-IgG1Fc

<400> SEQUENCE: 91

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg taccggcgc     540
ctacctgaga tcaccggcga aggagggcca ccatgtacag gatgcaactc ctgtcttgca     600
ttgcactaag tcttgcactt gtcacgaatt cgacccaagg tgtctttgag gactgctgcc     660
tggcctacca ctaccccatt gggtgggctg tgctccggca cgcctggact taccggatcc     720
aggaggtgag cggagctgc aatctgcctg ctgcgatatt ctacctcccc aagagacaca     780
ggaaggtgtg tgggaacccc aaaagcaggg aggtgcagag agccatgaag ctcctggatg     840
ctcgaaataa ggttttttgca agctccgcc acaacacgca gaccttccaa ggccctcatg     900
ctgtaaagaa gttgagttct ggaaactcca agttatcatc gtccaagttt agcaatccca     960
tcagcagcag caagaggaat gtctccgaca aaactcacac atgcccaccg tgcccagcac    1020
ctgaactcct ggggggaccg tcagtcttcc tcttcccccc aaaacccaag gacaccctca    1080
tgatctcccg gacccctgag gtcacatgcg tggtggtgga cgtgagccac gaagaccctg    1140
aggtcaagtt caactggtac gtggacggcg tggaggtgca taatgccaag acaaagccgc    1200
gggaggagca gtacaacagc acgtaccgtg tggtcagcgt cctcaccgtc ctgcaccagg    1260
actggctgaa tggcaaggag tacaagtgca aggtctccaa caaagccctc ccagccccca    1320
tcgagaaaac catctccaaa gccaagggc agccccgaga accacaggtg tacaccctgc    1380
ccccatcccg ggaggagatg accaagaacc aggtcagcct gacctgcctg gtcaaaggct    1440
tctatcccag cgacatcgcc gtggagtggg agagcaatgg gcagccggag aacaactaca    1500
agaccacgcc tcccgtgctg gactccgacg gctccttctt cctctacagc aagctcaccg    1560
tggacaagag caggtggcag caggggaacg tcttctcatg ctccgtgatg cacgaggctc    1620
tgcacaacca ctacacgcag aagagcctct ccctgtctcc gggtaaatga gtgctagctg    1680
gccagacatg ataagataca ttgatgagtt tggacaaacc acaactagaa tgcagtgaaa    1740
aaaatgcttt atttgtgaaa tttgtgatgc tattgcttta tttgtaacca ttataagctg    1800
caataaacaa gttaacaaca acaattgcat tcattttatg tttcaggttc agggggaggt    1860
gtgggaggtt ttttaaagca agtaaaacct ctacaaatgt ggtatggaat taattctaaa    1920
atacagcata gcaaacttt aacctccaaa tcaagcctct acttgaatcc tttttctgagg    1980
gatgaataag gcataggcat caggggctgt tgccaatgtg cattagctgt ttgcagcctc    2040
```

```
accttctttc atggagttta agatatagtg tattttccca aggtttgaac tagctcttca   2100
tttctttatg ttttaaatgc actgacctcc cacattccct ttttagtaaa atattcagaa   2160
ataatttaaa tacatcattg caatgaaaat aaatgttttt tattaggcag aatccagatg   2220
ctcaaggccc ttcataatat cccccagttt agtagttgga cttagggaac aaaggaacct   2280
ttaatagaaa ttggacagca agaaagcgag cttctagctt atcctcagtc ctgctcctct   2340
gccacaaagt gcacgcagtt gccggccggg tcgcgcaggg cgaactcccg cccccacggc   2400
tgctcgccga tctcggtcat ggccggcccg gaggcgtccc ggaagttcgt ggacacgacc   2460
tccgaccact cggcgtacag ctcgtccagg ccgcgcaccc acacccaggc cagggtgttg   2520
tccggcacca cctggtcctg gaccgcgctg atgaacaggg tcacgtcgtc ccggaccaca   2580
ccggcgaagt cgtcctccac gaagtcccgg gagaacccga gccggtcggt ccagaactcg   2640
accgctccgg cgacgtcgcg cgcggtgagc accggaacgg cactggtcaa cttggccatg   2700
atggctcctc ctgtcaggag aggaaagaga agaaggttag tacaattgct atagtgagtt   2760
gtattatact atgcagatat actatgccaa tgattaattg tcaaactagg gctgcagggt   2820
tcatagtgcc acttttcctg cactgcccca tctcctgccc acccttccc aggcatagac    2880
agtcagtgac ttaccaaact cacaggaggg agaaggcaga agcttgagac agacccgcgg   2940
gaccgccgaa ctgcgagggg acgtggctag ggcggcttct tttatggtgc gccggccctc   3000
ggaggcaggg cgctcgggga ggcctagcgg ccaatctgcg gtggcaggag gcggggccga   3060
aggccgtgcc tgaccaatcc ggagcacata ggagtctcag ccccccgccc caaagcaagg   3120
ggaagtcacg cgcctgtagc gccagcgtgt tgtgaaatgg gggcttgggg gggttggggc   3180
cctgactagt caaaacaaac tcccattgac gtcaatgggg tggagacttg aaatccccg    3240
tgagtcaaac cgctatccac gcccattgat gtactgccaa aaccgcatca tcatggtaat   3300
agcgatgact aatacgtaga tgtactgcca agtaggaaag tcccataagg tcatgtactg   3360
ggcataatgc caggcgggcc atttaccgtc attgacgtca ataggggcg tacttggcat    3420
atgatacact tgatgtactg ccaagtgggc agtttaccgt aaatactcca cccattgacg   3480
tcaatggaaa gtccctattg gcgttactat gggaacatac gtcattattg acgtcaatgg   3540
gcgggggtcg ttgggcggtc agccaggcgg gccatttacc gtaagttatg taacgcctgc   3600
aggttaatta agaacatgtg agcaaaaggc cagcaaaagg ccaggaaccg taaaaaggcc   3660
gcgttgctgg cgttttccca taggctccgc ccccctgacg agcatcacaa aaatcgacgc   3720
tcaagtcaga ggtggcgaaa cccgacagga ctataaagat accaggcgtt ccccctgga    3780
agctccctcg tgcgctctcc tgttccgacc ctgccgctta ccggatacct gtccgccttt   3840
ctcccttcgg gaagcgtggc gctttctcat agctcacgct gtaggtatct cagttcggtg   3900
taggtcgttc gctccaagct gggctgtgtg cacgaacccc ccgttcagcc cgaccgctgc   3960
gccttatccg gtaactatcg tcttgagtcc aacccggtaa gacacgactt atcgccactg   4020
gcagcagcca ctggtaacag gattagcaga gcgaggtatg taggcggtgc tacagagttc   4080
ttgaagtggt ggcctaacta cggctacact agaagaacag tatttggtat ctgcgctctg   4140
ctgaagccag ttaccttcgg aaaaagagtt ggtagctctt gatccggcaa acaaaccacc   4200
gctggtagcg gtggtttttt tgtttgcaag cagcagatta cgcgcagaaa aaaggatct   4260
caagaagatc ctttgatctt ttctacgggg tctgacgctc agtggaacga aaactcacgt   4320
taagggattt tggtcatggc tagttaatta acatttaaat cagcggccgc aataaaatat   4380
ctttattttc attacatctg tgtgttggtt ttttgtgtga atcgtaacta acatacgctc   4440
```

-continued

| | |
|---|---|
| tccatcaaaa caaaacgaaa caaaacaaac tagcaaaata ggctgtcccc agtgcaagtg | 4500 |
| caggtgccag aacatttctc tatcgaa | 4527 |

<210> SEQ ID NO 92
<211> LENGTH: 4518
<212> TYPE: DNA
<213> ORGANISM: Artificial Sequence
<220> FEATURE:
<223> OTHER INFORMATION: pCCL25(4-127)-IgG1Fc

<400> SEQUENCE: 92

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct cgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggtctttga ggactgctgc ctggcctacc | 660 |
| actacccat gggtgggct gtgctccggc acgcctggac ttaccggatc caggaggtga | 720 |
| gcggagctg caatctgcct gctgcgatat tctacctccc caagagacac aggaaggtgt | 780 |
| gtgggaaccc caaaagcagg gaggtgcaga gagccatgaa gctcctggat gctcgaaata | 840 |
| aggttttgc aaagctccgc cacaacacg agaccttcca aggccctcat gctgtaaaga | 900 |
| agttgagttc tggaaactcc aagttatcat cgtccaagtt tagcaatccc atcagcagca | 960 |
| gcaagaggaa tgtctccgac aaaactcaca catgcccacc gtgcccagca cctgaactcc | 1020 |
| tgggggggacc gtcagtcttc ctcttccccc caaaacccaa ggacaccctc atgatctccc | 1080 |
| ggacccctga ggtcacatgc gtggtggtgg acgtgagcca cgaagaccct gaggtcaagt | 1140 |
| tcaactggta cgtggacggc gtggaggtgc ataatgccaa gacaaagccg cgggaggagc | 1200 |
| agtacaacag cacgtaccgt gtggtcagcg tcctcaccgt cctgcaccag gactggctga | 1260 |
| atggcaagga gtacaagtgc aaggtctcca acaaagccct cccagccccc atcgagaaaa | 1320 |
| ccatctccaa agccaaaggg cagccccgag aaccacaggt gtacaccctg cccccatccc | 1380 |
| gggaggagat gaccaagaac caggtcagcc tgacctgcct ggtcaaaggc ttctatccca | 1440 |
| gcgacatcgc cgtggagtgg gagagcaatg ggcagccgga gaacaactac aagaccacgc | 1500 |
| ctcccgtgct ggactccgac ggctccttct cctctacag caagctcacc gtggacaaga | 1560 |
| gcaggtggca gcaggggaac gtcttctcat gctccgtgat gcacgaggct ctgcacaacc | 1620 |
| actacacgca gaagagcctc tccctgtctc cgggtaaatg agtgctagct ggccagacat | 1680 |
| gataagatac attgatgagt ttggacaaac cacaactaga atgcagtgaa aaaaatgctt | 1740 |
| tatttgtgaa atttgtgatg ctattgcttt atttgtaacc attataagct gcaataaaca | 1800 |
| agttaacaac aacaattgca ttcattttat gtttcaggtt cagggggagg tgtgggaggt | 1860 |
| tttttaaagc aagtaaaacc tctacaaatg tggtatggaa ttaattctaa aatacagcat | 1920 |

| | |
|---|---|
| agcaaaactt taacctccaa atcaagcctc tacttgaatc cttttctgag ggatgaataa | 1980 |
| ggcataggca tcaggggctg ttgccaatgt gcattagctg tttgcagcct caccttcttt | 2040 |
| catggagttt aagatatagt gtattttccc aaggtttgaa ctagctcttc atttctttat | 2100 |
| gttttaaatg cactgacctc ccacattccc tttttagtaa aatattcaga ataatttaa | 2160 |
| atacatcatt gcaatgaaaa taaatgtttt ttattaggca gaatccagat gctcaaggcc | 2220 |
| cttcataata tcccccagtt tagtagttgg acttagggaa caaggaacc tttaatagaa | 2280 |
| attggacagc aagaaagcga gcttctagct tatcctcagt cctgctcctc tgccacaaag | 2340 |
| tgcacgcagt gccggccgg gtcgcgcagg gcgaactccc gccccacgg ctgctcgccg | 2400 |
| atctcggtca tggccggccc ggaggcgtcc cggaagttcg tggacacgac ctccgaccac | 2460 |
| tcggcgtaca gctcgtccag gccgcgcacc cacacccagg ccagggtgtt gtccggcacc | 2520 |
| acctggtcct ggaccgcgct gatgaacagg gtcacgtcgt cccggaccac accggcgaag | 2580 |
| tcgtcctcca cgaagtcccg ggagaacccg agccggtcgg tccagaactc gaccgctccg | 2640 |
| gcgacgtcgc gcgcggtgag caccggaacg gcactggtca acttggccat gatggctcct | 2700 |
| cctgtcagga gaggaaagag aagaaggtta gtacaattgc tatagtgagt tgtattatac | 2760 |
| tatgcagata tactatgcca atgattaatt gtcaaactag ggctgcaggg ttcatagtgc | 2820 |
| cactttcct gcactgcccc atctcctgcc caccctttcc caggcataga cagtcagtga | 2880 |
| cttaccaaac tcacaggagg gagaaggcag aagcttgaga cagacccgcg ggaccgccga | 2940 |
| actgcgaggg gacgtggcta gggcggcttc ttttatggtg cgccggccct cggaggcagg | 3000 |
| gcgctcgggg aggcctagcg gccaatctgc ggtggcagga ggcggggccg aaggccgtgc | 3060 |
| ctgaccaatc cggagcacat aggagtctca gcccccgcc ccaaagcaag gggaagtcac | 3120 |
| gcgcctgtag cgccagcgtg ttgtgaaatg ggggcttggg ggggttgggg ccctgactag | 3180 |
| tcaaaacaaa ctcccattga cgtcaatggg gtggagactt ggaaatcccc gtgagtcaaa | 3240 |
| ccgctatcca cgcccattga tgtactgcca aaaccgcatc atcatggtaa tagcgatgac | 3300 |
| taatacgtag atgtactgcc aagtaggaaa gtcccataag gtcatgtact gggcataatg | 3360 |
| ccaggcgggc catttaccgt cattgacgtc aataggggc gtacttggca tatgatacac | 3420 |
| ttgatgtact gccaagtggg cagtttaccg taaatactcc acccattgac gtcaatggaa | 3480 |
| agtccctatt ggcgttacta tgggaacata cgtcattatt gacgtcaatg ggcggggtc | 3540 |
| gttgggcggt cagccaggcg ggccatttac cgtaagttat gtaacgcctg caggttaatt | 3600 |
| aagaacatgt gagcaaaagg ccagcaaaag gccaggaacc gtaaaaaggc cgcgttgctg | 3660 |
| gcgttttcc ataggctccg ccccctgac gagcatcaca aaaatcgacg ctcaagtcag | 3720 |
| aggtggcgaa acccgacagg actataaaga taccaggcgt ttcccctgg aagctccctc | 3780 |
| gtgcgctctc ctgttccgac cctgccgctt accggatacc tgtccgcctt tctcccttcg | 3840 |
| ggaagcgtgg cgctttctca tagctcacgc tgtaggtatc tcagttcggt gtaggtcgtt | 3900 |
| cgctccaagc tgggctgtgt gcacgaaccc cccgttcagc ccgaccgctg cgccttatcc | 3960 |
| ggtaactatc gtcttgagtc caacccggta agacacgact tatcgccact ggcagcagcc | 4020 |
| actggtaaca ggattagcag agcgaggtat gtaggcggtg ctacagagtt cttgaagtgg | 4080 |
| tggcctaact acggctacac tagaagaaca gtatttggta tctgcgctct gctgaagcca | 4140 |
| gttaccttcg gaaaaagagt tggtagctct tgatccggca aacaaaccac cgctggtagc | 4200 |
| ggtggttttt ttgtttgcaa gcagcagatt acgcgcagaa aaaaggatc tcaagaagat | 4260 |
| cctttgatct tttctacggg gtctgacgct cagtggaacg aaaactcacg ttaagggatt | 4320 |

```
ttggtcatgg ctagttaatt aacatttaaa tcagcggccg caataaaata tctttatttt    4380
cattacatct gtgtgttggt tttttgtgtg aatcgtaact aacatacgct ctccatcaaa    4440
acaaaacgaa acaaaacaaa ctagcaaaat aggctgtccc cagtgcaagt gcaggtgcca    4500
gaacatttct ctatcgaa                                                  4518

<210> SEQ ID NO 93
<211> LENGTH: 4518
<212> TYPE: DNA
<213> ORGANISM: Artificial Sequence
<220> FEATURE:
<223> OTHER INFORMATION: pCCL25(4-127K/H-A)-IgG1Fc

<400> SEQUENCE: 93
ggatctgcga tcgctccggt gcccgtcagt gggcagagcg cacatcgccc acagtccccg      60
agaagttggg gggagggggtc ggcaattgaa cgggtgccta gagaaggtgg cgcggggtaa   120
```



```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc tgtggtgcc tcctgaactg     360 cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggtctttga ggactgctgc ctggcctacc    660 actacccat gggtgggct gtgctccggc acgcctggac ttaccggatc caggaggtga     720
gcgggagctg caatctgcct gctgcgatat tctacctccc cgctgccgct gccgcggtgt    780
gtgggaaccc cgctagcgcc gaggtgcagg ctgccatggc cctcctggat gctgctaatg    840 ccgttttttgc agcgctcgct gccaacacg agaccttcca aggccctgcg gctgtagccg    900 cttttgagttc tggaaactcc gccttatcat cgtccgcgtt tagcaatccc atcagcagca    960
gcgctgccaa tgtctccgac aaaactcaca catgcccacc gtgcccagca cctgaactcc   1020
tggggggacc gtcagtcttc ctcttccccc caaaacccaa ggacaccctc atgatctccc   1080
ggacccctga ggtcacatgc gtggtggtgg acgtgagcca cgaagaccct gaggtcaagt   1140
tcaactggta cgtggacggc gtggaggtgc ataatgccaa gacaaagccg cgggaggagc   1200
agtacaacag cacgtaccgt gtggtcagcg tcctcaccgt cctgcaccag gactggctga   1260
atggcaagga gtacaagtgc aaggtctcca acaaagccct cccagccccc atcgagaaaa   1320
ccatctccaa agccaagggg cagccccgag aaccacaggt gtacaccctg cccccatccc   1380
gggaggagat gaccaagaac caggtcagcc tgacctgcct ggtcaaaggc ttctatccca   1440
gcgacatcgc cgtggagtgg gagagcaatg ggcagccgga gaacaactac aagaccacgc   1500
ctcccgtgct ggactccgac ggctccttct tcctctacag caagctcacc gtggacaaga   1560
gcaggtggca gcaggggaac gtcttctcat gctccgtgat gcacgaggct ctgcacaacc   1620
actacacgca gaagagcctc tccctgtctc cgggtaaatg agtgctagct ggccagacat   1680
gataagatac attgatgagt ttggacaaac cacaactaga atgcagtgaa aaaaatgctt   1740
tatttgtgaa atttgtgatg ctattgcttt atttgtaacc attataagct gcaataaaca   1800
```

```
agttaacaac aacaattgca ttcattttat gtttcaggtt caggggagg tgtgggaggt    1860 ttttttaaagc aagtaaaacc tctacaaatg tggtatggaa ttaattctaa aatacagcat    1920
agcaaaactt taacctccaa atcaagcctc tacttgaatc cttttctgag ggatgaataa    1980
ggcataggca tcaggggctg ttgccaatgt gcattagctg tttgcagcct caccttcttt    2040
catggagttt aagatatagt gtattttccc aaggtttgaa ctagctcttc atttctttat    2100
gttttaaatg cactgacctc ccacattccc tttttagtaa aatattcaga ataatttaa    2160 atacatcatt gcaatgaaaa taaatgtttt ttattaggca gaatccagat gctcaaggcc    2220
cttcataata tcccccagtt tagtagttgg acttagggaa caaaggaacc tttaatagaa    2280
attggacagc aagaaagcga gcttctagct tatcctcagt cctgctcctc tgccacaaag    2340
tgcacgcagt gccggccgg gtcgcgcagg gcgaactccc gccccacgg ctgctcgccg    2400 atctcggtca tggccggccc ggaggcgtcc cggaagttcg tggacacgac ctccgaccac    2460
tcggcgtaca gctcgtccag gccgcgcacc cacacccagg ccagggtgtt gtccggcacc    2520
acctggtcct ggaccgcgct gatgaacagg gtcacgtcgt cccggaccac accggcgaag    2580
tcgtcctcca cgaagtcccg ggagaacccg agccggtcgg tccagaactc gaccgctccg    2640
gcgacgtcgc gcgcggtgag caccggaacg gcactggtca acttggccat gatggctcct    2700
cctgtcagga gaggaaagag aagaaggtta gtacaattgc tatagtgagt tgtattatac    2760
tatgcagata tactatgcca atgattaatt gtcaaactag gctgcaggg ttcatagtgc    2820 cacttttcct gcactgcccc atctcctgcc cacccttcc caggcataga cagtcagtga    2880
cttaccaaac tcacaggagg gagaaggcag aagcttgaga cagacccgcg ggaccgccga    2940
actgcgaggg gacgtggcta gggcggcttc ttttatggtg cgccggccct cggaggcagg    3000
gcgctcgggg aggcctagcg gccaatctgc ggtggcagga ggcggggccg aaggccgtgc    3060
ctgaccaatc cggagcacat aggagtctca gcccccgcc ccaaagcaag gggaagtcac    3120
gcgcctgtag cgccagcgtg ttgtgaaatg ggggcttggg gggttgggg ccctgactag    3180 tcaaaacaaa ctcccattga cgtcaatggg gtggagactt ggaaatcccc gtgagtcaaa    3240
ccgctatcca cgcccattga tgtactgcca aaaccgcatc atcatggtaa tagcgatgac    3300
taatacgtag atgtactgcc aagtaggaaa gtcccataag gtcatgtact gggcataatg    3360
ccaggcgggc catttaccgt cattgacgtc aatagggggc gtacttggca tatgatacac    3420
ttgatgtact gccaagtggg cagtttaccg taaatactcc acccattgac gtcaatggaa    3480
agtccctatt ggcgttacta tgggaacata cgtcattatt gacgtcaatg ggcggggtc    3540 gttgggcggt cagccaggcg ggccatttac cgtaagttat gtaacgcctg caggttaatt    3600
aagaacatgt gagcaaaagg ccagcaaaag gccaggaacc gtaaaaaggc cgcgttgctg    3660 gcgttttttcc ataggctccg ccccctgac gagcatcaca aaaatcgacg ctcaagtcag    3720
aggtggcgaa acccgacagg actataaaga taccaggcgt ttccccctgg aagctccctc    3780
gtgcgctctc ctgttccgac cctgccgctt accggatacc tgtccgcctt tctcccttcg    3840
ggaagcgtgg cgctttctca tagctcacgc tgtaggtatc tcagttcggt gtaggtcgtt    3900
cgctccaagc tgggctgtgt gcacgaaccc ccgttcagc ccgaccgctg cgccttatcc    3960
ggtaactatc gtcttgagtc aacccggta agacacgact tatcgccact ggcagcagcc    4020
actggtaaca ggattagcag agcgaggtat gtaggcggtg ctacagagtt cttgaagtgg    4080
tggcctaact acggctacac tagaagaaca gtatttggta tctgcgctct gctgaagcca    4140
gttaccttcg gaaaaagagt tggtagctct tgatccggca aacaaaccac cgctggtagc    4200
```

```
ggtggttttt tgtttgcaa gcagcagatt acgcgcagaa aaaaaggatc tcaagaagat    4260
cctttgatct tttctacggg gtctgacgct cagtggaacg aaaactcacg ttaagggatt    4320
ttggtcatgg ctagttaatt aacatttaaa tcagcggccg caataaaata tctttatttt    4380
cattacatct gtgtgttggt tttttgtgtg aatcgtaact aacatacgct ctccatcaaa    4440
acaaaacgaa acaaaacaaa ctagcaaaat aggctgtccc cagtgcaagt gcaggtgcca    4500
gaacatttct ctatcgaa                                                  4518

<210> SEQ ID NO 94
<211> LENGTH: 4392
<212> TYPE: DNA
<213> ORGANISM: Artificial Sequence
<220> FEATURE:
<223> OTHER INFORMATION: pCXCL11-IgG1Fc

<400> SEQUENCE: 94
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct cgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgttccccat gttcaaaaga ggacgctgtc    660
tttgcatagg ccctggggta aaagcagtga agtggcaga tattgagaaa gcctccataa    720
tgtacccaag taacaactgt gacaaaatag aagtgattat taccctgaaa gaaaataaag    780
gacaacgatg cctaaatccc aaatcgaagc aagcaaggct tataatcaaa aaagttgaaa    840
gaaagaattt tgacaaaact cacacatgcc caccgtgccc agcacctgaa ctcctggggg    900
gaccgtcagt cttcctcttc cccccaaaac ccaaggacac cctcatgatc tcccggaccc    960
ctgaggtcac atgcgtggtg gtggacgtga gccacgaaga ccctgaggtc aagttcaact   1020
ggtacgtgga cggcgtggag gtgcataatg ccaagacaaa gccgcgggag gagcagtaca   1080
acagcacgta ccgtgtggtc agcgtcctca ccgtcctgca ccaggactgg ctgaatggca   1140
aggagtacaa gtgcaaggtc tccaacaaag ccctcccagc ccccatcgag aaaaccatct   1200
ccaaagccaa agggcagccc cgagaaccac aggtgtacac cctgccccca tcccgggagg   1260
agatgaccaa gaaccaggtc agcctgacct gcctggtcaa aggcttctat cccagcgaca   1320
tcgccgtgga gtgggagagc aatgggcagc cggagaacaa ctacaagacc acgcctcccg   1380
tgctggactc cgacggctcc ttcttcctct acagcaagct caccgtggac aagagcaggt   1440
ggcagcaggg gaacgtcttc tcatgctccg tgatgcacga ggctctgcac aaccactaca   1500
cgcagaagag cctctccctg tctccgggta aatgagtgct agctggccag acatgataag   1560
atacattgat gagtttggac aaaccacaac tagaatgcag tgaaaaaaat gctttatttg   1620
tgaaatttgt gatgctattg ctttatttgt aaccattata agctgcaata aacaagttaa   1680
```

```
caacaacaat tgcattcatt ttatgtttca ggttcagggg gaggtgtggg aggtttttta    1740
aagcaagtaa aacctctaca aatgtggtat ggaattaatt ctaaaataca gcatagcaaa    1800
actttaacct ccaaatcaag cctctacttg aatccttttc tgagggatga ataaggcata    1860
ggcatcaggg gctgttgcca atgtgcatta gctgtttgca gcctcacctt ctttcatgga    1920
gtttaagata tagtgtattt tcccaaggtt tgaactagct cttcatttct ttatgtttta    1980
aatgcactga cctcccacat tcccttttta gtaaaatatt cagaaataat ttaaatacat    2040
cattgcaatg aaaataaatg tttttattta ggcagaatcc agatgctcaa ggcccttcat    2100
aatatccccc agtttagtag ttggacttag ggaacaaagg aacctttaat agaaattgga    2160
cagcaagaaa gcgagcttct agcttatcct cagtcctgct cctctgccac aaagtgcacg    2220
cagttgccgg ccgggtcgcg cagggcgaac tcccgccccc acggctgctc gccgatctcg    2280
gtcatggccg gcccggaggc gtcccggaag ttcgtggaca cgacctccga ccactcggcg    2340
tacagctcgt ccaggccgcg cacccacacc caggccaggg tgttgtccgg caccacctgg    2400
tcctggaccg cgctgatgaa cagggtcacg tcgtcccgga ccacaccggc gaagtcgtcc    2460
tccacgaagt cccgggagaa cccgagccgg tcggtccaga actcgaccgc tccggcgacg    2520
tcgcgcgcgg tgagcaccgg aacggcactg gtcaacttgg ccatgatggc tcctcctgtc    2580
aggagaggaa agagaagaag gttagtacaa ttgctatagt gagttgtatt atactatgca    2640
gatatactat gccaatgatt aattgtcaaa ctagggctgc agggtcata gtgccacttt    2700
tcctgcactg ccccatctcc tgcccaccct ttcccaggca tagacagtca gtgacttacc    2760
aaactcacag gagggagaag gcagaagctt gagacagacc cgcgggaccg ccgaactgcg    2820
aggggacgtg gctagggcgg cttctttat ggtgcgccgg ccctcggagg cagggcgctc    2880
ggggaggcct agcggccaat ctgcggtggc aggaggcggg gccgaaggcc gtgcctgacc    2940
aatccggagc acataggagt ctcagccccc cgccccaaag caaggggaag tcacgcgcct    3000
gtagcgccag cgtgttgtga aatgggggct tgggggggtt ggggccctga ctagtcaaaa    3060
caaactccca ttgacgtcaa tggggtggag acttggaaat cccccgtgagt caaaccgcta    3120
tccacgccca ttgatgtact gccaaaaccg catcatcatg gtaatagcga tgactaatac    3180
gtagatgtac tgccaagtag gaaagtccca taaggtcatg tactgggcat aatgccaggc    3240
gggccattta ccgtcattga cgtcaatagg gggcgtactt ggcatatgat acacttgatg    3300
tactgccaag tgggcagttt accgtaaata ctccacccat tgacgtcaat ggaaagtccc    3360
tattggcgtt actatgggaa catacgtcat tattgacgtc aatgggcggg ggtcgttggg    3420
cggtcagcca ggcgggccat ttaccgtaag ttatgtaacg cctgcaggtt aattaagaac    3480
atgtgagcaa aaggccagca aaaggccagg aaccgtaaaa aggccgcgtt gctggcgttt    3540
ttccataggc tccgcccccc tgacgagcat cacaaaaatc gacgctcaag tcagaggtgg    3600
cgaaacccga caggactata aagataccag gcgtttcccc ctggaagctc cctcgtgcgc    3660
tctcctgttc cgaccctgcc gcttaccgga tacctgtccg cctttctccc ttcgggaagc    3720
gtggcgcttt ctcatagctc acgctgtagg tatctcagtt cggtgtaggt cgttcgctcc    3780
aagctgggct gtgtgcacga accccccgtt cagcccgacc gctgcgcctt atccggtaac    3840
tatcgtcttg agtccaaccc ggtaagacac gacttatcgc cactggcagc agccactggt    3900
aacaggatta gcagagcgag gtatgtaggc ggtgctacag agttcttgaa gtggtggcct    3960
aactacggct acactagaag aacagtattt ggtatctgcg ctctgctgaa gccagttacc    4020
ttcggaaaaa gagttggtag ctcttgatcc ggcaaacaaa ccaccgctgg tagcggtggt    4080
```

```
tttttttgttt gcaagcagca gattacgcgc agaaaaaaag gatctcaaga agatcctttg    4140
atcttttcta cggggtctga cgctcagtgg aacgaaaact cacgttaagg gattttggtc    4200
atggctagtt aattaacatt taaatcagcg gccgcaataa aatatcttta ttttcattac    4260
atctgtgtgt tggttttttg tgtgaatcgt aactaacata cgctctccat caaaacaaaa    4320
cgaaacaaaa caaactagca aaataggctg tccccagtgc aagtgcaggt gccagaacat    4380
ttctctatcg aa                                                       4392

<210> SEQ ID NO 95
<211> LENGTH: 4383
<212> TYPE: DNA
<213> ORGANISM: Artificial Sequence
<220> FEATURE:
<223> OTHER INFORMATION: pCXCL11(4-73)-IgG1Fc

<400> SEQUENCE: 95
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgttcaaaag aggacgctgt ctttgcatag     660
gccctggggt aaaagcagtg aaagtggcag atattgagaa agcctccata atgtacccaa     720
gtaacaactg tgacaaaata gaagtgatta ttaccctgaa agaaaataaa ggacaacgat     780
gcctaaatcc caaatcgaag caagcaaggc ttataatcaa aaaagttgaa agaaagaatt     840
ttgacaaaac tcacacatgc ccaccgtgcc cagcacctga actcctgggg ggaccgtcag     900
tcttcctctt ccccccaaaa cccaaggaca cctcatgat ctcccggacc cctgaggtca     960
catgcgtggt ggtggacgtg agccacgaag accctgaggt caagttcaac tggtacgtgg    1020
acggcgtgga ggtgcataat gccaagacaa agccgcggga ggagcagtac aacagcacgt    1080
accgtgtggt cagcgtcctc accgtcctgc accaggactg gctgaatggc aaggagtaca    1140
agtgcaaggt ctccaacaaa gccctcccag cccccatcga gaaaaccatc tccaaagcca    1200
aagggcagcc ccgagaacca caggtgtaca ccctgccccc atcccgggag gagatgacca    1260
agaaccaggt cagcctgacc tgcctggtca aaggcttcta tcccagcgac atcgccgtgg    1320
agtgggagag caatgggcag ccggagaaca actacaagac cacgcctccc gtgctggact    1380
ccgacggctc cttcttcctc tacagcaagc tcaccgtgga caagagcagg tggcagcagg    1440
ggaacgtctt ctcatgctcc gtgatgcacg aggctctgca caaccactac acgcagaaga    1500
gcctctccct gtctccgggt aaatgagtgc tagctggcca gacatgataa gatacattga    1560
tgagtttgga caaaccacaa ctagaatgca gtgaaaaaaa tgctttattt gtgaaatttg    1620
tgatgctatt gctttatttg taaccattat aagctgcaat aaacaagtta acaacaacaa    1680
```

```
ttgcattcat tttatgtttc aggttcaggg ggaggtgtgg gaggttttt  aaagcaagta   1740
aaacctctac aaatgtggta tggaattaat tctaaaatac agcatagcaa aactttaacc   1800
tccaaatcaa gcctctactt gaatcctttt ctgagggatg aataaggcat aggcatcagg   1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttccctttt  agtaaaatat tcagaaataa tttaaataca tcattgcaat   2040
gaaaataaat gttttttatt aggcagaatc cagatgctca aggcccttca taatatcccc   2100
cagtttagta gttggactta gggaacaaag gaaccttta  tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga cccgagccg  tcggtccag  aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gaggggacgt   2820
ggctagggcg gcttcttta  tggtgcgccg gccctcggag gcagggcgct cggggaggcc   2880
tagcggccaa tctgcggtgg caggaggcgg ggccgaaggc cgtgcctgac caatccggag   2940
cacataggag tctcagcccc ccgccccaaa gcaagggaa  gtcacgcgcc tgtagcgcca   3000
gcgtgttgtg aaatggggc  ttggggggt  tgggcccctg actagtcaaa caaactccc   3060
attgacgtca atggggtgga gacttggaaa tccccgtgag tcaaaccgct atccacgccc   3120
attgatgtac tgccaaaacc gcatcatcat ggtaatagcg atgactaata cgtagatgta   3180
ctgccaagta ggaaagtccc ataaggtcat gtactgggca taatgccagg cgggccattt   3240
accgtcattg acgtcaatag ggggcgtact tggcatatga tacacttgat gtactgccaa   3300
gtgggcagtt taccgtaaat actccaccca ttgacgtcaa tggaaagtcc ctattggcgt   3360
tactatggga acatacgtca ttattgacgt caatgggcgg gggtcgttgg gcggtcagcc   3420
aggcgggcca tttaccgtaa gttatgtaac gcctgcaggt taattaagaa catgtgagca   3480
aaaggccagc aaaaggccag gaaccgtaaa aaggccgcgt tgctggcgtt tttccatagg   3540
ctccgccccc ctgacgagca tcacaaaaat cgacgctcaa gtcagaggtg gcgaaacccg   3600
acaggactat aaagatacca ggcgtttccc cctggaagct ccctcgtgcg ctctcctgtt   3660
ccgaccctgc cgcttaccgg atacctgtcc gcctttctcc cttcgggaag cgtggcgctt   3720
tctcatagct cacgctgtag gtatctcagt tcggtgtagg tcgttcgctc caagctgggc   3780
tgtgtgcacg aaccccccgt tcagcccgac cgctgcgcct tatccggtaa ctatcgtctt   3840
gagtccaacc cggtaagaca cgacttatcg ccactggcag cagccactgg taacaggatt   3900
agcagagcga ggtatgtagg cggtgctaca gagttcttga agtggtggcc taactacggc   3960
tacactagaa gaacagtatt tggtatctgc gctctgctga agccagttac cttcggaaaa   4020
agagttggta gctcttgatc cggcaaacaa accaccgctg gtagcggtgg tttttttgtt   4080
```

```
tgcaagcagc agattacgcg cagaaaaaaa ggatctcaag aagatccttt gatcttttct    4140
acggggtctg acgctcagtg gaacgaaaac tcacgttaag ggattttggt catggctagt    4200
taattaacat ttaaatcagc ggccgcaata aaatatcttt attttcatta catctgtgtg    4260 ttggttttt  gtgtgaatcg taactaacat acgctctcca tcaaaacaaa acgaaacaaa    4320
acaaactagc aaaataggct gtccccagtg caagtgcagg tgccagaaca tttctctatc    4380
gaa                                                                 4383
```

<210> SEQ ID NO 96
<211> LENGTH: 4383
<212> TYPE: DNA
<213> ORGANISM: Artificial Sequence
<220> FEATURE:
<223> OTHER INFORMATION: pCXCL11(4-73K/H-A)-IgG1Fc

<400> SEQUENCE: 96

```
ggatctgcga tcgctccggt gcccgtcagt gggcagagcg cacatcgccc acagtccccg      60
agaagttggg gggagggggtc ggcaattgaa cgggtgccta gagaaggtgg cgcggggtaa    120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgttcaaaag gaggacgctgt ctttgcatag    660 gccctggggt aaaagcagtg aaagtggcag atattgaggc cgcctccata atgtacccaa    720
gtaacaactg tgacaaaata gaagtgatta ttaccctggc agaaaatgcc ggacaagcat    780
gcctaaatcc cgcctcggca caagcagccc ttataatcgc agccgttgaa gcagccaatt    840
ttgacaaaac tcacacatgc ccaccgtgcc cagcacctga actcctgggg ggaccgtcag    900
tcttcctctt ccccccaaaa cccaaggaca cctcatgat ctcccggacc cctgaggtca     960
catgcgtggt ggtggacgtg agccacgaag accctgaggt caagttcaac tggtacgtgg   1020
acggcgtgga ggtgcataat gccaagacaa agccgcggga ggagcagtac aacagcacgt   1080
accgtgtggt cagcgtcctc accgtcctgc accaggactg gctgaatggc aaggagtaca   1140
agtgcaaggt ctccaacaaa gccctcccag ccccatcga gaaaaccatc tccaaagcca    1200
aagggcagcc ccgagaacca caggtgtaca ccctgccccc atcccgggag gagatgacca   1260
agaaccaggt cagcctgacc tgcctggtca aaggcttcta tcccagcgac atcgccgtgg   1320
agtgggagag caatgggcag ccggagaaca actacaagac cacgcctccc gtgctggact   1380
ccgacggctc cttcttcctc tacagcaagc tcaccgtgga caagagcagg tggcagcagg   1440
ggaacgtctt ctcatgctcc gtgatgcacg aggctctgca caaccactac acgcagaaga   1500
gcctctccct gtctccgggt aaatgagtgc tagctggcca gacatgataa gatacattga   1560
tgagtttgga caaaccacaa ctagaatgca gtgaaaaaaa tgctttattt gtgaaatttg   1620
tgatgctatt gctttatttg taaccattat aagctgcaat aaacaagtta acaacaacaa   1680
```

```
ttgcattcat ttatgttc aggttcaggg ggaggtgtgg gaggttttt aaagcaagta      1740 aaacctctac aaatgtggta tggaattaat tctaaaatac agcatagcaa aactttaacc   1800
tccaaatcaa gcctctactt gaatcctttt ctgagggatg aataaggcat aggcatcagg   1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttcccttttt agtaaaatat tcagaaataa tttaaataca tcattgcaat   2040
gaaaataaat gttttttatt aggcagaatc cagatgctca aggcccttca taatatcccc   2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga acccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gaggggacgt   2820
ggctagggcg gcttcttta tggtgcgccg gccctcggag cagggcgct cggggaggcc     2880 tagcggccaa tctgcggtgg caggaggcgg ggccgaaggc cgtgcctgac caatccggag   2940
cacataggag tctcagcccc ccgcccaaa gcaagggaa gtcacgcgcc tgtagcgcca     3000
gcgtgttgtg aaatggggc ttggggggt tgggcccctg actagtcaaa caaactccc     3060 attgacgtca atggggtgga gacttggaaa tccccgtgag tcaaaccgct atccacgccc   3120
attgatgtac tgccaaaacc gcatcatcat ggtaatagcg atgactaata cgtagatgta   3180
ctgccaagta ggaaagtccc ataaggtcat gtactgggca taatgccagg cgggccattt   3240
accgtcattg acgtcaatag ggggcgtact tggcatatga tacacttgat gtactgccaa   3300
gtgggcagtt taccgtaaat actccaccca ttgacgtcaa tggaaagtcc ctattggcgt   3360
tactatggga acatacgtca ttattgacgt caatgggcgg gggtcgttgg gcggtcagcc   3420
aggcgggcca tttaccgtaa gttatgtaac gcctgcaggt taattaagaa catgtgagca   3480
aaaggccagc aaaaggccag gaaccgtaaa aaggccgcgt tgctggcgtt tttccatagg   3540
ctccgccccc ctgacgagca tcacaaaaat cgacgctcaa gtcagaggtg gcgaaacccg   3600
acaggactat aaagatacca ggcgtttccc cctggaagct ccctcgtgcg ctctcctgtt   3660
ccgaccctgc cgcttaccgg atacctgtcc gcctttctcc cttcgggaag cgtggcgctt   3720
tctcatagct cacgctgtag gtatctcagt tcggtgtagg tcgttcgctc caagctgggc   3780
tgtgtgcacg aaccccccgt tcagcccgac cgctgcgcct tatccggtaa ctatcgtctt   3840
gagtccaacc cggtaagaca cgacttatcg ccactggcag cagccactgg taacaggatt   3900
agcagagcga ggtatgtagg cggtgctaca gagttcttga agtggtggcc taactacggc   3960
tacactagaa gaacagtatt tggtatctgc gctctgctga agccagttac cttcggaaaa   4020
agagttggta gctcttgatc cggcaaacaa accaccgctg gtagcggtgg ttttttgtt    4080
```

```
tgcaagcagc agattacgcg cagaaaaaaa ggatctcaag aagatccttt gatcttttct    4140
acggggtctg acgctcagtg aacgaaaac tcacgttaag ggattttggt catggctagt     4200
taattaacat ttaaatcagc ggccgcaata aatatctttt attttcatta catctgtgtg    4260
ttggtttttt gtgtgaatcg taactaacat acgctctcca tcaaaacaaa acgaaacaaa    4320
acaaactagc aaaataggct gtccccagtg caagtgcagg tgccagaaca tttctctatc    4380
gaa                                                                  4383
```

<210> SEQ ID NO 97
<211> LENGTH: 4383
<212> TYPE: DNA
<213> ORGANISM: Artificial Sequence
<220> FEATURE:
<223> OTHER INFORMATION: pCXCL11-IgG4Fc

<400> SEQUENCE: 97

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttcc cgagggtggg ggagaaccgt      180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc      300
gccatccacg ccggttgagt cgcgttctgc cgcctccgc ctgtggtgcc tcctgaactg      360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cgttccccat gttcaaaaga ggacgctgtc     660
tttgcatagg ccctggggta aaagcagtga agtggcaga tattgagaaa gcctccataa      720
tgtacccaag taacaactgt gacaaaatag aagtgattat taccctgaaa gaaaataaag    780
gacaacgatg cctaaatccc aaatcgaagc aagcaaggct tataatcaaa aaagttgaaa     840
gaaagaattt tccccatgc ccatcatgcc cagcacctga gttcctgggg ggaccatcag     900
tcttcctgtt cccccaaaa cccaaggaca ctctcatgat ctcccggacc cctgaggtca    960
cgtgcgtggt ggtggacgtg agccaggaag accccgaggt ccagttcaac tggtacgtgg    1020
atggcgtgga ggtgcataat gccaagacaa agccgcggga ggagcagttc aacagcacgt    1080
accgtgtggt cagcgtcctc accgtcctgc accaggactg gctgaacggc aaggagtaca    1140
agtgcaaggt ctccaacaaa ggcctcccgt cctccatcga aaaccatc tccaaagcca     1200 aagggcagcc ccgagagcca caggtgtaca ccctgccccc atcccaggag gagatgacca    1260
agaaccaggt cagcctgacc tgcctggtca aaggcttcta ccccagcgac atcgccgtgg    1320
agtgggagag caatgggcag ccggagaaca actacaagac cacgcctccc gtgctggact    1380
ccgacggctc cttcttcctc tacagcaggc taaccgtgga caagagcagg tggcaggagg    1440
ggaatgtctt ctcatgctcc gtgatgcatg aggctctgca caaccactac acacagaaga    1500
gcctctccct gtctccgggt aaatgagtgc tagctggcca gacatgataa gatacattga    1560
tgagtttgga caaaccacaa ctagaatgca gtgaaaaaaa tgctttattt gtgaaatttg    1620
tgatgctatt gctttatttg taaccattat aagctgcaat aaacaagtta acaacaacaa    1680
```

```
ttgcattcat ttatgtttc aggttcaggg ggaggtgtgg gaggtttttt aaagcaagta    1740
aaacctctac aaatgtggta tggaattaat tctaaaatac agcatagcaa aactttaacc    1800
tccaaatcaa gcctctactt gaatcctttt ccgaggcatg aataaggcat aggcatcagg    1860
ggctgttgcc aatgtgcatt agctgtttgc agcctcacct tctttcatgg agtttaagat    1920
atagtgtatt ttcccaaggt ttgaactagc tcttcatttc tttatgtttt aaatgcactg    1980
acctcccaca ttcccttttt agtaaaatat tcagaaataa tttaaataca tcattgcaat    2040
gaaaataaat gttttttatt aggcagaatc cagatgctca aggcccttca taatatcccc    2100
cagtttagta gttggactta gggaacaaag gaacctttaa tagaaattgg acagcaagaa    2160
agcgagcttc tagcttatcc tcagtcctgc tcctctgcca caaagtgcac gcagttgccg    2220
gccgggtcgc gcagggcgaa ctcccgcccc cacggctgct cgccgatctc ggtcatggcc    2280
ggcccggagg cgtcccggaa gttcgtggac acgacctccg accactcggc gtacagctcg    2340
tccaggccgc gcacccacac ccaggccagg gtgttgtccg gcaccacctg gtcctggacc    2400
gcgctgatga acagggtcac gtcgtcccgg accacaccgg cgaagtcgtc ctccacgaag    2460
tcccgggaga acccgagccg gtcggtccag aactcgaccg ctccggcgac gtcgcgcgcg    2520
gtgagcaccg gaacggcact ggtcaacttg gccatgatgg ctcctcctgt caggagagga    2580
aagagaagaa ggttagtaca attgctatag tgagttgtat tatactatgc agatatacta    2640
tgccaatgat taattgtcaa actagggctg cagggttcat agtgccactt ttcctgcact    2700
gccccatctc ctgcccaccc tttcccaggc atagacagtc agtgacttac caaactcaca    2760
ggagggagaa ggcagaagct tgagacagac ccgcgggacc gccgaactgc gaggggacgt    2820
ggctagggcg gcttcttta tggtgcgccg gccctcggag cagggcgct cggggaggcc    2880 tagcggccaa tctgcggtgg caggaggcgg ggccgaaggc cgtgcctgac caatccggag    2940
cacataggag tctcagcccc ccgcccccaaa gcaagggaa gtcacgcgcc tgtagcgcca    3000
gcgtgttgtg aaatggggc ttggggggggt tggggccctg actagtcaaa acaaactccc    3060
attgacgtca atggggtgga gacttggaaa tccccgtgag tcaaaccgct atccacgccc    3120
attgatgtac tgccaaaacc gcatcatcat ggtaatagcg atgactaata cgtagatgta    3180
ctgccaagta ggaaagtccc ataaggtcat gtactgggca taatgccagg cgggccattt    3240
accgtcattg acgtcaatag ggggcgtact tggcatatga tacacttgat gtactgccaa    3300
gtgggcagtt taccgtaaat actccaccca ttgacgtcaa tggaaagtcc ctattggcgt    3360
tactatggga acatacgtca ttattgacgt caatgggcgg gggtcgttgg gcggtcagcc    3420
aggcgggcca tttaccgtaa gttatgtaac gcctgcaggt taattaagaa catgtgagca    3480
aaaggccagc aaaaggccag gaaccgtaaa aaggccgcgt tgctggcgtt tttccatagg    3540
ctccgccccc ctgacgagca tcacaaaaat cgacgctcaa gtcagaggtg gcgaaacccg    3600
acaggactat aaagatacca ggcgtttccc cctggaagct ccctcgtgcg ctctcctgtt    3660
ccgaccctgc cgcttaccgg atacctgtcc gcctttctcc cttcgggaag cgtggcgctt    3720
tctcatagct cacgctgtag gtatctcagt tcggtgtagg tcgttcgctc caagctgggc    3780
tgtgtgcacg aaccccccgt tcagcccgac cgctgcgcct tatccggtaa ctatcgtctt    3840
gagtccaacc cggtaagaca cgacttatcg ccactggcag cagccactgg taacaggatt    3900
agcagagcga ggtatgtagg cggtgctaca gagttcttga agtggtggcc taactacggc    3960
tacactagaa gaacagtatt tggtatctgc gctctgctga agccagttac cttcggaaaa    4020
agagttggta gctcttgatc cggcaaacaa accaccgctg gtagcggtgg tttttttgtt    4080
```

-continued

```
tgcaagcagc agattacgcg cagaaaaaaa ggatctcaag aagatccttt gatctttttct    4140 acggggtctg acgctcagtg aacgaaaac tcacgttaag ggattttggt catggctagt    4200
taattaacat ttaaatcagc ggccgcaata aaatatcttt attttcatta catctgtgtg    4260 ttggttttttt gtgtgaatcg taactaacat acgctctcca tcaaaacaaa acgaaacaaa    4320
acaaactagc aaaataggct gtccccagtg caagtgcagg tgccagaaca tttctctatc    4380
gaa                                                                   4383
```

<210> SEQ ID NO 98
<211> LENGTH: 4374
<212> TYPE: DNA
<213> ORGANISM: Artificial Sequence
<220> FEATURE:
<223> OTHER INFORMATION: pCXCL11(4-73)-IgG4Fc

<400> SEQUENCE: 98

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cgttcaaaag gaggacgctgt ctttgcatag    660 gccctggggt aaaagcagtg aaagtggcag atattgagaa agcctccata atgtacccaa    720
gtaacaactg tgacaaaata gaagtgatta ttaccctgaa agaaaataaa ggacaacgat    780
gcctaaatcc caaatcgaag caagcaaggc ttataatcaa aaaagttgaa agaaagaatt    840 ttccccccatg cccatcatgc ccagcacctg agttcctggg gggaccatca gtcttcctgt    900
tccccccaaa acccaaggac actctcatga tctcccggac ccctgaggtc acgtgcgtgg    960
tggtggacgt gagccaggaa gaccccgagg tccagttcaa ctggtacgtg gatggcgtgg   1020
aggtgcataa tgccaagaca aagccgcggg aggagcagtt caacagcacg taccgtgtgg   1080
tcagcgtcct caccgtcctg caccaggact ggctgaacgg caaggagtac aagtgcaagg   1140
tctccaacaa aggcctcccg tcctccatcg agaaaaccat ctccaaagcc aaagggcagc   1200
cccgagagcc acaggtgtac accctgcccc catcccagga ggagatgacc aagaaccagg   1260
tcagcctgac ctgcctggtc aaaggcttct accccagcga catcgccgtg gagtgggaga   1320
gcaatgggca gccggagaac aactacaaga ccacgcctcc cgtgctggac tccgacggct   1380
ccttcttcct ctacagcagg ctaaccgtgg acaagagcag gtggcaggag gggaatgtct   1440
tctcatgctc cgtgatgcat gaggctctgc acaaccacta cacacagaag agcctctccc   1500
tgtctccggg taaatgagtg ctagctggcc agacatgata agatacattg atgagtttgg   1560
acaaaccaca actagaatgc agtgaaaaaa atgctttatt tgtgaaattt gtgatgctat   1620
tgctttattt gtaaccatta taagctgcaa taaacaagtt aacaacaaca attgcattca   1680
```

| | |
|---|---|
| ttttatgttt caggttcagg gggaggtgtg ggaggttttt taaagcaagt aaaacctcta | 1740 |
| caaatgtggt atggaattaa ttctaaaata cagcatagca aaactttaac ctccaaatca | 1800 |
| agcctctact tgaatccttt tctgagggat gaataaggca taggcatcag gggctgttgc | 1860 |
| caatgtgcat tagctgtttg cagcctcacc ttctttcatg gagtttaaga tatagtgtat | 1920 |
| tttcccaagg tttgaactag ctcttcattt ctttatgttt taaatgcact gacctcccac | 1980 |
| attccctttt tagtaaaata ttcagaaata atttaaatac atcattgcaa tgaaaataaa | 2040 |
| tgttttttat taggcagaat ccagatgctc aaggcccttc ataatatccc ccagtttagt | 2100 |
| agttggactt agggaacaaa ggaacccttta atagaaattg gacagcaaga aagcgagctt | 2160 |
| ctagcttatc ctcagtcctg ctcctctgcc acaaagtgca cgcagttgcc ggccgggtcg | 2220 |
| cgcagggcga actcccgccc ccacggctgc tcgccgatct cggtcatggc cggcccggag | 2280 |
| gcgtcccgga agttcgtgga cacgacctcc gaccactcgg cgtacagctc gtccaggccg | 2340 |
| cgcacccaca cccaggccag ggtgttgtcc ggcaccacct ggtcctggac cgcgctgatg | 2400 |
| aacagggtca cgtcgtcccg gaccacaccg gcgaagtcgt cctccacgaa gtcccgggag | 2460 |
| aacccgagcc ggtcggtcca gaactcgacc gctccggcga cgtcgcgcgc ggtgagcacc | 2520 |
| ggaacggcac tggtcaactt ggccatgatg gctcctcctg tcaggagagg aaagagaaga | 2580 |
| aggttagtac aattgctata gtgagttgta ttatactatg cagatatact atgccaatga | 2640 |
| ttaattgtca aactagggct gcagggttca tagtgccact tttcctgcac tgccccatct | 2700 |
| cctgcccacc ctttcccagg catagacagt cagtgactta ccaaactcac aggagggaga | 2760 |
| aggcagaagc ttgagacaga cccgcgggac cgccgaactg cgaggggacg tggctagggc | 2820 |
| ggcttctttt atggtgcgcc ggccctcgga ggcagggcgc tcggggaggc ctagcggcca | 2880 |
| atctgcggtg gcaggaggcg gggccgaagg ccgtgcctga ccaatccgga gcacatagga | 2940 |
| gtctcagccc cccgccccaa agcaagggga agtcacgcgc ctgtagcgcc agcgtgttgt | 3000 |
| gaaatggggg cttgggggggg ttggggcccct gactagtcaa aacaaactcc cattgacgtc | 3060 |
| aatggggtgg agacttggaa atccccgtga gtcaaaccgc tatccacgcc cattgatgta | 3120 |
| ctgccaaaac cgcatcatca tggtaatagc gatgactaat acgtagatgt actgccaagt | 3180 |
| aggaaagtcc cataaggtca tgtactgggc ataatgccag gcgggccatt taccgtcatt | 3240 |
| gacgtcaata gggggcgtac ttggcatatg atacacttga tgtactgcca agtgggcagt | 3300 |
| ttaccgtaaa tactccaccc attgacgtca atggaaagtc cctattggcg ttactatggg | 3360 |
| aacatacgtc attattgacg tcaatggcg ggggtcgttg ggcggtcagc caggcgggcc | 3420 |
| atttaccgta agttatgtaa cgcctgcagg ttaattaaga acatgtgagc aaaaggccag | 3480 |
| caaaaggcca ggaaccgtaa aaaggccgcg ttgctggcgt ttttccatag gctccgcccc | 3540 |
| cctgacgagc atcacaaaaa tcgacgctca agtcagaggt ggcgaaaccc gacaggacta | 3600 |
| taaagatacc aggcgtttcc ccctggaagc tccctcgtgc gctctcctgt tccgaccctg | 3660 |
| ccgcttaccg gatacctgtc cgcctttctc ccttcgggaa gcgtggcgct ttctcatagc | 3720 |
| tcacgctgta ggtatctcag ttcggtgtag gtcgttcgct ccaagctggg ctgtgtgcac | 3780 |
| gaaccccccg ttcagcccga ccgctgcgcc ttatccggta actatcgtct gagtccaac | 3840 |
| ccggtaagac acgacttatc gccactggca gcagccactg gtaacaggat tagcagagcg | 3900 |
| aggtatgtag gcggtgctac agagttcttg aagtggtggc ctaactacgg ctacactaga | 3960 |
| agaacagtat ttggtatctg cgctctgctg aagccagtta ccttcggaaa aagagttggt | 4020 |
| agctcttgat ccggcaaaca aaccaccgct ggtagcggtg gtttttttgt ttgcaagcag | 4080 |

| | | |
|---|---|---|
| cagattacgc gcagaaaaaa aggatctcaa gaagatcctt tgatcttttc tacggggtct | 4140 | |
| gacgctcagt ggaacgaaaa ctcacgttaa gggattttgg tcatggctag ttaattaaca | 4200 | |
| tttaaatcag cggccgcaat aaaatatctt tattttcatt acatctgtgt gttggttttt | 4260 | |
| tgtgtgaatc gtaactaaca tacgctctcc atcaaaacaa aacgaaacaa aacaaactag | 4320 | |
| caaaataggc tgtccccagt gcaagtgcag gtgccagaac atttctctat cgaa | 4374 | |

<210> SEQ ID NO 99
<211> LENGTH: 4374
<212> TYPE: DNA
<213> ORGANISM: Artificial Sequence
<220> FEATURE:
<223> OTHER INFORMATION: pCXCL11(4-73K/H-A)-IgG4Fc

<400> SEQUENCE: 99

| | | |
|---|---|---|
| ggatctgcga tcgctccggt gcccgtcagt gggcagagcg cacatcgccc acagtccccg | 60 | |
| agaagttggg gggaggggtc ggcaattgaa cgggtgccta gagaaggtgg cgcggggtaa | 120 | |
| actgggaaag tgatgtcgtg tactggctcc gcctttttcc cgagggtggg ggagaaccgt | 180 | |
| atataagtgc agtagtcgcc gtgaacgttc ttttcgcaa cgggtttgcc gccagaacac | 240 | |
| agctgaagct tcgaggggct cgcatctctc cttcacgcgc ccgccgccct acctgaggcc | 300 | |
| gccatccacg ccggttgagt cgcgttctgc gcctcccgc ctgtggtgcc tcctgaactg | 360 | |
| cgtccgccgt ctaggtaagt ttaaagctca ggtcgagacc gggcctttgt ccggcgctcc | 420 | |
| cttggagcct acctagactc agccggctct ccacgctttg cctgaccctg cttgctcaac | 480 | |
| tctacgtctt tgtttcgttt tctgttctgc gccgttacag atccaagctg tgaccggcgc | 540 | |
| ctacctgaga tcaccggcga aggagggcca ccatgtacag gatgcaactc ctgtcttgca | 600 | |
| ttgcactaag tcttgcactt gtcacgaatt cgttcaaaag gaggacgctgt ctttgcatag | 660 | |
| gccctggggt aaaagcagtg aaagtggcag atattgaggc gcctccata atgtacccaa | 720 | |
| gtaacaactg tgacaaaata gaagtgatta ttaccctggc agaaaatgcc ggacaagcat | 780 | |
| gcctaaatcc cgcctcggca caagcagccc ttataatcgc agccgttgaa gcagccaatt | 840 | |
| ttccccccatg cccatcatgc ccagcacctg agttcctggg ggaccatca gtcttcctgt | 900 | |
| tcccccaaa acccaaggac actctcatga tctcccggac ccctgaggtc acgtgcgtgg | 960 | |
| tggtggacgt gagccaggaa gaccccgagg tccagttcaa ctggtacgtg gatggcgtgg | 1020 | |
| aggtgcataa tgccaagaca aagccgcggg aggagcagtt caacagcacg taccgtgtgg | 1080 | |
| tcagcgtcct caccgtcctg caccaggact ggctgaacgg caaggagtac aagtgcaagg | 1140 | |
| tctccaacaa aggcctcccg tcctccatcg agaaaccat ctccaaagcc aaagggcagc | 1200 | |
| cccgagagcc acaggtgtac accctgcccc catcccagga ggagatgacc aagaaccagg | 1260 | |
| tcagcctgac ctgcctggtc aaaggcttct accccagcga catcgccgtg gagtgggaga | 1320 | |
| gcaatgggca gccggagaac aactacaaga ccacgcctcc cgtgctggac tcgacggct | 1380 | |
| ccttcttcct ctacagcagg ctaaccgtgg acaagagcag gtggcaggag gggaatgtct | 1440 | |
| tctcatgctc cgtgatgcat gaggctctgc acaaccacta cacacagaag agcctctccc | 1500 | |
| tgtctccggg taaatgagtg ctagctgcc agacatgata agatacattg atgagtttgg | 1560 | |
| acaaaccaca actagaatgc agtgaaaaaa atgctttatt tgtgaaattt gtgatgctat | 1620 | |
| tgctttattt gtaaccatta taagctgcaa taaacaagtt aacaacaaca attgcattca | 1680 | |
| ttttatgttt caggttcagg gggaggtgtg ggaggttttt taaagcaagt aaaacctcta | 1740 | |

```
caaatgtggt atggaattaa ttctaaaata cagcatagca aaactttaac ctccaaatca    1800
agcctctact tgaatccttt tctgagggat gaataaggca taggcatcag gggctgttgc    1860
caatgtgcat tagctgtttg cagcctcacc ttctttcatg gagtttaaga tatagtgtat    1920
tttcccaagg tttgaactag ctcttcattt ctttatgttt taaatgcact gacctcccac    1980
attccctttt tagtaaaata ttcagaaata atttaaatac atcattgcaa tgaaaataaa    2040
tgtttttttat taggcagaat ccagatgctc aaggcccttc ataatatccc ccagtttagt    2100
agttggactt agggaacaaa ggaaccttta atagaaattg acagcaaga aagcgagctt    2160
ctagcttatc ctcagtcctg ctcctctgcc acaaagtgca cgcagttgcc ggccgggtcg    2220
cgcagggcga actcccgccc ccacggctgc tcgccgatct cggtcatggc cggcccggag    2280
gcgtcccgga agttcgtgga cacgacctcc gaccactcgg cgtacagctc gtccaggccg    2340
cgcacccaca cccaggccag ggtgttgtcc ggcaccacct ggtcctggac cgcgctgatg    2400
aacagggtca cgtcgtcccg gaccacaccg gcgaagtcgt cctccacgaa gtcccgggag    2460
aacccgagcc ggtcggtcca gaactcgacc gctccggcga cgtcgcgcgc ggtgagcacc    2520
ggaacggcac tggtcaactt ggccatgatg gctcctcctg tcaggagagg aaagagaaga    2580
aggttagtac aattgctata gtgagttgta ttatactatg cagatatact atgccaatga    2640
ttaattgtca aactagggct gcagggttca tagtgccact tttcctgcac tgccccatct    2700
cctgcccacc ctttcccagg catagacagt cagtgactta ccaaactcac aggagggaga    2760
aggcagaagc ttgagacaga cccgcgggac cgccgaactg cgaggggacg tggctagggc    2820
ggcttctttt atggtgcgcc ggccctcgga ggcaggcgc tcggggaggc ctagcggcca    2880
atctgcggtg gcaggaggcg gggccgaagg ccgtgcctga ccaatccgga gcacatagga    2940
gtctcagccc cccgccccaa agcaagggga agtcacgcgc ctgtagcgcc agcgtgttgt    3000
gaaatggggg cttggggggg ttggggccct gactagtcaa acaaactcc cattgacgtc    3060
aatgggtgg agacttggaa atccccgtga gtcaaaccgc tatccacgcc cattgatgta    3120
ctgccaaaac cgcatcatca tggtaatagc gatgactaat acgtagatgt actgccaagt    3180
aggaaagtcc cataaggtca tgtactgggc ataatgccag gcgggccatt taccgtcatt    3240
gacgtcaata gggggcgtac ttggcatatg atacacttga tgtactgcca agtgggcagt    3300
ttaccgtaaa tactccaccc attgacgtca atggaaagtc cctattggcg ttactatggg    3360
aacatacgtc attattgacg tcaatgggcg ggggtcgttg ggcggtcagc caggcgggcc    3420
atttaccgta agttatgtaa cgcctgcagg ttaattaaga acatgtgagc aaaaggccag    3480
caaaaggcca ggaaccgtaa aaaggccgcg ttgctggcgt ttttccatag gctccgcccc    3540
cctgacgagc atcacaaaaa tcgacgctca agtcagaggt ggcgaaaccc gacaggacta    3600
taaagatacc aggcgtttcc ccctggaagc tccctcgtgc gctctcctgt tccgaccctg    3660
ccgcttaccg gatacctgtc cgcctttctc ccttcgggaa gcgtggcgct ttctcatagc    3720
tcacgctgta ggtatctcag ttcggtgtag gtcgttcgct ccaagctggg ctgtgtgcac    3780
gaaccccccg ttcagcccga ccgctgcgcc ttatccggta actatcgtct gagtccaac    3840
ccggtaagac acgacttatc gccactggca gcagccactg gtaacaggat tagcagagcg    3900
aggtatgtag gcggtgctac agagttcttg aagtggtggc ctaactacgg ctacactaga    3960
agaacagtat ttggtatctg cgctctgctg aagccagtta ccttcggaaa aagagttggt    4020
agctcttgat ccggcaaaca aaccaccgct ggtagcggtg gttttttgt ttgcaagcag    4080
cagattacgc gcagaaaaaa aggatctcaa gaagatcctt tgatcttttc tacggggtct    4140
```

```
gacgctcagt ggaacgaaaa ctcacgttaa gggattttgg tcatggctag ttaattaaca    4200
tttaaatcag cggccgcaat aaaatatctt tattttcatt acatctgtgt gttggttttt    4260
tgtgtgaatc gtaactaaca tacgctctcc atcaaaacaa aacgaaacaa aacaaactag    4320
caaaataggc tgtccccagt gcaagtgcag gtgccagaac atttctctat cgaa          4374

<210> SEQ ID NO 100
<211> LENGTH: 4434
<212> TYPE: DNA
<213> ORGANISM: Artificial Sequence
<220> FEATURE:
<223> OTHER INFORMATION: pCXCL13-IgG1Fc

<400> SEQUENCE: 100
ggatctgcga tcgctccggt gcccgtcagt gggcagagcg cacatcgccc acagtccccg      60
agaagttggg gggagggtc ggcaattgaa cgggtgccta gagaaggtgg cgcggggtaa     120
actgggaaag tgatgtcgtg tactggctcc gccttttcc cgagggtggg ggagaaccgt     180
atataagtgc agtagtcgcc gtgaacgttc ttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggttctgga ggtctattac acaagcttga     660
ggtgtagatg tgtccaagag agctcagtct ttatccctag acgcttcatt gatcgaattc     720
aaatcttgcc ccgtgggaat ggttgtccaa gaaagaaat catagtctgg aagaagaaca     780
agtcaattgt gtgtgtggac cctcaagctg aatggataca agaatgatg gaagtattga     840 gaaaagaag ttcttcaact ctaccagttc cagtgtttaa gagaaagatt cccgacaaaa     900
ctcacacatg cccaccgtgc ccagcacctg aactcctggg gggaccgtca gtcttcctct    960 tcccccaaa acccaaggac accctcatga tctcccggac ccctgaggtc acatgcgtgg    1020
tggtggacgt gagccacgaa gaccctgagg tcaagttcaa ctggtacgtg gacggcgtgg    1080
aggtgcataa tgccaagaca aagccgcggg aggagcagta caacagcacg taccgtgtgg    1140
tcagcgtcct caccgtcctg caccaggact ggctgaatgg caaggagtac aagtgcaagg    1200
tctccaacaa agccctccca gccccatcg agaaaaccat ctccaaagcc aaagggcagc    1260
cccgagaacc acaggtgtac accctgcccc catcccggga ggagatgacc aagaaccagg    1320
tcagcctgac ctgcctggtc aaaggcttct atcccagcga catcgccgtg gagtgggaga    1380
gcaatgggca gccggagaac aactacaaga ccacgcctcc cgtgctggac tccgacggct    1440
ccttcttcct ctacagcaag ctcaccgtgg acaagagcag gtggcagcag gggaacgtct    1500
tctcatgctc cgtgatgcac gaggctctgc acaaccacta cacgcagaag agcctctccc    1560
tgtctccggg taaatgagtg ctagctgggc agacatgata agatacattg atgagtttgg    1620
acaaaccaca actagaatgc agtgaaaaaa atgctttatt tgtgaaattt gtgatgctat    1680
tgctttattt gtaaccatta taagctgcaa taaacaagtt aacaacaaca attgcattca    1740
ttttatgttt caggttcagg gggaggtgtg ggaggttttt taaagcaagt aaaacctcta    1800
```

-continued

```
caaatgtggt atggaattaa ttctaaaata cagcatagca aaactttaac ctccaaatca    1860
agcctctact tgaatccttt tctgagggat gaataaggca taggcatcag gggctgttgc    1920
caatgtgcat tagctgtttg cagcctcacc ttctttcatg gagtttaaga tatagtgtat    1980
tttcccaagg tttgaactag ctcttcattt ctttatgttt taaatgcact gacctcccac    2040
attccctttt tagtaaaata ttcagaaata atttaaatac atcattgcaa tgaaaataaa    2100
tgtttttat taggcagaat ccagatgctc aaggcccttc ataatatccc ccagtttagt     2160
agttggactt agggaacaaa ggaacccttta atagaaattg acagcaaga aagcgagctt    2220
ctagcttatc ctcagtcctg ctcctctgcc acaaagtgca cgcagttgcc ggccgggtcg    2280
cgcagggcga actcccgccc ccacggctgc tcgccgatct cggtcatggc cggcccggag    2340
gcgtcccgga agttcgtgga cacgacctcc gaccactcgg cgtacagctc gtccaggccg    2400
cgcacccaca cccaggccag ggtgttgtcc ggcaccacct ggtcctggac cgcgctgatg    2460
aacagggtca cgtcgtcccg gaccacaccg gcgaagtcgt cctccacgaa gtcccgggag    2520
aacccgagcc ggtcggtcca gaactcgacc gctccggcga cgtcgcgcgc ggtgagcacc    2580
ggaacggcac tggtcaactt ggccatgatg gctcctcctg tcaggagagg aaagagaaga    2640
aggttagtac aattgctata gtgagttgta ttatactatg cagatatact atgccaatga    2700
ttaattgtca aactagggct gcagggttca tagtgccact tttcctgcac tgccccatct    2760
cctgcccacc ctttcccagg catagacagt cagtgactta ccaaactcac aggagggaga    2820
aggcagaagc ttgagacaga cccgcgggac cgccgaactg cgaggggacg tggctagggc    2880
ggcttctttt atggtgcgcc ggccctcgga ggcagggcgc tcggggaggc ctagcggcca    2940
atctgcggtg gcaggaggcg gggccgaagg ccgtgcctga ccaatccgga gcacatagga    3000
gtctcagccc cccgccccaa agcaagggga agtcacgcgc ctgtagcgcc agcgtgttgt    3060
gaaatggggg cttggggggg ttggggccct gactagtcaa acaaactcc cattgacgtc     3120
aatggggtgg agacttggaa atccccgtga gtcaaaccgc tatccacgcc cattgatgta    3180
ctgccaaaac cgcatcatca tggtaatagc gatgactaat acgtagatgt actgccaagt    3240
aggaaagtcc cataaggtca tgtactgggc ataatgccag gcgggccatt taccgtcatt    3300
gacgtcaata ggggggcgtac ttggcatatg atacacttga tgtactgcca agtgggcagt    3360
ttaccgtaaa tactccaccc attgacgtca atggaaagtc cctattggcg ttactatggg    3420
aacatacgtc attattgacg tcaatgggcg ggggtcgttg ggcggtcagc caggcgggcc    3480
atttaccgta agttatgtaa cgcctgcagg ttaattaaga acatgtgagc aaaaggccag    3540
caaaaggcca ggaaccgtaa aaaggccgcg ttgctggcgt ttttccatag gctccgcccc    3600
cctgacgagc atcacaaaaa tcgacgctca agtcagaggt ggcgaaaccc gacaggacta    3660
taaagatacc aggcgtttcc ccctggaagc tccctcgtgc gctctcctgt tccgaccctg    3720
ccgcttaccg gatacctgtc cgcctttctc ccttcgggaa gcgtggcgct ttctcatagc    3780
tcacgctgta ggtatctcag ttcggtgtag tcgttcgct ccaagctggg ctgtgtgcac     3840
gaaccccccg ttcagcccga ccgctgcgcc ttatccggta actatcgtct tgagtccaac    3900
ccggtaagac acgacttatc gccactggca gcagccactg gtaacaggat tagcagagcg    3960
aggtatgtag gcggtgctac agagttcttg aagtggtggc ctaactacgg ctacactaga    4020
agaacagtat ttggtatctg cgctctgctg aagccagtta ccttcggaaa aagagttggt    4080
agctcttgat ccggcaaaca aaccaccgct ggtagcggtg ttttttgt ttgcaagcag      4140
cagattacgc gcagaaaaaa aggatctcaa gaagatcctt tgatcttttc tacggggtct    4200
```

```
gacgctcagt ggaacgaaaa ctcacgttaa gggattttgg tcatggctag ttaattaaca    4260
tttaaatcag cggccgcaat aaaatatctt tattttcatt acatctgtgt gttggttttt    4320
tgtgtgaatc gtaactaaca tacgctctcc atcaaaacaa aacgaaacaa aacaaactag    4380
caaaataggc tgtccccagt gcaagtgcag gtgccagaac atttctctat cgaa          4434
```

<210> SEQ ID NO 101
<211> LENGTH: 4428
<212> TYPE: DNA
<213> ORGANISM: Artificial Sequence
<220> FEATURE:
<223> OTHER INFORMATION: pCXCL13(3-87)-IgG1Fc

<400> SEQUENCE: 101

```
ggatctgcga tcgctccggt gcccgtcagt gggcagagcg cacatcgccc acagtccccg      60
agaagttggg gggagggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc ttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggaggtcta ttacaaagc ttgaggtgta    660 gatgtgtcca agagagctca gtctttatcc ctagacgctt cattgatcga attcaaatct    720
tgccccgtgg gaatggttgt ccaagaaaag aaatcatagt ctggaagaag aacaagtcaa    780
ttgtgtgtgt ggaccctcaa gctgaatgga tacaaagaat gatggaagta ttgagaaaaa    840
gaagttcttc aactctacca gttccagtgt ttaagagaaa gattcccgac aaaactcaca    900
catgcccacc gtgcccagca cctgaactcc tggggggacc gtcagtcttc ctcttcccc    960 caaaacccaa ggacaccctc atgatctccc ggaccctga ggtcacatgc gtggtggtgg    1020
acgtgagcca cgaagaccct gaggtcaagt tcaactggta cgtggacggc gtggaggtgc    1080
ataatgccaa gacaaagccg cgggaggagc agtacaacag cacgtaccgt gtggtcagcg    1140
tcctcaccgt cctgcaccag gactggctga atggcaagga gtacaagtgc aaggtctcca    1200
acaaagccct cccagccccc atcgagaaaa ccatctccaa agccaagggg cagccccgag    1260
aaccacaggt gtacaccctg cccccatccc gggaggagat gaccaagaac caggtcagcc    1320
tgacctgcct ggtcaaaggc ttctatccca gcgacatcgc cgtggagtgg gagagcaatg    1380
ggcagccgga gaacaactac aagaccacgc ctcccgtgct ggactccgac ggctccttct    1440
tcctctacag caagctcacc gtggacaaga gcaggtggca gcaggggaac gtcttctcat    1500
gctccgtgat gcacgaggct ctgcacaacc actacacgca gaagagcctc tccctgtctc    1560
cgggtaaatg agtgctagct ggccagacat gataagatac attgatgagt ttggacaaac    1620
cacaactaga atgcagtgaa aaaaatgctt tatttgtgaa atttgtgatg ctattgcttt    1680
atttgtaacc attataagct gcaataaaca agttaacaac aacaattgca ttcattttat    1740
gtttcaggtt cagggggagg tgtgggaggt tttttaaagc aagtaaaacc tctacaaatg    1800
```

```
tggtatggaa ttaattctaa atacagcat agcaaaactt taacctccaa atcaagcctc    1860
tacttgaatc cttttctgag ggatgaataa ggcataggca tcaggggctg ttgccaatgt    1920
gcattagctg tttgcagcct caccttcttt catggagttt aagatatagt gtattttccc    1980
aaggtttgaa ctagctcttc atttctttat gttttaaatg cactgacctc ccacattccc    2040
tttttagtaa aatattcaga aataatttaa atacatcatt gcaatgaaaa taaatgtttt    2100
ttattaggca gaatccagat gctcaaggcc cttcataata tcccccagtt tagtagttgg    2160
acttagggaa caaaggaacc tttaatagaa attggacagc aagaaagcga gcttctagct    2220
tatcctcagt cctgctcctc tgccacaaag tgcacgcagt tgccggccgg gtcgcgcagg    2280
gcgaactccc gcccccacgg ctgctcgccg atctcggtca tggccggccc ggaggcgtcc    2340
cggaagttcg tggacacgac ctccgaccac tcggcgtaca gctcgtccag gccgcgcacc    2400
cacacccagg ccagggtgtt gtccggcacc acctggtcct ggaccgcgct gatgaacagg    2460
gtcacgtcgt cccggaccac accggcgaag tcgtcctcca cgaagtcccg ggagaacccg    2520
agccggtcgg tccagaactc gaccgctccg gcgacgtcgc gcgcggtgag caccggaacg    2580
gcactggtca acttggccat gatggctcct cctgtcagga gaggaaagag aagaaggtta    2640
gtacaattgc tatagtgagt tgtattatac tatgcagata tactatgcca atgattaatt    2700
gtcaaactag ggctgcaggg ttcatagtgc cacttttcct gcactgcccc atctcctgcc    2760
caccctttcc caggcataga cagtcagtga cttaccaaac tcacaggagg gagaaggcag    2820
aagcttgaga cagacccgcg ggaccgccga actgcgaggg gacgtggcta gggcggcttc    2880
ttttatggtg cgccggccct cggaggcagg gcgctcgggg aggcctagcg gccaatctgc    2940
ggtggcagga ggcggggccg aaggccgtgc ctgaccaatc cggagcacat aggagtctca    3000 gcccccgcc ccaaagcaag gggaagtcac gcgcctgtag cgccagcgtg ttgtgaaatg    3060
ggggcttggg ggggttgggg ccctgactag tcaaaacaaa ctcccattga cgtcaatggg    3120
gtggagactt ggaaatcccc gtgagtcaaa ccgctatcca cgcccattga tgtactgcca    3180
aaaccgcatc atcatggtaa tagcgatgac taatacgtag atgtactgcc aagtaggaaa    3240
gtcccataag gtcatgtact gggcataatg ccaggcgggc catttaccgt cattgacgtc    3300
aatagggggc gtacttggca tatgatacac ttgatgtact gccaagtggg cagtttaccg    3360
taaatactcc acccattgac gtcaatggaa agtccctatt ggcgttacta tgggaacata    3420
cgtcattatt gacgtcaatg ggcggggggtc gttgggcggt cagccaggcg ggccatttac    3480
cgtaagttat gtaacgcctg caggttaatt aagaacatgt gagcaaaagg ccagcaaaag    3540
gccaggaacc gtaaaaaggc cgcgttgctg gcgttttttcc ataggctccg ccccctgac    3600 gagcatcaca aaaatcgacg ctcaagtcag aggtggcgaa acccgacagg actataaaga    3660
taccaggcgt ttccccctgg aagctccctc gtgcgctctc ctgttccgac cctgccgctt    3720
accggatacc tgtccgcctt tctcccttcg ggaagcgtgg cgctttctca tagctcacgc    3780
tgtaggtatc tcagttcggt gtaggtcgtt cgctccaagc tgggctgtgt gcacgaaccc    3840
cccgttcagc ccgaccgctg cgccttatcc ggtaactatc gtcttgagtc aacccggta    3900 agacacgact tatcgccact ggcagcagcc actggtaaca ggattagcag agcgaggtat    3960
gtaggcggtg ctacagagtt cttgaagtgg tggcctaact acggctacac tagaagaaca    4020
gtatttggta tctgcgctct gctgaagcca gttaccttcg gaaaagagt tggtagctct    4080 tgatccggca aacaaaccac cgctggtagc ggtggttttt ttgtttgcaa gcagcagatt    4140
acgcgcagaa aaaaggatc tcaagaagat cctttgatct tttctacggg gtctgacgct    4200
```

| | |
|---|---|
| cagtggaacg aaaactcacg ttaagggatt ttggtcatgg ctagttaatt aacatttaaa | 4260 |
| tcagcggccg caataaaata tctttatttt cattacatct gtgtgttggt tttttgtgtg | 4320 |
| aatcgtaact aacatacgct ctccatcaaa acaaaacgaa acaaaacaaa ctagcaaaat | 4380 |
| aggctgtccc cagtgcaagt gcaggtgcca gaacatttct ctatcgaa | 4428 |

<210> SEQ ID NO 102
<211> LENGTH: 4428
<212> TYPE: DNA
<213> ORGANISM: Artificial Sequence
<220> FEATURE:
<223> OTHER INFORMATION: pCXCL13(3-87K/H-A)-IgG1Fc

<400> SEQUENCE: 102

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg taccggcgc | 540 |
| ctacctgaga tcaccggcga aggagggcca ccatgtacag gatgcaactc ctgtcttgca | 600 |
| ttgcactaag tcttgcactt gtcacgaatt cggaggtcta ttacaagc ttgaggtgta | 660 |
| gatgtgtcca agagagctca gtctttatcc ctagacgctt cattgatgcc attcaaatct | 720 |
| tgccccgtgg gaatggttgt ccaagaaaag aaatcatagt ctgggctgcg aacgcttcaa | 780 |
| ttgtgtgtgt ggaccctcaa gctgaatgga tacaagccat gatggaagta ttggctgcgg | 840 |
| ctagttcttc aactctacca gttccagtgt ttgccgctgc gattcccgac aaaactcaca | 900 |
| catgcccacc gtgcccagca cctgaactcc tggggggacc gtcagtcttc ctcttccccc | 960 |
| caaaacccaa ggacaccctc atgatctccc ggacccctga ggtcacatgc gtggtggtgg | 1020 |
| acgtgagcca cgaagaccct gaggtcaagt tcaactggta cgtggacggc gtggaggtgc | 1080 |
| ataatgccaa gacaaagccg cgggaggagc agtacaacag cacgtaccgt gtggtcagcg | 1140 |
| tcctcaccgt cctgcaccag gactggctga atggcaagga gtacaagtgc aaggtctcca | 1200 |
| acaaagccct cccagccccc atcgagaaaa ccatctccaa agccaagggg cagccccgag | 1260 |
| aaccacaggt gtacaccctg cccccatccc gggaggagat gaccaagaac caggtcagcc | 1320 |
| tgacctgcct ggtcaaaggc ttctatccca gcgacatcgc cgtggagtgg gagagcaatg | 1380 |
| ggcagccgga gaacaactac aagaccacgc ctcccgtgct ggactccgac ggctccttct | 1440 |
| tcctctacag caagctcacc gtggacaaga gcaggtggca gcagggaac gtcttctcat | 1500 |
| gctccgtgat gcacgaggct ctgcacaacc actacacgca gaagagcctc tccctgtctc | 1560 |
| cgggtaaatg agtgctagct ggccagacat gataagatac attgatgagt ttggacaaac | 1620 |
| cacaactaga atgcagtgaa aaaaatgctt tatttgtgaa atttgtgatg ctattgcttt | 1680 |
| atttgtaacc attataagct gcaataaaca agttaacaac aacaattgca ttcattttat | 1740 |
| gtttcaggtt cagggggagg tgtgggaggt tttttaaagc aagtaaaacc tctacaaatg | 1800 |

```
tggtatggaa ttaattctaa atacagcat agcaaaactt taacctccaa atcaagcctc   1860
tacttgaatc cttttctgag ggatgaataa ggcataggca tcaggggctg ttgccaatgt   1920
gcattagctg tttgcagcct caccttcttt catggagttt aagatatagt gtattttccc   1980
aaggtttgaa ctagctcttc atttctttat gttttaaatg cactgacctc ccacattccc   2040
tttttagtaa aatattcaga aataatttaa atacatcatt gcaatgaaaa taaatgtttt   2100
ttattaggca gaatccagat gctcaaggcc cttcataata tcccccagtt tagtagttgg   2160
acttagggaa caaaggaacc tttaatagaa attggacagc aagaaagcga gcttctagct   2220
tatcctcagt cctgctcctc tgccacaaag tgcacgcagt tgccggccgg gtcgcgcagg   2280
gcgaactccc gccccacgg ctgctcgccg atctcggtca tggccggccc ggaggcgtcc   2340
cggaagttcg tggacacgac ctccgaccac tcggcgtaca gctcgtccag gccgcgcacc   2400
cacacccagg ccagggtgtt gtccggcacc acctggtcct ggaccgcgct gatgaacagg   2460
gtcacgtcgt cccggaccac accggcgaag tcgtcctcca cgaagtcccg ggagaacccg   2520
agccggtcgg tccagaactc gaccgctccg gcgacgtcgc gcgcggtgag caccggaacg   2580
gcactggtca acttggccat gatggctcct cctgtcagga gaggaaagag aagaaggtta   2640
gtacaattgc tatagtgagt tgtattatac tatgcagata tactatgcca atgattaatt   2700
gtcaaactag ggctgcaggg ttcatagtgc cacttttcct gcactgcccc atctcctgcc   2760 cacccttttcc caggcatagaa cagtcagtga cttaccaaac tcacaggagg gagaaggcag   2820
aagcttgaga cagacccgcg ggaccgccga actgcgaggg gacgtggcta gggcggcttc   2880
ttttatggtg cgccggccct cggaggcagg gcgctcgggg aggcctagcg gccaatctgc   2940
ggtggcagga ggcggggccg aaggccgtgc ctgaccaatc cggagcacat aggagtctca   3000 gcccccgcc ccaaagcaag gggaagtcac gcgcctgtag cgccagcgtg ttgtgaaatg   3060
ggggcttggg ggggttgggg ccctgactag tcaaaacaaa ctcccattga cgtcaatggg   3120
gtggagactt ggaaatcccc gtgagtcaaa ccgctatcca cgcccattga tgtactgcca   3180
aaaccgcatc atcatggtaa tagcgatgac taatacgtag atgtactgcc aagtaggaaa   3240
gtcccataag gtcatgtact gggcataatg ccaggcgggc catttaccgt cattgacgtc   3300 aataggggc gtacttggca tatgatacac ttgatgtact gccaagtggg cagtttaccg   3360
taaatactcc acccattgac gtcaatggaa agtccctatt ggcgttacta tgggaacata   3420
cgtcattatt gacgtcaatg gcggggggtc gttgggcggt cagccaggcg ggccatttac   3480
cgtaagttat gtaacgcctg caggttaatt aagaacatgt gagcaaaagg ccagcaaaag   3540
gccaggaacc gtaaaaaggc cgcgttgctg gcgttttttcc ataggctccg ccccccctgac   3600 gagcatcaca aaaatcgacg ctcaagtcag aggtggcgaa acccgacagg actataaaga   3660
taccaggcgt ttccccctgg aagctccctc gtgcgctctc ctgttccgac cctgccgctt   3720
accggatacc tgtccgcctt tctcccttcg ggaagcgtgg cgctttctca tagctcacgc   3780
tgtaggtatc tcagttcggt gtaggtcgtt cgctccaagc tgggctgtgt gcacgaaccc   3840
cccgttcagc ccgaccgctg cgccttatcc ggtaactatc gtcttgagtc caacccggta   3900
agacacgact tatcgccact ggcagcagcc actggtaaca ggattagcag agcgaggtat   3960
gtaggcggtg ctacagagtt cttgaagtgg tggcctaact acggctacac tagaagaaca   4020
gtatttggta tctgcgctct gctgaagcca gttaccttcg gaaaaagagt tggtagctct   4080
tgatccggca aacaaaccac cgctggtagc ggtggttttt ttgtttgcaa gcagcagatt   4140
acgcgcagaa aaaaggatc tcaagaagat cctttgatct tttctacggg gtctgacgct   4200
```

-continued

| | |
|---|---|
| cagtggaacg aaaactcacg ttaagggatt ttggtcatgg ctagttaatt aacatttaaa | 4260 |
| tcagcggccg caataaaata tctttatttt cattacatct gtgtgttggt tttttgtgtg | 4320 |
| aatcgtaact aacatacgct ctccatcaaa acaaaacgaa acaaaacaaa ctagcaaaat | 4380 |
| aggctgtccc cagtgcaagt gcaggtgcca gaacatttct ctatcgaa | 4428 |

<210> SEQ ID NO 103
<211> LENGTH: 4425
<212> TYPE: DNA
<213> ORGANISM: Artificial Sequence
<220> FEATURE:
<223> OTHER INFORMATION: pCXCL13-IgG4Fc

<400> SEQUENCE: 103

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggttctgga ggtctattac acaagcttga | 660 |
| ggtgtagatg tgtccaagag agctcagtct ttatccctag acgcttcatt gatcgaattc | 720 |
| aaatcttgcc ccgtgggaat ggttgtccaa gaaaagaaat catagtctgg aagaagaaca | 780 |
| agtcaattgt gtgtgtggac cctcaagctg aatggataca agaatgatg gaagtattga | 840 |
| gaaaagaag ttcttcaact ctaccagttc cagtgtttaa gagaaagatt ccccccccat | 900 |
| gcccatcatg cccagcacct gagttcctgg ggggaccatc agtcttcctg ttcccccaa | 960 |
| aacccaagga cactctcatg atctcccgga cccctgaggt cacgtgcgtg gtggtggacg | 1020 |
| tgagccagga agaccccgag gtccagttca actggtacgt ggatggcgtg gaggtgcata | 1080 |
| atgccaagac aaagccgcgg gaggagcagt tcaacagcac gtaccgtgtg gtcagcgtcc | 1140 |
| tcaccgtcct gcaccaggac tggctgaacg gcaaggagta caagtgcaag gtctccaaca | 1200 |
| aaggcctccc gtcctccatc gagaaaacca tctccaaagc caaagggcag ccccgagagc | 1260 |
| cacaggtgta caccctgccc ccatcccagg aggagatgac caagaaccag gtcagcctga | 1320 |
| cctgcctggt caaaggcttc taccccagcg acatcgccgt ggagtgggag agcaatgggc | 1380 |
| agccggagaa caactacaag accacgcctc ccgtgctgga ctccgacggc tccttcttcc | 1440 |
| tctacagcag gctaaccgtg gacaagagca ggtggcagga ggggaatgtc ttctcatgct | 1500 |
| ccgtgatgca tgaggctctg cacaaccact acacacagaa gagcctctcc ctgtctccgg | 1560 |
| gtaaatgagt gctagctggc cagacatgat aagatacatt gatgagtttg gacaaaccac | 1620 |
| aactagaatg cagtgaaaaa aatgctttat ttgtgaaatt tgtgatgcta ttgctttatt | 1680 |
| tgtaaccatt ataagctgca ataaacaagt taacaacaac aattgcattc attttatgtt | 1740 |
| tcaggttcag ggggaggtgt gggaggtttt ttaaagcaag taaaacctct acaaatgtgg | 1800 |

```
tatggaatta attctaaaat acagcatagc aaaactttaa cctccaaatc aagcctctac    1860
ttgaatcctt ttctgaggga tgaataaggc ataggcatca ggggctgttg ccaatgtgca    1920
ttagctgttt gcagcctcac cttctttcat ggagtttaag atatagtgta ttttcccaag    1980
gtttgaacta gctcttcatt tctttatgtt ttaaatgcac tgacctccca cattcccttt    2040
ttagtaaaat attcagaaat aatttaaata catcattgca atgaaaataa atgttttta    2100 ttaggcagaa tccagatgct caaggccctt cataatatcc cccagtttag tagttggact    2160
tagggaacaa aggaaccttt aatagaaatt ggacagcaag aaagcgagct tctagcttat    2220
cctcagtcct gctcctctgc cacaaagtgc acgcagttgc cggccgggtc gcgcagggcg    2280
aactcccgcc cccacggctg ctcgccgatc tcggtcatgg ccggcccgga ggcgtcccgg    2340
aagttcgtgg acacgacctc cgaccactcg gcgtacagct cgtccaggcc gcgcacccac    2400
acccaggcca gggtgttgtc cggcaccacc tggtcctgga ccgcgctgat gaacagggtc    2460
acgtcgtccc ggaccacacc ggcgaagtcg tcctccacga agtcccggga gaacccgagc    2520
cggtcggtcc agaactcgac cgctccggcg acgtcgcgcg cggtgagcac cggaacggca    2580
ctggtcaact tggccatgat ggctcctcct gtcaggagag gaaagagaag aaggttagta    2640
caattgctat agtgagttgt attatactat gcagatatac tatgccaatg attaattgtc    2700
aaactagggc tgcagggttc atagtgccac ttttcctgca ctgccccatc tcctgcccac    2760
cctttcccag gcatagacag tcagtgactt accaaactca caggagggag aaggcagaag    2820
cttgagacag acccgcggga ccgccgaact gcgagggac gtggctaggg cggcttcttt    2880
tatggtgcgc cggccctcgg aggcagggcg ctcggggagg cctagcggcc aatctgcggt    2940
ggcaggaggc ggggccgaag gccgtgcctg accaatccgg agcacatagg agtctcagcc    3000
ccccgcccca aagcaagggg aagtcacgcg cctgtagcgc cagcgtgttg tgaaatgggg    3060
gcttgggggg gttgggggccc tgactagtca aaacaaactc ccattgacgt caatgggtg    3120 gagacttgga aatccccgtg agtcaaaccg ctatccacgc ccattgatgt actgccaaaa    3180
ccgcatcatc atggtaatag cgatgactaa tacgtagatg tactgccaag taggaaagtc    3240
ccataaggtc atgtactggg cataatgcca ggcgggccat ttaccgtcat tgacgtcaat    3300 aggggggcgta cttggcatat gatacacttg atgtactgcc aagtgggcag tttaccgtaa    3360
atactccacc cattgacgtc aatggaaagt ccctattggc gttactatgg aacatacgt    3420 cattattgac gtcaatgggc gggggtcgtt gggcggtcag ccaggcgggc catttaccgt    3480
aagttatgta acgcctgcag gttaattaag aacatgtgag caaaaggcca gcaaaaggcc    3540
aggaaccgta aaaaggccgc gttgctggcg ttttccata ggctccgccc cctgacgag    3600 catcacaaaa atcgacgctc aagtcagagg tggcgaaacc cgacaggact ataaagatac    3660
caggcgtttc ccctggaag ctccctcgtg cgctctcctg ttccgaccct gccgcttacc    3720
ggatacctgt ccgcctttct cccttcggga agcgtggcgc tttctcatag ctcacgctgt    3780
aggtatctca gttcggtgta ggtcgttcgc tccaagctgg gctgtgtgca cgaaccccc    3840 gttcagcccg accgctgcgc cttatccggt aactatcgtc ttgagtccaa cccggtaaga    3900
cacgacttat cgccactggc agcagccact ggtaacagga ttagcagagc gaggtatgta    3960
ggcggtgcta cagagttctt gaagtggtgg cctaactacg gctacactag aagaacagta    4020
tttggtatct gcgctctgct gaagccagtt accttcggaa aaagagttgg tagctcttga    4080
tccggcaaac aaaccaccgc tggtagcggt ggtttttttg tttgcaagca gcagattacg    4140
cgcagaaaaa aaggatctca agaagatcct ttgatctttt ctacggggtc tgacgctcag    4200
```

```
tggaacgaaa actcacgtta agggattttg gtcatggcta gttaattaac atttaaatca    4260
gcggccgcaa taaaatatct ttattttcat tacatctgtg tgttggtttt ttgtgtgaat    4320
cgtaactaac atacgctctc catcaaaaca aaacgaaaca aaacaaacta gcaaaatagg    4380
ctgtccccag tgcaagtgca ggtgccagaa catttctcta tcgaa                    4425

<210> SEQ ID NO 104
<211> LENGTH: 4419
<212> TYPE: DNA
<213> ORGANISM: Artificial Sequence
<220> FEATURE:
<223> OTHER INFORMATION: pCXCL13(3-87)-IgG4Fc

<400> SEQUENCE: 104
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct cgaggggct cgcatctctc cttcacgcgc ccgccgccct acctgaggcc     300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggaggtcta ttacacaagc ttgaggtgta    660
gatgtgtcca agagagctca gtctttatcc ctagacgctt cattgatcga attcaaatct    720
tgccccgtgg gaatggttgt ccaagaaaag aaatcatagt ctggaagaag aacaagtcaa    780
ttgtgtgtgt ggaccctcaa gctgaatgga tacaaagaat gatggaagta ttgagaaaaa    840
gaagttcttc aactctacca gttccagtgt ttaagagaaa gattcccccc ccatgcccat    900
catgcccagc acctgagttc ctggggggac catcagtctt cctgttcccc ccaaaaccca    960
aggacactct catgatctcc cggacccctg aggtcacgtg cgtggtggtg gacgtgagcc   1020
aggaagaccc cgaggtccag ttcaactggt acgtggatgg cgtggaggtg cataatgcca   1080
agacaaagcc gcgggaggag cagttcaaca gcacgtaccg tgtggtcagc gtcctcaccg   1140
tcctgcacca ggactggctg aacggcaagg agtacaagtg caaggtctcc aacaaaggcc   1200
tcccgtcctc catcgagaaa accatctcca aagccaaagg gcagccccga gagccacagg   1260
tgtacaccct gcccccatcc caggaggaga tgaccaagaa ccaggtcagc ctgacctgcc   1320
tggtcaaagg cttctacccc agcgacatcg ccgtggagtg ggagagcaat gggcagccgg   1380
agaacaacta caagaccacg cctcccgtgc tggactccga cggctccttc ttcctctaca   1440
gcaggctaac cgtggacaag agcaggtggc aggaggggaa tgtcttctca tgctccgtga   1500
tgcatgaggc tctgcacaac cactacacac agaagagcct ctccctgtct ccgggtaaat   1560
gagtgctagc tggccagaca tgataagata cattgatgag tttggacaaa ccacaactag   1620
aatgcagtga aaaaaatgct ttatttgtga aatttgtgat gctattgctt tatttgtaac   1680
cattataagc tgcaataaac aagttaacaa caacaattgc attcatttta tgtttcaggt   1740
tcagggggag gtgtgggagg ttttttaaag caagtaaaac ctctacaaat gtggtatgga   1800
```

```
attaattcta aaatacagca tagcaaaact ttaacctcca aatcaagcct ctacttgaat    1860
ccttttctga gggatgaata aggcataggc atcaggggct gttgccaatg tgcattagct    1920
gtttgcagcc tcaccttctt tcatggagtt taagatatag tgtattttcc caaggtttga    1980
actagctctt catttcttta tgttttaaat gcactgacct cccacattcc ctttttagta    2040
aaatattcag aaataattta aatacatcat tgcaatgaaa ataaatgttt tttattaggc    2100
agaatccaga tgctcaaggc ccttcataat atcccccagt ttagtagttg gacttaggga    2160
acaaaggaac ctttaataga aattggacag caagaaagcg agcttctagc ttatcctcag    2220
tcctgctcct ctgccacaaa gtgcacgcag ttgccggccg ggtcgcgcag ggcgaactcc    2280
cgcccccacg gctgctcgcc gatctcggtc atggccggcc cggaggcgtc ccggaagttc    2340
gtggacacga cctccgacca ctcggcgtac agctcgtcca ggccgcgcac ccacacccag    2400
gccagggtgt tgtccggcac cacctggtcc tggaccgcgc tgatgaacag ggtcacgtcg    2460
tcccggacca caccggcgaa gtcgtcctcc acgaagtccc gggagaaccc gagccggtcg    2520
gtccagaact cgaccgctcc ggcgacgtcg cgcgcggtga gcaccggaac ggcactggtc    2580
aacttggcca tgatggctcc tcctgtcagg agaggaaaga gaagaaggtt agtacaattg    2640
ctatagtgag ttgtattata ctatgcagat atactatgcc aatgattaat tgtcaaacta    2700
gggctgcagg gttcatagtg ccacttttcc tgcactgccc catctcctgc ccacccttc     2760
ccaggcatag acagtcagtg acttaccaaa ctcacaggag ggagaaggca gaagcttgag    2820
acagacccgc gggaccgccg aactgcgagg ggacgtggct agggcggctt cttttatggt    2880
gcgccggccc tcgaggcag ggcgctcggg gaggcctagc ggccaatctg cggtggcagg     2940
aggcggggcc gaaggccgtg cctgaccaat ccggagcaca taggagtctc agccccccgc    3000
cccaaagcaa ggggaagtca cgcgcctgta gcgccagcgt gttgtgaaat gggggcttgg    3060
gggggttggg gccctgacta gtcaaaacaa actcccattg acgtcaatgg ggtggagact    3120
tggaaatccc cgtgagtcaa accgctatcc acgcccattg atgtactgcc aaaaccgcat    3180
catcatggta atagcgatga ctaatacgta gatgtactgc caagtaggaa agtcccataa    3240
ggtcatgtac tgggcataat gccaggcggg ccatttaccg tcattgacgt caataggggg    3300
cgtacttggc atatgataca cttgatgtac tgccaagtgg gcagtttacc gtaaatactc    3360
cacccattga cgtcaatgga aagtccctat tggcgttact atgggaacat acgtcattat    3420
tgacgtcaat gggcggggt cgttgggcgg tcagccaggc gggccattta ccgtaagtta     3480
tgtaacgcct gcaggttaat taagaacatg tgagcaaaag gccagcaaaa ggccaggaac    3540
cgtaaaaagg ccgcgttgct ggcgtttttc cataggctcc gcccccctga cgagcatcac    3600
aaaaatcgac gctcaagtca gaggtggcga acccgacag gactataaag ataccaggcg     3660
tttccccctg gaagctccct cgtgcgctct cctgttccga ccctgccgct taccggatac    3720
ctgtccgcct ttctcccttc gggaagcgtg gcgctttctc atagctcacg ctgtaggtat    3780
ctcagttcgg tgtaggtcgt tcgctccaag ctgggctgtg tgcacgaacc ccccgttcag    3840
cccgaccgct gcgccttatc cggtaactat cgtcttgagt ccaacccggt aagacacgac    3900
ttatcgccac tggcagcagc cactggtaac aggattagca gagcgaggta tgtaggcggt    3960
gctacagagt tcttgaagtg gtggcctaac tacggctaca ctagaagaac agtatttggt    4020
atctgcgctc tgctgaagcc agttaccttc ggaaaaagag ttggtagctc ttgatccggc    4080
aaacaaacca ccgctggtag cggtggtttt tttgtttgca agcagcagat tacgcgcaga    4140
aaaaaaggat ctcaagaaga tccttttgatc ttttctacgg ggtctgacgc tcagtggaac    4200
```

```
gaaaactcac gttaagggat tttggtcatg gctagttaat taacatttaa atcagcggcc    4260
gcaataaaat atctttattt tcattacatc tgtgtgttgg ttttttgtgt gaatcgtaac    4320
taacatacgc tctccatcaa aacaaaacga aacaaaacaa actagcaaaa taggctgtcc    4380
ccagtgcaag tgcaggtgcc agaacatttc tctatcgaa                          4419
```

<210> SEQ ID NO 105
<211> LENGTH: 4419
<212> TYPE: DNA
<213> ORGANISM: Artificial Sequence
<220> FEATURE:
<223> OTHER INFORMATION: pCXCL13(3-87K/H-A)-IgG4Fc

<400> SEQUENCE: 105

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac      240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggaggtcta ttacaagc ttgaggtgta      660 gatgtgtcca agagagctca gtctttatcc ctagacgctt cattgatgcc attcaaatct     720
tgccccgtgg gaatggttgt ccaagaaaag aaatcatagt ctgggctgcg aacgcttcaa     780
ttgtgtgtgt ggaccctcaa gctgaatgga tacaagccat gatggaagta ttggctgcgg     840
ctagttcttc aactctacca gttccagtgt ttgccgctgc gattccccc ccatgcccat      900 catgcccagc acctgagttc ctggggggac atcagtctt cctgttcccc ccaaaaccca      960
aggacactct catgatctcc cggacccctg aggtcacgtg cgtggtggtg gacgtgagcc    1020
aggaagaccc cgaggtccag ttcaactggt acgtggatgg cgtggaggtg cataatgcca    1080
agacaaagcc gcgggaggag cagttcaaca gcacgtaccg tgtggtcagc gtcctcaccg    1140
tcctgcacca ggactggctg aacggcaagg agtacaagtg caaggtctcc aacaaaggcc    1200
tcccgtcctc catcgagaaa accatctcca aagccaaagg gcagcccga gagccacagg     1260 tgtacaccct gcccccatcc caggaggaga tgaccaagaa ccaggtcagc ctgacctgcc    1320
tggtcaaagg cttctacccc agcgacatcg ccgtggagtg ggagagcaat gggcagccgg    1380
agaacaacta caagaccacg cctcccgtgc tggactccga cggctccttc ttcctctaca    1440
gcaggctaac cgtggacaag agcaggtggc aggaggggaa tgtcttctca tgctccgtga    1500
tgcatgaggc tctgcacaac cactacacac agaagagcct ctccctgtct ccgggtaaat    1560
gagtgctagc tggccagaca tgataagata cattgatgag tttggacaaa ccacaactag    1620
aatgcagtga aaaaaatgct ttatttgtga aatttgtgat gctattgctt tatttgtaac    1680
cattataagc tgcaataaac aagttaacaa caacaattgc attcatttta tgtttcaggt    1740
tcagggggag gtgtgggagg ttttttaaag caagtaaaac ctctacaaat gtggtatgga    1800
```

-continued

| | | | | | |
|---|---|---|---|---|---|
| attaattcta | aaatacagca | tagcaaaact | ttaacctcca | aatcaagcct | ctacttgaat | 1860 |
| ccttttctga | gggatgaata | aggcataggc | atcaggggct | gttgccaatg | tgcattagct | 1920 |
| gtttgcagcc | tcaccttctt | tcatggagtt | taagatatag | tgtattttcc | caaggtttga | 1980 |
| actagctctt | catttcttta | tgttttaaat | gcactgacct | cccacattcc | cttttagta | 2040 |
| aaatattcag | aaataattta | aatacatcat | tgcaatgaaa | ataaatgttt | tttattaggc | 2100 |
| agaatccaga | tgctcaaggc | ccttcataat | atcccccagt | ttagtagttg | gacttaggga | 2160 |
| acaaaggaac | ctttaataga | aattggacag | caagaaagcg | agcttctagc | ttatcctcag | 2220 |
| tcctgctcct | ctgccacaaa | gtgcacgcag | ttgccggccg | ggtcgcgcag | ggcgaactcc | 2280 |
| cgcccccacg | gctgctcgcc | gatctcggtc | atggccggcc | cggaggcgtc | ccggaagttc | 2340 |
| gtggacacga | cctccgacca | ctcggcgtac | agctcgtcca | ggccgcgcac | ccacacccag | 2400 |
| gccagggtgt | tgtccggcac | cacctggtcc | tggaccgcgc | tgatgaacag | ggtcacgtcg | 2460 |
| tcccggacca | caccggcgaa | gtcgtcctcc | acgaagtccc | gggagaaccc | gagccggtcg | 2520 |
| gtccagaact | cgaccgctcc | ggcgacgtcg | cgcgcggtga | gcaccggaac | ggcactggtc | 2580 |
| aacttggcca | tgatggctcc | tcctgtcagg | agaggaaaga | gaagaaggtt | agtacaattg | 2640 |
| ctatagtgag | ttgtattata | ctatgcagat | atactatgcc | aatgattaat | tgtcaaacta | 2700 |
| gggctgcagg | gttcatagtg | ccacttttcc | tgcactgccc | catctcctgc | ccacccttc | 2760 |
| ccaggcatag | acagtcagtg | acttaccaaa | ctcacaggag | ggagaaggca | gaagcttgag | 2820 |
| acagacccgc | gggaccgccg | aactgcgagg | ggacgtggct | agggcggctt | cttttatggt | 2880 |
| gcgccggccc | tcggaggcag | ggcgctcggg | gaggcctagc | ggccaatctg | cggtggcagg | 2940 |
| aggcggggcc | gaaggccgtg | cctgaccaat | ccggagcaca | taggagtctc | agcccccgc | 3000 |
| cccaaagcaa | ggggaagtca | cgcgcctgta | gcgccagcgt | gttgtgaaat | ggggcttgg | 3060 |
| gggggttggg | gccctgacta | gtcaaaacaa | actcccattg | acgtcaatgg | ggtggagact | 3120 |
| tggaaatccc | cgtgagtcaa | accgctatcc | acgcccattg | atgtactgcc | aaaaccgcat | 3180 |
| catcatggta | atagcgatga | ctaatacgta | gatgtactgc | caagtaggaa | agtcccataa | 3240 |
| ggtcatgtac | tgggcataat | gccaggcggg | ccatttaccg | tcattgacgt | caataggggg | 3300 |
| cgtacttggc | atatgataca | cttgatgtac | tgccaagtgg | gcagtttacc | gtaaatactc | 3360 |
| cacccattga | cgtcaatgga | aagtccctat | tggcgttact | atgggaacat | acgtcattat | 3420 |
| tgacgtcaat | gggcgggggt | cgttgggcgg | tcagccaggc | gggccattta | ccgtaagtta | 3480 |
| tgtaacgcct | gcaggttaat | taagaacatg | tgagcaaaag | gccagcaaaa | ggccaggaac | 3540 |
| cgtaaaaagg | ccgcgttgct | ggcgtttttc | cataggctcc | gcccccctga | cgagcatcac | 3600 |
| aaaaatcgac | gctcaagtca | gaggtggcga | aacccgacag | gactataaag | ataccaggcg | 3660 |
| tttccccctg | gaagctccct | cgtgcgctct | cctgttccga | ccctgccgct | taccggatac | 3720 |
| ctgtccgcct | ttctcccttc | gggaagcgtg | gcgctttctc | atagctcacg | ctgtaggtat | 3780 |
| ctcagttcgg | tgtaggtcgt | tcgctccaag | ctgggctgtg | tgcacgaacc | ccccgttcag | 3840 |
| cccgaccgct | gcgccttatc | cggtaactat | cgtcttgagt | ccaacccggt | aagacacgac | 3900 |
| ttatcgccac | tggcagcagc | cactggtaac | aggattagca | gagcgaggta | tgtaggcggt | 3960 |
| gctacagagt | tcttgaagtg | gtggcctaac | tacggctaca | ctagaagaac | agtatttggt | 4020 |
| atctgcgctc | tgctgaagcc | agttaccttc | ggaaaaagag | ttggtagctc | ttgatccggc | 4080 |
| aaacaaacca | ccgctggtag | cggtggtttt | tttgtttgca | agcagcagat | tacgcgcaga | 4140 |
| aaaaaaggat | ctcaagaaga | tcctttgatc | ttttctacgg | ggtctgacgc | tcagtggaac | 4200 |

```
gaaaactcac gttaagggat tttggtcatg gctagttaat taacatttaa atcagcggcc    4260
gcaataaaat atctttattt tcattacatc tgtgtgttgg tttttgtgt gaatcgtaac    4320 taacatacgc tctccatcaa aacaaaacga aacaaaacaa actagcaaaa taggctgtcc    4380
ccagtgcaag tgcaggtgcc agaacatttc tctatcgaa                          4419
```

<210> SEQ ID NO 106
<211> LENGTH: 20
<212> TYPE: PRT
<213> ORGANISM: Artificial Sequence
<220> FEATURE:
<223> OTHER INFORMATION: IL-2 Secretion Signal

<400> SEQUENCE: 106

```
Met Tyr Arg Met Gln Leu Leu Ser Cys Ile Ala Leu Ser Leu Ala Leu
1               5                   10                  15

Val Thr Asn Ser
            20
```